US012788749B2

(12) United States Patent
Goetz et al.

(10) Patent No.: US 12,788,749 B2
(45) Date of Patent: Nov. 10, 2026

(54) DEGRADING PKCB1 TO TREAT CANCER

(71) Applicant: Mayo Foundation for Medical Education and Research, Rochester, MN (US)

(72) Inventors: Matthew P. Goetz, Rochester, MN (US); Thomas R. Caulfield, Jacksonville, FL (US); John Randolph Hawse, IV, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 685 days.

(21) Appl. No.: 18/266,375

(22) PCT Filed: Dec. 10, 2021

(86) PCT No.: PCT/US2021/062953
§ 371 (c)(1),
(2) Date: Jun. 9, 2023

(87) PCT Pub. No.: WO2022/125988
PCT Pub. Date: Jun. 16, 2022

(65) Prior Publication Data

US 2024/0058318 A1 Feb. 22, 2024

Related U.S. Application Data

(60) Provisional application No. 63/123,983, filed on Dec. 10, 2020.

(51) Int. Cl.

| | |
|---|---|
| ***A61K 31/452*** | (2006.01) |
| ***A61K 31/138*** | (2006.01) |
| ***A61P 35/00*** | (2006.01) |

(52) U.S. Cl.
CPC .......... *A61K 31/452* (2013.01); *A61K 31/138* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 7,014,866 | B2 | 3/2006 | Infeld et al. |
| 9,353,132 | B2 | 5/2016 | Wang et al. |

(Continued)

FOREIGN PATENT DOCUMENTS

| | | |
|---|---|---|
| CN | 104367581 | 2/2015 |
| WO | WO 2016/197032 | 12/2016 |
| WO | WO 2018/102725 | 6/2018 |

OTHER PUBLICATIONS

Kareva et al., Frontiers in Ecology and Evolution (2021), 9, Article 673082 (15 pages) (Year: 2021).*

(Continued)

*Primary Examiner* — Adam C Milligan
*Assistant Examiner* — Jason M. Nolan
(74) *Attorney, Agent, or Firm* — Fish & Richardson P.C.

(57) ABSTRACT

Methods and material for treating cancer (e.g., estrogen receptor negative (ER−) and estrogen receptor positive (ER+) breast cancer) are described herein. For example, methods and materials for targeting degradation of protein kinase C type beta (PKCβ1) polypeptides in mammals with ER− cancers are described.

21 Claims, 54 Drawing Sheets

TC-Pr-001

(56) References Cited

U.S. PATENT DOCUMENTS

| | | | |
|---|---|---|---|
| 9,821,068 | B2 | 11/2017 | Bradner et al. |
| 2006/0079502 | A1 | 4/2006 | Lang |
| 2006/0094744 | A1 | 5/2006 | Maryanoff et al. |
| 2017/0144975 | A1 | 5/2017 | Cushman et al. |
| 2019/0263823 | A1 | 8/2019 | Bradner et al. |
| 2020/0157078 | A1 | 5/2020 | Fan et al. |

OTHER PUBLICATIONS

Dai et al., Journal of Cancer (2017), 8, 3131-3141 (Year: 2017).*
Extended European Search Report in European Appln. No. 21904523.4, dated Oct. 15, 2024, 8 pages.
Ali et al., "Endoxifen is a new potent inhibitor of PKC: a potential therapeutic agent for bipolar disorder," Bioorg. Med. Chem. Lett., Apr. 2010, 20(8):2665-2667.
Al-Saffar et al., "Metabolic biomarkers of response to the AKT inhibitor MK-2206 in pre-clinical models of human colorectal and prostate carcinoma," Br. J. Cancer, Oct. 2018, 119(9):1118-1128.
Borges et al., "Quantitative effect of CYP2D6 genotype and inhibitors on tamoxifen metabolism: implication for optimization of breast cancer treatment," Clin. Pharmacol. Ther., Jul. 2006, 80(1):61-74.
Burstein et al., "Adjuvant Endocrine Therapy for Women with Hormone Receptor- Positive Breast Cancer: ASCO Clinical Practice Guideline Focused Update," J. Clin. Oncol., Feb. 2019, 37(5):423-438.
Casado et al., "Kinase-substrate enrichment analysis provides insights into the heterogeneity of signaling pathway activation in leukemia cells," Sci. Signal., Mar. 2013, 6(268):rs6.
Chen et al., "AKT inhibitor MK-2206 sensitizes breast cancer cells to MLN4924, a first-in-class NEDD8-activating enzyme (NAE) inhibitor," Cell Cycle, Sep. 2018, 17(16):2069-2079.
Cheng et al., "MoMo: discovery of statistically significant post-translational modification motifs," Bioinformatics, Aug. 2019, 35(16):2774-2782.
Cicenas, "The potential role of Akt phosphorylation in human cancers," Int. J. Biol. Markers, Jan.-Mar. 2008, 23(1):1-9.
Clemons et al., "Phase II, double-blind, randomized trial of capecitabine plus enzastaurin versus capecitabine plus placebo in patients with metastatic or recurrent breast cancer after prior anthracycline and taxane therapy," Breast Cancer Res. Treat., Nov. 2010, 124(1):177-186.
Corazzari et al., "Endoplasmic Reticulum Stress, Unfolded Protein Response, and Cancer Cell Fate," Front. Oncol., Apr. 2017, 7:78.
Curtis et al., "The genomic and transcriptomic architecture of 2,000 breast tumours reveals novel subgroups," Nature, Apr. 2012, 486(7403):346-352.
Demizu et al., "Design and synthesis of estrogen receptor degradation inducer based on a protein knockdown strategy," Bioorg. Med. Chem. Lett., Feb. 2012, 22(4):1793-1796.
Dennis Jr. et al., "DAVID: Database for Annotation, Visualization, and Integrated Discovery," Genome Biol., Apr. 2003, 4(5):P3.
Dobrikov et al., "Ribosomal RACK1:Protein Kinase C βII Phosphorylates Eukaryotic Initiation Factor 4G1 at S1093 to Modulate Cap-Dependent and -Independent Translation Initiation," Mol. Cell. Biol., Oct. 2018, 38(19):e00304-18.
Dowsett et al., "Proliferation and Apoptosis as Markers of Benefit in Neoadjuvant Endocrine Therapy of Breast Cancer," Clin. Cancer Res., Feb. 2006, 12(3):1024s-1030s.
Duronio, "The life of a cell: apoptosis regulation by the PI3K/PKB pathway," Biochem. J., Nov. 2008, 415(3):333-344.
Early Breast Cancer Trialists' Collaborative Group (EBCTCG), "Relevance of breast cancer hormone receptors and other factors to the efficacy of adjuvant tamoxifen: patient-level meta-analysis of randomised trials," Lancet, Aug. 2011, 378(9793):771-784.
Early Breast Cancer Trialists' Collaborative Group (EBCTCG), "Aromatase inhibitors versus tamoxifen in early breast cancer: patient-level meta-analysis of the randomised trials," Lancet, Oct. 2015, 386(10001):1341-1352.
Early Breast Cancer Trialists' Collaborative Group (EBCTCG), "Effects of chemotherapy and hormonal therapy for early breast cancer on recurrence and 15-year survival: an overview of the randomised trials," Lancet, May 2005, 365(9472):1687-1717.
Franke et al., "PI3K/Akt and apoptosis: size matters," Oncogene, Dec. 2003, 22(56):8983-8998.
Fusco et al., "PIK3CA Mutations as a Molecular Target for Hormone Receptor-Positive, HER2-Negative Metastatic Breast Cancer," Front. Oncol., Mar. 2021, 11:644737.
Gingery et al., "Skeletal and Uterotrophic Effects of Endoxifen in Female Rats," Endocrinology, Oct. 2017, 158(10):3354-3368.
Gingery et al., "The effects of a novel hormonal breast cancer therapy, endoxifen, on the mouse skeleton, " PLoS One, May 2014, 9(5):e98219.
Goetz et al., "Abstract PD7-06: A randomized phase II trial of tamoxifen versus Z-endoxifen HCL in postmenopausal women with metastatic estrogen receptor positive, HER2 negative breast cancer," Cancer Res., Feb. 2020, 80(4_Supplement):PD7-06.
Goetz et al., "First-in-Human Phase I Study of the Tamoxifen Metabolite Z-Endoxifen in Women with Endocrine-Refractory Metastatic Breast Cancer," J. Clin. Oncol., Oct. 2017, 35(30):3391-3400.
Goetz et al., "Tumor Sequencing and Patient-Derived Xenografts in the Neoadjuvant Treatment of Breast Cancer," J. Natl. Cancer Inst., Jul. 2017, 109(7):djw306.
Guo et al., "Identification and Characterization of a Novel Endoxifen Substrate, PKCβ1, and its Interactions with the Estrogen Receptor," Poster, Presented at proceedings of the San Antonio Breast Cancer Symposium, San Antonio, TX, Dec. 9-13, 2016, 1 page.
Hawse et al., "Endoxifen's molecular mechanisms of action are concentration dependent and different than that of other anti-estrogens," PLoS One, Jan. 2013, 8(1):e54613.
Heider et al., "The IMID-Target Cereblon Determines Transmembrane Protein Quality Control Promoting Tumor Metabolism," Blood, Nov. 2019, 134(Suppl. 1):314.
Hill et al., "Insulin-stimulated protein kinase B phosphorylation on Ser-473 is independent of its activity and occurs through a staurosporine-insensitive kinase," J. Biol. Chem., Jul. 2001, 276(28):25643-25646.
Hollestelle et al., "Phosphatidylinositol-3-OH kinase or RAS pathway mutations in human breast cancer cell lines," Mol. Cancer Res., Feb. 2007, 5(2):195-201.
Horn et al., "KinomeXplorer: an integrated platform for kinome biology studies," Nat. Methods, Jun. 2014, 11(6):603-604.
Hornbeck et al., "PhosphoSitePlus, 2014: mutations, PTMs and recalibrations," Nucleic Acids Res., Jan. 2015, 43(Database issue):D512-D520.
Jayaraman et al., "Abstract P6-04-06: Protein kinase C beta 1 (PKCβ1), a novel drug target of Z-endoxifen, inhibits growth of estrogen receptor positive (ER+) breast cancer via activation of the NF-κB transcription factor RelA," Cancer Res., Feb. 2020, 80(4_Supplement):P6-04-06.
Jayaraman et al., "Abstract PD8-04: Antitumor activity of Z-endoxifen (ENDX) is mediated via PKCβ1-dependent ERα loss and cell cycle arrest in ERα-positive breast cancer," Cancer Res., Feb. 2021, 81(4_Supplement):PD8-04.
Jayaraman et al., "Antitumor Activity of Z-endoxifen (ENDX) is Mediated via PKCβ1-Dependent ERα Loss and Cell Cycle Arrest in ERα-Positive Breast Cancer," Poster, Presented at the proceedings of the San Antonio Breast Cancer Symposium, San Antonio, TX, Dec. 8-11, 2020, 1 page.
Jayaraman et al., "Antitumor activity of Z-endoxifen in aromatase inhibitor-sensitive and aromatase inhibitor-resistant estrogen receptor-positive breast cancer," Breast Cancer Res., May 2020, 22(1):51.
Jayaraman et al., "Endoxifen downregulates AKT phosphorylation through protein kinase C beta 1 inhibition in ERα+ breast cancer," NPJ Breast Cancer, Dec. 2023, 9:101.
Jayaraman et al., "Endoxifen, an Estrogen Receptor Targeted Therapy: From Bench to Bedside," Endocrinology, Dec. 2021, 162(12):bqab191.
Jayaraman et al., "Protein Kinase C Beta 1 (PKCβ1), a novel drug target of Z-endoxifen, inhibits growth of estrogen receptor positive (ER+) breast cancer via activation of the NF-κB transcription factor

(56) References Cited

OTHER PUBLICATIONS

RelA," Poster, Presented at proceedings of the San Antonio Breast Cancer Symposium, San Antonio, TX, Dec. 10-14, 2019, 1 page.
Jiao et al., "DAVID-WS: a stateful web service to facilitate gene/protein list analysis," Bioinformatics, Jul. 2012, 28(13):1805-1806.
Jiao et al., "MK-2206 induces cell cycle arrest and apoptosis in HepG2 cells and sensitizes TRAIL-mediated cell death," Mol. Cell. Biochem., Oct. 2013, 382(1-2):217-224.
Jin et al., "CYP2D6 genotype, antidepressant use, and tamoxifen metabolism during adjuvant breast cancer treatment," J. Natl. Cancer Inst., Jan. 2005, 97(1):30-39.
Johnson et al., "Pharmacological characterization of 4-hydroxy-N-desmethyl tamoxifen, a novel active metabolite of tamoxifen," Breast Cancer Res. Treat., May 2004, 85(2):151-159.
Kennedy et al., "The PI 3-kinase/Akt signaling pathway delivers an anti-apoptotic signal," Genes Dev., Mar. 1997, 11(6):701-713.
Kuleshov et al., "KEA3: improved kinase enrichment analysis via data integration," Nucleic Acids Res., Jul. 2021, 49(W1):W304-W316.
Li et al., "Fulvestrant in the treatment of hormone receptor-positive/human epidermal growth factor receptor 2-negative advanced breast cancer: A review," Cancer Med., May 2019, 8(5):1943-1957.
Li et al., "Protein Kinase C β Enhances Growth and Expression of Cyclin D1 in Human Breast Cancer Cells," Cancer Res., Dec. 2006, 66(23):11399-11408.
Lim et al., "Endoxifen (4-hydroxy-N-desmethyl-tamoxifen) has anti-estrogenic effects in breast cancer cells with potency similar to 4-hydroxy-tamoxifen," Cancer Chemother. Pharmacol., May 2005, 55(5):471-478.
Long et al., "Therapeutic strategies using the aromatase inhibitor letrozole and tamoxifen in a breast cancer model," J. Natl. Cancer Inst., Mar. 2004, 96(6):456-465.
Lu et al., "MK-2206 induces apoptosis of AML cells and enhances the cytotoxicity of cytarabine," Med. Oncol., Jul. 2015, 32(7):206.
Macedo et al., "Combination of anastrozole with fulvestrant in the intratumoral aromatase xenograft model," Cancer Res., May 2008, 68(9):3516-3522.
Maximov et al., "Pharmacological relevance of endoxifen in a laboratory simulation of breast cancer in postmenopausal patients," J. Natl. Cancer Inst., Sep. 2014, 106(10):dju283.
Maximov et al., "Simulation with cells in vitro of tamoxifen treatment in premenopausal breast cancer patients with different CYP2D6 genotypes," Br. J. Pharmacol., Dec. 2014, 171(24):5624-5635.
Mina et al., "A phase II study of oral enzastaurin in patients with metastatic breast cancer previously treated with an anthracycline and a taxane containing regimen," Invest. New Drugs, Dec. 2009, 27(6):565-570.
Monroe et al., "Estrogen receptor isoform-specific regulation of endogenous gene expression in human osteoblastic cell lines expressing either ERα or ERβ," J. Cell. Biochem., Oct. 2003, 90(2):315-326.
Mosele et al., "Outcome and molecular landscape of patients with PIK3CA-mutated metastatic breast cancer," Ann. Oncol., Mar. 2020, 31(3):377-386.
Murdter et al., "Activity levels of tamoxifen metabolites at the estrogen receptor and the impact of genetic polymorphisms of phase I and II enzymes on their concentration levels in plasma," Clin. Pharmacol. Ther., May 2011, 89(5):708-717.
Murray et al., "Overexpression of protein kinase C betaII induces colonic hyperproliferation and increased sensitivity to colon carcinogenesis," J. Cell. Biol., May 1999, 145(4):699-711.
O'Brian et al., "Inhibition of Protein Kinase C by Tamoxifen," Cancer Res., Jun. 1985, 45(6):2462-2465.
O'Sullivan et al., "Abstract PS5-24: Novel genomic variants and pathways associated with baseline serum thymidine kinase 1 levels in HR-positive HER2-negative MBC patients commencing palbociclib and letrozole," Cancer Res., Feb. 2021, 81(4_Supplement):PS5-24.
Ogata et al., "KEGG: Kyoto Encyclopedia of Genes and Genomes," Nucleic Acids Res., Jan. 1999, 27(1):29-34.
Okuhira et al., "Development of hybrid small molecules that induce degradation of estrogen receptor-alpha and necrotic cell death in breast cancer cells," Cancer Sci., Nov. 2013, 104(11):1492-1498.
PCT International Search Report and Written Opinion in International Appln. No. PCT/US2021/062953, mailed on May 16, 2022, 11 pages.
PCT Preliminary Report on Patentability in International Appln. No. PCT/US2021/062953, mailed on Jun. 22, 2023, 8 pages.
Reese et al., "ERB-mediated induction of cystatins results in suppression of TGFβ signaling and inhibition of triple-negative breast cancer metastasis, " Proc. Natl. Acad. Sci. USA, Sep. 2018, 115(41):E9580-E9589.
Reid et al., "Pharmacokinetics of endoxifen and tamoxifen in female mice: implications for comparative in vivo activity studies," Cancer Chemother. Pharmacol., Dec. 2014, 74(6):1271-1278.
Riester et al., "PureCN: copy number calling and SNV classification using targeted short read sequencing," Source Code Biol. Med., Dec. 2016, 11:13.
Sabbah et al., "Estrogen induction of the cyclin D1 promoter: involvement of a cAMP response-like element," Proc. Natl. Acad. Sci. USA, Sep. 1999, 96(20):11217-11222.
Schroth et al., "Improved Prediction of Endoxifen Metabolism by CYP2D6 Genotype in Breast Cancer Patients Treated with Tamoxifen," Front. Pharmacol., Aug. 2017, 8:582.
Schwartz et al., "An iterative statistical approach to the identification of protein phosphorylation motifs from large-scale data sets," Nat. Biotechnol., Nov. 2005, 23(11):1391-1398.
Schweikart et al., "Comparative uterotrophic effects of endoxifen and tamoxifen in ovariectomized Sprague-Dawley rats," Toxicol. Pathol., Dec. 2014, 42(8):1188-1196.
Sherman et al., "DAVID: a web server for functional enrichment analysis and functional annotation of gene lists (2021 update), " Nucleic Acids Res., Jul. 2022, 50(W1):W216-W221.
Steinebach et al., "Systematic exploration of different E3 ubiquitin ligases: an approach towards potent and selective CDK6 degraders," Chem. Sci., Mar. 2020, 11(13):3474-3486.
Takebe et al., "Phase 1 study of Z-endoxifen in patients with advanced gynecologic, desmoid, and hormone receptor-positive solid tumors," Oncotarget, Feb. 2021, 12(4): 268-277.
Tao et al., "Akt inhibitor MK-2206 enhances the effect of cisplatin in gastric cancer cells," Biomed. Rep., Mar. 2016, 4(3):365-368.
The Cancer Genome Atlas Network, "Comprehensive molecular portraits of human breast tumours," Nature, Oct. 2012, 490(7418):61-70.
Wallace et al., "Protein kinase C Beta in the tumor microenvironment promotes mammary tumorigenesis," Front. Oncol., Apr. 2014, 4:87.
Wang et al., "Transcriptional Activation of E2F1 Gene Expression by 17β-Estradiol in MCF-7 Cells is Regulated by NF-Y-Sp1/Estrogen Receptor Interactions," Mol. Endocrinol., Aug. 1999, 13(8):1373-1387.
Wu et al., "PKC-β1 Mediates Glucose-Induced Akt Activation and TGF-β1 Upregulation in Mesangial Cells," J. Am. Soc. Nephrol., Mar. 2009, 20(3):554-566.
Wu et al., "Somatic mutation and gain of copy number of PIK3CA in human breast cancer," Breast Cancer Res., May 2005, 7(5):R609-R616.
Wu et al., "The tamoxifen metabolite, endoxifen, is a potent antiestrogen that targets estrogen receptor alpha for degradation in breast cancer cells," Cancer Res., Mar. 2009, 69(5):1722-1727.
Yilmaz et al., "Robust inference of kinase activity using functional networks," Nat. Commun., Feb. 2021, 12(1):1177.
Yue et al., "A New Nude Mouse Model for Postmenopausal Breast Cancer Using MCF-7 Cells Transfected with the Human Aromatase Gene," Cancer Res., Oct. 1994, 54(19):5092-5095.

* cited by examiner

TC-Pr-001

TC-Pr-003

TC-Pr-002

TC-Pr-004

TC-Pr-005

TC-Pr-006

TC-Pr-007

TC-Pr-008

TC-Pr-009

1
2
2
3
3
TC-Pr-009

MCF7AC1

TC-Pr-009 analog 1: IC50 ≤ 0.01 μM

TC-Pr-009 analog 4: IC50 ≤ 0.01 μM

| | | | TC-Pr-009 analog 1 (μM) | | | | TC-Pr-009 analog 4 (μM) | | | |
|---|---|---|---|---|---|---|---|---|---|---|
| **MCF7AC1 cells (2000 cells/well):** | **No treat** | **DMSO** | **0.01** | **0.1** | **1** | **10** | **0.01** | **0.1** | **1** | **10** |
| | 0.6014 | 0.5745 | 0.2036 | 0.1232 | 0.1443 | 0.1244 | 0.2193 | 0.1216 | 0.1414 | 0.1473 |
| | 0.6012 | 0.5855 | 0.2186 | 0.1218 | 0.1487 | 0.1217 | 0.2256 | 0.1173 | 0.1370 | 0.1380 |
| | 0.6067 | 0.5745 | 0.2111 | 0.1236 | 0.1469 | 0.1216 | 0.2515 | 0.1178 | 0.1347 | 0.1388 |
| | 0.5946 | 0.5820 | 0.2253 | 0.1283 | 0.1440 | 0.1243 | 0.2367 | 0.1146 | 0.1294 | 0.1245 |
| | 0.5835 | 0.5763 | 0.2140 | 0.1252 | 0.1372 | 0.1247 | 0.2383 | 0.1123 | 0.1235 | 0.1298 |
| | 0.5912 | 0.5848 | 0.2044 | 0.1146 | 0.1418 | 0.1287 | 0.2111 | 0.1179 | 0.1339 | 0.1385 |
| **Average:** | **0.5964** | **0.5796** | **0.2128** | **0.1228** | **0.1438** | **0.1242** | **0.2304** | **0.1169** | **0.1333** | **0.1361** |
| ***Stdev:*** | ***0.0084*** | ***0.0051*** | ***0.0084*** | ***0.0046*** | ***0.0040*** | ***0.0026*** | ***0.0146*** | ***0.0032*** | ***0.0062*** | ***0.0080*** |
| **% inhibition of DMSO:** | | **100** | **37** | **21** | **25** | **21** | **40** | **20** | **23** | **23** |

FIG. 9B

| | | | TC-Pr-009 analog 1 (μM) | | | | TC-Pr-009 analog 4 (μM) | | | |
|---|---|---|---|---|---|---|---|---|---|---|
| **MDAMB231 cells (2000 cells/well):** | **No treat** | **DMSO** | **0.01** | **0.1** | **1** | **10** | **0.01** | **0.1** | **1** | **10** |
| | 0.1979 | 0.2327 | 0.1958 | 0.1977 | 0.2191 | 0.1361 | 0.2357 | 0.2222 | 0.2035 | 0.1077 |
| | 0.1853 | 0.2140 | 0.2013 | 0.1895 | 0.1980 | 0.1711 | 0.2287 | 0.2216 | 0.2000 | 0.1001 |
| | 0.2219 | 0.1999 | 0.2235 | 0.2095 | 0.2262 | 0.1468 | 0.2307 | 0.2041 | 0.1939 | 0.0970 |
| | 0.2070 | 0.1923 | 0.2040 | 0.2064 | 0.2168 | 0.1631 | 0.2341 | 0.2312 | 0.1876 | 0.0929 |
| | 0.2031 | 0.2112 | 0.2283 | 0.2007 | 0.2236 | 0.1563 | 0.2352 | 0.2240 | 0.2026 | 0.1050 |
| | 0.2067 | 0.2074 | 0.2123 | 0.2083 | 0.2178 | 0.1675 | 0.2247 | 0.2130 | 0.1906 | 0.0812 |
| **Average:** | **0.2037** | **0.2096** | **0.2109** | **0.2021** | **0.2170** | **0.1569** | **0.2316** | **0.2194** | **0.1964** | **0.0974** |
| ***Stdev:*** | ***0.0120*** | ***0.0138*** | ***0.0129*** | ***0.0076*** | ***0.0099*** | ***0.0133*** | ***0.0043*** | ***0.0095*** | ***0.0066*** | ***0.0095*** |
| **% inhibition of DMSO:** | | **100** | **101** | **96** | **103** | **75** | **110** | **105** | **94** | **46** |

FIG. 9D

| | | | TC-Pr-009 analog 1 (μM) | | | | TC-Pr-009 analog 4 (μM) | | | |
|---|---|---|---|---|---|---|---|---|---|---|
| **BT549 cells (2000 cells/well):** | **No treat** | **DMSO** | **0.01** | **0.1** | **1** | **10** | **0.01** | **0.1** | **1** | **10** |
| | 0.1509 | 0.1566 | 0.1740 | 0.1550 | 0.1799 | 0.1296 | 0.2014 | 0.1686 | 0.1270 | 0.0738 |
| | 0.1693 | 0.1646 | 0.1782 | 0.1723 | 0.1699 | 0.1369 | 0.2477 | 0.1822 | 0.1274 | 0.0759 |
| | 0.1731 | 0.1519 | 0.1694 | 0.1832 | 0.1545 | 0.1336 | 0.1771 | 0.1593 | 0.1192 | 0.0758 |
| | 0.1514 | 0.1370 | 0.1435 | 0.1571 | 0.1496 | 0.1319 | 0.1711 | 0.1547 | 0.1148 | 0.0779 |
| | 0.1514 | 0.1512 | 0.1504 | 0.1400 | 0.1535 | 0.1172 | 0.1578 | 0.1573 | 0.1066 | 0.0705 |
| | 0.1411 | 0.1567 | 0.1441 | 0.1569 | 0.1435 | 0.1101 | 0.1715 | 0.1460 | 0.1113 | 0.0630 |
| Average: | **0.1562** | **0.1530** | **0.1599** | **0.1607** | **0.1584** | **0.1265** | **0.1877** | **0.1613** | **0.1177** | **0.0728** |
| *Stdev:* | ***0.0123*** | ***0.0092*** | ***0.0157*** | ***0.0150*** | ***0.0137*** | ***0.0105*** | ***0.0327*** | ***0.0126*** | ***0.0084*** | ***0.0054*** |
| % inhibition of DMSO: | | 100 | 105 | 105 | 104 | 83 | 123 | 105 | 77 | 48 |

FIG. 9F

| | | | TC-Pr-009 analog 1 (μM) | | | | TC-Pr-009 analog 4 (μM) | | | |
|---|---|---|---|---|---|---|---|---|---|---|
| **BT549 cells (4000 cells/well):** | **No treat** | **DMSO** | **0.01** | **0.1** | **1** | **10** | **0.01** | **0.1** | **1** | **10** |
| | 0.3187 | 0.3176 | 0.3301 | 0.3288 | 0.3292 | 0.2613 | 0.3382 | 0.3206 | 0.2140 | 0.1494 |
| | 0.3166 | 0.3016 | 0.3392 | 0.3326 | 0.3254 | 0.2665 | 0.3438 | 0.3387 | 0.2461 | 0.1564 |
| | 0.3406 | 0.3126 | 0.3407 | 0.3169 | 0.3347 | 0.2516 | 0.3623 | 0.3269 | 0.2328 | 0.1565 |
| | 0.3116 | 0.3130 | 0.3339 | 0.3261 | 0.3298 | 0.2730 | 0.3361 | 0.3159 | 0.2278 | 0.1309 |
| | 0.2893 | 0.3085 | 0.2990 | 0.3029 | 0.2803 | 0.2488 | 0.3204 | 0.3158 | 0.2187 | 0.1452 |
| | 0.2735 | 0.2771 | 0.3220 | 0.3144 | 0.3163 | 0.2430 | 0.3221 | 0.3348 | 0.2268 | 0.1492 |
| **Average:** | **0.3084** | **0.3051** | **0.3275** | **0.3203** | **0.3193** | **0.2574** | **0.3371** | **0.3254** | **0.2277** | **0.1479** |
| ***Stdev:*** | ***0.0237*** | ***0.0147*** | ***0.0155*** | ***0.0110*** | ***0.0201*** | ***0.0115*** | ***0.0154*** | ***0.0097*** | ***0.0113*** | ***0.0094*** |
| **% inhibition of DMSO:** | | **100** | **107** | **105** | **105** | **84** | **111** | **107** | **75** | **48** |

FIG. 9H

TC-Pr-009 analog 1: No major kill

TC-Pr-009 analog 4: IC50 between 1 – 10 μM

| | | | TC-Pr-009 analog 1 (μM) | | | | TC-Pr-009 analog 4 (μM) | | | |
|---|---|---|---|---|---|---|---|---|---|---|
| **MDAMB436 cells (4000 cells/well):** | **No treat** | **DMSO** | **0.01** | **0.1** | **1** | **10** | **0.01** | **0.1** | **1** | **10** |
| | 0.2931 | 0.2828 | 0.2632 | 0.2907 | 0.2865 | 0.2679 | 0.2851 | 0.2774 | 0.1887 | 0.1175 |
| | 0.2957 | 0.2581 | 0.3191 | 0.2637 | 0.2927 | 0.2675 | 0.2942 | 0.2823 | 0.1871 | 0.1142 |
| | 0.2959 | 0.2646 | 0.2789 | 0.2512 | 0.2805 | 0.2589 | 0.3186 | 0.2823 | 0.2019 | 0.1159 |
| | 0.2716 | 0.2613 | 0.2777 | 0.2648 | 0.2494 | 0.2571 | 0.3031 | 0.2773 | 0.1769 | 0.1184 |
| | 0.2679 | 0.2690 | 0.2531 | 0.2737 | 0.2544 | 0.2398 | 0.2862 | 0.2541 | 0.1668 | 0.1161 |
| | 0.2563 | 0.2517 | 0.2568 | 0.2581 | 0.2517 | 0.2466 | 0.2999 | 0.2717 | 0.1816 | 0.1058 |
| **Average:** | **0.2801** | **0.2646** | **0.2748** | **0.2671** | **0.2692** | **0.2563** | **0.2979** | **0.2742** | **0.1839** | **0.1147** |
| ***Stdev:*** | ***0.0170*** | ***0.0107*** | ***0.0242*** | ***0.0138*** | ***0.0195*** | ***0.0113*** | ***0.0124*** | ***0.0106*** | ***0.0119*** | ***0.0046*** |
| **% inhibition of DMSO:** | | **100** | **104** | **101** | **102** | **97** | **113** | **104** | **69** | **43** |

FIG. 9J

Xbp-1

Bax

DEGRADING PKCB1 TO TREAT CANCER

CROSS-REFERENCE TO RELATED APPLICATIONS

This application is a National Stage application under 35 U.S.C. § 371 of International Application No. PCT/US2021/062953, having an International Filing Date of Dec. 10, 2021, which claims priority from U.S. Provisional Application Ser. No. 63/123,983, filed Dec. 10, 2020. The disclosures of the prior applications are considered part of (and are incorporated by reference in) the disclosure of this application.

STATEMENT AS TO FEDERALLY SPONSORED RESEARCH

This invention was made with government support under CA015083 and CA116201 awarded by the National Institutes of Health. The government has certain rights in the invention.

TECHNICAL FIELD

This document relates to methods and materials for treating cancer (e.g., estrogen receptor negative (ER−) or estrogen receptor positive (ER+) breast cancer). For example, this document provides methods and materials for targeting degradation of protein kinase C type beta (PKCβ1) in mammals with breast cancer (e.g., ER− or ER+ breast cancer).

BACKGROUND

Breast cancer can be classified as hormone receptor-positive or hormone-receptor negative. About 80% of all breast cancers are estrogen receptor alpha positive (ERα+), meaning that the cancer cells grow in response to estrogen, while about 20% of all breast cancers are estrogen receptor alpha negative (ERα−). About 65% of ER positive breast cancers also are progesterone receptor (PR) positive. In addition, cancer cells in about 20% of breast cancers have increased levels of the HER2 protein; these cancers tend to be aggressive and fast-growing. On the other hand, between about 10% and about 20% of breast cancers are referred to as "triple negative" because they don't have estrogen or progesterone receptors and they don't overexpress HER2. Tumors that are ER+ and/or PR+ can be treated with hormone therapy, while tumors that are ER− and PR− cannot; hormone negative cancers are more typically treated with surgery, chemotherapy, and/or radiation.

SUMMARY

This document is based, at least in part, on the discovery that mammals identified as having ER− or ER+ breast cancer can be treated with bifunctional compounds containing a small molecule targeted to protein kinase C type beta (PKCβ1), where binding of the bifunctional compounds to PKCβ1 leads to PKCβ1 polypeptide degradation. In general, the bifunctional compounds include a polypeptide-binding moiety and an E3 ubiquitin ligase-binding moiety that can induce proteasome-mediated degradation of the targeted polypeptide. In some cases, this document provides compounds that target a PKCβ1 polypeptide as well as methods for using such compounds to treat mammals identified as having breast cancer (e.g., ER− or ER+ breast cancer).

In a first aspect, this document features a method for killing an ER− cancer cell. The method can include contacting the cell with a bifunctional compound that includes (a) a first molecule component capable of interacting with a PKCβ1 polypeptide, (b) a second molecule component capable of interacting with an E3 ubiquitin ligase polypeptide, and (c) a linker covalently coupling the first molecule component to the second molecule component. The cancer cell can be a breast cancer cell or an ovarian cancer cell. The first molecule component can include an endoxifen residue. The second molecule component can include an immunomodulatory drug (IMiD) residue. The second molecule component can include a thalidomide residue. The bifunctional compound can have an $IC_{50}$ of less than 500 nM in a crystal violet proliferation assay using triple negative cells (e.g., BT549 cells or MDAMB436 cells). The bifunctional compound can be a compound of Formula (A):

(A)

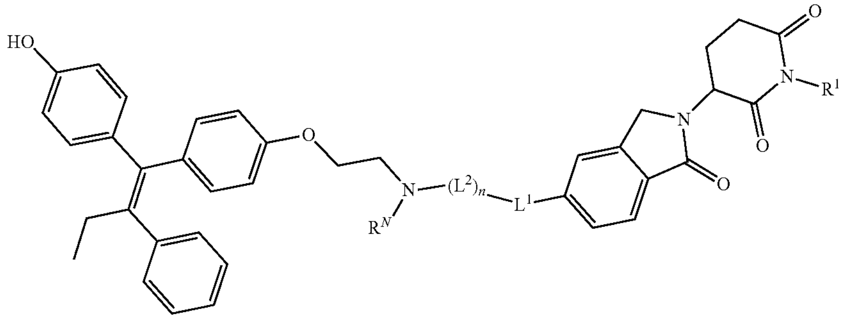

or a pharmaceutically acceptable salt thereof, wherein $L^1$ is $C_{1-3}$ alkylene, optionally substituted with 1, 2, or 3 substituents independently selected from OH, $NO_2$, CN, halo, amino, and carboxy; n is an integer selected from 1 to 10; each $L^2$ is independently selected from C(═O), $N(R^N)$, O, $(—C_{1-3}$ alkylene-O—$)_x$, (—O—$C_{1-3}$ alkylene-$)_x$, —$C_{1-3}$ alkylene-, and 4-6 membered heterocycloalkylene, wherein each x is independently an integer from 1 to 10, and wherein said $C_{1-3}$ alkylene and 4-6 membered heterocycloalkylene are each optionally substituted with 1, 2, or 3 substituents independently selected from OH, $NO_2$, CN, halo, amino, and carboxy; each $R^N$ is independently selected from H and $C_{1-3}$ alkyl; and $R^1$ is selected from H and $C_{1-3}$ alkyl, optionally substituted with a group selected from —OC (=O)O—$C_{1-6}$ alkyl, —OC(=O)$NH_2$, —OC(=O)NH($C_{1-6}$ alkyl), —OC(=O)N($C_{1-6}$ alkyl)$_2$, NHC(=O)O—$C_{1-6}$ alkyl, NHC(=O)$NH_2$, NHC(=O)NH($C_{1-6}$ alkyl), and NHC(=O)N($C_{1-6}$ alkyl)$_2$. The bifunctional compound can be a compound of Formula (I):

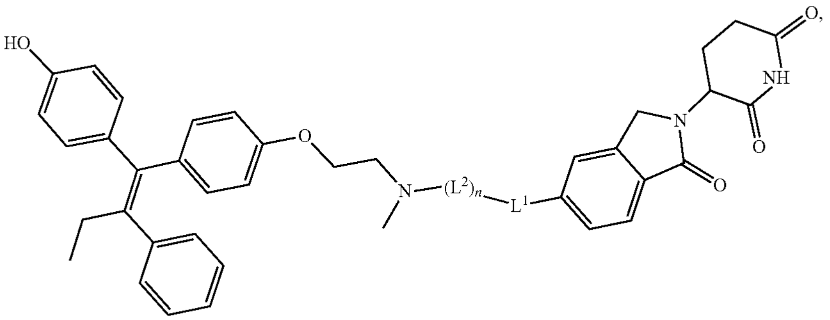

(I)

or a pharmaceutically acceptable salt thereof, wherein $L^1$ is $C_{1-3}$ alkylene, optionally substituted with 1, 2, or 3 substituents independently selected from OH, $NO_2$, CN, halo, amino, and carboxy; n is an integer selected from 1 to 10; each $L^2$ is independently selected from C(=O), N($R^N$), O, (—$C_{1-3}$ alkylene-O—)$_x$, (—O—$C_{1-3}$ alkylene-)$_x$, and —$C_{1-3}$ alkylene-, wherein each x is independently an integer from 1 to 10 and each $C_{1-3}$ alkylene is optionally substituted with 1, 2, or 3 substituents independently selected from OH, $NO_2$, CN, halo, amino, and carboxy; and each $R^N$ is independently selected from H and $C_{1-3}$ alkyl. The bifunctional compound can be a compound of Formula (II):

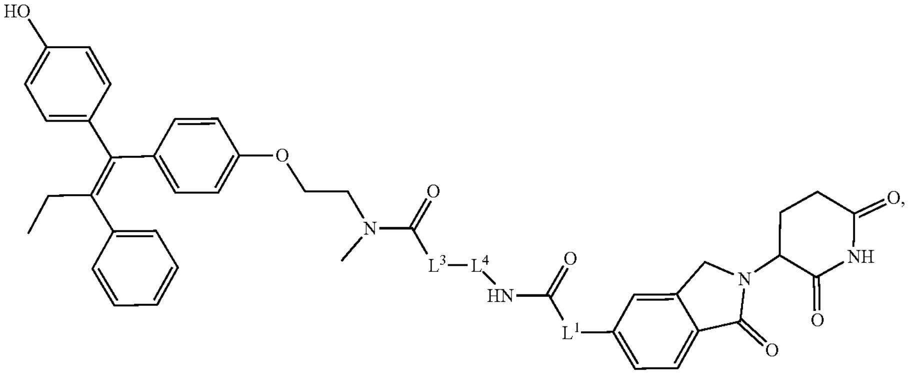

(II)

or a pharmaceutically acceptable salt thereof, wherein $L^3$ is $C_{1-3}$ alkylene; and $L^4$ is (—O—$C_{1-3}$ alkylene-)$_x$. The bifunctional compound can have Formula (III), Formula (IV), or Formula (V):

(III)
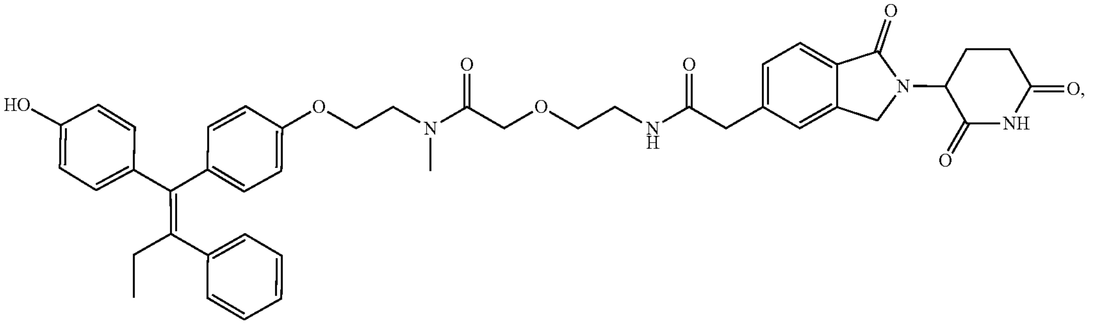
(IV)
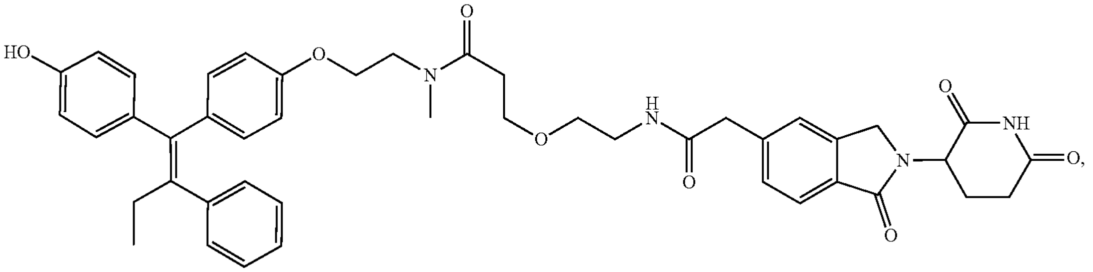
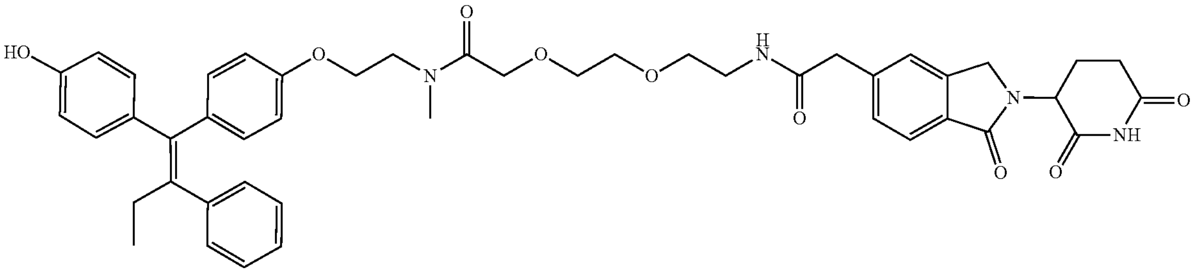
(V), or a pharmaceutically acceptable salt thereof. The bifunctional compound can have Formula (VI):
(VI)
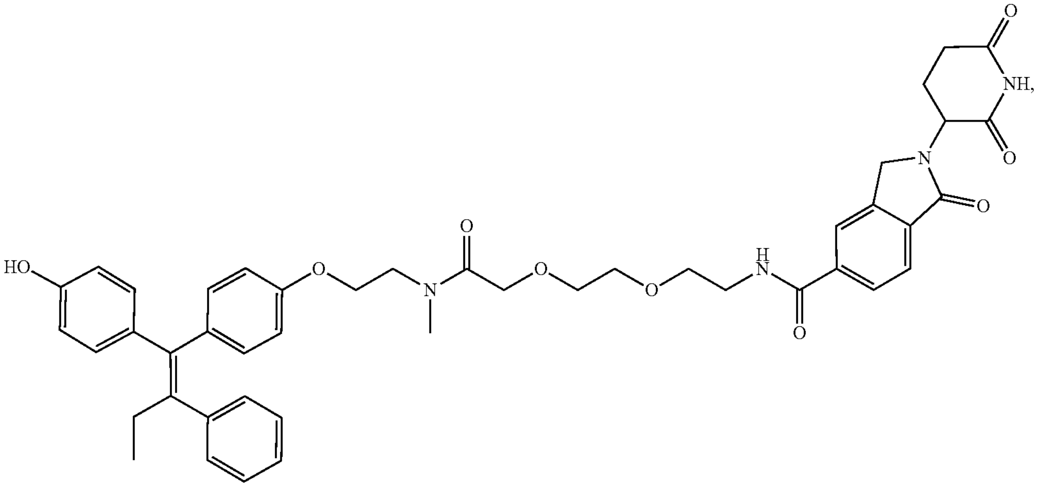
or a pharmaceutically acceptable salt thereof. The bifunctional compound can have Formula (VII), Formula (VIII), or Formula (IX):

(VII)

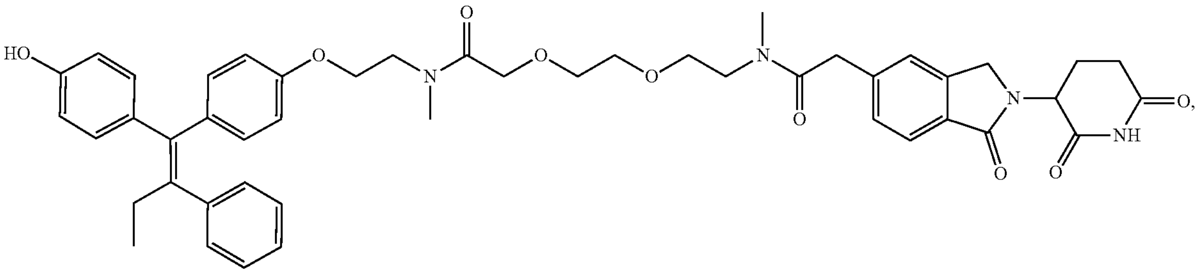

(VIII)

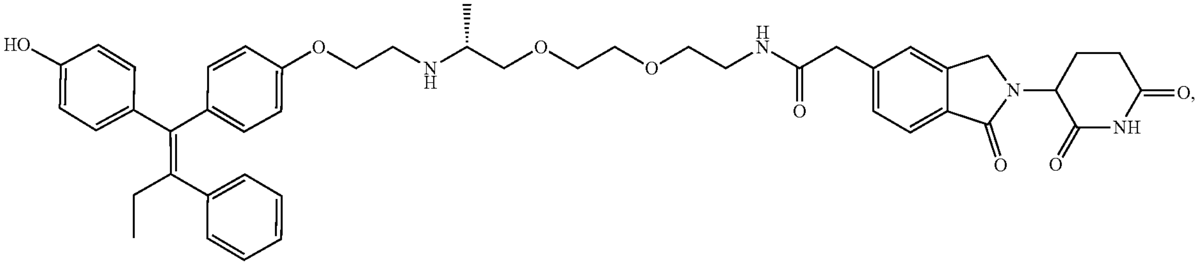

(IX)

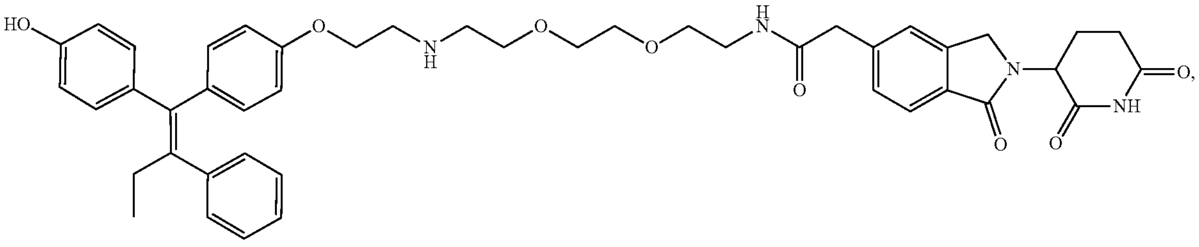

or a pharmaceutically acceptable salt thereof. The bifunctional compound can be a compound of Formula (B):

(B)

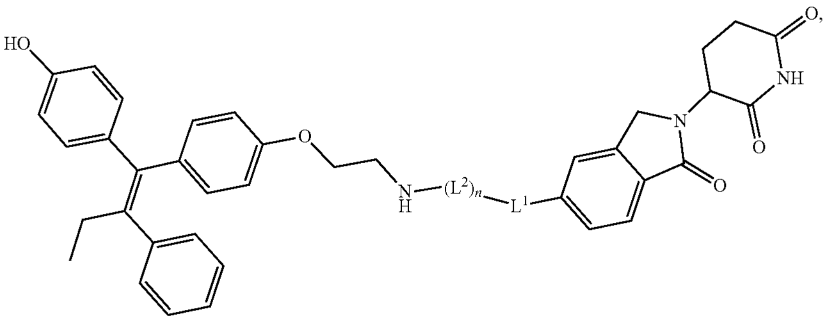

or a pharmaceutically acceptable salt thereof, wherein $L^1$ is $C_{1-3}$ alkylene, optionally substituted with 1, 2, or 3 substituents independently selected from OH, $NO_2$, CN, halo, amino, and carboxy; n is an integer selected from 1 to 10; each $L^2$ is independently selected from C(═O), $N(R^N)$, O, (—$C_{1-3}$ alkylene-O—$)_x$, (—O—$C_{1-3}$ alkylene-$)_x$, —$C_{1-3}$ alkylene-, and 4-6 membered heterocycloalkylene, wherein each x is independently an integer from 1 to 10, wherein said $C_{1-3}$ alkylene and 4-6 membered heterocycloalkylene are each optionally substituted with 1, 2, or 3 substituents independently selected from OH, $NO_2$, CN, halo, amino, and carboxy; and wherein each $R^N$ is independently selected from H and $C_{1-3}$ alkyl. The bifunctional compound can have Formula (X):

(X)

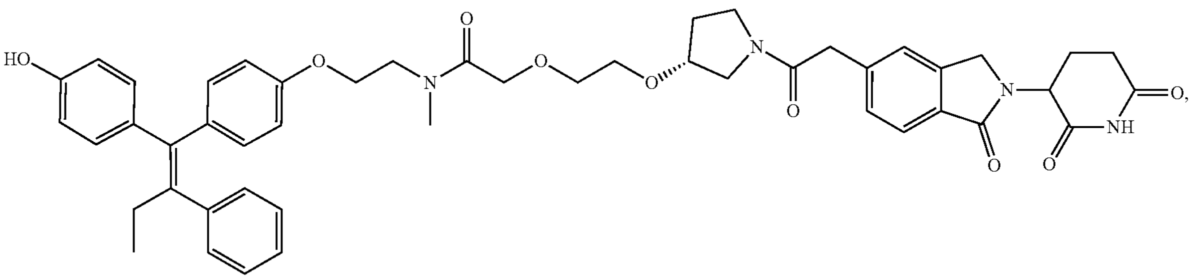

or a pharmaceutically acceptable salt thereof. The bifunctional compound can be a compound of Formula (C):

(C)

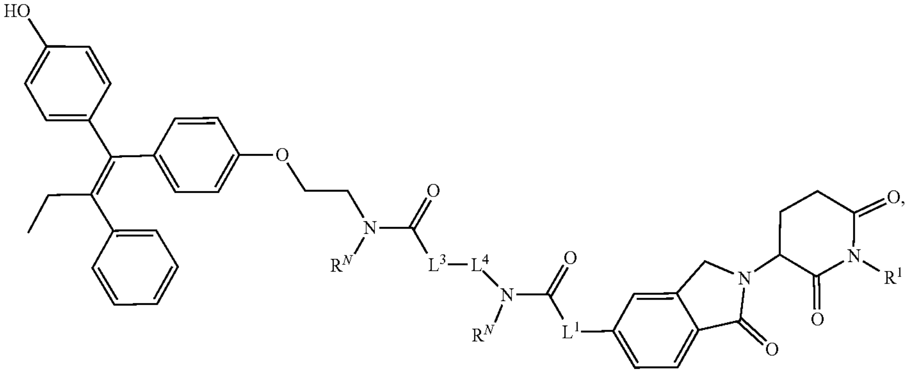

or a pharmaceutically acceptable salt thereof, wherein each $R^N$ is independently selected from H and $C_{1-3}$ alkyl; $L^1$ is $C_{1-3}$ alkylene; $L^3$ is $C_{1-3}$ alkylene and $L^4$ is $(—O—C_{1-3}\text{ alkylene-})_x$; and $R^1$ is $C_{1-3}$ alkyl substituted with $—OC(=O)O—C_{1-6}$ alkyl. The bifunctional compound can have Formula (XI) or Formula (XII):

(XI)

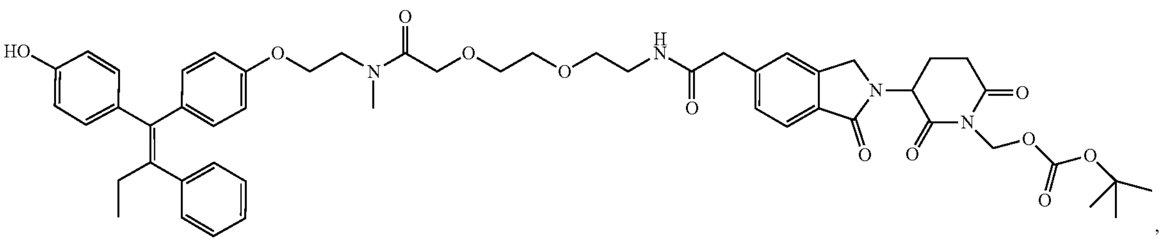

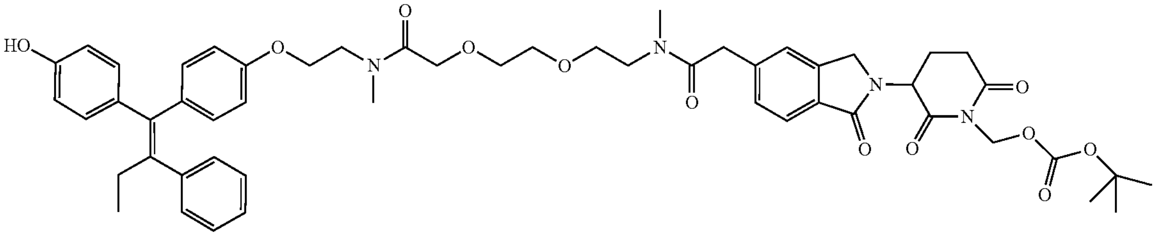

(XII), or a pharmaceutically acceptable salt thereof. The ER− cancer cell can be in a tumor within a mammal (e.g., a human).

In another aspect, this document features a method for reducing proliferation of ER− cancer cells. The method can include contacting the cells with a bifunctional compound that includes (a) a first molecule component capable of interacting with a PKCβ1 polypeptide, (b) a second molecule component capable of interacting with an E3 ubiquitin ligase polypeptide, and (c) a linker covalently coupling the first molecule component to the second molecule component. The cancer cells can be breast cancer cells or ovarian cancer cells. The first molecule component can include an endoxifen residue. The second molecule component can include an IMiD residue. The second molecule component can include a thalidomide residue. The bifunctional compound can have an $IC_{50}$ of less than 500 nM in a crystal violet proliferation assay using triple negative cells (e.g., BT549 cells or MDAMB436 cells). The bifunctional compound can be a compound of Formula (A):

(A)

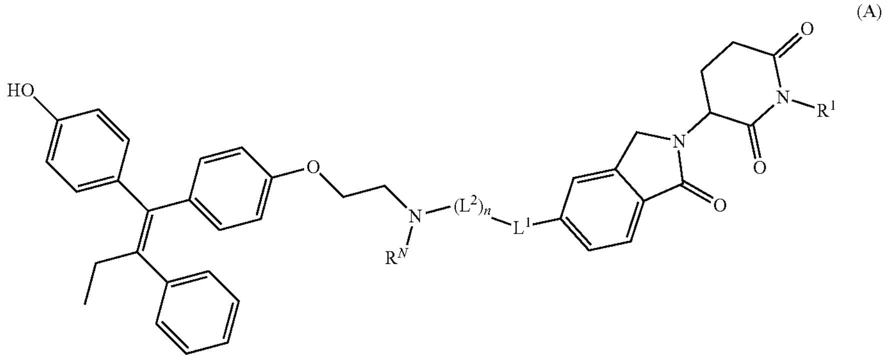

or a pharmaceutically acceptable salt thereof, wherein $L^1$ is $C_{1-3}$ alkylene, optionally substituted with 1, 2, or 3 substituents independently selected from OH, $NO_2$, CN, halo, amino, and carboxy; n is an integer selected from 1 to 10; each $L^2$ is independently selected from C(═O), N($R^N$), O, (—$C_{1-3}$ alkylene-O—$)_x$, (—O—$C_{1-3}$ alkylene-$)_x$, —$C_{1-3}$ alkylene-, and 4-6 membered heterocycloalkylene, wherein each x is independently an integer from 1 to 10, and wherein said $C_{1-3}$ alkylene and 4-6 membered heterocycloalkylene are each optionally substituted with 1, 2, or 3 substituents independently selected from OH, $NO_2$, CN, halo, amino, and carboxy; each $R^N$ is independently selected from H and $C_{1-3}$ alkyl; and $R^1$ is selected from H and $C_{1-3}$ alkyl, optionally substituted with a group selected from —OC(═O)O—$C_{1-6}$ alkyl, —OC(═O)$NH_2$, —OC(═O)NH($C_{1-6}$ alkyl), —OC(═O)N($C_{1-6}$ alkyl$)_2$, NHC(═O)O—$C_{1-6}$ alkyl, NHC(═O)$NH_2$, NHC(═O)NH($C_{1-6}$ alkyl), and NHC(═O)N($C_{1-6}$ alkyl$)_2$. The bifunctional compound can be a compound of Formula (I):

(I)

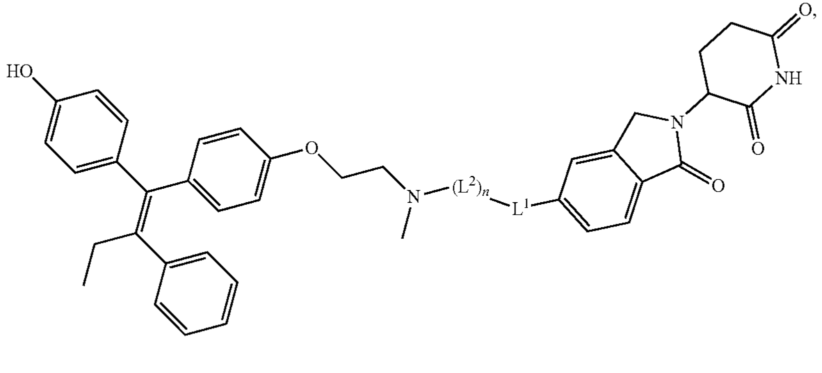

or a pharmaceutically acceptable salt thereof, wherein $L^1$ is $C_{1-3}$ alkylene, optionally substituted with 1, 2, or 3 substituents independently selected from OH, $NO_2$, CN, halo, amino, and carboxy; n is an integer selected from 1 to 10; each $L^2$ is independently selected from C(═O), N($R^N$), O, (—$C_{1-3}$ alkylene-O—$)_x$, (—O—$C_{1-3}$ alkylene-$)_x$, and —$C_{1-3}$ alkylene-, wherein each x is independently an integer from 1 to 10 and each $C_{1-3}$ alkylene is optionally substituted with 1, 2, or 3 substituents independently selected from OH, $NO_2$, CN, halo, amino, and carboxy; and each $R^N$ is independently selected from H and $C_{1-3}$ alkyl. The bifunctional compound can be a compound of Formula (II):

(II)

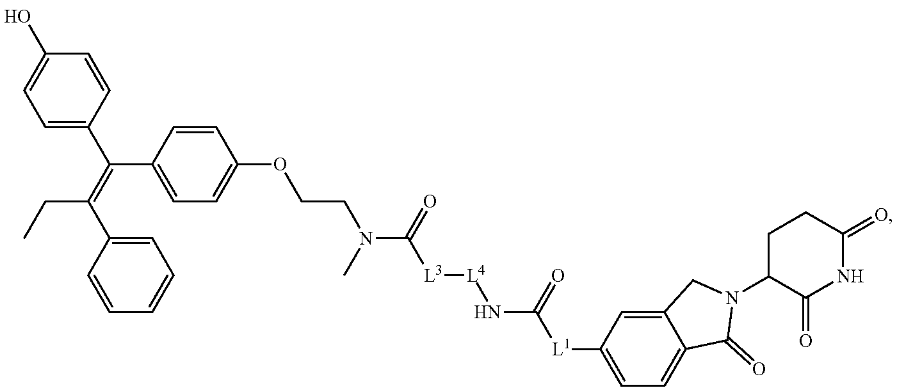

or a pharmaceutically acceptable salt thereof, wherein $L^3$ is $C_{1-3}$ alkylene; and $L^4$ is (—O—$C_{1-3}$ alkylene-$)_x$. The bifunctional compound can have Formula (III), Formula (IV), or Formula (V):

(III)

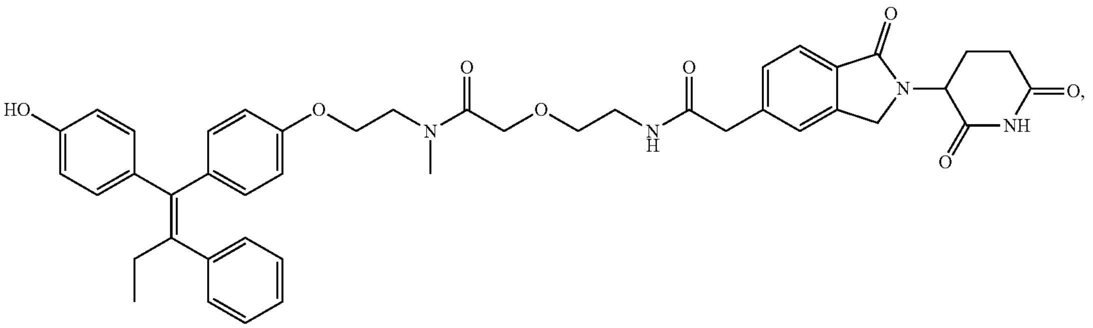

(IV)

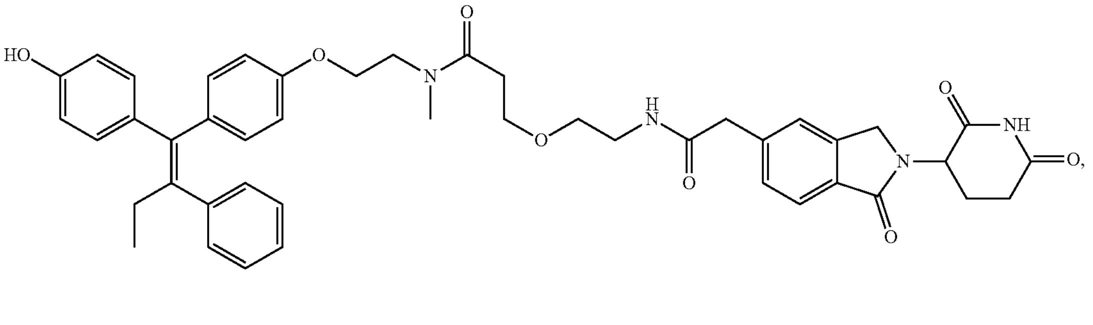

-continued
(V)
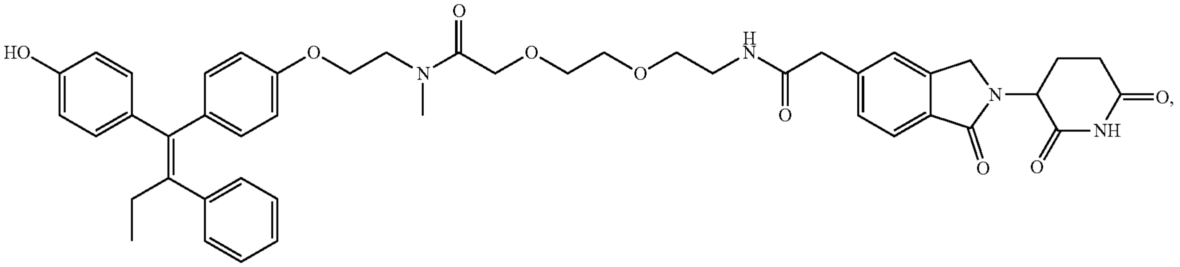
or a pharmaceutically acceptable salt thereof. The bifunctional compound can have Formula (VI):
(VI)
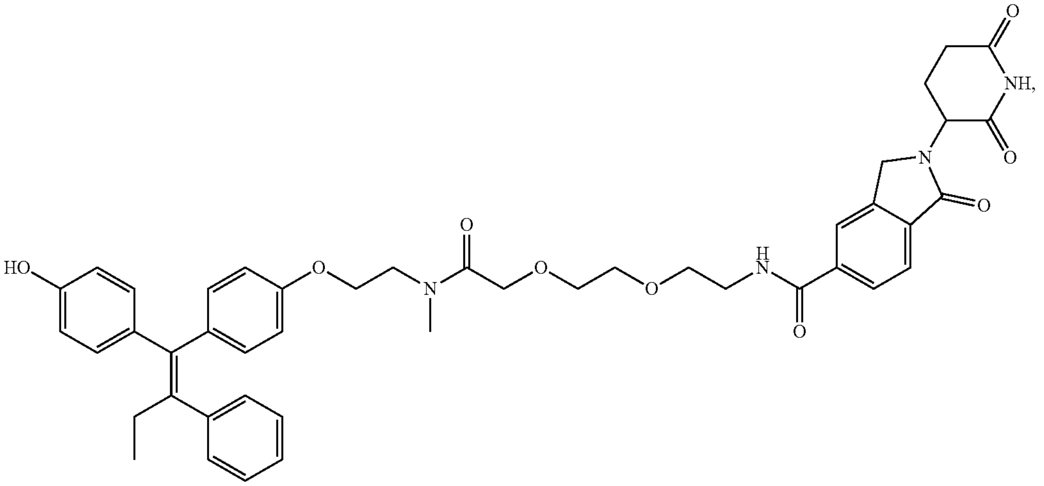
or a pharmaceutically acceptable salt thereof. The bifunctional compound can have Formula (VII), Formula (VIII), or Formula (IX):
(VII)
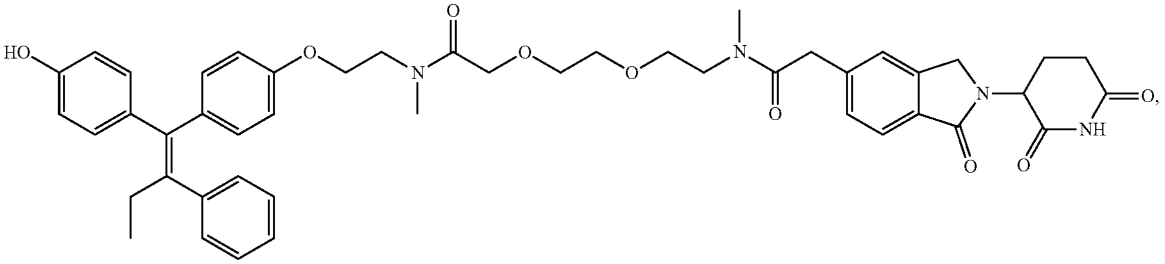

-continued (VIII)

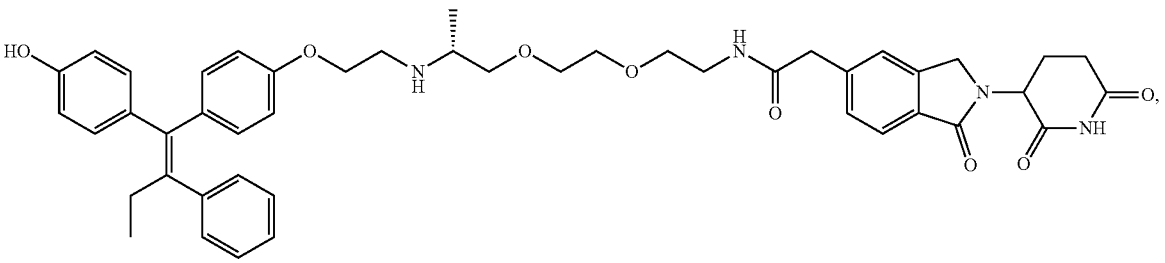

(IX)

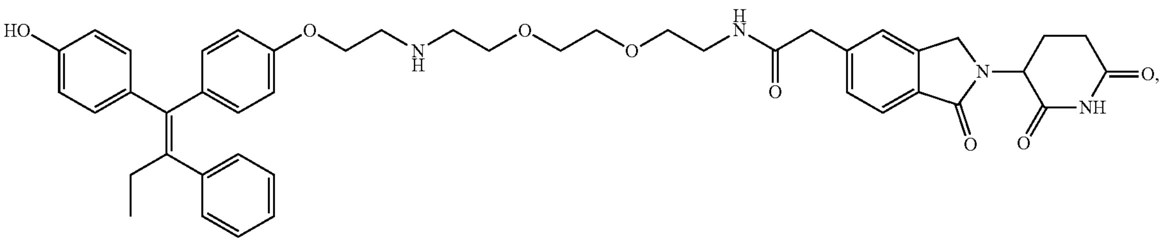

or a pharmaceutically acceptable salt thereof. The bifunctional compound can be a compound of Formula (B):

(B)

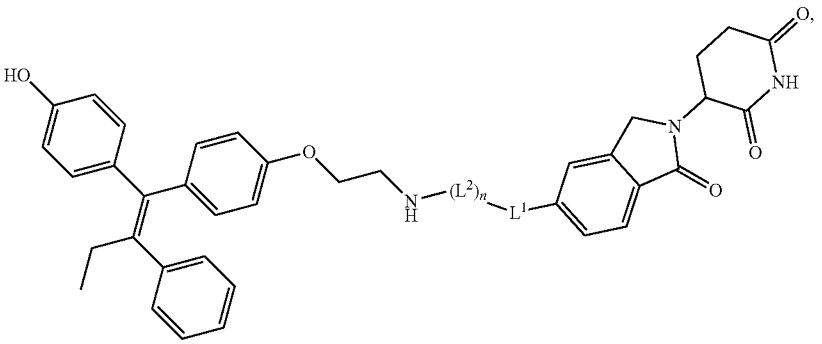

or a pharmaceutically acceptable salt thereof, wherein $L^1$ is $C_{1-3}$ alkylene, optionally substituted with 1, 2, or 3 substituents independently selected from OH, $NO_2$, CN, halo, amino, and carboxy; n is an integer selected from 1 to 10; each $L^2$ is independently selected from C(═O), N($R^N$), O, (—$C_{1-3}$ alkylene-O—$)_x$, (—O—$C_{1-3}$ alkylene-$)_x$, —$C_{1-3}$ alkylene-, and 4-6 membered heterocycloalkylene, wherein each x is independently an integer from 1 to 10, wherein said $C_{1-3}$ alkylene and 4-6 membered heterocycloalkylene are each optionally substituted with 1, 2, or 3 substituents independently selected from OH, $NO_2$, CN, halo, amino, and carboxy; and wherein each $R^N$ is independently selected from H and $C_{1-3}$ alkyl. The bifunctional compound can have Formula (X):

(X)

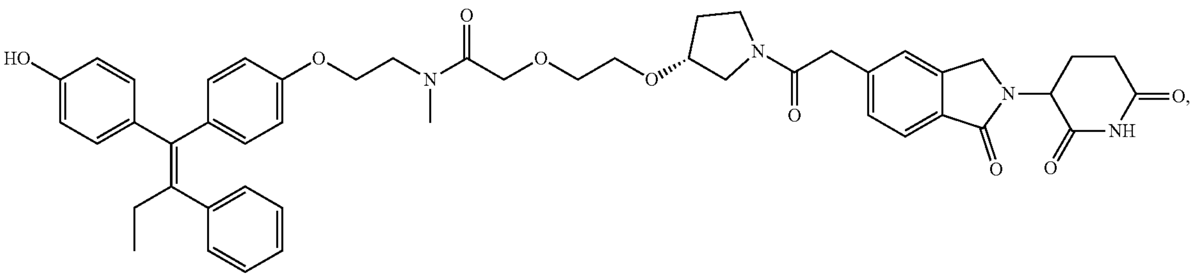

or a pharmaceutically acceptable salt thereof. The bifunctional compound can be a compound of Formula (C):

(C)

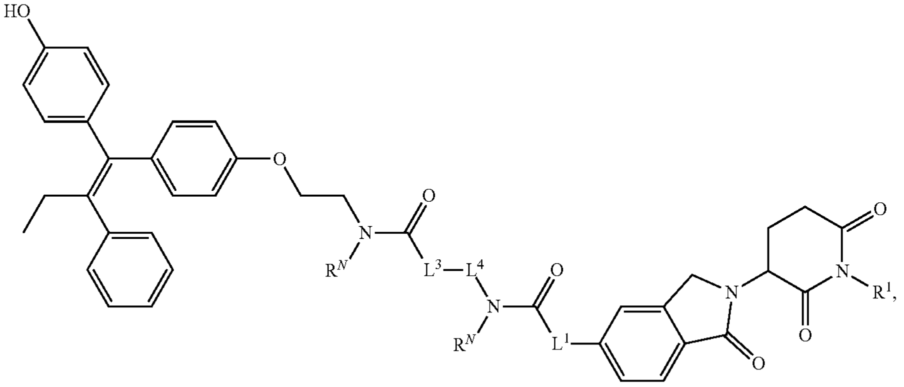

or a pharmaceutically acceptable salt thereof, wherein each $R^N$ is independently selected from H and $C_{1-3}$ alkyl; $L^1$ is $C_{1-3}$ alkylene; $L^3$ is $C_{1-3}$ alkylene and $L^4$ is $(—O—C_{1-3}$ alkylene-$)_x$; and $R^1$ is $C_{1-3}$ alkyl substituted with —OC(=O)O—$C_{1-6}$ alkyl. The bifunctional compound can have Formula (XI) or Formula (XII):

(XI)

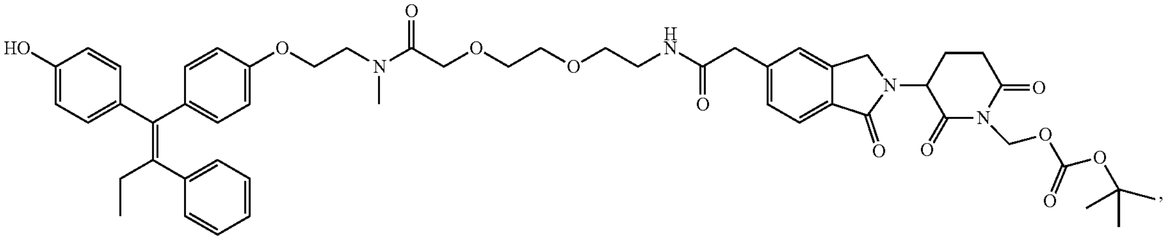

(XII)

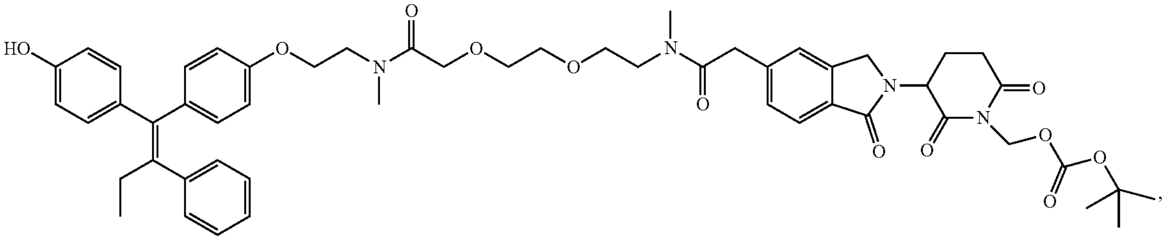

(XII), or a pharmaceutically acceptable salt thereof. The ER− cancer cells can be in a tumor within a mammal (e.g., a human).

In another aspect, this document features a method for treating a mammal identified as having ER− cancer. The method can include administering to the mammal a composition containing a bifunctional compound, where the bifunctional compound comprises (a) a first molecule component capable of interacting with a PKCβ1 polypeptide, (b) a second molecule component capable of interacting with an E3 ubiquitin ligase polypeptide, and (c) a linker covalently coupling the first molecule component to the second molecule component. The cancer can be breast cancer or ovarian cancer. The first molecule component can include an endoxifen residue. The second molecule component can include an IMiD residue. The second molecule component can include a thalidomide residue. The bifunctional compound can have an $IC_{50}$ of less than 500 nM in a crystal violet proliferation assay using triple negative cells (e.g., BT549 cells or MDAMB436 cells). The bifunctional compound can be a compound of Formula (A):

(A)

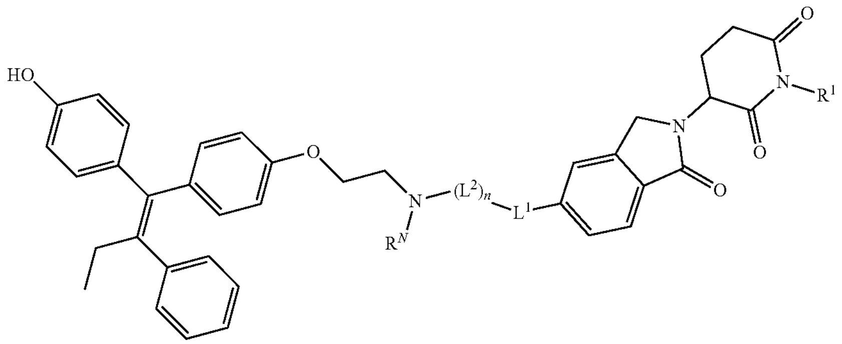

or a pharmaceutically acceptable salt thereof, wherein $L^1$ is $C_{1-3}$ alkylene, optionally substituted with 1, 2, or 3 substituents independently selected from OH, $NO_2$, CN, halo, amino, and carboxy; n is an integer selected from 1 to 10; each $L^2$ is independently selected from C(═O), N($R^N$), O, (—$C_{1-3}$ alkylene-O—)$_x$, (—O—$C_{1-3}$ alkylene-)$_x$, —$C_{1-3}$ alkylene-, and 4-6 membered heterocycloalkylene, wherein each x is independently an integer from 1 to 10, and wherein said $C_{1-3}$ alkylene and 4-6 membered heterocycloalkylene are each optionally substituted with 1, 2, or 3 substituents independently selected from OH, $NO_2$, CN, halo, amino, and carboxy; each $R^N$ is independently selected from H and $C_{1-3}$ alkyl; and $R^1$ is selected from H and $C_{1-3}$ alkyl, optionally substituted with a group selected from —OC(═O)O—$C_{1-6}$ alkyl, —OC(═O)$NH_2$, —OC(═O)NH($C_{1-6}$ alkyl), —OC(═O)N($C_{1-6}$ alkyl)$_2$, NHC(═O)O—$C_{1-6}$ alkyl, NHC(═O)$NH_2$, NHC(═O)NH($C_{1-6}$ alkyl), and NHC(═O)N($C_{1-6}$ alkyl)$_2$. The bifunctional compound can be a compound of Formula (I):

(I)

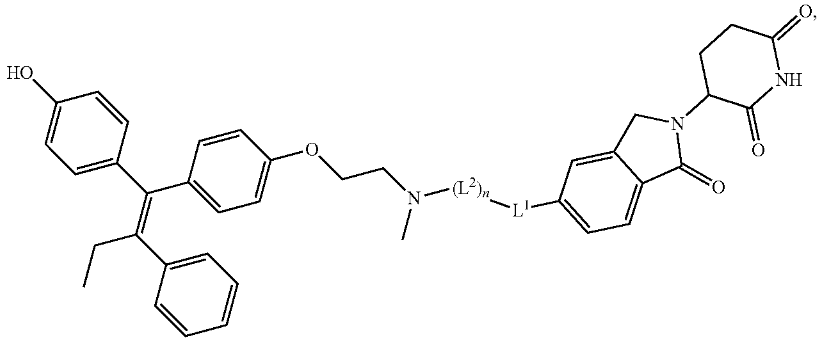

or a pharmaceutically acceptable salt thereof, wherein $L^1$ is $C_{1-3}$ alkylene, optionally substituted with 1, 2, or 3 substituents independently selected from OH, $NO_2$, CN, halo, amino, and carboxy; n is an integer selected from 1 to 10; each $L^2$ is independently selected from C(=O), $N(R^N)$, O, ($-C_{1-3}$ alkylene-O$-$)$_x$, ($-$O$-C_{1-3}$ alkylene-)$_x$, and $-C_{1-3}$ alkylene-, wherein each x is independently an integer from 1 to 10 and each $C_{1-3}$ OH, $NO_2$, CN, halo, amino, and carboxy; and each $R^N$ is independently selected from H and $C_{1-3}$ alkyl. The bifunctional compound can be a compound of Formula (II):

(II)

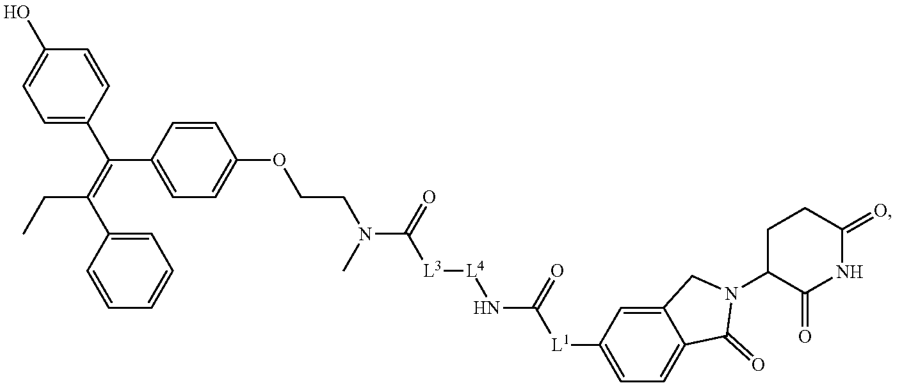

or a pharmaceutically acceptable salt thereof, wherein $L^3$ is $C_{1-3}$ alkylene; and $L^4$ is ($-$O$-C_{1-3}$ alkylene-)$_x$. The bifunctional compound can have Formula (III), Formula (IV), or Formula (V):

(III)

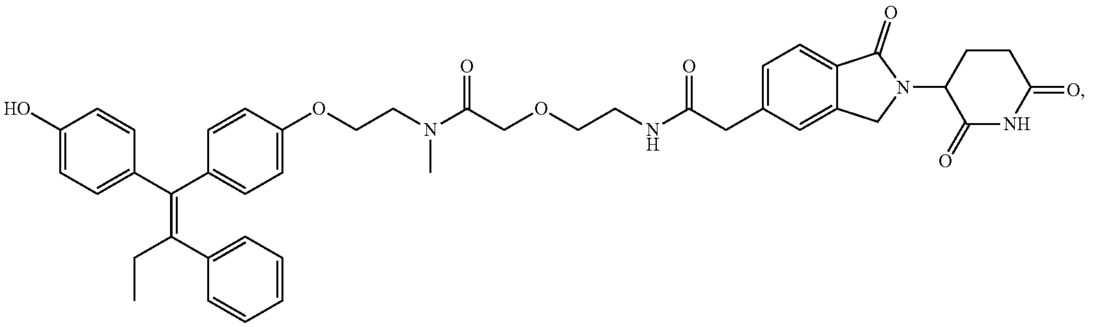

(IV)

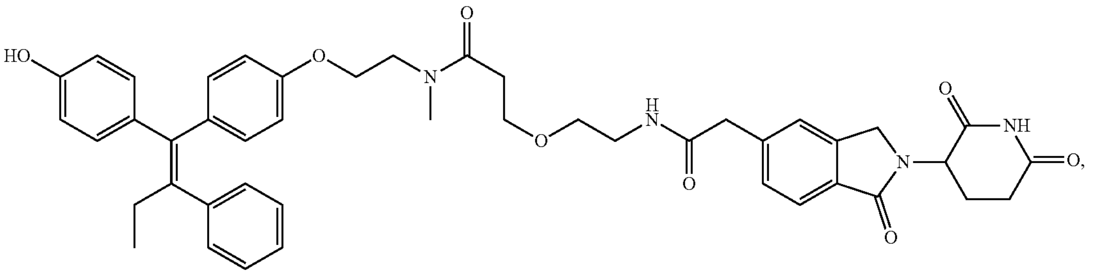

-continued
(V)
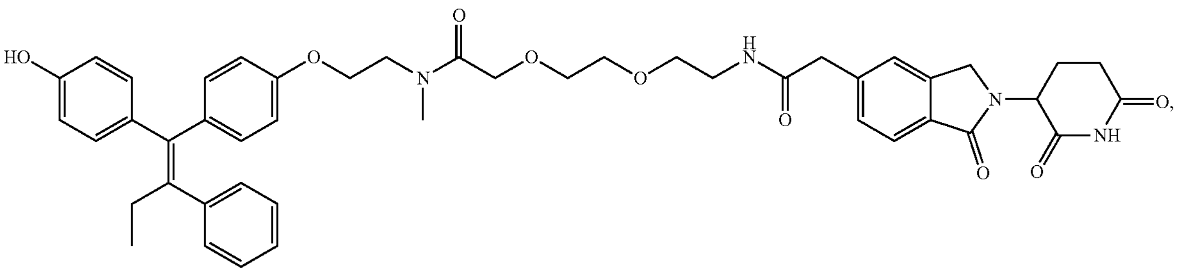
or a pharmaceutically acceptable salt thereof. The bifunctional compound can have Formula (VI):
(VI)
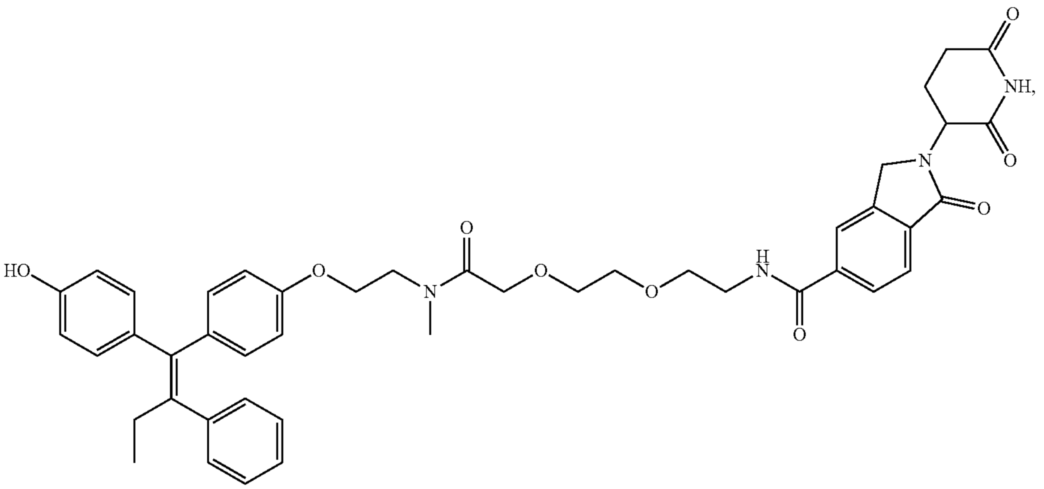
or a pharmaceutically acceptable salt thereof. The bifunctional compound can have Formula (VII), Formula (VIII), or Formula (IX):
(VII)
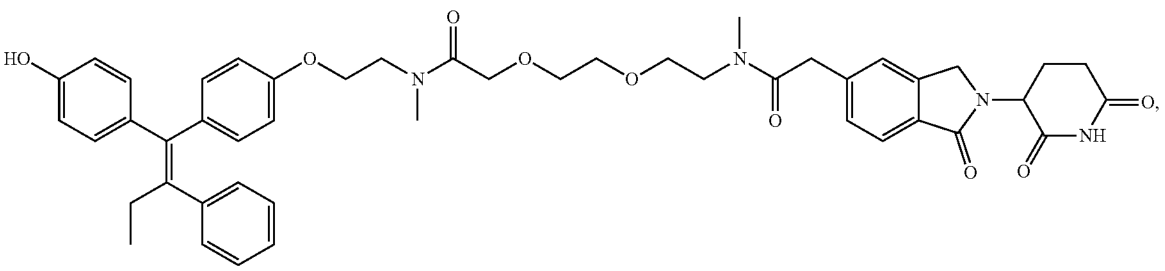

-continued (VIII)

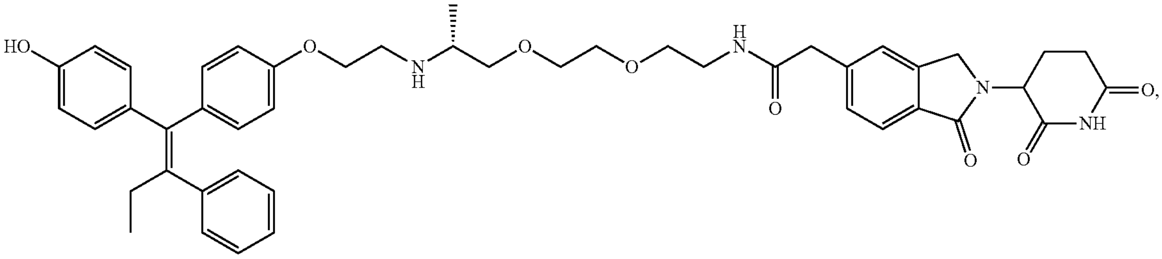

(IX)

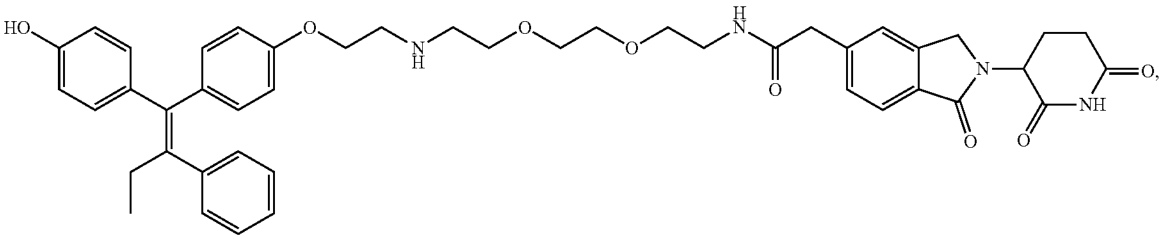

or a pharmaceutically acceptable salt thereof. The bifunctional compound can be a compound of Formula (B):

(B)

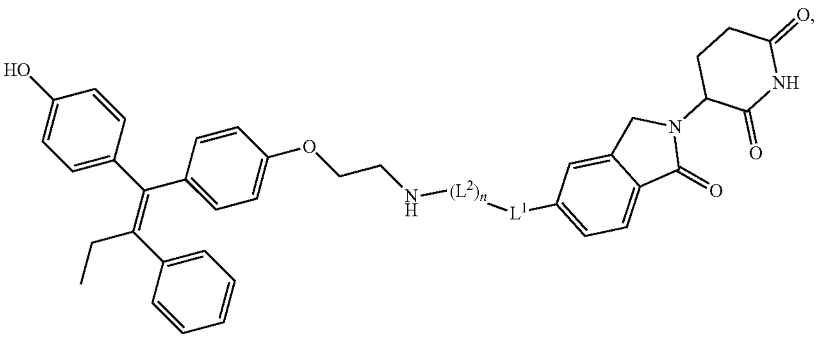

or a pharmaceutically acceptable salt thereof, wherein $L^1$ is $C_{1-3}$ alkylene, optionally substituted with 1, 2, or 3 substituents independently selected from OH, $NO_2$, CN, halo, amino, and carboxy; n is an integer selected from 1 to 10; each $L^2$ is independently selected from C(=O), N($R^N$), O, (—$C_{1-3}$ alkylene-O—$)_x$, (—O—$C_{1-3}$ alkylene-$)_x$, —$C_{1-3}$ alkylene-, and 4-6 membered heterocycloalkylene, wherein each x is independently an integer from 1 to 10, wherein said $C_{1-3}$ alkylene and 4-6 membered heterocycloalkylene are each optionally substituted with 1, 2, or 3 substituents independently selected from OH, $NO_2$, CN, halo, amino, and carboxy; and wherein each $R^N$ is independently selected from H and $C_{1-3}$ alkyl. The bifunctional compound can have Formula (X):

(X)

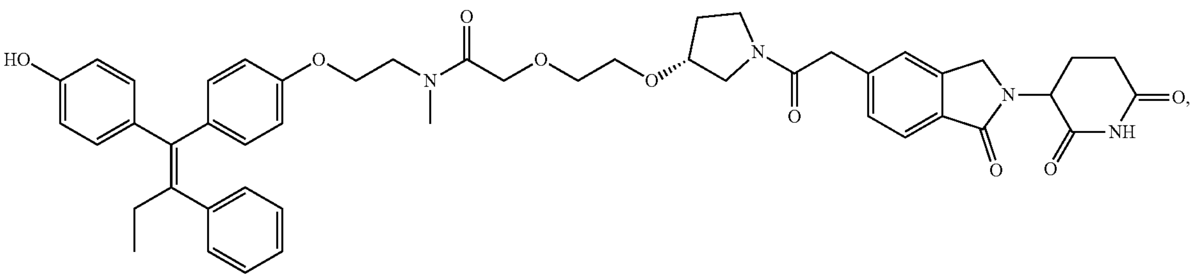

or a pharmaceutically acceptable salt thereof. The bifunctional compound can be a compound of Formula (C):

(C)

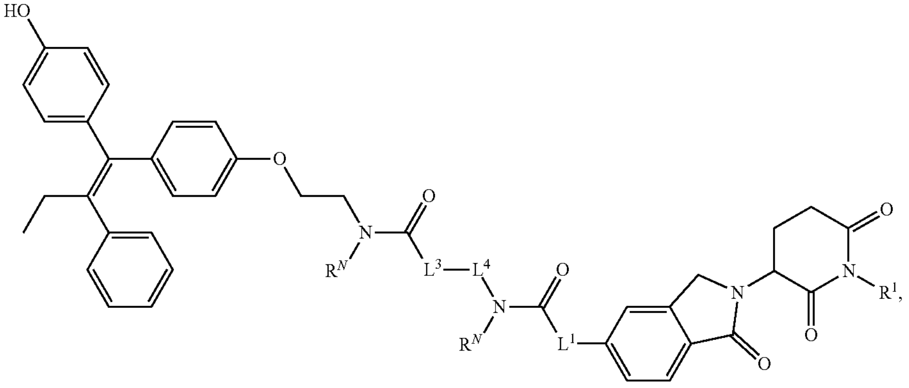

or a pharmaceutically acceptable salt thereof, wherein each $R^N$ is independently selected from H and $C_{1-3}$ alkyl; $L^1$ is $C_{1-3}$ alkylene; $L^3$ is $C_{1-3}$ alkylene and $L^4$ is (—O—$C_{1-3}$ alkylene-$)_x$; and $R^1$ is $C_{1-3}$ alkyl substituted with —OC(═O)O—$C_{1-6}$ alkyl. The bifunctional compound can have Formula (XI) or Formula (XII):

(XI)

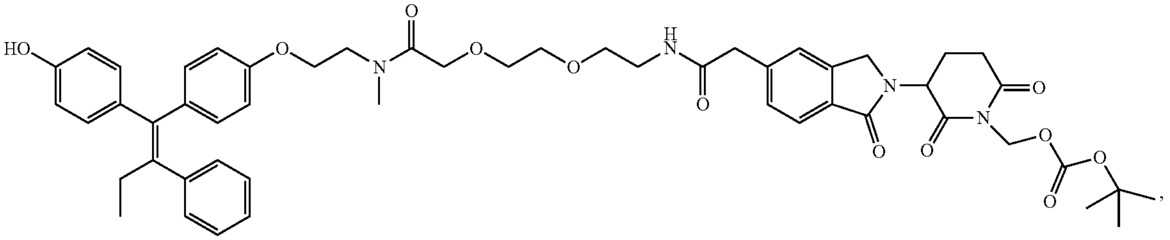

(XII)

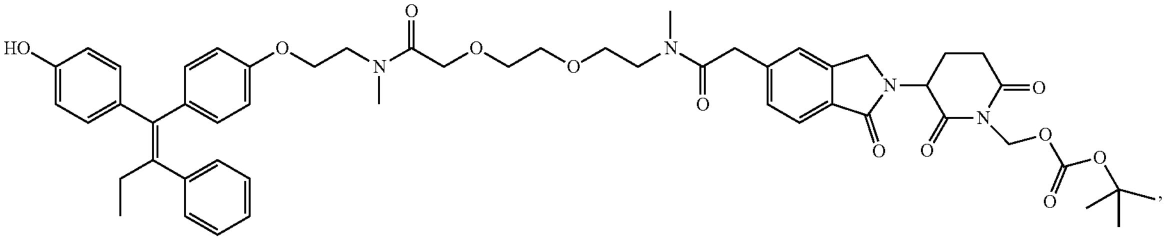

or a pharmaceutically acceptable salt thereof. The mammal can be a human.

In still another aspect, this document features a method for inhibiting the growth of a tumor containing ER− cancer cells. The method can include contacting the tumor with a bifunctional compound that includes (a) a first molecule component capable of interacting with a PKCβ1 polypeptide, (b) a second molecule component capable of interacting with an E3 ubiquitin ligase polypeptide, and (c) a linker covalently coupling the first molecule component to the second molecule component. The cancer cells can be breast cancer cells or ovarian cancer cells. The first molecule component can include an endoxifen residue. The second molecule component can include an IMiD residue. The second molecule component can include a thalidomide residue. The bifunctional compound can have an $IC_{50}$ of less than 500 nM in a crystal violet proliferation assay using triple negative cells (e.g., BT549 cells or MDAMB436 cells). The bifunctional compound can be a compound of Formula (A):

(A)

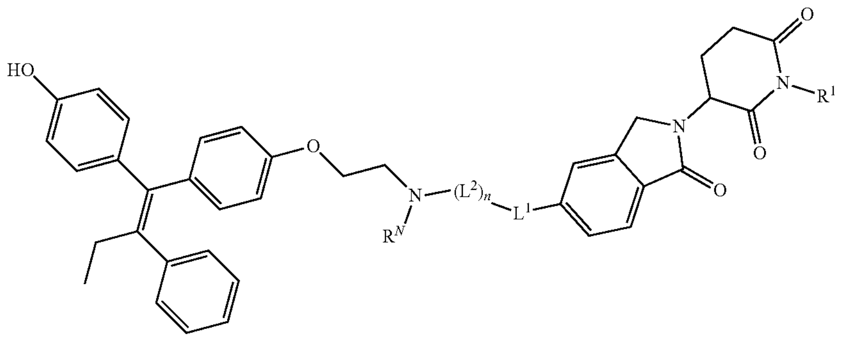

or a pharmaceutically acceptable salt thereof, wherein $L^1$ is $C_{1-3}$ alkylene, optionally substituted with 1, 2, or 3 substituents independently selected from OH, $NO_2$, CN, halo, amino, and carboxy; n is an integer selected from 1 to 10; each $L^2$ is independently selected from C(═O), N($R^N$), O, (—$C_{1-3}$ alkylene-O—)$_x$, (—O—$C_{1-3}$ alkylene-)$_x$, —$C_{1-3}$ alkylene-, and 4-6 membered heterocycloalkylene, wherein each x is independently an integer from 1 to 10, and wherein said $C_{1-3}$ alkylene and 4-6 membered heterocycloalkylene are each optionally substituted with 1, 2, or 3 substituents independently selected from OH, $NO_2$, CN, halo, amino, and carboxy; each $R^N$ is independently selected from H and $C_{1-3}$ alkyl; and $R^1$ is selected from H and $C_{1-3}$ alkyl, optionally substituted with a group selected from —OC(═O)O—$C_{1-6}$ alkyl, —OC(═O)$NH_2$, —OC(═O)NH($C_{1-6}$ alkyl), —OC(═O)N($C_{1-6}$ alkyl)$_2$, NHC(═O)O—$C_{1-6}$ alkyl, NHC(═O)$NH_2$, NHC(═O)NH($C_{1-6}$ alkyl), and NHC(═O)N($C_{1-6}$ alkyl)$_2$. The bifunctional compound can be a compound of Formula (I):

(I)

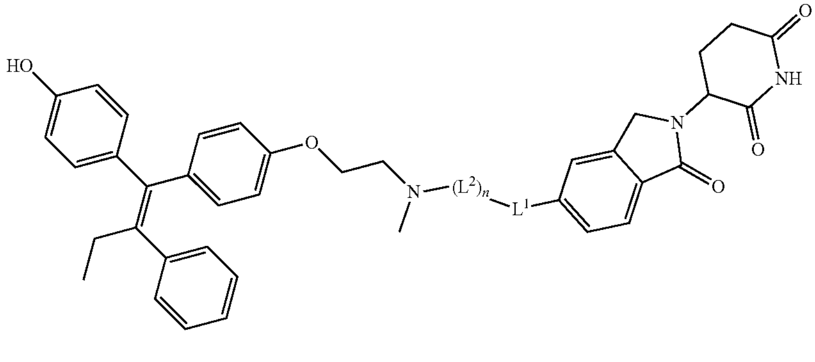

or a pharmaceutically acceptable salt thereof, wherein $L^1$ is $C_{1-3}$ alkylene, optionally substituted with 1, 2, or 3 substituents independently selected from OH, $NO_2$, CN, halo, amino, and carboxy; n is an integer selected from 1 to 10; each $L^2$ is independently selected from C(=O), $N(R^N)$, O, $(—C_{1-3}$ alkylene-O—$)_x$, (—O—$C_{1-3}$ alkylene-$)_x$, and —$C_{1-3}$ alkylene-, wherein each x is independently an integer from 1 to 10 and each $C_{1-3}$ OH, $NO_2$, CN, halo, amino, and carboxy; and each $R^N$ is independently selected from H and $C_{1-3}$ alkyl. The bifunctional compound can be a compound of Formula (II):

(II)

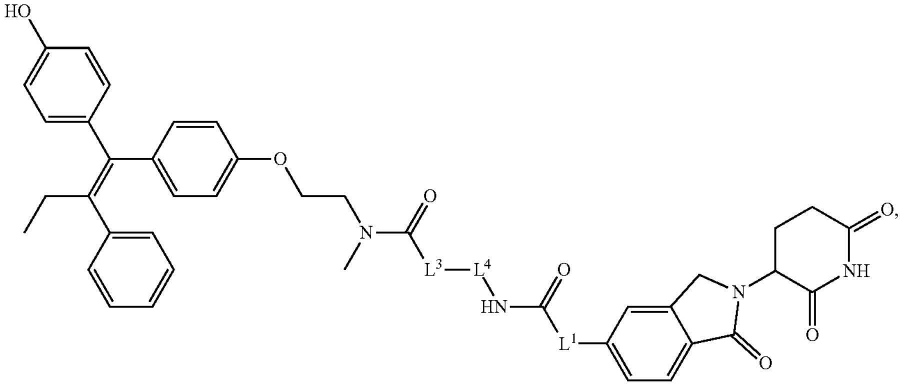

or a pharmaceutically acceptable salt thereof, wherein $L^3$ is $C_{1-3}$ alkylene; and $L^4$ is (—O—$C_{1-3}$ alkylene-$)_x$. The bifunctional compound can have Formula (III), Formula (IV), or Formula (V):

(III)

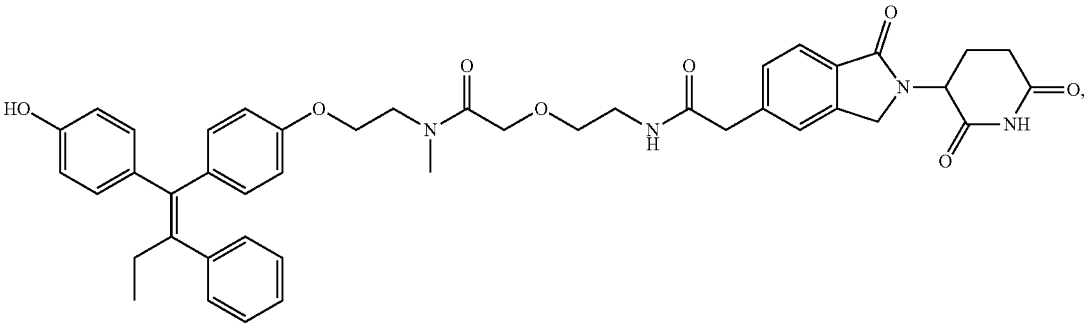

(IV)

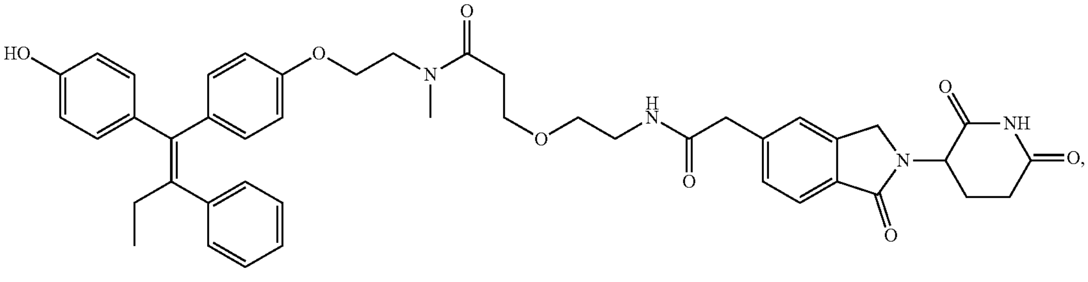

(V)

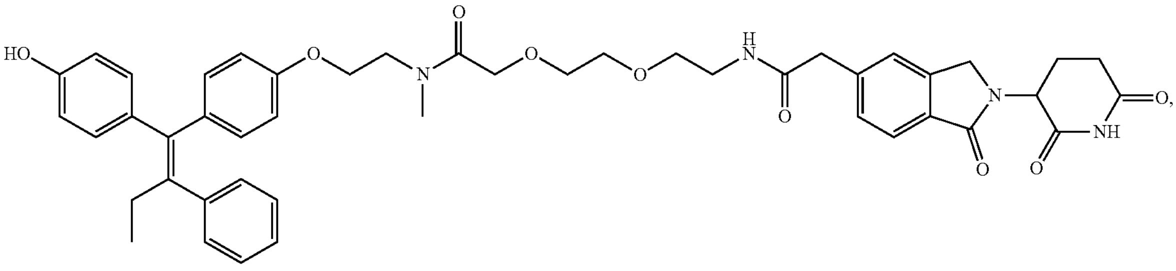

or a pharmaceutically acceptable salt thereof. The bifunctional compound can have Formula (VI):
(VI)
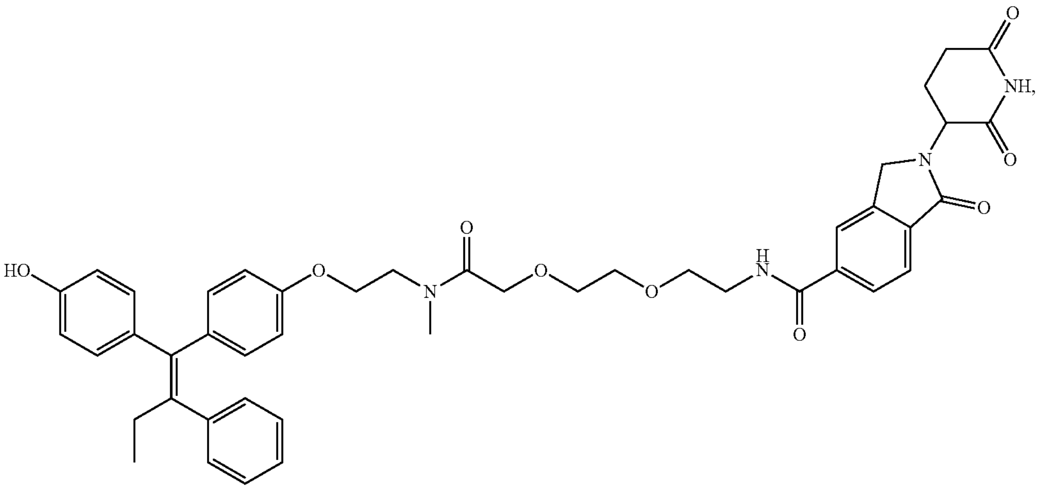
or a pharmaceutically acceptable salt thereof. The bifunctional compound can have Formula (VII), Formula (VIII), or Formula (IX):
(VII)
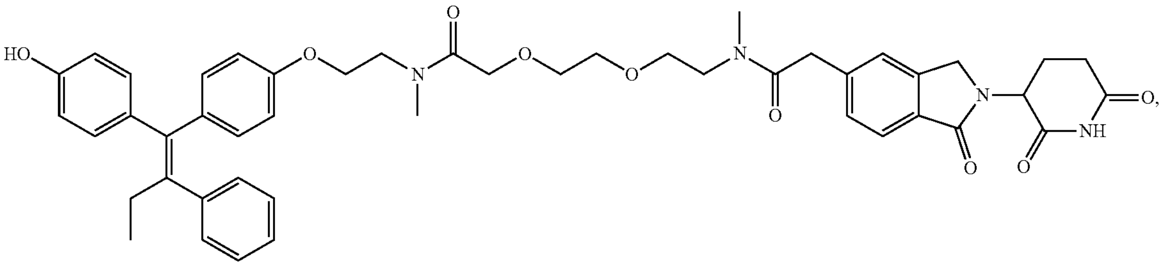
(VIII)
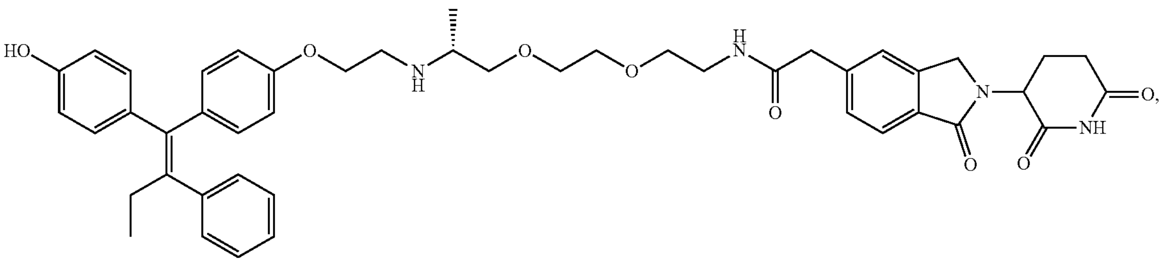
(IX)
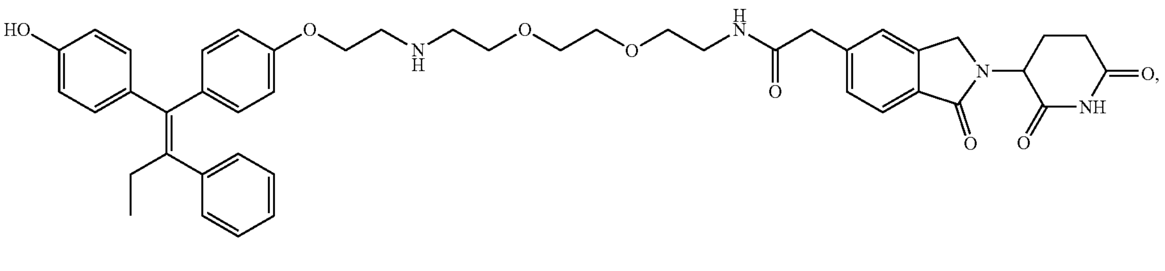
or a pharmaceutically acceptable salt thereof. The bifunctional compound can be a compound of Formula (B):

(B)

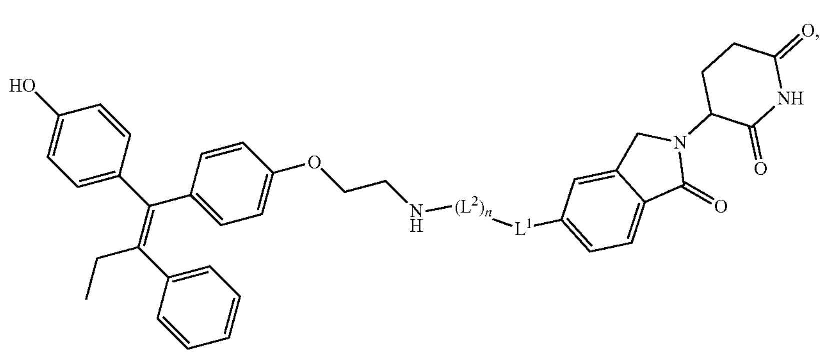

or a pharmaceutically acceptable salt thereof, wherein $L^1$ is $C_{1-3}$ alkylene, optionally substituted with 1, 2, or 3 substituents independently selected from OH, $NO_2$, CN, halo, amino, and carboxy; n is an integer selected from 1 to 10; each $L^2$ is independently selected from C(=O), $N(R^N)$, O, $(—C_{1-3}$ alkylene-O—$)_x$, (—O—$C_{1-3}$ alkylene-$)_x$, —$C_{1-3}$ alkylene-, and 4-6 membered heterocycloalkylene, wherein each x is independently an integer from 1 to 10, wherein said $C_{1-3}$ alkylene and 4-6 membered heterocycloalkylene are each optionally substituted with 1, 2, or 3 substituents independently selected from OH, $NO_2$, CN, halo, amino, and carboxy; and wherein each $R^N$ is independently selected from H and $C_{1-3}$ alkyl. The bifunctional compound can have Formula (X):

(X)

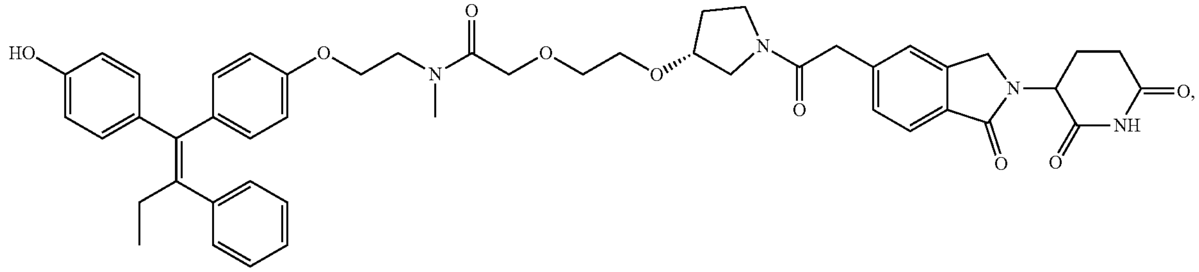

or a pharmaceutically acceptable salt thereof. The bifunctional compound can be a compound of Formula (C):

(C)

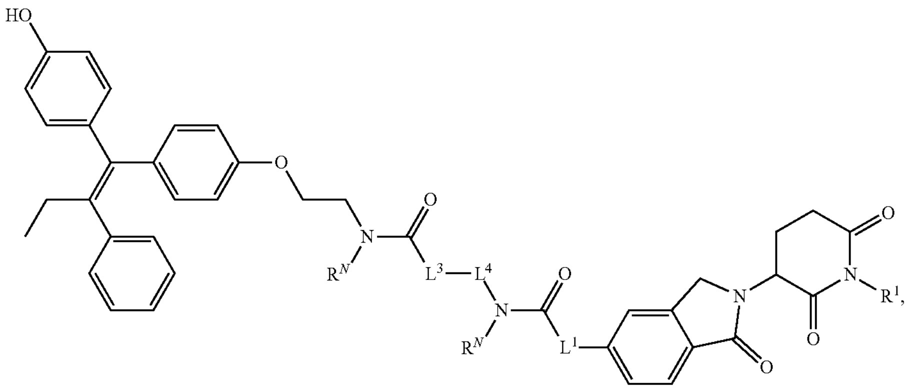

or a pharmaceutically acceptable salt thereof, wherein each $R^N$ is independently selected from H and $C_{1-3}$ alkyl; $L^1$ is $C_{1-3}$ alkylene; $L^3$ is $C_{1-3}$ alkylene and $L^4$ is $(—O—C_{1-3}$ alkylene-$)_x$; and $R^1$ is $C_{1-3}$ alkyl substituted with —OC(═O)O—$C_{1-6}$ alkyl. The bifunctional compound can have Formula (XI) or Formula (XII):

(XI)

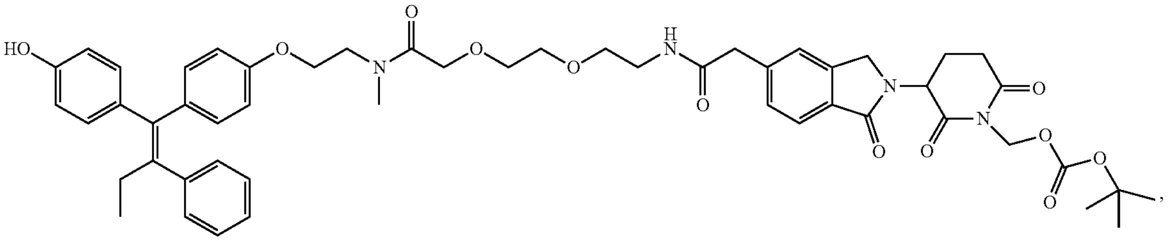

(XII)

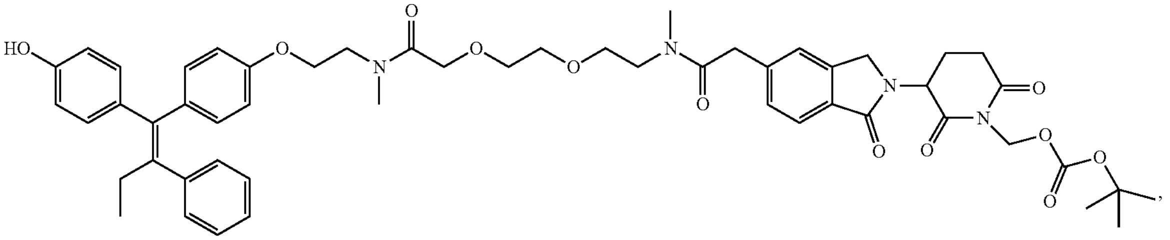

or a pharmaceutically acceptable salt thereof. The tumor can be within a mammal (e.g., a human).

This document also features a compound of Formula (A):

(A)

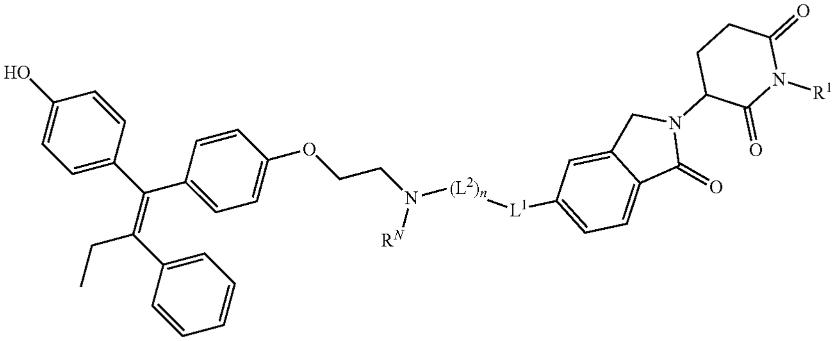

or a pharmaceutically acceptable salt thereof, wherein $L^1$ is $C_{1-3}$ alkylene, optionally substituted with 1, 2, or 3 substituents independently selected from OH, $NO_2$, CN, halo, amino, and carboxy; n is an integer selected from 1 to 10; each $L^2$ is independently selected from C(═O), N($R^N$), O, $(—C_{1-3}$ alkylene-O—$)_x$, $(—O—C_{1-3}$ alkylene-$)_x$, —$C_{1-3}$ alkylene-, and 4-6 membered heterocycloalkylene, wherein each x is independently an integer from 1 to 10, and wherein said $C_{1-3}$ alkylene and 4-6 membered heterocycloalkylene are each optionally substituted with 1, 2, or 3 substituents independently selected from OH, $NO_2$, CN, halo, amino, and carboxy; each $R^N$ is independently selected from H and $C_{1-3}$ alkyl; and $R^1$ is selected from H and $C_{1-3}$ alkyl, optionally substituted with a group selected from —OC(═O)O—$C_{1-6}$ alkyl, —OC(═O)$NH_2$, —OC(═O)NH($C_{1-6}$ alkyl), —OC(═O)N($C_{1-6}$ alkyl$)_2$, NHC(═O)O—$C_{1-6}$ alkyl, NHC(═O)$NH_2$, NHC(═O)NH($C_{1-6}$ alkyl), and NHC(═O)N($C_{1-6}$ alkyl$)_2$. The compound can have Formula (I):

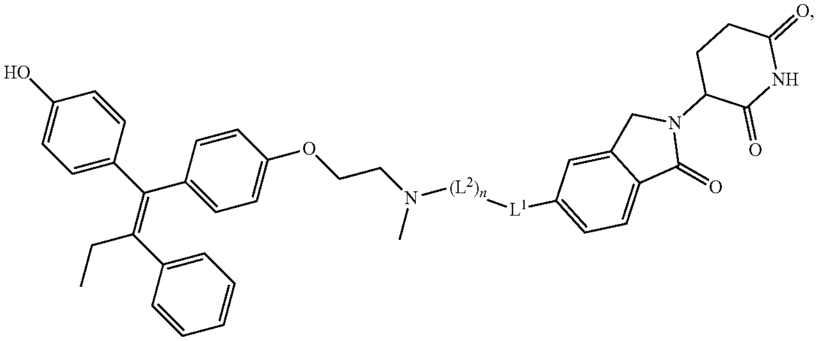

(I)

or a pharmaceutically acceptable salt thereof, wherein $L^1$ is $C_{1-3}$ alkylene, optionally substituted with 1, 2, or 3 substituents independently selected from OH, $NO_2$, CN, halo, amino, and carboxy; n is an integer selected from 1 to 10; each $L^2$ is independently selected from C(═O), $N(R^N)$, O, $(—C_{1-3}$ alkylene-O—$)_x$, (—O—$C_{1-3}$ alkylene-$)_x$, and —$C_{1-3}$ alkylene-, wherein each x is independently an integer from 1 to 10 and each $C_{1-3}$ alkylene is optionally substituted with 1, 2, or 3 substituents independently selected from OH, $NO_2$, CN, halo, amino, and carboxy; and each $R^N$ is independently selected from H and $C_{1-3}$ alkyl. The compound can have Formula (II):

(II)

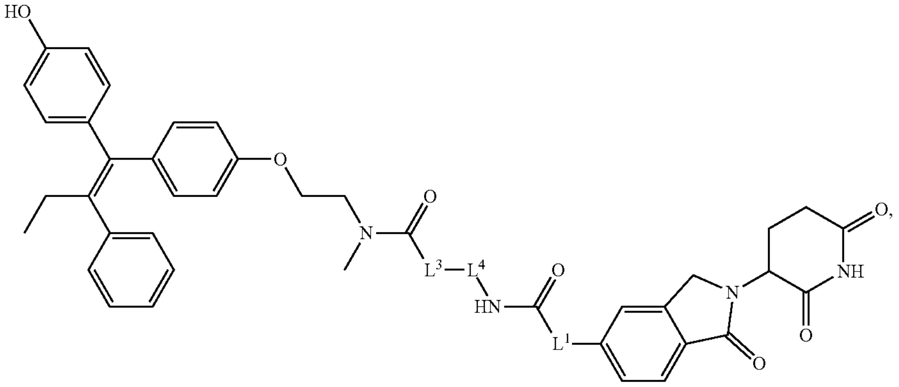

or a pharmaceutically acceptable salt thereof, wherein $L^3$ is $C_{1-3}$ alkylene; and $L^4$ is (—O—$C_{1-3}$ alkylene-$)_x$. The compound can have Formula (III), Formula (IV), or Formula (V):

(III)

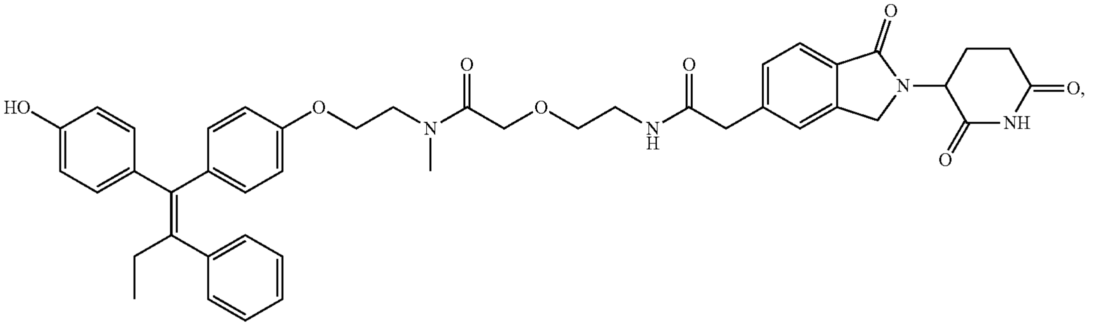

-continued
(IV)
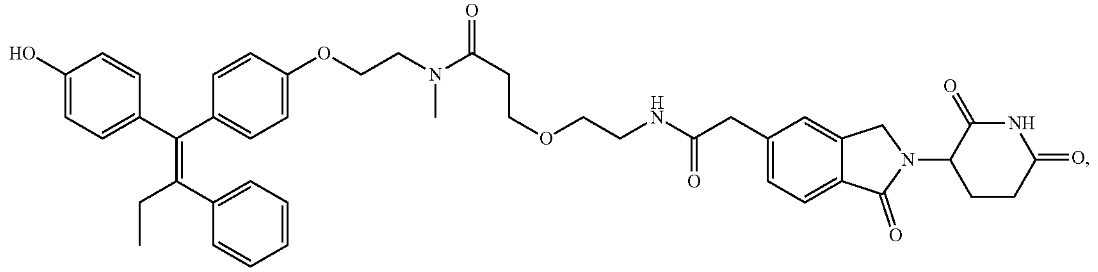
(V)
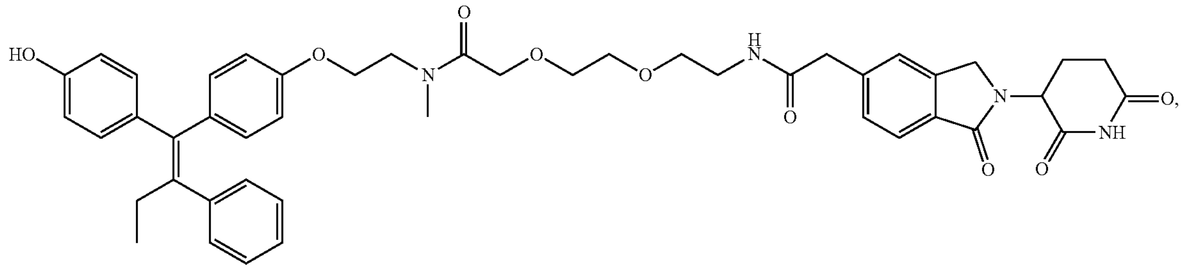
or a pharmaceutically acceptable salt thereof. The compound can have Formula (VII), Formula (VIII), or Formula (IX):
(VII)
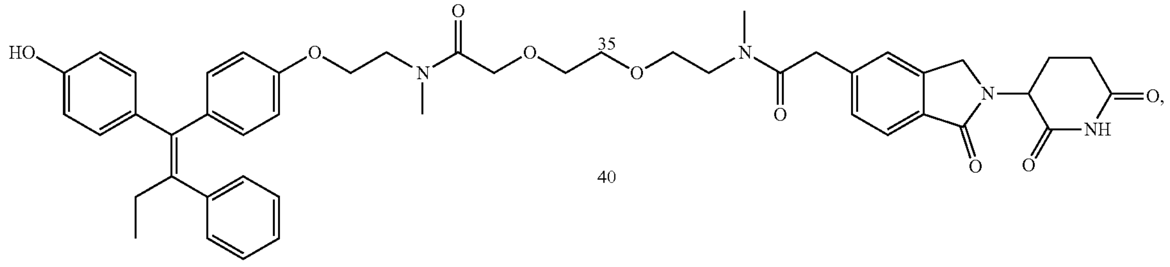
(VIII)
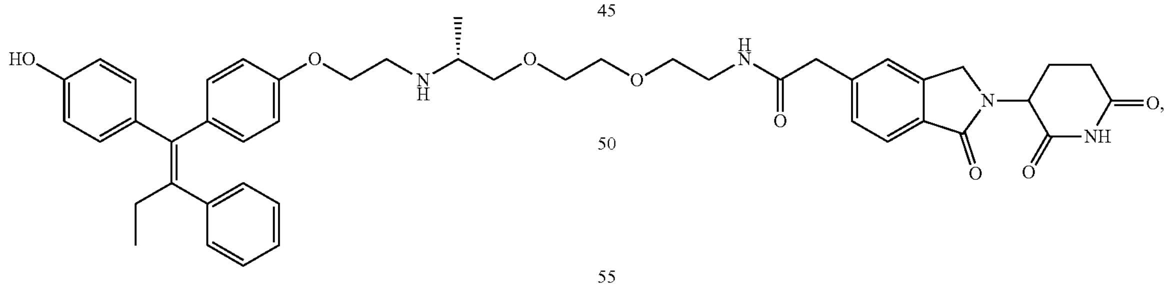
(IX)
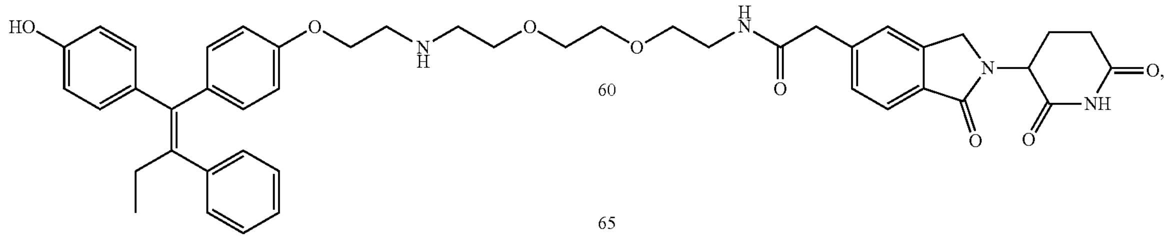

or a pharmaceutically acceptable salt thereof. The compound can be a compound of Formula (B):

(B)

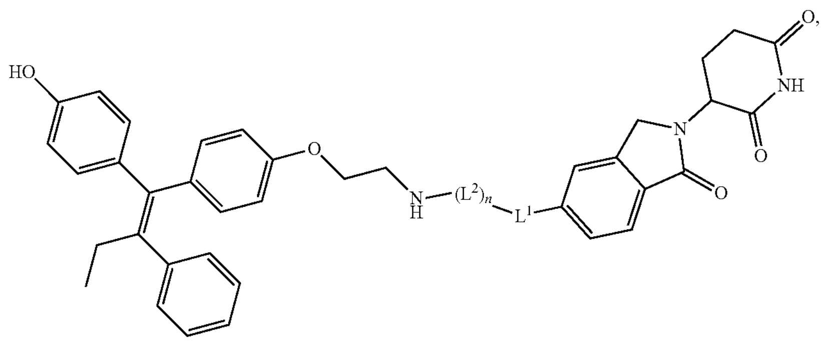

or a pharmaceutically acceptable salt thereof, wherein L' is $C_{1-3}$ alkylene, optionally substituted with 1, 2, or 3 substituents independently selected from OH, $NO_2$, CN, halo, amino, and carboxy; n is an integer selected from 1 to 10; each $L^2$ is independently selected from C(═O), N($R^N$), O, (—$C_{1-3}$ alkylene-O—$)_x$, (—O—$C_{1-3}$ alkylene-$)_x$, —$C_{1-3}$ alkylene-, and 4-6 membered heterocycloalkylene, wherein each x is independently an integer from 1 to 10, wherein said $C_{1-3}$ alkylene and 4-6 membered heterocycloalkylene are each optionally substituted with 1, 2, or 3 substituents independently selected from OH, $NO_2$, CN, halo, amino, and carboxy; and wherein each $R^N$ is independently selected from H and $C_{1-3}$ alkyl. The compound can have Formula (X):

(X)

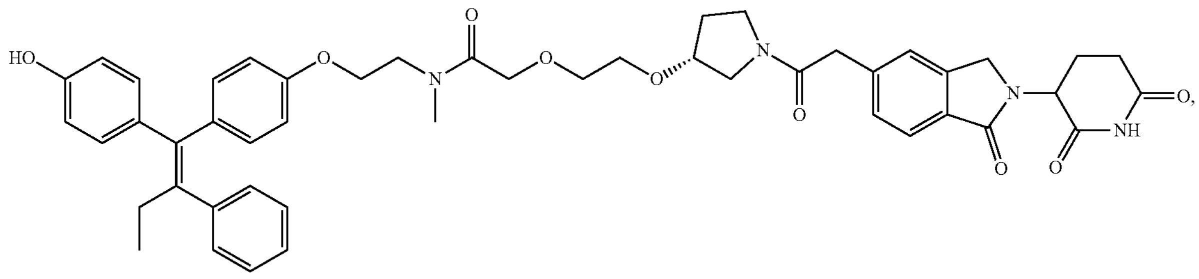

or a pharmaceutically acceptable salt thereof. The compound can be a compound of Formula (C):

(C)

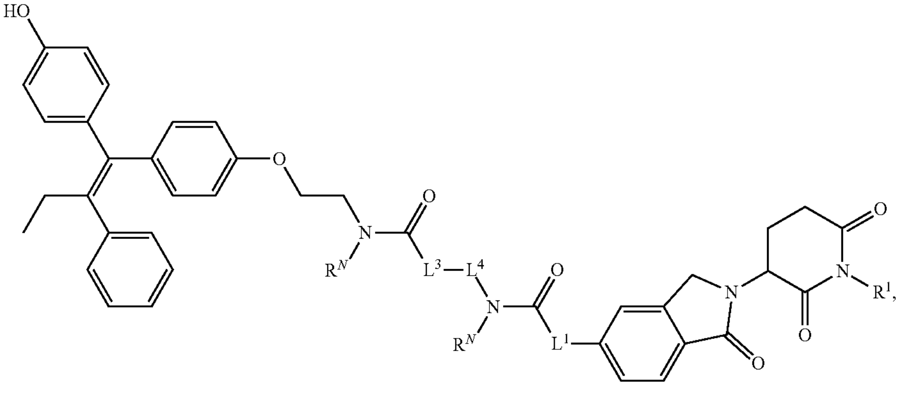

or a pharmaceutically acceptable salt thereof, wherein each $R^N$ is independently selected from H and $C_{1-3}$ alkyl; $L^1$ is $C_{1-3}$ alkylene; $L^3$ is $C_{1-3}$ alkylene and $L^4$ is $(—O—C_{1-3}$ alkylene-$)_x$; and $R^1$ is $C_{1-3}$ alkyl substituted with —OC(=O)O—$C_{1-6}$ alkyl. The compound can have Formula (XI) or Formula (XII):

(XI)

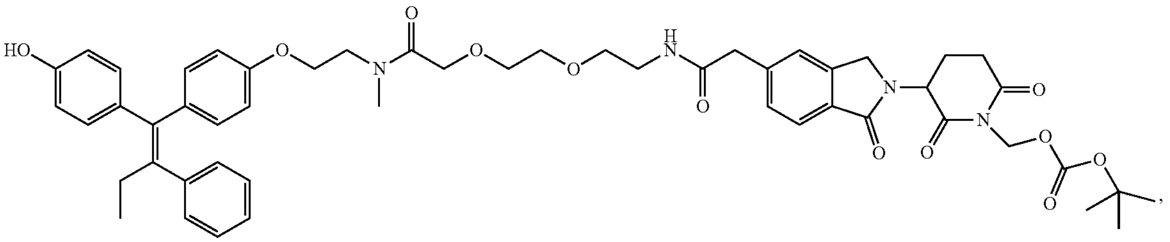

(XII)

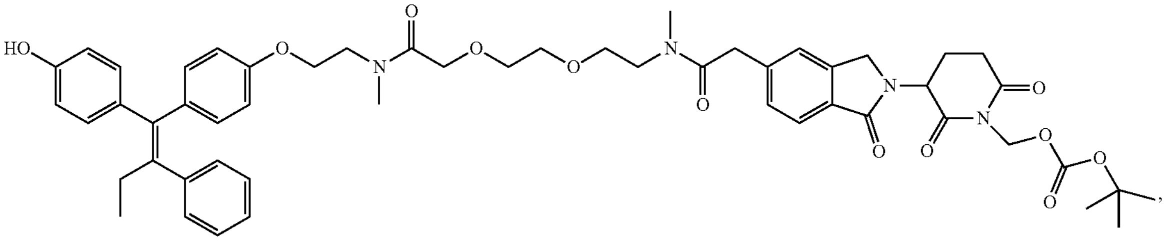

or a pharmaceutically acceptable salt thereof.

In another aspect, this document features a compound of Formula VI:

(VI)

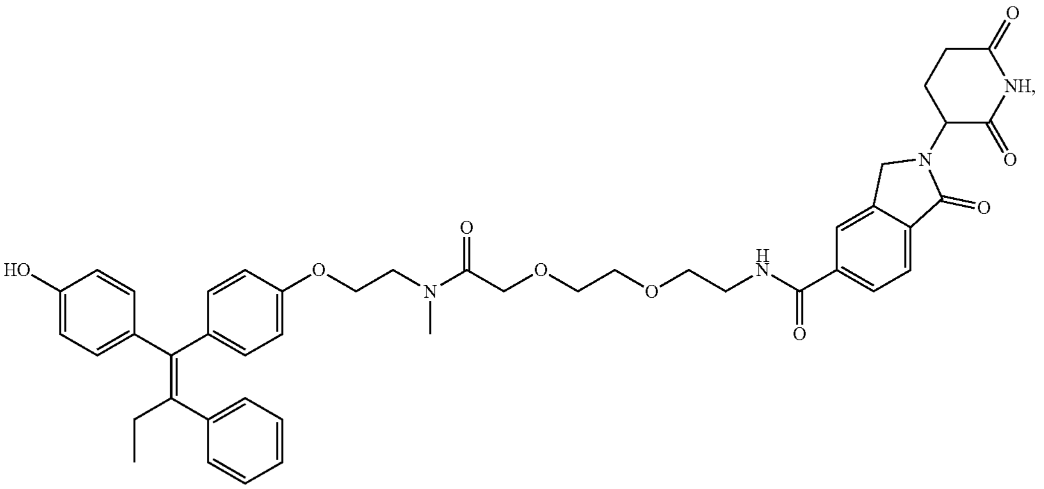

a pharmaceutically acceptable salt thereof.

In another aspect, this document features a composition containing a pharmaceutically acceptable carrier and a bifunctional compound of Formula (A):

(A)

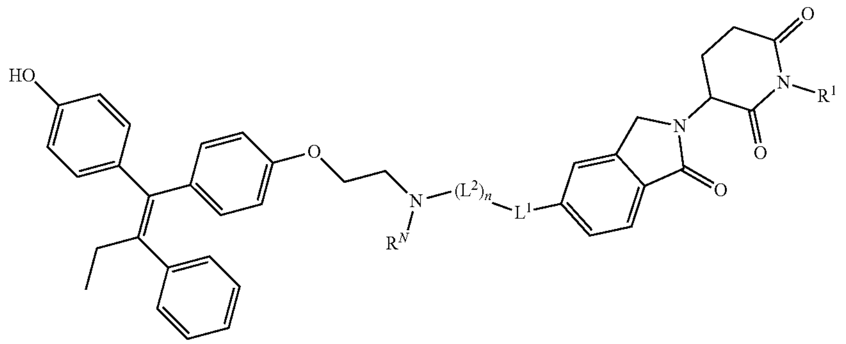

or a pharmaceutically acceptable salt thereof, wherein $L^1$ is $C_{1-3}$ alkylene, optionally substituted with 1, 2, or 3 substituents independently selected from OH, $NO_2$, CN, halo, amino, and carboxy; n is an integer selected from 1 to 10; each $L^2$ is independently selected from C(═O), N($R^N$), O, (—$C_{1-3}$ alkylene-O—$)_x$, (—O—$C_{1-3}$ alkylene-$)_x$, —$C_{1-3}$ alkylene-, and 4-6 membered heterocycloalkylene, wherein each x is independently an integer from 1 to 10, and wherein said $C_{1-3}$ alkylene and 4-6 membered heterocycloalkylene are each optionally substituted with 1, 2, or 3 substituents independently selected from OH, $NO_2$, CN, halo, amino, and carboxy; each $R^N$ is independently selected from H and $C_{1-3}$ alkyl; and $R^1$ is selected from H and $C_{1-3}$ alkyl, optionally substituted with a group selected from —OC(═O)O—$C_{1-6}$ alkyl, —OC(═O)$NH_2$, —OC(═O)NH($C_{1-6}$ alkyl), —OC(═O)N($C_{1-6}$ alkyl$)_2$, NHC(═O)O—$C_{1-6}$ alkyl, NHC(═O)$NH_2$, NHC(═O)NH($C_{1-6}$ alkyl), and NHC(═O)N($C_{1-6}$ alkyl$)_2$. The bifunctional compound can be a compound of Formula (I):

(I)

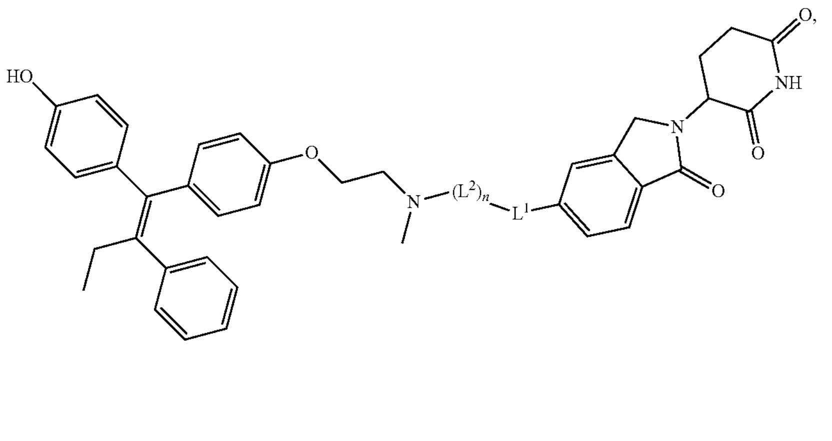

or a pharmaceutically acceptable salt thereof, wherein $L^1$ is $C_{1-3}$ alkylene, optionally substituted with 1, 2, or 3 substituents independently selected from OH, $NO_2$, CN, halo, amino, and carboxy; n is an integer selected from 1 to 10; each $L^2$ is independently selected from C(═O), N($R^N$), O, (—$C_{1-3}$ alkylene-O—$)_x$, (—O—$C_{1-3}$ alkylene-$)_x$, and —$C_{1-3}$ alkylene-, wherein each x is independently an integer from 1 to 10 and each $C_{1-3}$ alkylene is optionally substituted with 1, 2, or 3 substituents independently selected from OH, $NO_2$, CN, halo, amino, and carboxy; and each $R^N$ is independently selected from H and $C_{1-3}$ alkyl. The bifunctional compound can be a compound of Formula (II):

(II)
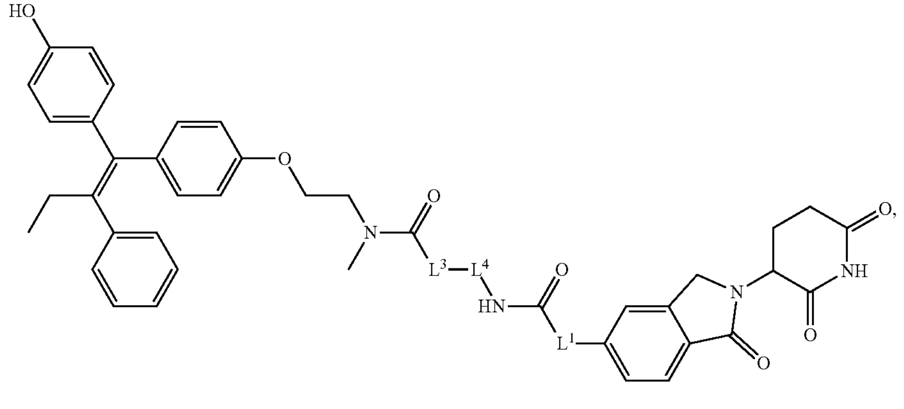
or a pharmaceutically acceptable salt thereof, wherein $L^3$ is $C_{1-3}$ alkylene; and $L^4$ is $(—O—C_{1-3}$ alkylene-$)_x$. The bifunctional compound can have Formula (III), Formula (IV), or Formula (V):
(III)
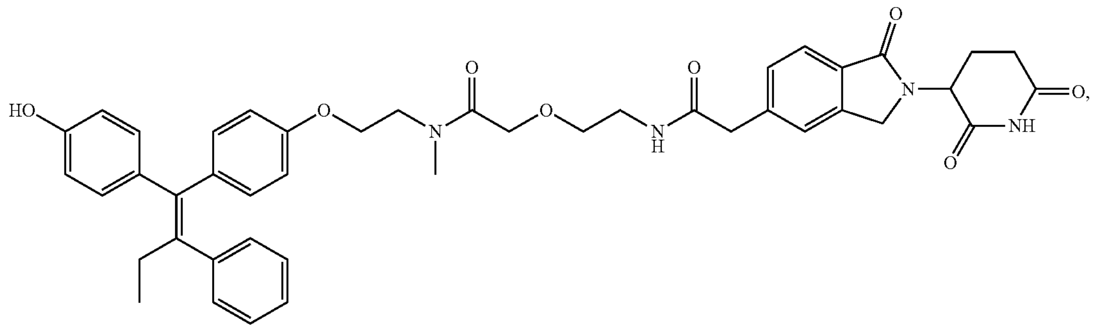
(IV)
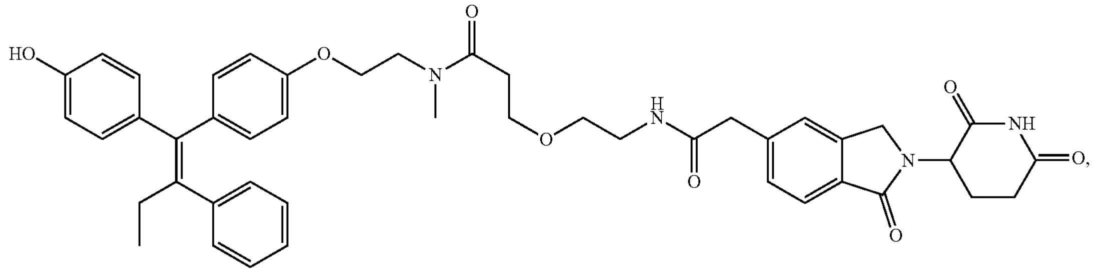
(V)
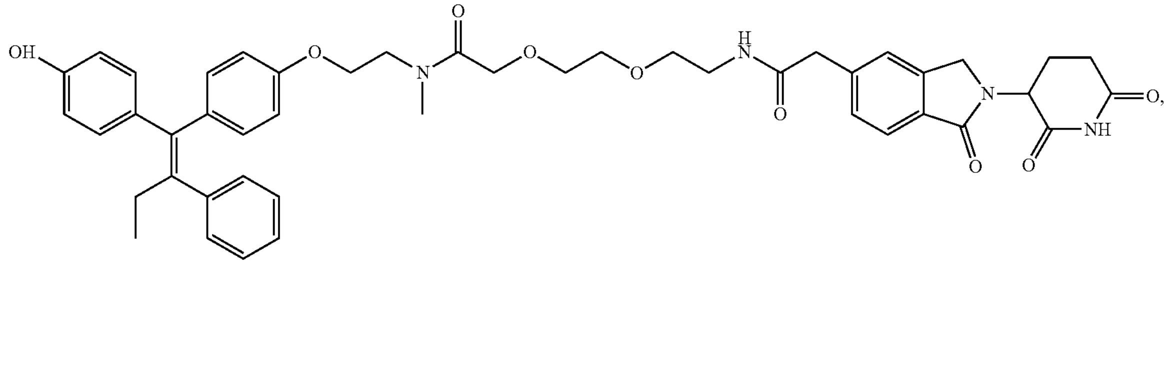

or a pharmaceutically acceptable salt thereof. The bifunctional compound can have Formula (VI):
(VI)
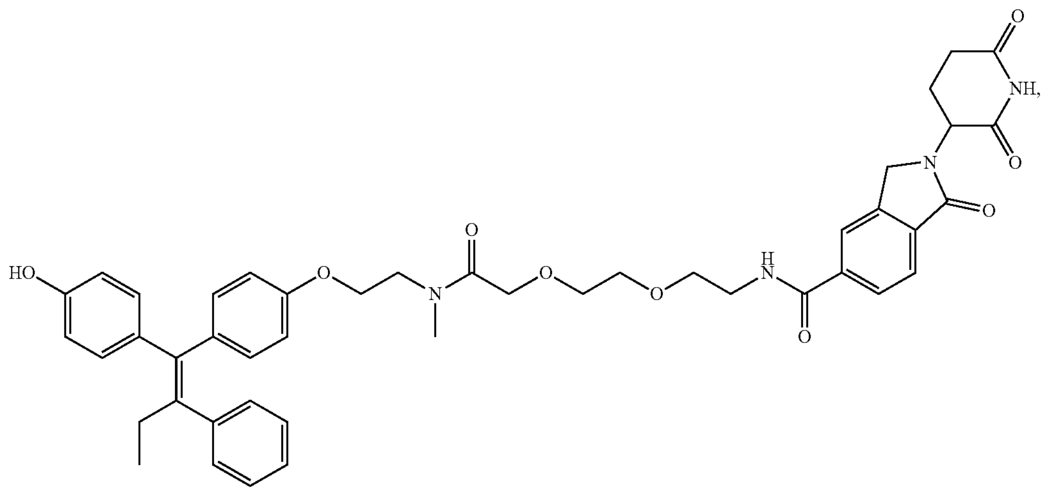
or a pharmaceutically acceptable salt thereof. The bifunctional compound can have Formula (VII), Formula (VIII), or Formula (IX):
(VII)
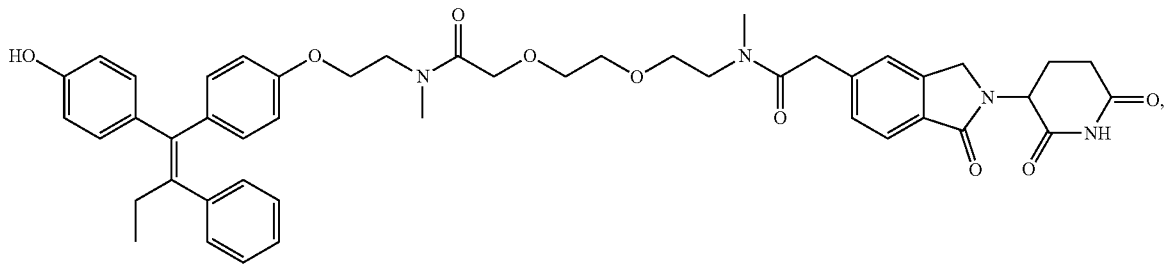
(VIII)
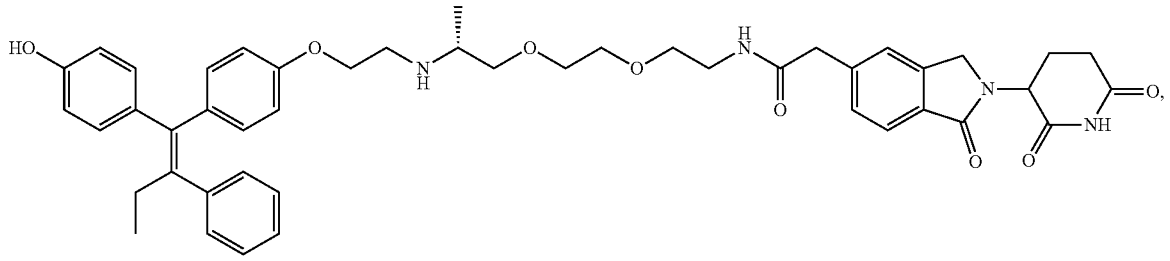
(IX)
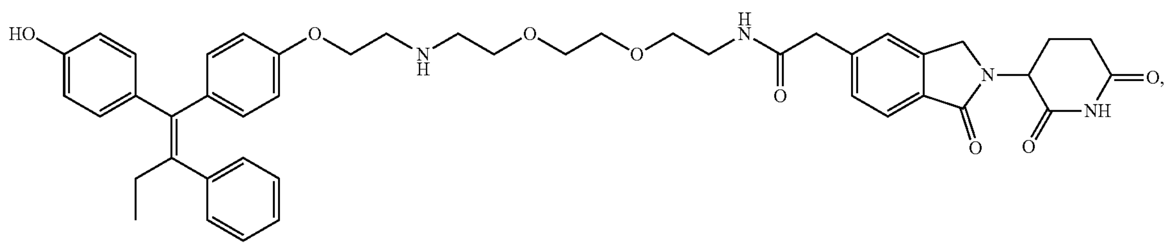

or a pharmaceutically acceptable salt thereof. The bifunctional compound can be a compound of Formula (B):

(B)

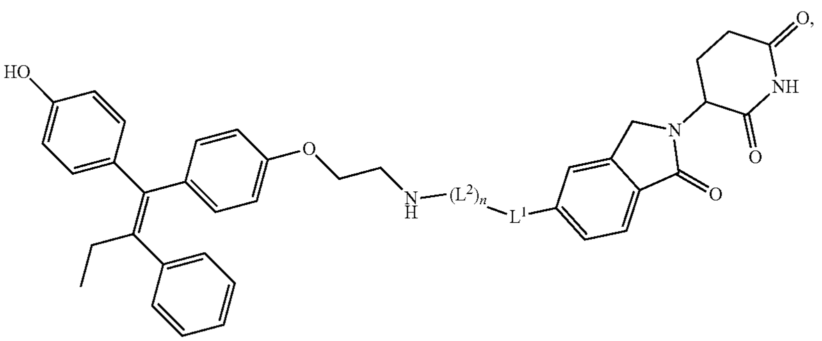

or a pharmaceutically acceptable salt thereof, wherein $L^1$ is $C_{1-3}$ alkylene, optionally substituted with 1, 2, or 3 substituents independently selected from OH, $NO_2$, CN, halo, amino, and carboxy; n is an integer selected from 1 to 10; each $L^2$ is independently selected from C(=O), $N(R^N)$, O, $(—C_{1-3}$ alkylene-O—$)_x$, (—O—$C_{1-3}$ alkylene-$)_x$, —$C_{1-3}$ alkylene-, and 4-6 membered heterocycloalkylene, wherein each x is independently an integer from 1 to 10, wherein said $C_{1-3}$ alkylene and 4-6 membered heterocycloalkylene are each optionally substituted with 1, 2, or 3 substituents independently selected from OH, $NO_2$, CN, halo, amino, and carboxy; and wherein each $R^N$ is independently selected from H and $C_{1-3}$ alkyl. The bifunctional compound can have Formula (X):

(X)

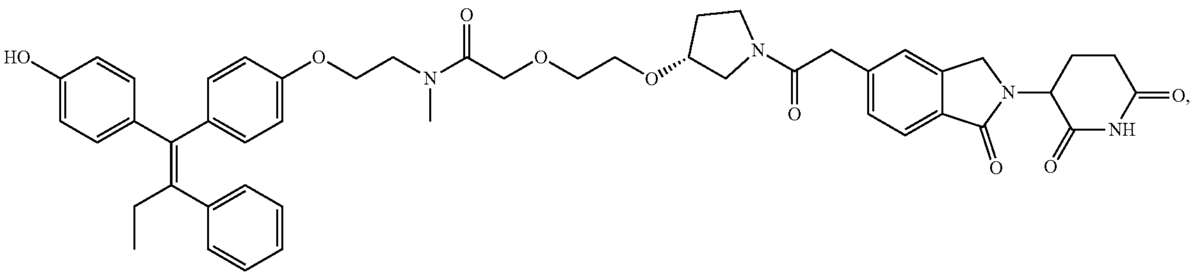

or a pharmaceutically acceptable salt thereof. The bifunctional compound can be a compound of Formula (C):

(C)

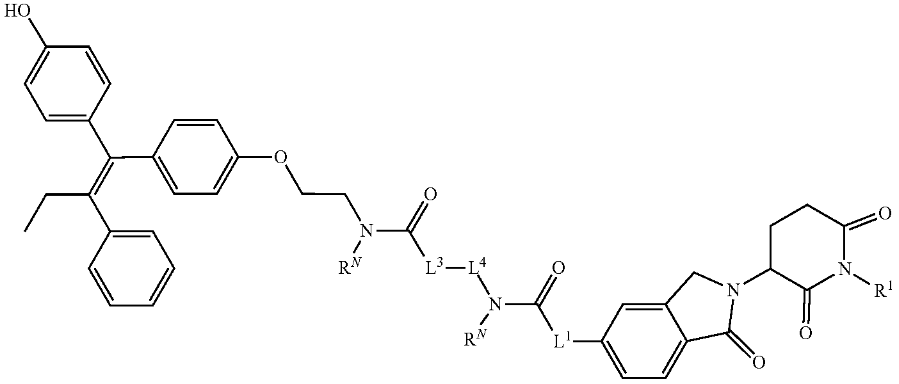

or a pharmaceutically acceptable salt thereof, wherein each $R^N$ is independently selected from H and $C_{1-3}$ alkyl; $L^1$ is $C_{1-3}$ alkylene; $L^3$ is $C_{1-3}$ alkylene and $L^4$ is $(—O—C_{1-3}$ alkylene-$)_x$; and $R^1$ is $C_{1-3}$ alkyl substituted with —OC(=O)O—$C_{1-6}$ alkyl. The bifunctional compound can have Formula (XI) or Formula (XII):

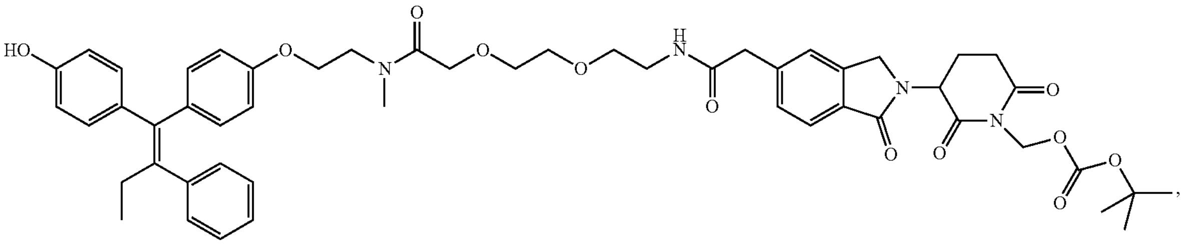

,

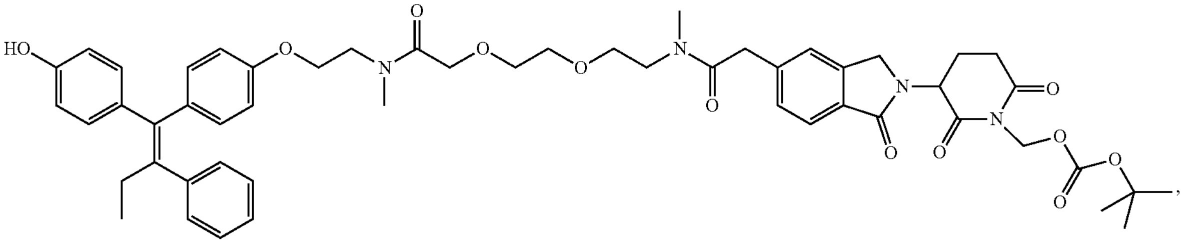

, or a pharmaceutically acceptable salt thereof.

In addition, this document features a method for killing a cancer cell, where the method includes contacting the cancer cell with a compound provided herein. The cancer cell can be an ER− cancer cell or an ER+ cancer cell. The cancer cell can be in a tumor within a mammal (e.g., a human).

In another aspect, this document features a method for reducing proliferation of cancer cells, where the method includes contacting the cancer cells with a compound provided herein. The cancer cells can be ER− cancer cells or ER+ cancer cells. The cancer cells can be in a tumor within a mammal (e.g., a human).

In yet another aspect, this document features a method for treating a cancer, where the method includes administering a composition containing a compound provided herein to a mammal having cancer. The cancer can be an ER− cancer or an ER+ cancer. The mammal can be a human.

In another aspect, this document features a method for inhibiting the growth of a tumor, where the method includes contacting the tumor with a compound provided herein. The tumor can be an ER− tumor or an ER+ tumor. The tumor can be within a mammal (e.g., a human).

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 6A-7E are graphs plotting plasma concentrations of ENDX PROTAC 9 (TC-Pr-009) in mice after oral (PO) administration at a dose of 10 mg/kg (FIG. 6A), after intravenous (IV) administration at a dose of 1 mg/kg with blood collected in an EDTA tube without NaF (FIG. 6B), after IV administration at a dose of 1 mg/kg with blood collected in an EDTA tube with NaF (FIG. 6C), or after intraperitoneal (IP) administration at a dose of 4 mg/kg (FIG. 6E). Combined results from the IV studies are plotted in FIG. 6D.

FIGS. 9A-9J show results from CV proliferation assays evaluating the efficacy of ENDX-PROTAC analogs Pr-9 analog 1 (Pr-9-1) and Pr-9 analog 4 (Pr-9-4) on growth of breast cancer cells. FIG. 9A is an image of a representative CV proliferation assay, showing the efficacy of the Pr-9-1 and Pr-9-4 molecules on growth of MCF7AC1 cells plated at 2000 cells per well. $IC_{50}$ estimates are included on the right. FIG. 9B shows the raw absorbance values calculated from the CV proliferation plate in FIG. 9A, and a calculation of the percentage of proliferation relative to DMSO control treatment. FIG. 9C is an image of a representative CV proliferation assay, showing the efficacy of the Pr-9-1 and Pr-9-4 molecules on growth of MDAMB231 cells plated at 2000 cells per well. $IC_{50}$ estimates are included on the right. FIG. 9D shows the raw absorbance values calculated from the CV proliferation plate in FIG. 9C, and a calculation of the percentage of proliferation relative to DMSO control treatment. FIG. 9E is an image of a representative crystal CV proliferation assay, showing the efficacy of the Pr-9-1 and Pr-9-4 molecules on growth of BT549 cells plated at 2000 cells per well. $IC_{50}$ estimates are included on the right. FIG. 9F shows the raw absorbance values calculated from the CV proliferation plate in FIG. 9E, and a calculation of the percentage of proliferation relative to DMSO control treatment. FIG. 9G is an image of a representative CV proliferation assay, showing the efficacy of the Pr-9-1 and Pr-9-4 molecules on growth of BT549 cells plated at 4000 cells per well. $IC_{50}$ estimates are included on the right. FIG. 9H shows the raw absorbance values calculated from the CV proliferation plate in FIG. 9G, and a calculation of the percentage of proliferation relative to DMSO control treatment. FIG. 9I is an image of a representative CV proliferation assay, showing the efficacy of the Pr-9-1 and Pr-9-4 molecules on growth of MDAMB436 cells plated at 4000 cells per well. $IC_{50}$ estimates are included on the right. FIG. 9J shows the raw absorbance values calculated from the CV proliferation plate in FIG. 9I, and a calculation of the percentage of proliferation relative to DMSO control treatment.

FIG. 11A, BIP; FIG. 11Q, PKCB1.

DETAILED DESCRIPTION

The ubiquitin-proteasome pathway causes covalent attachment of ubiquitin to lysine residues on polypeptide targets, leading to degradation of the targeted polypeptides. Attachment of ubiquitin to polypeptide substrates is achieved through the action of E3 ubiquitin ligases, which include more than 500 different proteins and are categorized into classes based on the structural element of their E3 functional activity. The pathway is naturally involved in regulating polypeptides, as it can lead to degradation of misfolded or abnormal polypeptides.

Figure 1A:
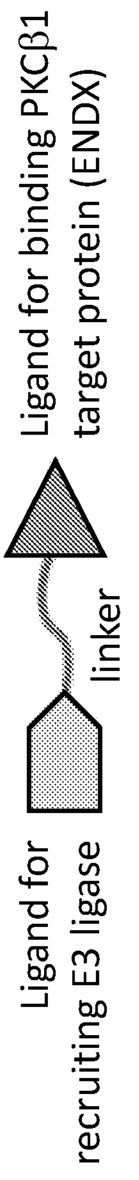
FIG. 1A is a diagram depicting the components of a bifunctional compound containing a first small molecule having the ability to bind to a PKCβ1 polypeptide and a second small molecule having the ability to bind to an E3 ubiquitin ligase polypeptide.
Figure 1B:
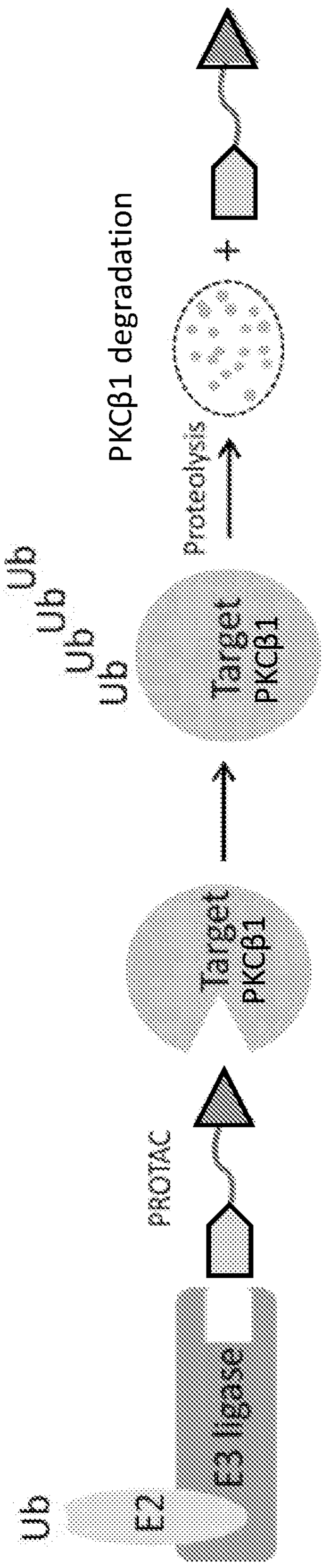
FIG. 1B is a diagram depicting the mechanism of action for the bifunctional compound of FIG. 1A, as the bifunctional compound leads to degradation of a PKCβ1 polypeptide.

The ubiquitin-proteasome pathway also can be employed as a mechanism for targeted polypeptide degradation through the use of proteolysis targeting chimera (PROTAC) molecules. A PROTAC is a heterobifunctional small molecule composed of two active domains coupled by a linker, where one active domain interacts with a selected target polypeptide, and the other active domain interacts with an E3 ubiquitin ligase polypeptide (see, e.g., FIG. 1A). Rather than acting as a conventional enzyme inhibitor, a PROTAC can work by inducing intracellular proteolysis of the selected target polypeptide (FIG. 1B).

As described herein, targeted proteolysis of a PKCβ1 polypeptide can be achieved using PROTAC molecules and, surprisingly, targeted proteolysis of PKCβ1 polypeptides can reduce the viability of ER− breast cancer cells. As such, this document provides methods and materials for treating ER− breast cancer, reducing the proliferation and/or viability of (e.g., by killing) ER− breast cancer cells, and improving the prognosis of mammals having ER− breast cancer, based on targeting of a PKCβ1 polypeptide for degradation. In some cases, this document also provides heterobifunctional PROTAC compounds that contain a first small molecule targeted to a PKCβ1 polypeptide and a second small molecule that binds to an E3 ubiquitin ligase, where the PKCβ1-targeted small molecule is coupled to the E3 ubiquitin ligase-binding small molecule via a linker. Interaction of the bifunctional compounds with a PKCβ1 polypeptide and an E3 ligase can lead to ubiquitination of the PKCβ1 polypeptide via the E3 ubiquitin ligase-binding moiety, followed by PKCβ1 polypeptide degradation.

The compounds provided herein contain a moiety, such as a small molecule, that is capable of binding to an E3 ubiquitin ligase. The small molecule can have a molecular weight less than 2000 Da (e.g., less than 1000 Da, less than 500 Da, less than 200 Da, about 1000 to about 2000 Da, about 500 to about 1000 Da, or about 200 to about 500 Da). Any appropriate E3 ligase can be targeted. The E3 ligases are classified based on the structural element of their E3 functional activity. For example, cereblon interacts with damaged DNA binding protein 1 and forms an E3 ubiquitin ligase complex with Cullin 4, leading to ubiquitination and proteasomal degradation of the proteins recognized by cereblon. Compounds such as thalidomide and lenalidomide can bind to cereblon and modulate its role in ubiquitination and degradation. In some cases, therefore, the bifunctional compounds provided herein can include a thalidomide residue (the entire thalidomide molecule but for the functional group used for conjugation to a linker) that is capable of binding to the cereblon E3 ubiquitin ligase. Examples of other E3 ligases that can be targeted include, without limitation, other cullin-RING E3 ubiquitin ligases (CRL) such as von Hippel Lindau (VHL), as well as non-CRL ligases such as cellular inhibitor of apoptosis protein 1 (cIAP1), mouse double minute 2 homolog (MDM2), and the HECT, TRAF6 RING, and BIRC7 E3 ligases. Examples of other E3 ubiquitin ligase binding molecules include, without limitation, immunomodulatory drugs (IMiDs) such as pomalidomide and lenalidomide (which target cereblon), VH298 (which targets VHL), ligands targeted to IAPB (including bestatin), and nutlin and idasanutlin (MDM2 antagonists). See, e.g., Steinebach et al., *Chem. Sci.* 2020, 11:3474-3486; and Heider et al., *Blood* 2019, 134 (Suppl. 1):314. In some cases, the moiety capable of binding to an E3 ubiquitin ligase is referred to herein as the "PROTAC warhead."

The compounds provided herein also contain a ligand moiety, such as a small molecule, that is capable of binding to a PKCβ1 polypeptide in such a way that the PKCβ1 polypeptide is placed in proximity to the E3 ubiquitin ligase to effect degradation of the PKCβ1 polypeptide. The small molecule can have a molecular weight less than 2000 Da (e.g., less than 1000 Da, less than 500 Da, less than 200 Da, 1000 to 2000 Da, 500 to 1000 Da, or 200 to 500 Da). In some cases, the PKCβ1-targeted small molecule can be an endoxifen residue. A "residue" of a molecule refers to the entire molecule but for the functional group used for conjugation to a linker; the residue functions as a molecular "guide" that targets the entire molecule, including the warhead, to the intended protein. In some cases, the PKCβ1-targeted small molecule can be an endoxifen derivative residue, a tamoxifen residue, a tamoxifen derivative residue, a 4-hydroxytamoxifen residue, or a 4-hydroxytamoxifen derivative residue. A derivative of a molecule can include a modification at one or more positions, and in some cases, can bind to a target (e.g., a PKCβ1 polypeptide) with increased affinity as compared to the unmodified molecule.

In the bifunctional compounds provided herein, the residue moiety can be covalently coupled to the E3 ubiquitin ligase-binding moiety via a linker. Any suitable linker can be used.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

At various places in the present specification various aryl, heteroaryl, cycloalkyl, and heterocycloalkyl rings are described. Unless otherwise specified, these rings can be attached to the rest of the molecule at any ring member as permitted by valency. For example, the term "a pyridine ring" or "pyridinyl" may refer to a pyridin-2-yl, pyridin-3-yl, or pyridin-4-yl ring.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

As used herein, the phrase "optionally substituted" means unsubstituted or substituted. The substituents are independently selected, and substitution may be at any chemically accessible position. As used herein, the term "substituted" means that a hydrogen atom is removed and replaced by a substituent. A single divalent substituent, e.g., oxo, can replace two hydrogen atoms. It is to be understood that substitution at a given atom is limited by valency.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, the term "$C_{n-m}$ alkylene", employed alone or in combination with other terms, refers to a divalent alkyl linking group having n to m carbons. Examples of alkylene groups include, but are not limited to, ethan-1,1-diyl, ethan-1,2-diyl, propan-1,1-diyl, propan-1,3-diyl, propan-1,2-diyl, butan-1,4-diyl, butan-1,3-diyl, butan-1,2-diyl, 2-methyl-propan-1,3-diyl, and the like. In some embodiments, the alkylene moiety contains 2 to 6, 2 to 4, 2 to 3, 1 to 6, 1 to 4, or 1 to 2 carbon atoms.

As used herein, the term "amino" refers to a group of formula $—NH_2$.

As used herein, the term "carboxy" refers to a —C(O)OH group.

As used herein, "halo" refers to F, Cl, Br, or I. In some embodiments, a halo is F, Cl, or Br.

As used herein, "heterocycloalkyl" refers to non-aromatic monocyclic or polycyclic heterocycles having one or more ring-forming heteroatoms selected from O, N, or S. Included in heterocycloalkyl are monocyclic 4-, 5-, 6-, 7-, 8-, 9- or 10-membered heterocycloalkyl groups. Heterocycloalkyl groups can also include spirocycles. Example heterocycloalkyl groups include pyrrolidin-2-one, 1,3-isoxazolidin-2-one, pyranyl, tetrahydropuran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by 1 or 2 independently selected oxo or sulfido groups (e.g., C(O), S(O), C(S), or $S(O)_2$, etc.). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the cycloalkyl ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl is a monocyclic 4-6 membered heterocycloalkyl having 1 or 2 heteroatoms independently selected from nitrogen, oxygen, or sulfur and having one or more oxidized ring members. In some embodiments, the heterocycloalkyl is a monocyclic or bicyclic 4-10 membered heterocycloalkyl having 1, 2, 3, or 4 heteroatoms independently selected from nitrogen, oxygen, or sulfur and having one or more oxidized ring members. The term "heterocycloalkylene" refers to a divalent heterocycloalkyl group.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C═N double bonds, N═N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. In some embodiments, the compound has the (R)-configuration. In some embodiments, the compound has the (S)-configuration.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

In some cases, a bifunctional PKCβ1-targeted compound provided herein can be a compound of Formula (A):

(A)

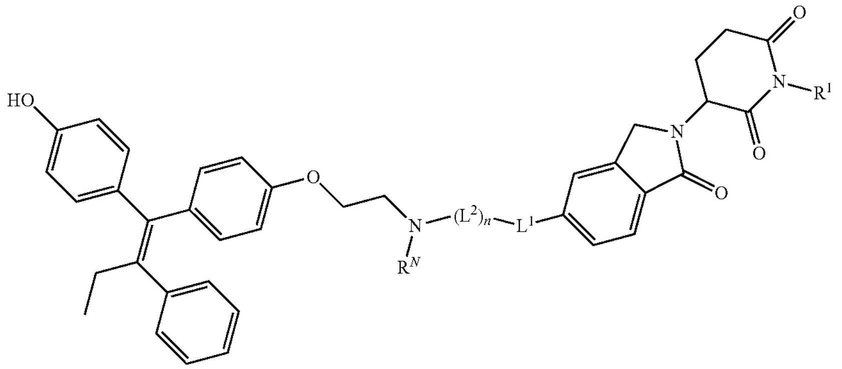

or a pharmaceutically acceptable salt thereof, wherein:

$L^1$ can be $C_{1-3}$ alkylene, optionally substituted with 1, 2, or 3 substituents independently selected from OH, $NO_2$, CN, halo, amino, and carboxy.

n can be an integer selected from 1 to 10.

Each $L^2$ can be independently selected from C(═O), $N(R^N)$, O, $(—C_{1-3}$ alkylene-O—$)_x$, $(—O—C_{1-3}$ alkylene-$)_x$, $—C_{1-3}$ alkylene-, and 4-6 membered heterocycloalkylene, where each x is independently an integer from 1 to 10, and said $C_{1-3}$ alkylene and 4-6 membered heterocycloalkylene are each optionally substituted with 1, 2, or 3 substituents independently selected from OH, $NO_2$, CN, halo, amino, and carboxy;

each $R^N$ is independently selected from H and $C_{1-3}$ alkyl; and $R^1$ is selected from H and $C_{1-3}$ alkyl, optionally substituted with a group selected from —OC(═O)O—$C_{1-6}$ alkyl, —OC(═O)$NH_2$, —OC(═O)NH($C_{1-6}$ alkyl), —OC(═O)N($C_{1-6}$ alkyl$)_2$, NHC(═O)O—$C_{1-6}$ alkyl, NHC(═O)$NH_2$, NHC(═O)NH($C_{1-6}$ alkyl), and NHC(═O)N($C_{1-6}$ alkyl$)_2$.

In some embodiments, $R^1$ is H.

In some embodiments, $R^1$ is $C_{1-3}$ alkyl.

In some embodiments, $R^1$ is $C_{1-3}$ alkyl substituted with a group selected from —OC(═O)O—$C_{1-6}$ alkyl, —OC(═O)$NH_2$, —OC(═O)NH($C_{1-6}$ alkyl), —OC(═O)N($C_{1-6}$ alkyl$)_2$, NHC(═O)O—$C_{1-6}$ alkyl, NHC(═O)$NH_2$, NHC(═O)NH($C_{1-6}$ alkyl), and NHC(═O)N($C_{1-6}$ alkyl$)_2$.

In some embodiments, $R^1$ is $C_{1-3}$ alkyl substituted with a group selected from —OC(═O)O—$C_{1-6}$ alkyl, —OC(═O)$NH_2$, and —OC(═O)NH($C_{1-6}$ alkyl).

In some embodiments, $R^1$ is $C_{1-3}$ alkyl substituted with —OC(═O)O—$C_{1-6}$ alkyl.

In some embodiments, $R^1$ is selected from H and $C_{1-3}$ alkyl substituted with —OC(═O)O—$C_{1-6}$ alkyl.

In some embodiments, $R^1$ is selected from H and —$CH_2$OC(═O)O-tert-butyl.

In some embodiments, $R^1$ is —$CH_2$OC(═O)O-tert-butyl.

In some embodiments, $R^N$ is H.

In some embodiments, $R^N$ is $C_{1-3}$ alkyl.

In some cases, the compound of Formula (A) can have Formula (I):

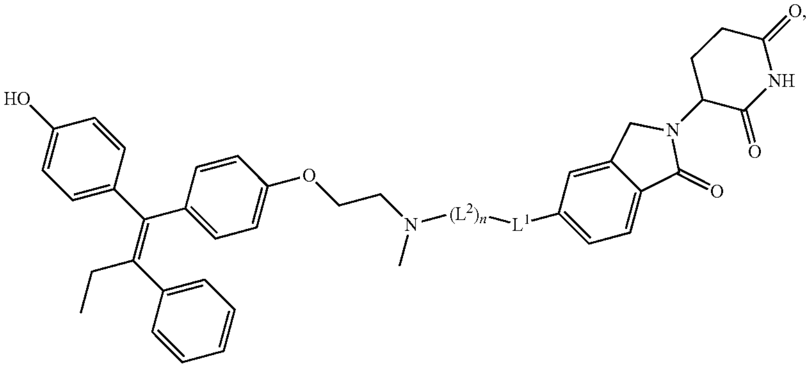

(I)

or a pharmaceutically acceptable salt thereof.

In some embodiments of Formula (I):

$L^1$ can be $C_{1-3}$ alkylene, optionally substituted with 1, 2, or 3 substituents independently selected from OH, $NO_2$, CN, halo, amino, and carboxy;

n can be an integer selected from 1 to 10; and each $L^2$ can be independently selected from C(═O), N($R^N$), O, (—$C_{1-3}$ alkylene-O—$)_x$, (—O—$C_{1-3}$ alkylene-$)_x$, and —$C_{1-3}$ alkylene-, where each x is independently an integer from 1 to 10 and each $C_{1-3}$ alkylene is optionally substituted with 1, 2, or 3 substituents independently selected from OH, $NO_2$, CN, halo, amino, and carboxy; and each $R^N$ is independently selected from H and $C_{1-3}$ alkyl.

In some cases, the compound of Formula (A) can have Formula (B):

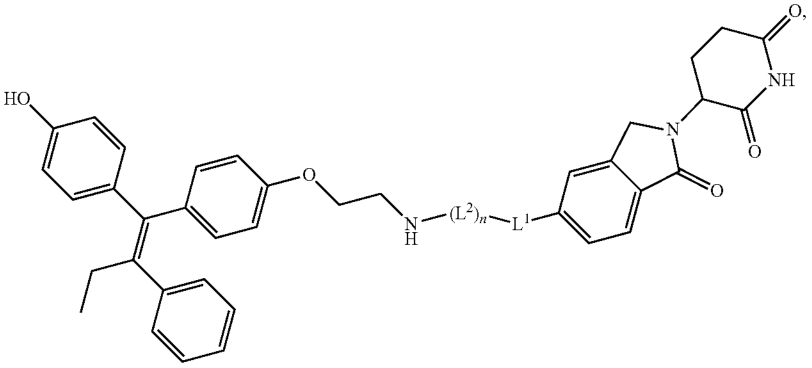

(B)

or a pharmaceutically acceptable salt thereof, wherein:

$L^1$ can be $C_{1-3}$ alkylene, optionally substituted with 1, 2, or 3 substituents independently selected from OH, $NO_2$, CN, halo, amino, and carboxy.

n can be an integer selected from 1 to 10.

Each $L^2$ can be independently selected from C(═O), $N(R^N)$, O, (—$C_{1-3}$ alkylene-O—$)_x$, (—O—$C_{1-3}$ alkylene-$)_x$, —$C_{1-3}$ alkylene-, and 4-6 membered heterocycloalkylene, where each x is independently an integer from 1 to 10, and said $C_{1-3}$ alkylene and 4-6 membered heterocycloalkylene are each optionally substituted with 1, 2, or 3 substituents independently selected from OH, $NO_2$, CN, halo, amino, and carboxy; and each $R^N$ is independently selected from H and $C_{1-3}$ alkyl.

In some cases, the compound of Formula (I) can have Formula (II):

In some cases, in the compounds of Formula (A), Formula (B), Formula (C), Formula (I), and/or Formula (II), $L^1$ can be ethylene.

In some cases, in the compounds of Formula (A), Formula (B), and/or Formula (I), n can be 5.

In some cases, in the compounds of Formula (A), Formula (B), and/or Formula (I), n can be 6.

In some cases, in the compounds of Formula (A), Formula (B), and/or Formula (I), at least one $L^2$ can be C(═O).

In some cases, in the compounds of Formula (A), Formula (B), and/or Formula (I), at least one $L^2$ can be NH.

In some cases, in the compounds of Formula (A), Formula (B), and/or Formula (I), at least one $L^2$ can be $NCH_3$.

In some cases, in the compounds of Formula (A), Formula (B), and/or Formula (I), at least one $L^2$ can be O.

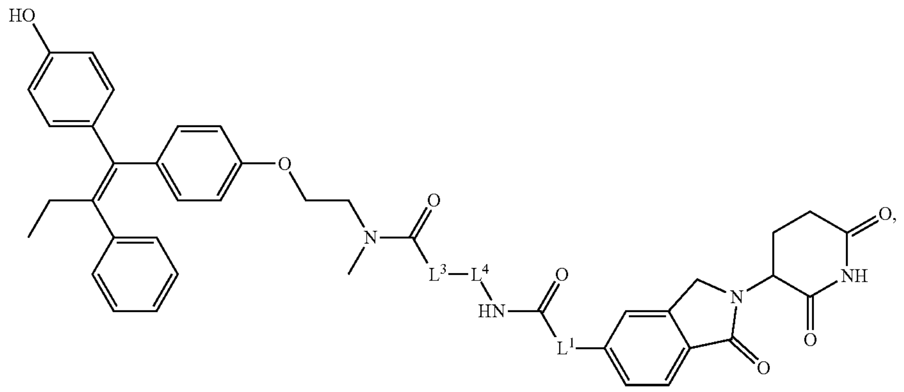

(II)

or a pharmaceutically acceptable salt thereof, wherein:

$L^3$ is $C_{1-3}$ alkylene and $L^4$ is (—O—$C_{1-3}$ alkylene-$)_x$.

In some cases, the compound of Formula (A) can have Formula (C):

In some cases, in the compounds of Formula (A), Formula (B), and/or Formula (I), at least one $L^2$ can be (—$C_{1-3}$ alkylene-O—$)_x$.

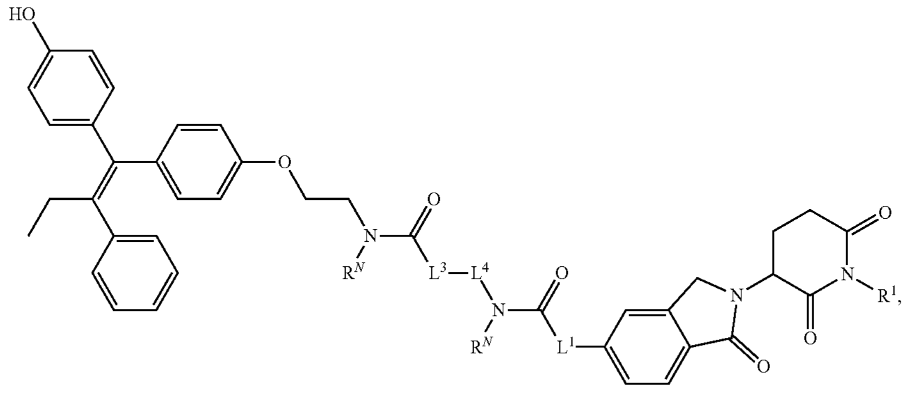

(C)

or a pharmaceutically acceptable salt thereof, wherein:

each $R^N$ is independently selected from H and $C_{1-3}$ alkyl;

$L^1$ is $C_{1-3}$ alkylene;

$L^3$ is $C_{1-3}$ alkylene and $L^4$ is (—O—$C_{1-3}$ alkylene-$)_x$; and $R^1$ is $C_{1-3}$ alkyl substituted with —OC(═O)O—$C_{1-6}$ alkyl.

In some cases, in the compounds of Formula (A), Formula (B), Formula (C), Formula (I), and/or Formula (II), $L^1$ can be methylene.

In some cases, in the compounds of Formula (A), Formula (B), and/or Formula (I), at least one $L^2$ can be (—O—$C_{1-3}$ alkylene-$)_x$.

In some cases, in the compounds of Formula (A), Formula (B), and/or Formula (I), at least one $L^2$ can be —$C_{1-3}$ alkylene-.

In some cases, in the compounds of Formula (A), Formula (B), and/or Formula (I), at least one $L^2$ can be 4-6 membered heterocycloalkylene.

In some cases, in the compounds of Formula (A), Formula (B), and/or Formula (I), at least one $L^2$ can be pyrrolidinylene.

In some cases, in the compounds of Formula (A), Formula (B), and/or Formula (I), at least one $L^2$ can have formula:

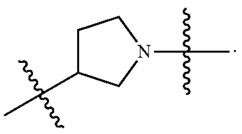 [SMILES: *C1CCN(*)C1]

In some cases, in the compounds of Formula (A), Formula (B), Formula (C), Formula (I), and/or Formula (II), x can be an integer from 1 to 5.

In some cases, in the compounds of Formula (A), Formula (B), Formula (C), Formula (I), and/or Formula (II), x can be 1, 2, or 3.

In some cases, a bifunctional PKCβ1-targeted compound provided herein can have Formula (III):

(III)

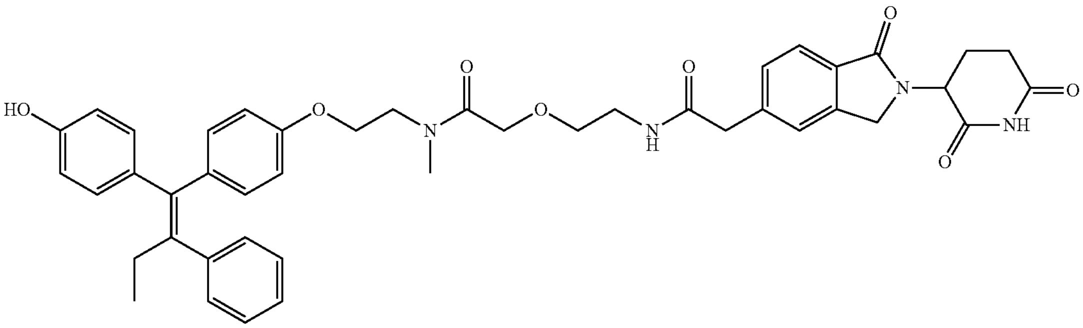

or a pharmaceutically acceptable salt thereof.

In some cases, a bifunctional PKCβ1-targeted compound provided herein can have Formula (IV):

(IV)

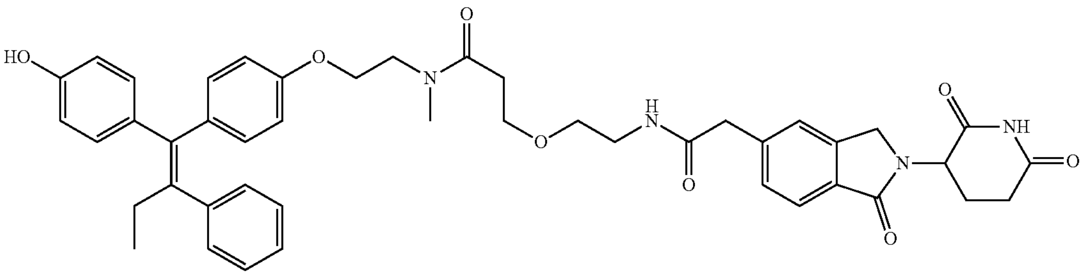

or a pharmaceutically acceptable salt thereof.

In some cases, a bifunctional PKCβ1-targeted compound provided herein can have Formula (V):

(V)

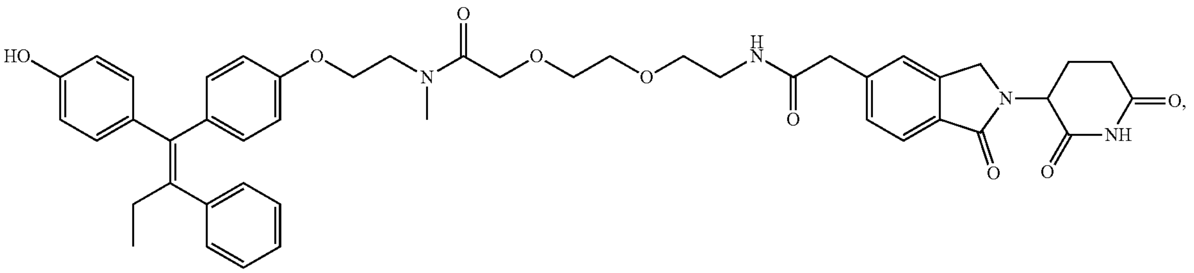

or a pharmaceutically acceptable salt thereof.

In some cases, a bifunctional PKCβ1-targeted compound provided herein can have Formula (VI):

(VI)

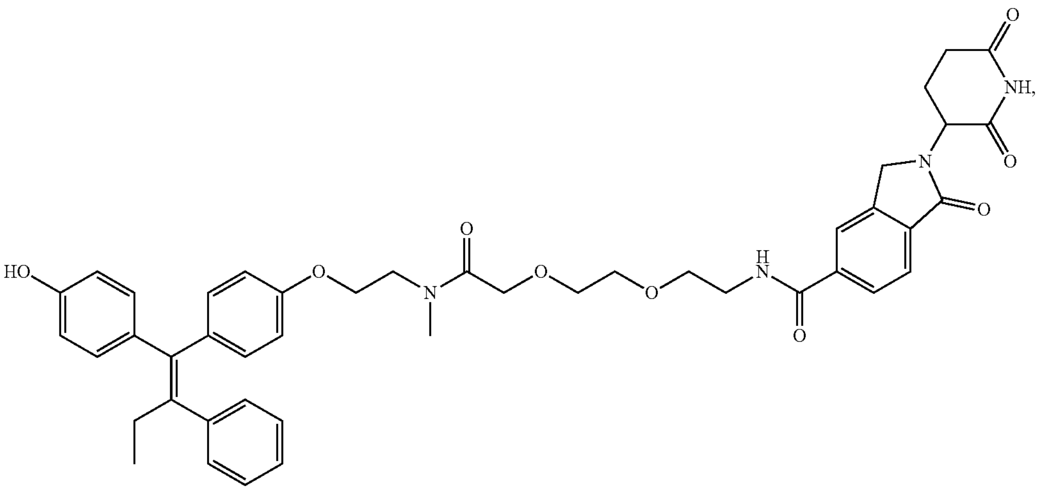

or a pharmaceutically acceptable salt thereof.

In some cases, a bifunctional PKCβ1-targeted compound provided herein can have Formula (VII):

(VII)

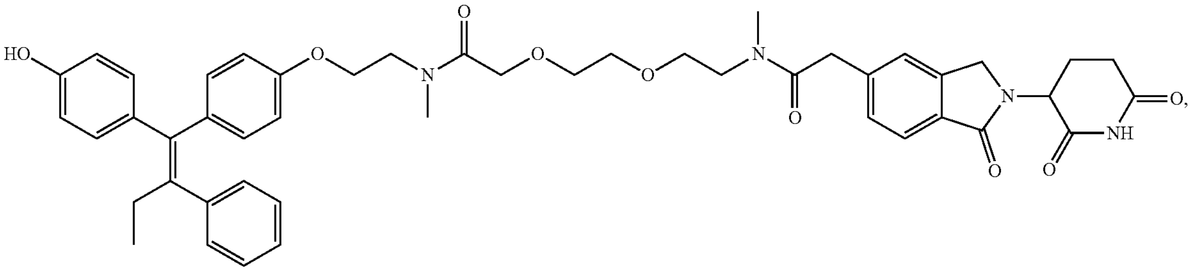

or a pharmaceutically acceptable salt thereof.

In some cases, a bifunctional PKCβ1-targeted compound provided herein can have Formula (VIII):

(VIII)

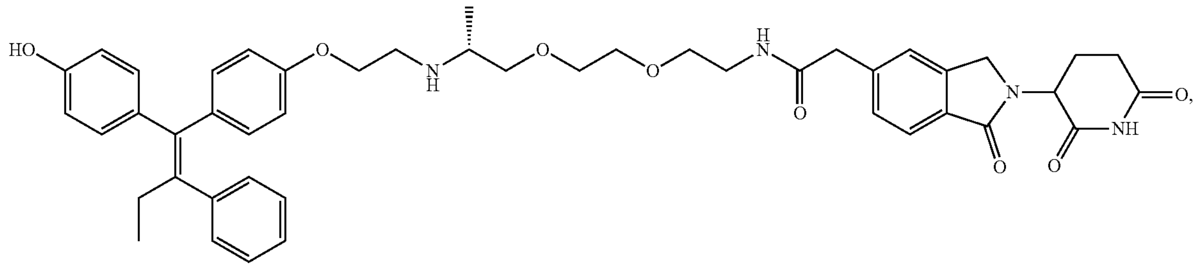

or a pharmaceutically acceptable salt thereof.

In some cases, a bifunctional PKCβ1-targeted compound provided herein can have Formula (IX):

(IX)

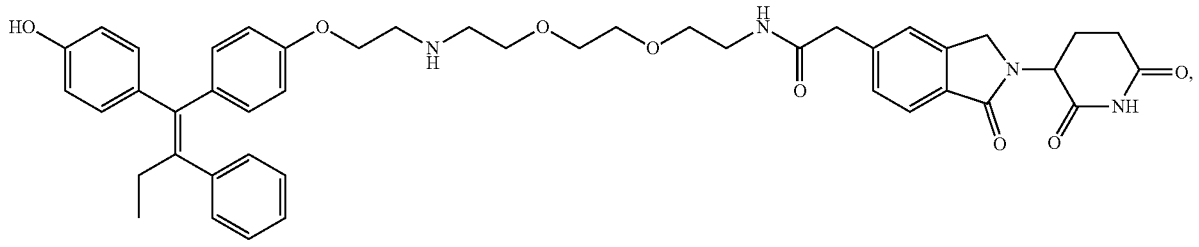

or a pharmaceutically acceptable salt thereof.

In some cases, a bifunctional PKCβ1-targeted compound provided herein can have Formula (X):

(X)

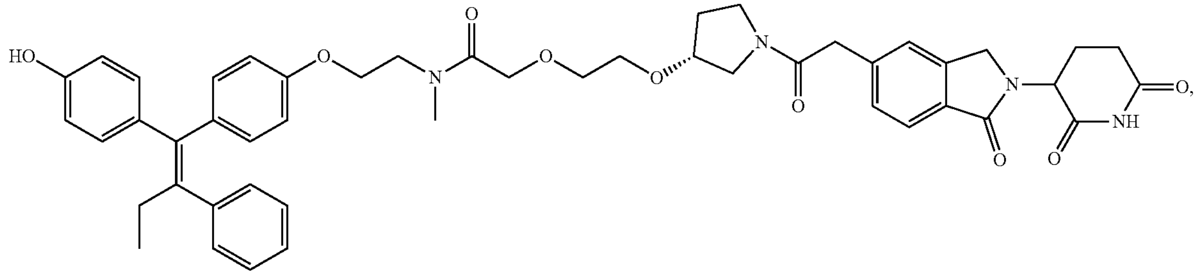

or a pharmaceutically acceptable salt thereof.

In some cases, a bifunctional PKCβ1-targeted compound provided herein can have Formula (XI):

(XI)

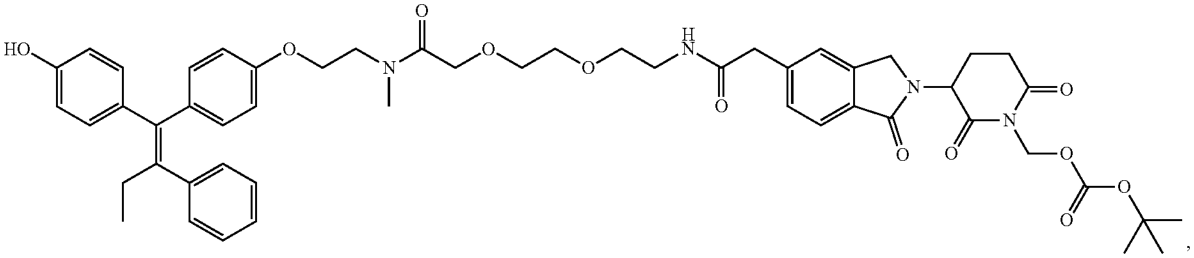

or a pharmaceutically acceptable salt thereof.

In some cases, a bifunctional PKCβ1-targeted compound provided herein can have Formula (XII):

(XII)

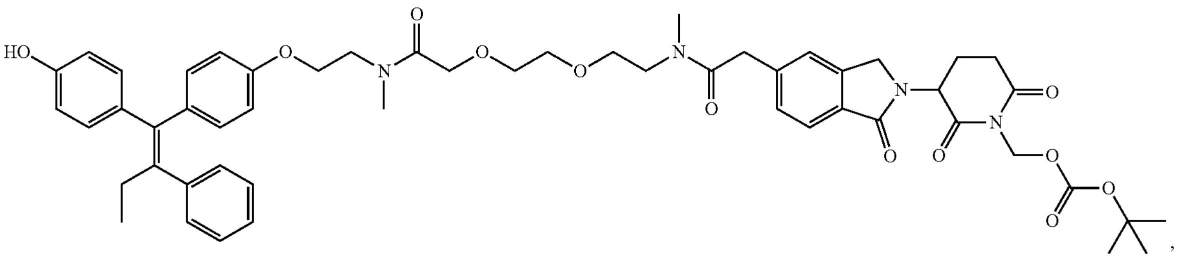

or a pharmaceutically acceptable salt thereof.

Any appropriate method can be used to synthesize the heterobifunctional PKCβ1-targeting compounds provided herein. Methods for making the compounds provided herein are disclosed in the Examples below, for example. See, also, U.S. Pat. No. 9,821,068, and U.S. Patent Application Publication No. 2019/0263823.

The bifunctional PKCβ1-targeted compounds provided herein can be effective for reducing the proliferation and/or viability of (e.g., by killing) ER− breast cancer cells, for reducing the size of ER− breast tumors, and/or for treating mammals having ER− breast cancer. In some cases, the bifunctional PKCβ1-targeted compounds provided herein can be more effective for reducing the proliferation and/or viability of (e.g., by killing) ER− breast cancer cells, reducing the size of ER− breast tumors, and/or treating mammals having ER− breast cancer than the PKCβ1-targeted molecule when used alone (without the linker and E3 ligase-binding component).

In some cases, the effectiveness of the compounds provided herein can be determined based on their $IC_{50}$ value for killing or inhibiting proliferation of cancer cells (e.g., the concentration at which the compound inhibits or kills 50% of the ER− breast cancer cells in a sample). In general, a compound with a lower $IC_{50}$ value, as determined under substantially similar conditions, is a more potent inhibitor than a compound with a higher $IC_{50}$ value.

This document also provides methods and materials involved in killing and/or reducing proliferation of ER− or ER+ cancer cells (e.g., ER− breast cancer cells, ER+ breast cancer cells, ER− ovarian cancer cells, or ER+ ovarian cancer cells), and treating mammals identified as having ER− or ER+ cancer (e.g., ER− breast cancer, ER+ breast cancer, ER− ovarian cancer, or ER+ ovarian cancer). For example, in some cases, this document provides methods and materials for using the bifunctional compounds described herein to kill ER− breast cancer cells or to reduce proliferation of ER− breast cancer cells. This document also provides methods and materials for using the bifunctional compounds described herein to treat mammals identified as having ER− or ER+ cancer (e.g., ER− breast cancer, ER+ breast cancer, ER− ovarian cancer, or ER+ ovarian cancer). The bifunctional compounds described herein also can be used to slow the progression of tumor growth in mammals who have cancer (e.g., ER− breast cancer, ER+ breast cancer, ER− ovarian cancer, or ER+ ovarian cancer).

Any type of mammal having cancer (e.g., ER− or ER+ breast cancer) can be treated as described herein. For example, humans and other primates such as monkeys having ER− breast cancer can be treated with a bifunctional compound described herein. In some cases, dogs, cats, horses, cows, pigs, sheep, rabbits, mice, or rats having ER− breast cancer can be treated with a bifunctional compound described herein. The mammal can be female or, in some cases, the mammal can be male.

Once identified as having cancer (e.g., ER− or ER+ breast cancer), a mammal can be administered one or more bifunctional compounds targeted to a PKCβ1 polypeptide as described herein. In some cases, a PKCβ1 polypeptide-targeted bifunctional compound, or a combination of PKCβ1 polypeptide-targeted bifunctional compounds, can be formulated into a pharmaceutically acceptable composition. For example, a therapeutically effective amount of a PKCβ1 polypeptide-targeted bifunctional compound can be formulated together with one or more pharmaceutically acceptable carriers (additives) and/or diluents. A pharmaceutical composition can be formulated for administration in solid or liquid form including, without limitation, sterile solutions, suspensions, sustained-release formulations, tablets, capsules, pills, powders, and granules.

Pharmaceutically acceptable carriers, adjuvants and vehicles that may be used in the pharmaceutical compositions described herein include, without limitation, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. If required, the solubility and bioavailability of a PKCβ1-targeted bifunctional compound in a pharmaceutical composition can be enhanced using lipid excipients and/or block copolymers of ethylene oxide and propylene oxide. See, e.g., U.S. Pat. No. 7,014,866 and U.S. Patent Publication Nos. 2006/0094744 and 2006/0079502.

A pharmaceutical composition described herein can be designed for oral or parenteral (including subcutaneous, intramuscular, intravenous, and intradermal) administration. Compositions suitable for parenteral administration include aqueous and non-aqueous sterile injection solutions that can contain anti-oxidants, buffers, bacteriostats, and solutes which render the formulation isotonic with the blood of the intended recipient; and aqueous and non-aqueous sterile suspensions which may include suspending agents and thickening agents. The formulations can be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules, and tablets.

Such injection solutions can be in the form, for example, of a sterile injectable aqueous or oleaginous suspension. This suspension may be formulated according to techniques using suitable dispersing or wetting agents (such as, for example, TWEEN® 80) and suspending agents. The sterile injectable preparation can be a sterile injectable solution or suspension in a non-toxic parenterally-acceptable diluent or solvent, for example, as a solution in 1,3-butanediol. Among the acceptable vehicles and solvents that can be used are mannitol, water, Ringer's solution, and isotonic sodium chloride solution. In addition, sterile, fixed oils are conventionally employed as a solvent or suspending medium. For this purpose, any bland fixed oil can be used including synthetic mono- or di-glycerides. Fatty acids, such as oleic acid and its glyceride derivatives can be used in the preparation of injectables, as can natural pharmaceutically-acceptable oils, such as olive oil or castor oil, including those in their polyoxyethylated versions. These oil solutions or suspensions can contain a long-chain alcohol diluent or dispersant.

Any suitable route of administration can be used for a composition containing a PKCβ1 polypeptide-targeted bifunctional compound. For example, a pharmaceutical composition containing one or more PKCβ1 polypeptide-targeted bifunctional compounds can be administered locally (e.g., to the vicinity of a tumor or directly to the tumor) or systemically. Administration can be, for example, oral, parenteral (e.g., by subcutaneous, intrathecal, intraventricular, intramuscular, or intraperitoneal injection, or by intravenous drip), or topical (e.g., transdermal, sublingual, ophthalmic, or intranasal), or can occur by a combination of such methods. For example, a composition containing a PKCβ1 polypeptide-targeted bifunctional compound can be administered systemically by intravenous injection into a mammal (e.g., a human). When two or more PKCβ1 polypeptide-targeted bifunctional compounds are to be administered, each compound can be administered by the same or different routes, and can be delivered simultaneously in the same composition or sequentially in separate compositions. Administration can be rapid (e.g., by injection) or can occur over a period of time (e.g., by slow infusion or administration of a slow release formulation).

Compositions containing one or more PKCβ1 polypeptide-targeted bifunctional compounds can be administered to a mammal in any amount, at any frequency, and for any duration effective to achieve a desired outcome. For example, a composition containing a PKCβ1 polypeptide-targeted bifunctional compound can be administered in an amount, at a frequency, and for a duration that is sufficient to reduce the proliferation of ER− breast cancer cells, to reduce the viability of (e.g., by killing) ER− breast cancer cells, and/or to reduce the size of an ER− breast tumor in a mammal.

Effective doses can vary, as recognized by those skilled in the art, depending on the severity of the mammal's condition, the route of administration, the age and general health of the mammal, the excipient usage, the possibility of co-usage with other therapeutic treatments (e.g., the use of other agents or treatments such as radiation), and the judgment of the treating clinician.

An effective amount of a composition containing one or more PKCβ1 polypeptide-targeted bifunctional compounds can be any amount that reduces the proliferation or viability of cancer cells (e.g., ER− or ER+ breast cancer cells in a mammal), and/or reduces the size of a tumor (e.g., an ER− or ER+ breast tumor) in a mammal, without producing significant toxicity to the mammal (e.g., in non-cancerous tissues within the mammal). For example, an effective amount of a PKCβ1 polypeptide-targeted bifunctional molecule can be an amount sufficient to reduce the size of a tumor (e.g., an ER− or ER+ breast tumor or an ER− or ER+ ovarian tumor), measured at the tumor's widest point, by at least 5% (e.g., at least 10%, at least 20%, at least 25%, at least 50%, at least 75%, or at least 100%), as compared to the size of the tumor prior to treatment or at an earlier time point during treatment. Any appropriate method can be used to measure the size of a tumor in a mammal. Suitable methods include, without limitation, imaging methods such as a computed tomography (CT) scans, magnetic resonance imaging (MM) scans, X-rays or other radiographic tests, mammography, positron emission tomograph (PET) scans, and ultrasound. In some cases, an effective amount of a PKCβ1-targeted bifunctional molecule can be an amount sufficient to reduce the proliferation or viability of cancer cells (e.g., ER− or ER+ breast cancer cells, or ER− or ER+ ovarian cancer cells) by at least 5% (e.g., at least 10%, at least 20%, at least 25%, at least 50%, at least 75%, or at least 100%), as compared to the rate of proliferation or the viability of the cancer cells prior to treatment or at an earlier time point during treatment. Any appropriate method can be used to assess the rate of proliferation or the viability of cancer cells (e.g., cells from a tumor biopsy), including methods used to measure tumor size at various time points (e.g., before, during, and/or after treatment).

In some cases, an effective amount of a PKCβ1 polypeptide-targeted bifunctional compound (e.g., a compound having the structure of Formula (I), Formula (II), Formula (III), Formula (IV), Formula (V), or Formula (VI)) can be from about 0.1 mg to about 500 mg. In some cases, for example, about 0.1 mg and about 500 mg (e.g., about 0.1 mg to about 0.5 mg, about 0.5 mg to about 1 mg, about 1 mg to about 10 mg, about 10 mg to about 25 mg, about 25 mg to about 50 mg, about 50 mg to about 100 mg, about 100 mg to about 200 mg, about 200 mg to about 300 mg, about 300 mg to about 400 mg, about 400 mg to about 500 mg, or about 1 mg to about 360 mg) of a PKCβ1 polypeptide-targeted bifunctional compound can be administered to a mammal (e.g., a human) per day for a suitable length of time. If a mammal fails to respond to a particular dosage, then the amount of a PKCβ1 polypeptide-targeted bifunctional compound can be increased by, for example, two fold. After receiving this higher amount, the mammal can be monitored for both responsiveness to the treatment and toxicity symptoms, and adjustments made accordingly.

The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the ER− cancer may require an increase or decrease in the actual effective amount administered.

The frequency of administration for a composition containing one or more PKCβ1 polypeptide-targeted bifunctional compounds can be any frequency that reduces the proliferation or viability of ER− breast cancer cells (e.g., in a mammal), and/or reduces the size of an ER− breast tumor in a mammal, without producing significant toxicity to the mammal (e.g., in non-cancerous tissues within the mammal). For example, the frequency of administration can be from about once a week to about three times a day, or from about twice a month to about six times a day, or from about twice a week to about once a day. The frequency of administration can remain constant or can be variable during the duration of treatment. In some cases, a course of treatment of a mammal with a composition containing one or more PKCβ1 polypeptide-targeted bifunctional compound can include rest periods. For example, a composition containing one or more PKCβ1 polypeptide-targeted bifunctional compound can be administered daily over a two week period followed by a two week rest period, and such a regimen can be repeated multiple times. As with the effective amount, various factors can influence the actual frequency of administration used for a particular application. For example, the effective amount, duration of treatment, use of multiple treatment agents, route of administration, and severity of the ER− cancer may require an increase or decrease in administration frequency.

An effective duration for administering a composition containing one or more PKCβ1 polypeptide-targeted bifunctional compounds can be any duration that reduces the proliferation or viability of ER− breast cancer cells (e.g., in a mammal), and/or reduces the size of an ER− breast tumor in a mammal, without producing significant toxicity to the mammal (e.g., in non-cancerous tissues within the mammal). The effective duration can vary from several days to several weeks or months. In general, the effective duration for the treatment of ER− breast cancer can range in duration from several weeks to several months. Multiple factors can influence the actual effective treatment duration. For example, an effective duration can vary with the frequency of administration, effective amount, use of multiple treatment agents, route of administration, and severity of the cancer being treated.

In some cases, a course of treatment and its effect on the ER− cancer being treated can be monitored. Any appropriate method can be used to determine the effect of treatment with a PKCβ1 polypeptide-targeted bifunctional molecule is effective (e.g., to reduce the proliferation and/or viability of cancer cells, or to reduce the size of a tumor). For example, tumor size can be assessed using imaging techniques at different time points.

In some cases, a PKCβ1 polypeptide-targeted bifunctional compound can be administered to a mammal in combination with one or more additional agents. The one or more additional agents can, for example, be targeted to ER− breast cancer cells, or can enhance the effectiveness of the PKCβ1 polypeptide-targeted bifunctional compound against the ER− cancer.

In some cases, the one or more additional agents can be UPR-targeted inhibitors. Examples of UPR-targeted inhibitors include, without limitation, eeyarestatin I, mycolactone, exotoxin A, NSC 630668-R/1, MAL3-39, MAL3-101, E6 berbamine, ophiobolin A, equisetin, CJ-21058, Rose Bengal, erythrosin B, bisthiouracil, SCA-21, HUN-7293, cotransin, CAM741, apratoxin A, decatransin, valinomycin, CADA, kinase inhibiting RNase attenuator6 (KIRA6), 3-hydroxy-2-naphthoic acid (3HNA), MKC-3946, 4-Phenylbutyric acid (4-PBA), taurine-conjugated ursodeoxycholic acid (TUDCA), olmesartan, N-acetylcysteine, (NAC), oleanolic acid (OA), ursolic acid, telmisartan, quercetin, 4118C, STF-083010, B-109, GSK2606414, GSK2656157, AMG PERK44, melatonin, ceapin, IRSIB, AID 2732, salubrinal, ISRIB, guanabenz, sephin1, salicylaldimines, APY29, sunitinib, toyocamycin, 3-ethoxy-5,6-dibromosalicylal-dehyde, apigenin, FIRE peptide, baicalein, kaempferol, compound 147, compound 263, 16F16, ONC201, 3-methoxy-6-bromosalicylaldehyde, MKC-3946, STF-803010, toyocamycin, 3,6-DMAD, hydroxy-aryl-aldehydes, irestatin, versipelostatin, AMG52, AMG44, ISRIB, Trazodone, salubrinal, guanabenz, sephin1, PF429242, AEBSF, ceapin-A7, trans-ISRIB, 2-[(3-amino-2-pyridinyl)methylene]-hydrazinecarbothioamide, CB-5083, tunicamycin, MLN7243, STF-083010, ML291, azoramide, and sandoz 58-035. The one or more additional agents can be administered to a mammal at the same time as a PKCβ1 polypeptide-targeted bifunctional compound (e.g., in the same composition, or in separate compositions co-administered at the same time), or the one or more additional agents can be administered to a mammal before or after a PKCβ1 polypeptide-targeted bifunctional compound. As described above for the PKCβ1 polypeptide-targeted bifunctional compound, the one or more additional agents can be administered in any appropriate dose, and by any appropriate route.

In some cases, the one or more additional agents can be UPR-targeted activators. Examples of UPR-targeted activators include, without limitation, tunicamycin, thapsigargin, brefeldin A, dithiothreitol, MG132, IXA1, IXA6, IXA4, CCT020312, MK-28, BiX, AA147, AA263, and ethyl 2-[3,5-bis(trifluoromethyl)phenyl]-3-oxo-1H-pyrazole-4-carboxylate. The one or more additional agents can be administered to a mammal at the same time as a PKCβ1 polypeptide-targeted bifunctional compound (e.g., in the same composition, or in separate compositions co-administered at the same time), or the one or more additional agents can be administered to a mammal before or after a PKCβ1 polypeptide-targeted bifunctional compound. As described above for the PKCβ1 polypeptide-targeted bifunctional compound, the one or more additional agents can be administered in any appropriate dose, and by any appropriate route.

The invention will be further described in the following examples, which do not limit the scope of the invention described in the claims.

EXAMPLES

Example 1—Development of Novel Therapeutic Compounds Targeted to PKCβ1

Nine first-generation ENDX-PROTACs were designed and synthesized to bind to and degrade PKCβ1 polypeptides. The structures of the nine PROTAC-based ENDX compounds (TC-Pr-001 through TC-Pr-009) are shown in FIGS. 2A-2I. All nine included thalidomide for binding to an E3 ubiquitin ligase, and were synthesized by deprotonation of the ENDX amine and placement of the linker and conjugated thalidomide to extrude away from the enzyme into solvent. The synthesized compounds were confirmed by analytical chemistry techniques including high-performance liquid chromatography with ultraviolet detection (HPLC-UV), total ion count mass spectroscopy (MS), evaporative light scattering detection (EVSD), positive and negative ion mode MS, and full proton nuclear magnetic resistance (NMR) with an inset zooming into the 6 to 10 ppm range.

Figure 2A:
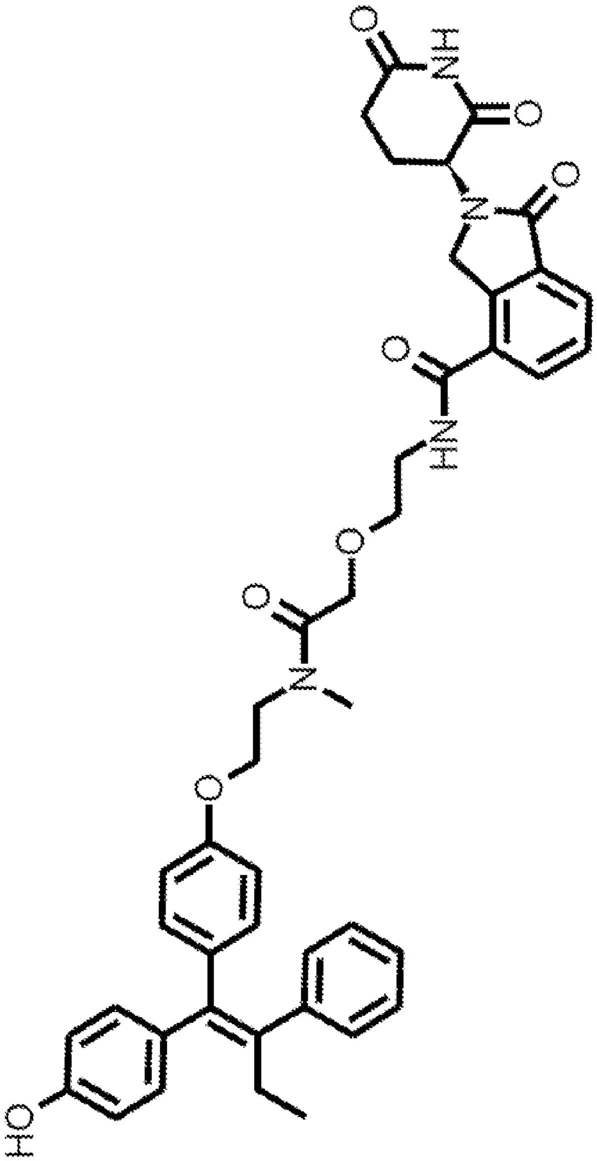
FIGS. 2A-2I show the structures of ENDX-PROTAC molecules TC-Pr-001 to TC-Pr-009, respectively.
Figure 2C:
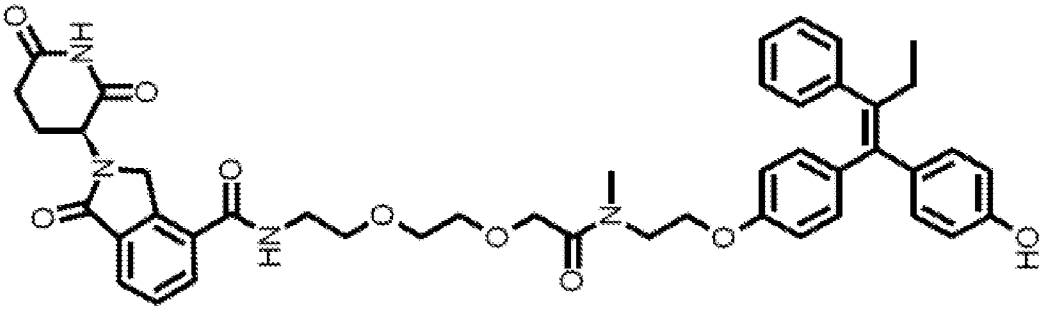
Figure 2B:
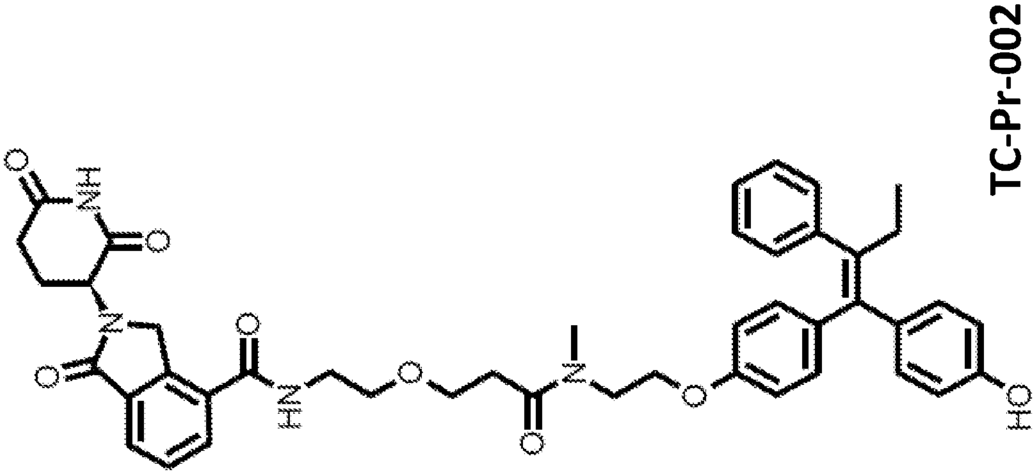
Figure 2D:
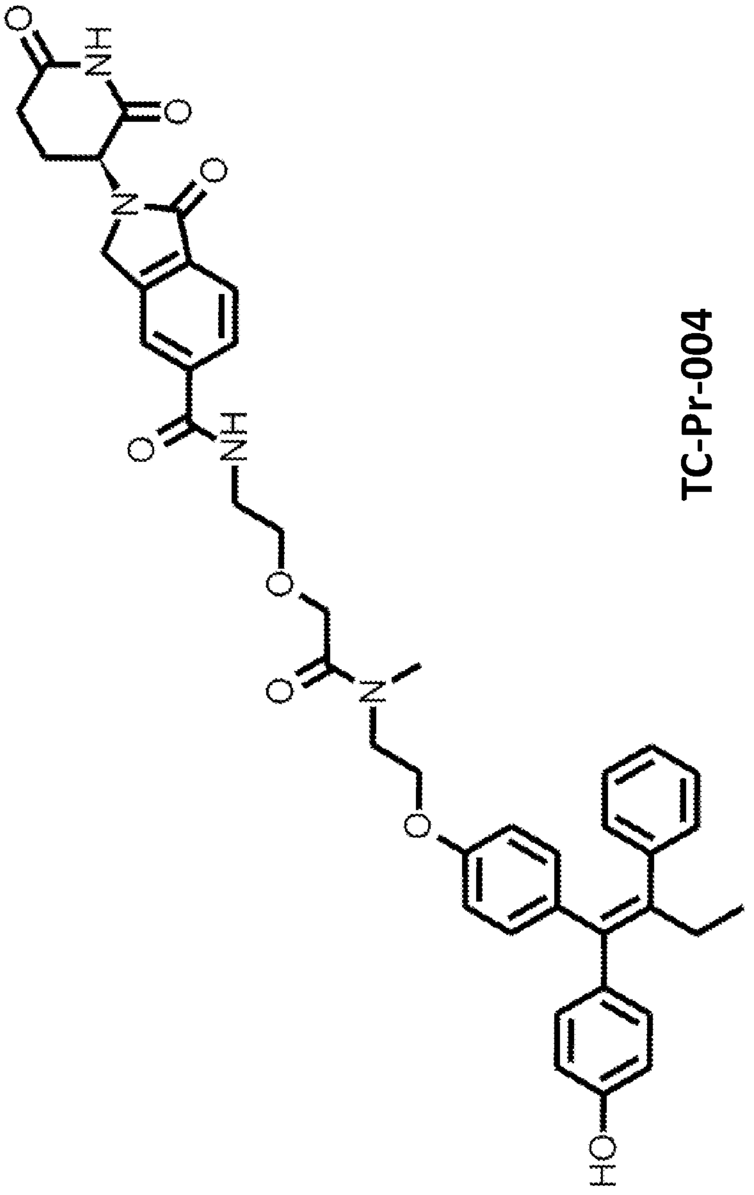
Figure 2E:
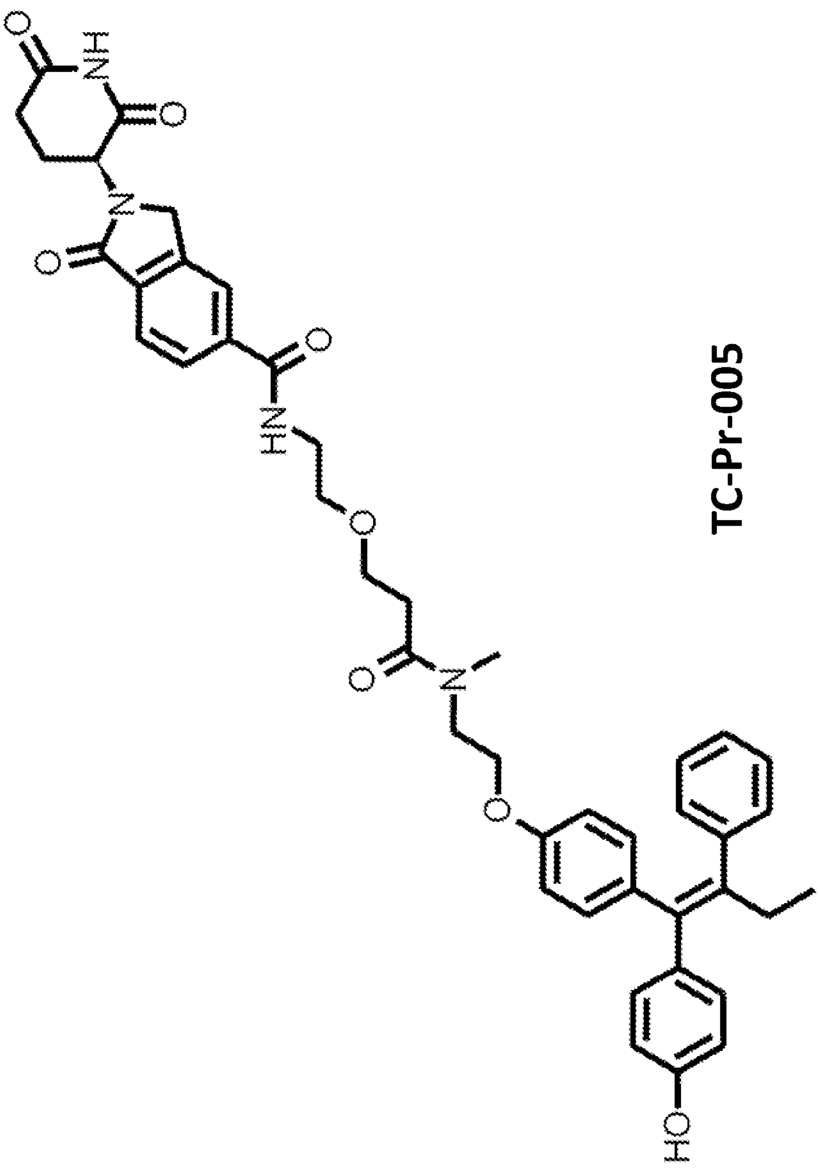
Figure 2F:
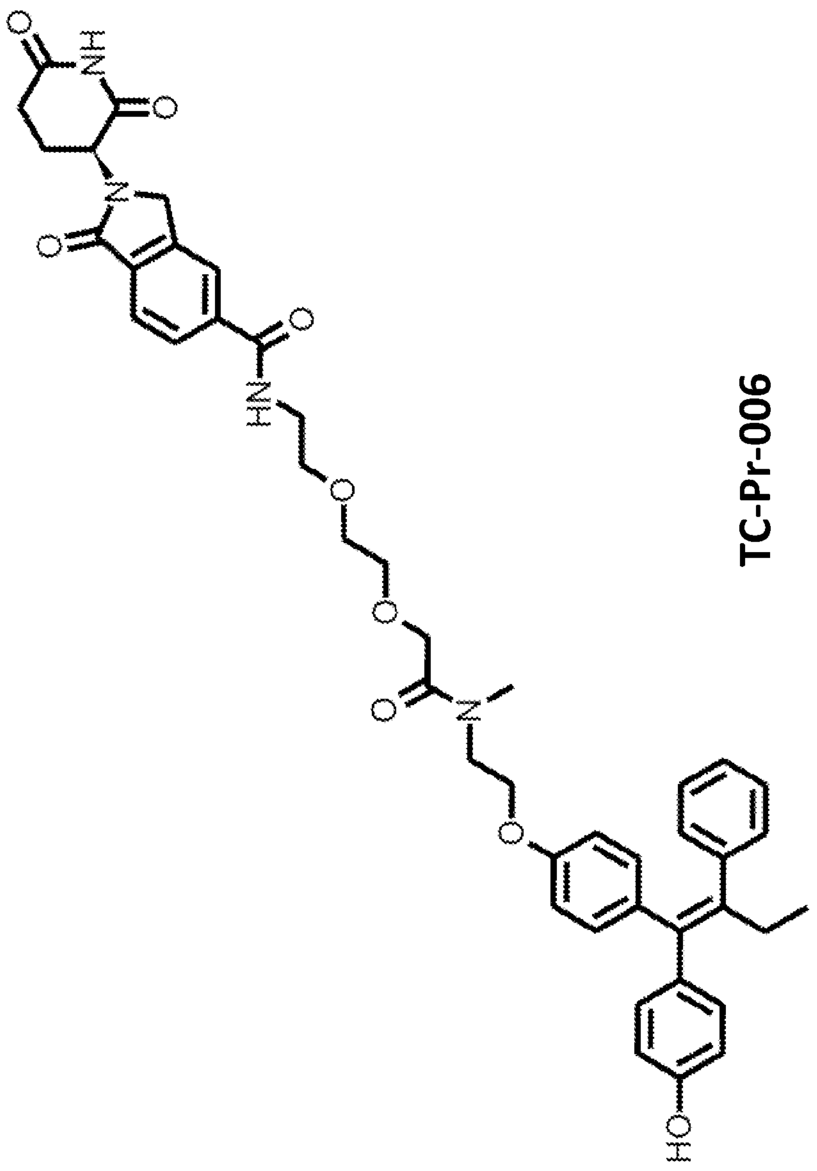
Figure 2G:
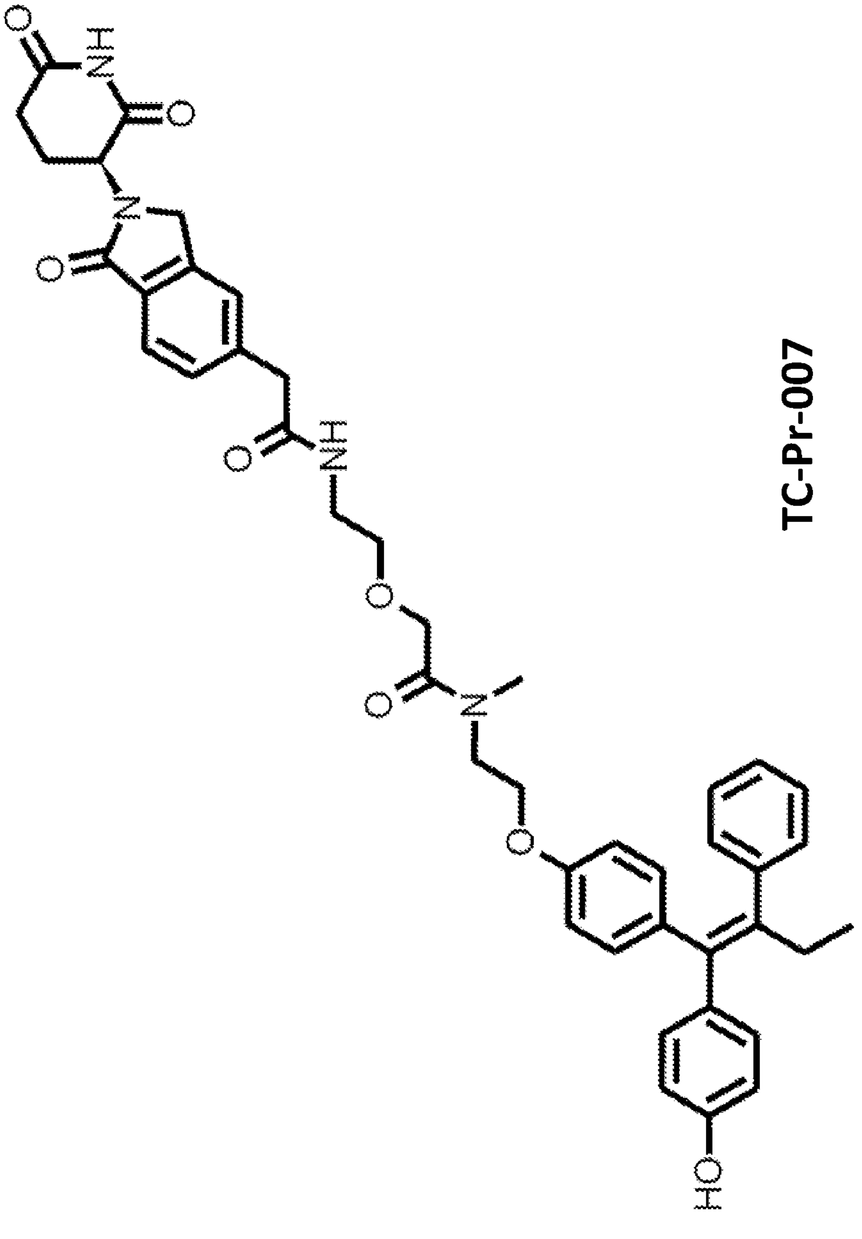
Figure 2H:
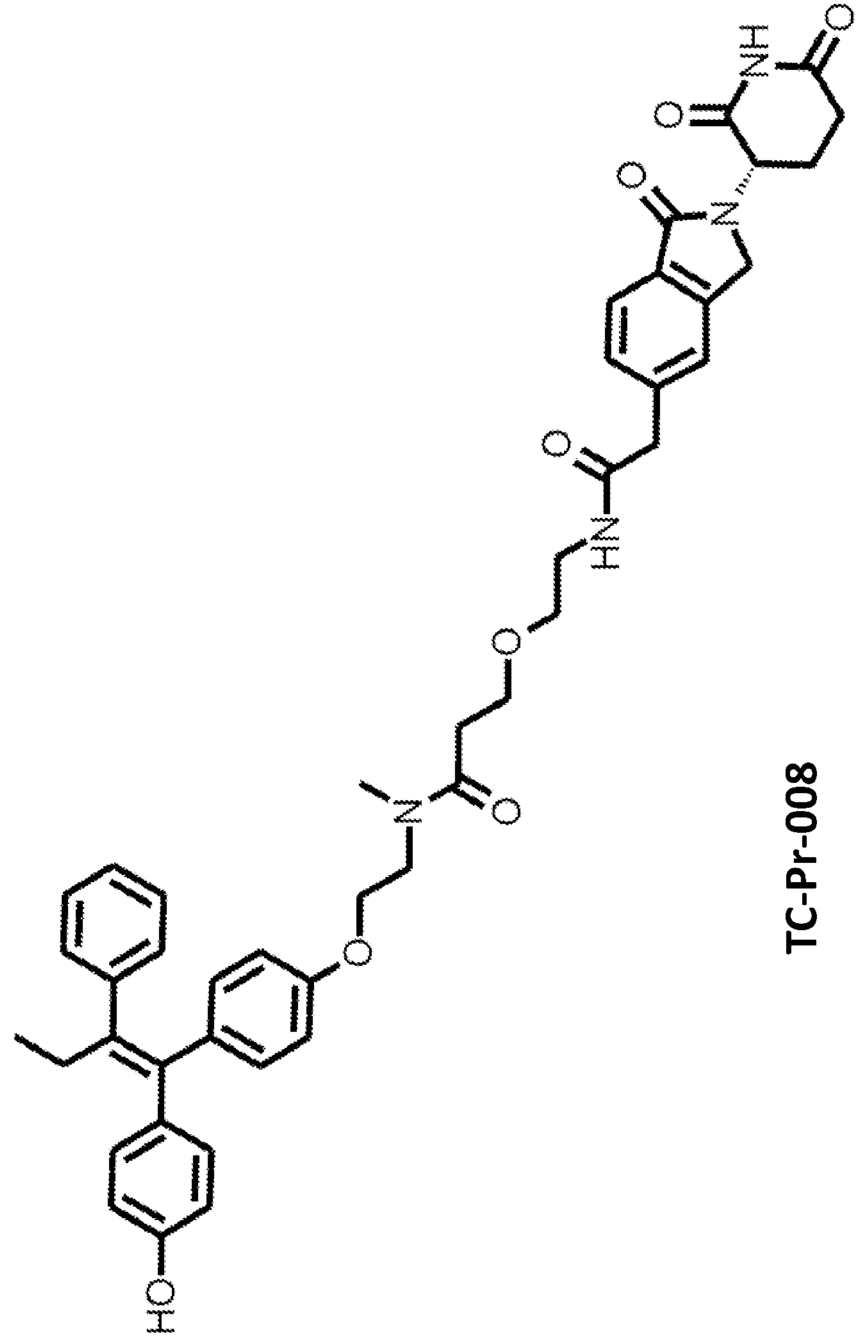
Figure 2I:
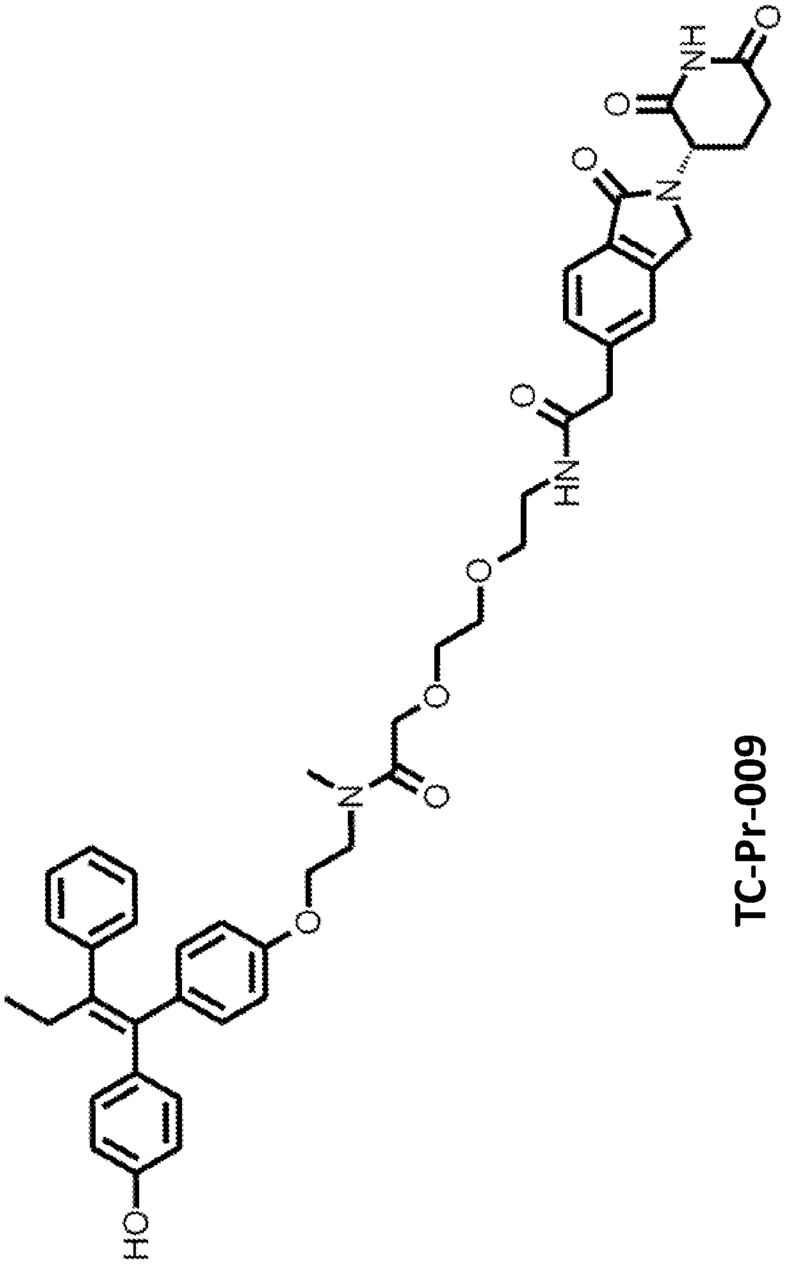
Figure 2J:
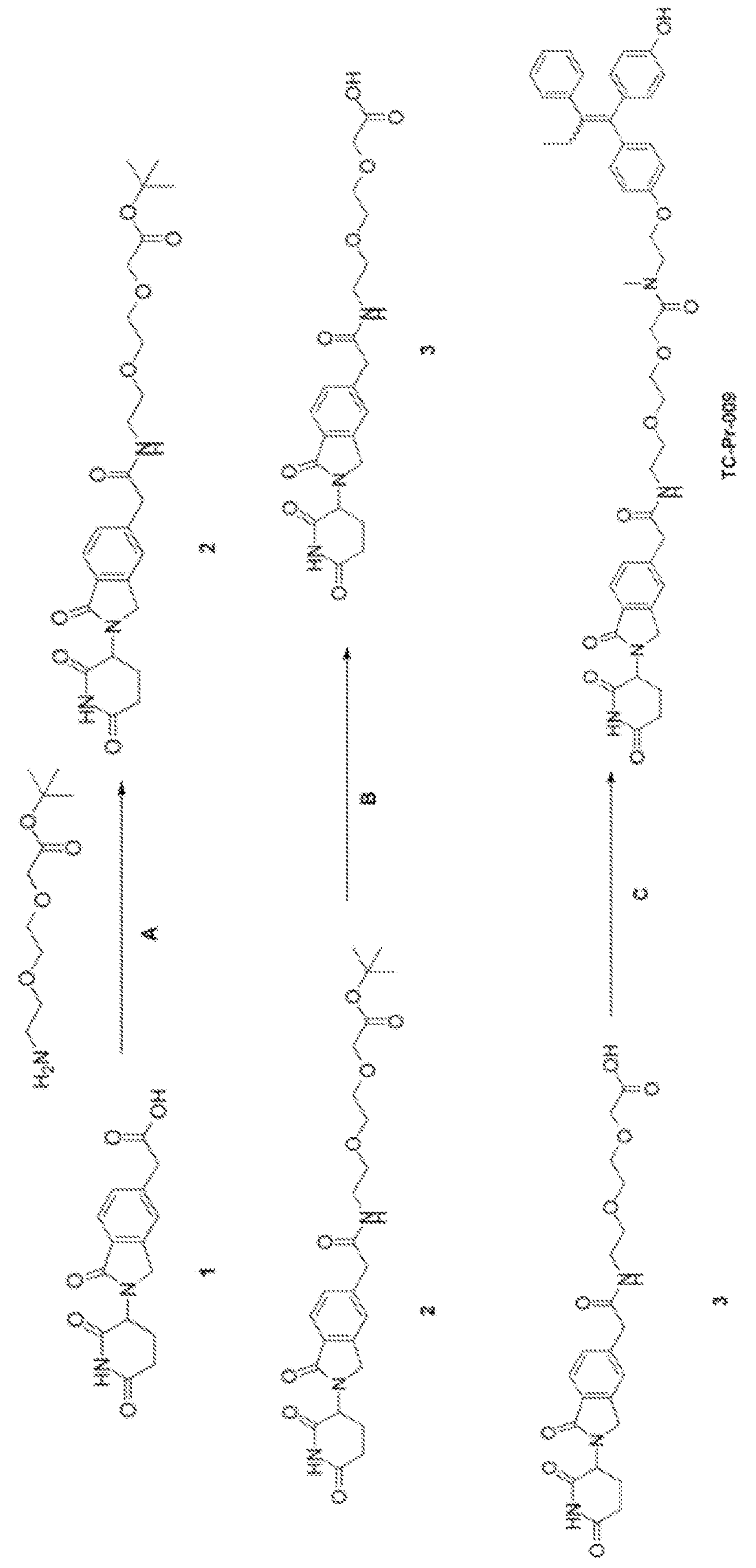
FIG. 2J depicts a synthesis scheme for TC-Pr-009.

In particular, TC-Pr-001 through TC-Pr-009 were produced as follows (using TC-Pr-009 as an example; depicted in FIG. 2J).

Step A (synthesis of 2): [(dimethylamino)(3H-[1,2,3]triazolo[4,5-b]pyridin-3-yloxy)methylidene]dimethylazanium; hexafluoro-lambda5-phosphanuide (286.56 mg, 753.66 μmol, 1.15 eq.) and ethylbis(propan-2-yl)amine (296.8 mg, 400.0 μl, 3.5 eq.) was added to a stirred solution of 2-[2-(2,6-dioxopiperidin-3-yl)-1-oxo-2,3-dihydro-1H-isoindol-5-yl]acetic acid (198.1 mg, 655.35 μmol, 1 eq.) in DMF (15 mL). The reaction mixture was stirred at room temperature for 10 minutes. A solution of tert-butyl 2-[2-(2-aminoethoxy)ethoxy]acetate hydrochloride (167.6 mg, 655.35 μmol, 1 eq.) in DMF (3 mL) was then added and the reaction mixture was stirred at room temperature for 12 hours. After completion of the reaction (LCMS control), the reaction mixture was concentrated under reduced pressure. The residue was treated with water (40 mL) and product was extracted with ethyl acetate (15 mL×4). The organic layers were separated, washed with water (20 mL×3), saturated aqueous citric acid solution (20 mL×2), saturated aqueous $NaHCO_3$ solution (20 mL), and brine (20 mL), and then dried over sodium sulfate, filtered, and concentrated under reduced pressure to yield the (tert-butyl 2-[2-(2-2-[2-(2,6-dioxopiperidin-3-yl)-1-oxo-2,3-dihydro-1H-isoindol-5-yl]acetamidoethoxy)ethoxy]acetate (190.0 mg, 377.32 μmol, 57.6% yield).

Step-B (synthesis of 3): 2,2,2-trifluoroacetic acid (4.43 g, 3.0 ml, 102.8 eq) was added to a solution of tert-butyl 2-[2-(2-2-[2-(2,6-dioxopiperidin-3-yl)-1-oxo-2,3-dihydro-1H-isoindol-5-yl]acetamidoethoxy)ethoxy]acetate (190.0 mg, 377.71 μmol, 1 eq.) and in DCM (5 mL). The resulting reaction mixture was stirred at room temperature for 10 hours. The progress of the reaction was monitored by TLC. After completion of the reaction, it was evaporated to dryness in vacuo to afford 2-[2-(2-2-[2-(2,6-dioxopiperidin-3-yl)-1-oxo-2,3-dihydro-1H-isoindol-5-yl]acetamidoethoxy)ethoxy]acetic acid (154.3 mg, 344.18 μmol, 91.1% yield).

Step-C (synthesis of TC-Pr-009): 4-(1-4-[2-(methylamino)ethoxy]phenyl-2-phenylbut-1-en-1-yl)phenol (128.85 mg, 345 μmol, 1 eq.), [(dimethylamino)(3H-[1,2,3]triazolo[4,5-b]pyridin-3-yloxy)methylidene]dimethylazanium; hexafluoro-lambda5-phosphanuide (150.85 mg, 396.7 μmol, 1.15 eq.) and ethylbis(propan-2-10 yl)amine (111.3 mg, 150.0 μl, 2.5 eq.) were added to a stirred solution of 2-[2-(2-2-[2-(2,6-dioxopiperidin-3-yl)-1-oxo-2,3-dihydro-1H-isoindol-5-yl]acetamidoethoxy) ethoxy]acetic acid (154.3 mg, 345 μmol, 1 eq.) in DMF (8 mL). The reaction mixture was stirred at room temperature for 16 hours and evaporated to dryness. The residue was dissolved in DMSO (0.5 mL) and subjected to HPLC purification (deionized water/HPLC-grade acetonitrile) to give 2-[2-(2-2-[2-(2,6-dioxopiperidin-3-yl)-1-oxo-2,3-dihydro-1H-isoindol-5-yl]acetamidoethoxy)ethoxy]-N-(2-4-[1-(4-hydroxyphenyl)-2-phenylbut-1-en-1-yl]phenoxyethyl)-N-methylacetamide as a beige solid (0.016 g, 0.0199 mmol, 95% purity, 5.8% yield). $^1H$ NMR (500 MHz, DMSO-d6) δ1H NMR (500 MHz, DMSO-d6) δ10.96 (s, 1H), 9.25 (m, 1H), 8.18 (d, J=6.8 Hz, 1H), 7.62 (d, J=7.8 Hz, 1H), 7.45 (s, 1H), 7.36 (d, J=7.9 Hz, 1H), 7.14 (t, J=6.5 Hz, 2H), 7.07 (m, 4H), 6.93 (m, 2H), 6.70 (m, 2H), 6.57 (d, J=6.6 Hz, 2H), 6.37 (d, J=8.0 Hz, 1H), 5.08 (m, 1H), 4.49-3.77 (m, 6H), 3.64-3.36 (m, 10H), 3.23-3.02 (m, 2H), 3.02-2.71 (m, 4H), 2.36 (m, 4H), 1.96 (s, 1H), 0.82 (m, 3H).

HPLC purity: 100%; LCMS Calculated for $C_{46}H_{50}N_4O_9$: 802.36; Observed: 802.91 [M+H]+.

Example 2—Effects of ENDX-PROTACs on ER+ and ER− Breast Cancer Cells

The efficacy of the synthesized ENDX-PROTAC molecules for inhibiting growth of ER+ and ER− breast cancer and ER− ovarian cancer cells was evaluated.

Cell proliferation rates were determined using crystal violet assays. One thousand cells per well were plated in 96 well tissue culture plates and treated the following day with a bifunctional compound or control for 7 days in replicates of 8. Cells were fixed with 25% glutaraldehyde for 10 minutes with shaking, washed 5 times with distilled water, stained with a 1% crystal violet solution (solubilized in 25% methanol) for 10 minutes, washed again 5 times and allowed to dry. De-staining was performed using 100 nM sodium citrate in 50% ethanol followed by quantification using a 96 well spectrophotometer set at an absorbance of 550 nM.

For western blotting analysis, cells were treated with vehicle (DMSO) or 1 μM of the indicated ENDX-PROTAC's or parent drug ENDX for 24, 48 and 72 hours with the drugs replenished every 24 hours. 25 μg of protein lysates were run on 10% Bis-Tris XT Criterion precast SDS-PAGE gels and transferred on to PVDF membrane. Following blocking with TB ST-5% milk, the membranes were probed with primary antibodies (1:500-1:2000 dilutions) for PKCβ1 (Abcam #136917), ERα (SC #8002), E2F1 (SC #251) and Actin (CS #8457) in TBST-5% BSA and secondary antibodies (1:2000 dilution) in TBST-5% milk. Membranes were developed using chemiluminescent WestPico or West-Femto detection solutions on the Li-Cor Imaging system.

Figure 3A:
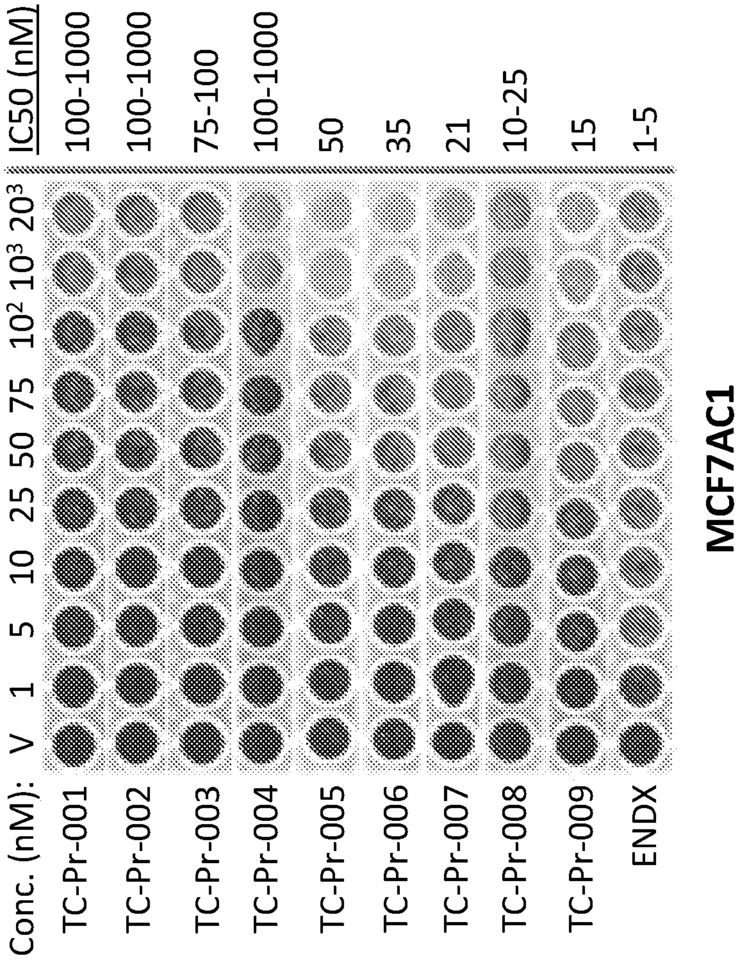
FIG. 3A is an image of a representative crystal violet (CV) proliferation assay, showing the efficacy of the ENDX-PROTAC molecules on growth of MCF7AC1 cells, which are ER+. The $IC_{50}$ concentrations of these molecules are shown at the right.
Figure 3B:
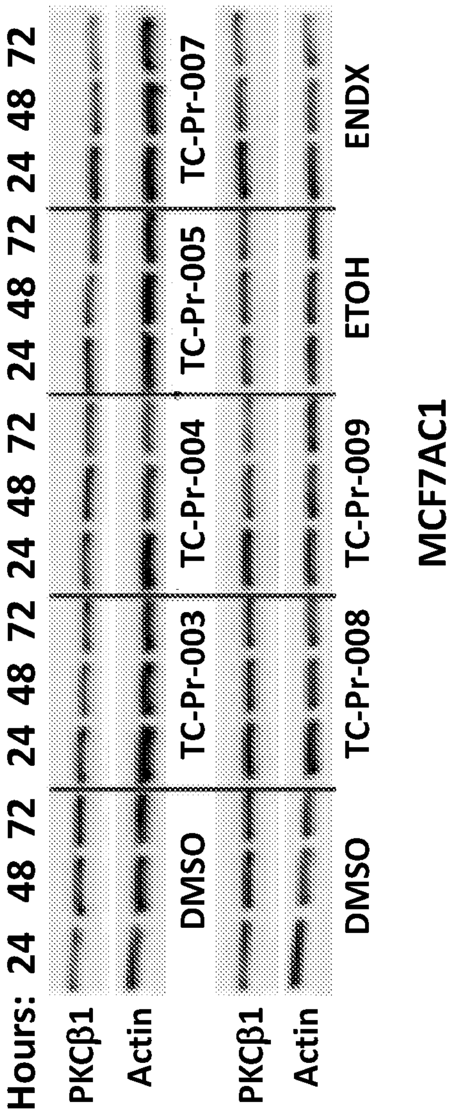
FIG. 3B is an image of representative western blots showing expression of PKCβ1 in MCF7AC1 cells treated with 1 μM concentration of the ENDX-PROTACs or ENDX for the indicated time points, with the drugs replenished every 24 hours.
Figure 3C:
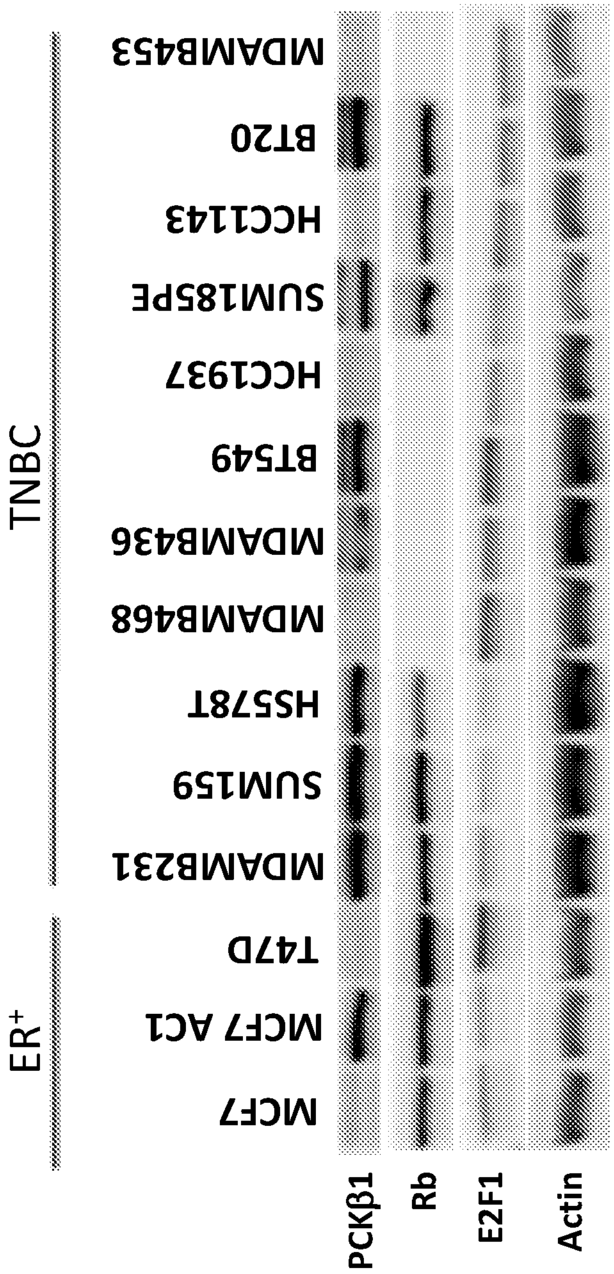
FIG. 3C is an image of representative western blots showing basal expression of PKCβ1, Rb, and E2F1 in the indicated ER+ and triple negative breast cancer (TNBC) cell lines. Actin was used as a loading control.
Figure 3D:
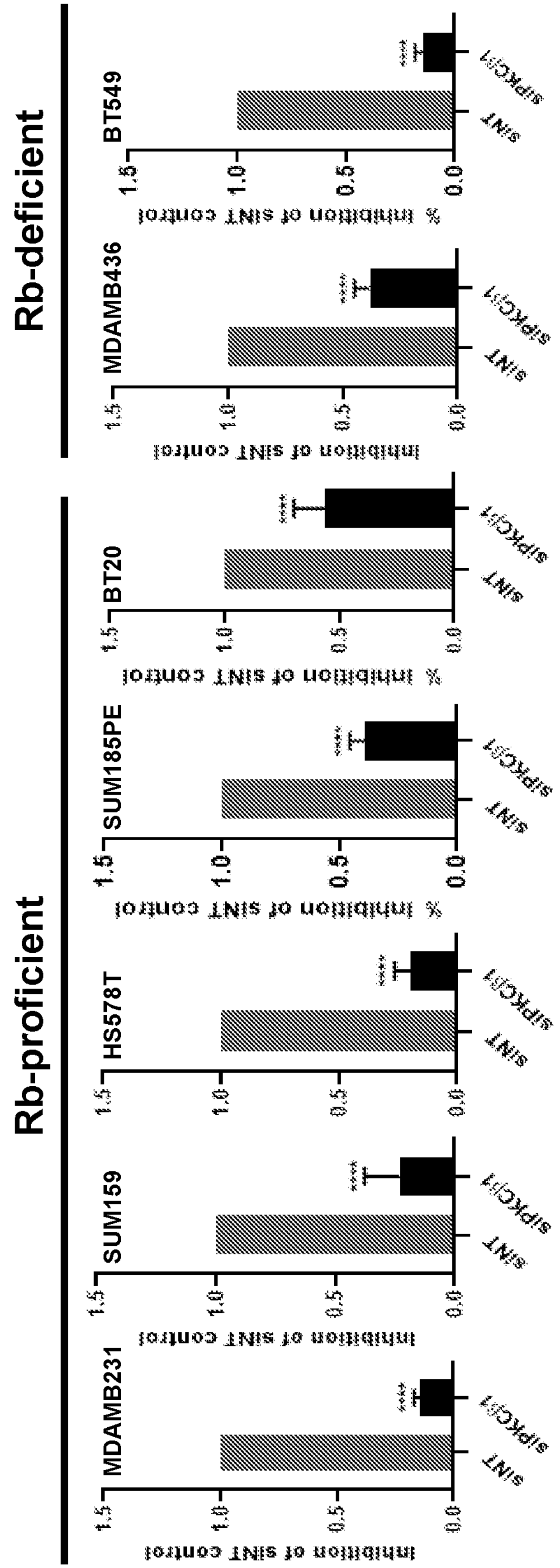
FIG. 3D is a graph plotting the level of cell proliferation for the indicated Rb-proficient and Rb-deficient TNBC cells upon PKCβ1 silencing. **** $p<0.0001$.

All nine ENDX-PROTACs exhibited varying potency in inhibiting growth of ER+ MCF7AC1 cells, with TC-Pr-005 to TC-Pr-009 inhibiting growth of the MCF7AC1 cells at concentrations in the range near to that of ENDX, TC-Pr-001 to TC-Pr-004 having a less potent effect (FIG. 3A). Evaluation of the ENDX-PROTAC effects on expression of PKCβ1 indicated that TC-Pr-007, TC-Pr-008, and TC-Pr-009 rapidly degraded PKCβ1 polypeptides following short-term treatment (within 72 hours), an effect that not observed with ENDX treatment at similar concentration and time points (FIG. 3B). These results prompted further investigation of ENDX-PROTAC's anticancer effects in other cancer cell sub-types, including TNBC cells. PKCβ1 polypeptide levels were generally higher in TNBC cells than in ERα+ breast cancer cells (FIG. 3C). As with the ER+ breast cancer models, PKCβ1 silencing profoundly inhibited the growth of multiple TNBC cell lines, including in models of Rb deficiency (MDAMB436 and BT549 cells; FIG. 3D), a biomarker associated with CDk4/6i resistance.

Figure 4A:
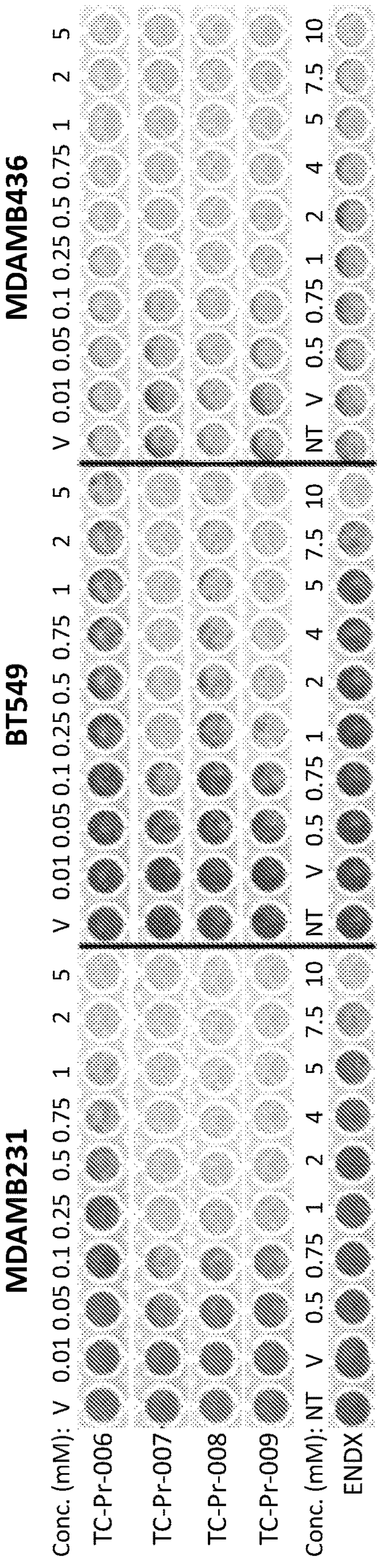
FIG. 4A is an image of a representative CV proliferation assay, showing the efficacy of the indicated ENDX-PROTAC molecules on the growth of Rb-proficient (MDAMB231) and Rb-deficient (BT549 and MDAMB436) TNBC cells.
Figure 4B:
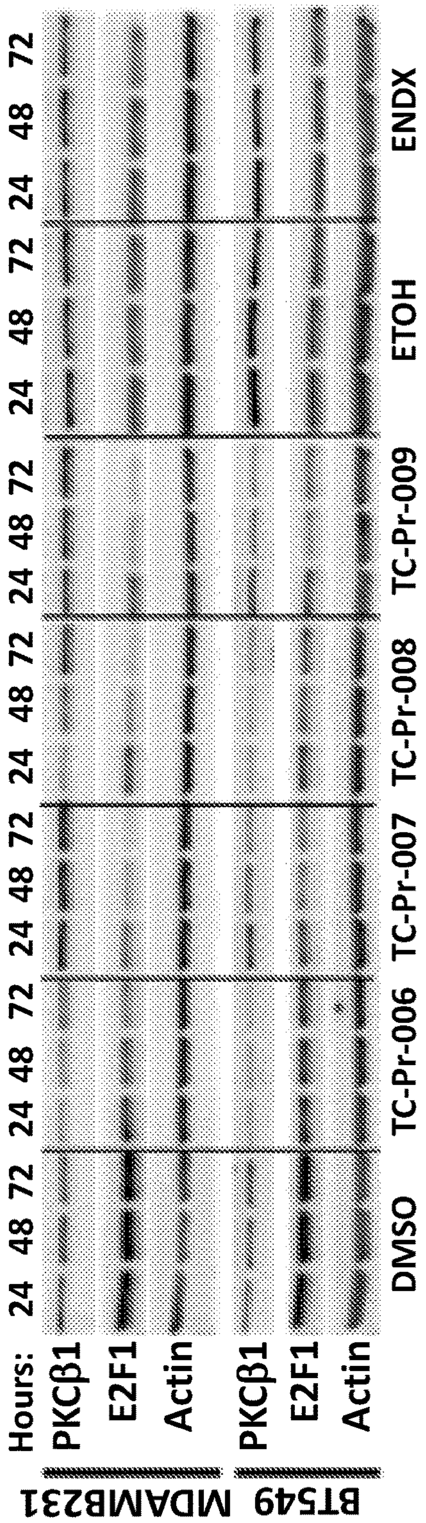
FIG. 4B is an image of representative western blots indicating the level of PKCβ1 and E2F1 protein expression in MDAMB231 and BT549 cells treated with 1 μM concentration of ENDX-PROTACs or ENDX for the indicated time points, with the drugs replenished every 24 hours. Actin was used as a loading control.

The effects of all the nine ENDX-PROTACs were then analyzed in Rb-proficient MDAMB231 and Rb-deficient BT549 and MDAMB436 cells. While ENDX-PROTACs TC-Pr-001 to TC-Pr-005 showed little to no effect in inhibiting growth, and ENDX inhibited growth only at higher concentrations (>5 μM), ENDX-PROTACs TC-Pr-006, TC-Pr-007, TC-Pr-008, and TC-Pr-009 potently inhibited the growth of both Rb-proficient and Rb-deficient TNBC cells at low concentrations (<1 μM). In fact, the $IC_{50}$ of these ENDX-PROTACs was at least 10- to 50-fold lower than that of ENDX (FIG. 4A and TABLE 1). Evaluation of PKCβ1 polypeptide expression in MDAMB231 and BT549 cells showed that these ENDX-PROTACs impacted PKCβ1 polypeptide degradation to varying extents within 72 hours (FIG. 4B). Remarkably, ENDX-PROTACs TC-Pr-006 to TC-Pr-009 also robustly reduced the polypeptide levels of E2F1 (FIG. 4B), which had higher basal expression in TNBC cells than in ER+ breast cancer cells (FIG. 3C). In contrast, ENDX impacted neither PKCβ1 polypeptide nor E2F1 polypeptide expression in these cells (FIG. 4B).

Collectively, these results demonstrated profound anti-proliferative effects for ENDX-PROTACs TC-Pr-006 to TC-Pr-009 in TNBC cells, including models of Rb-deficiency. These effects are likely related at least in part to the ability of ENDX-PROTACS to disrupt the ability of PKCβ1 polypeptides to chaperone cell proteins such as E2F1. The inclusion of ENDX in the PROTACs described herein is particularly useful, given that ENDX specifically interacts with PKCβ1 polypeptides but not with other PKC family members or off-target proteins, as is the case for PKCβ1 kinase inhibitors such as enzastaurin. Further, the use of ENDX has the added benefit of dually targeting ERα, which is involved in survival of ERα+ breast cancers.

TABLE 1

Growth inhibiting activity in ER- cell lines ($IC_{50}$, CV assay)

| Compound | $IC_{50}$ MDAMB231 (PKCβ1$^{high}$, Rb$^{positive}$) 2000 cells | BT549 (PKCβ1$^{high}$, Rb$^{negative}$) 2000 cells | MDAMB436 (PKCβ1$^{low}$, Rb$^{negative}$) 2000 cells |
|---|---|---|---|
| TC-Pr-001 | No major killing | No major killing | 10 μM |
| TC-Pr-002 | No major killing | No major killing | No major killing |
| TC-Pr-003 | No major killing | No major killing | No major killing |
| TC-Pr-004 | No major killing | No major killing, slightly growth promoting | 10 μM |
| TC-Pr-005 | >10 μM | >10 μM | 0.1-1 μM |
| TC-Pr-006 | 532 nM | 482 nM | 333 nM |
| TC-Pr-007 | 87 nM | 43 nM | 40 nM |
| TC-Pr-008 | 131 nM | 225 nM | 74 nM |

TABLE 1-continued

Growth inhibiting activity in ER- cell lines ($IC_{50}$, CV assay)

| Compound | $IC_{50}$ MDAMB231 (PKCβ1$^{high}$, Rb$^{positive}$) 2000 cells | BT549 (PKCβ1$^{high}$, Rb$^{negative}$) 2000 cells | MDAMB436 (PKCβ1$^{low}$, Rb$^{negative}$) 2000 cells |
|---|---|---|---|
| TC-Pr-009 | 131 nM | 67 nM | 64 nM |
| ENDX (NCI) | >5 μM | >5 μM | >5 μM |

Example 3—Effects of ENDX-PROTACs on ER− Ovarian Cancer Cells

Figure 5A:
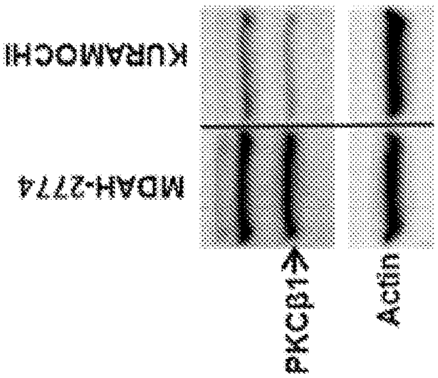
FIG. 5A is an image of western blots showing basal polypeptide expression of PKCβ1 in the indicated ovarian cancer cell lines. Actin was used as a loading control.
Figure 5B:
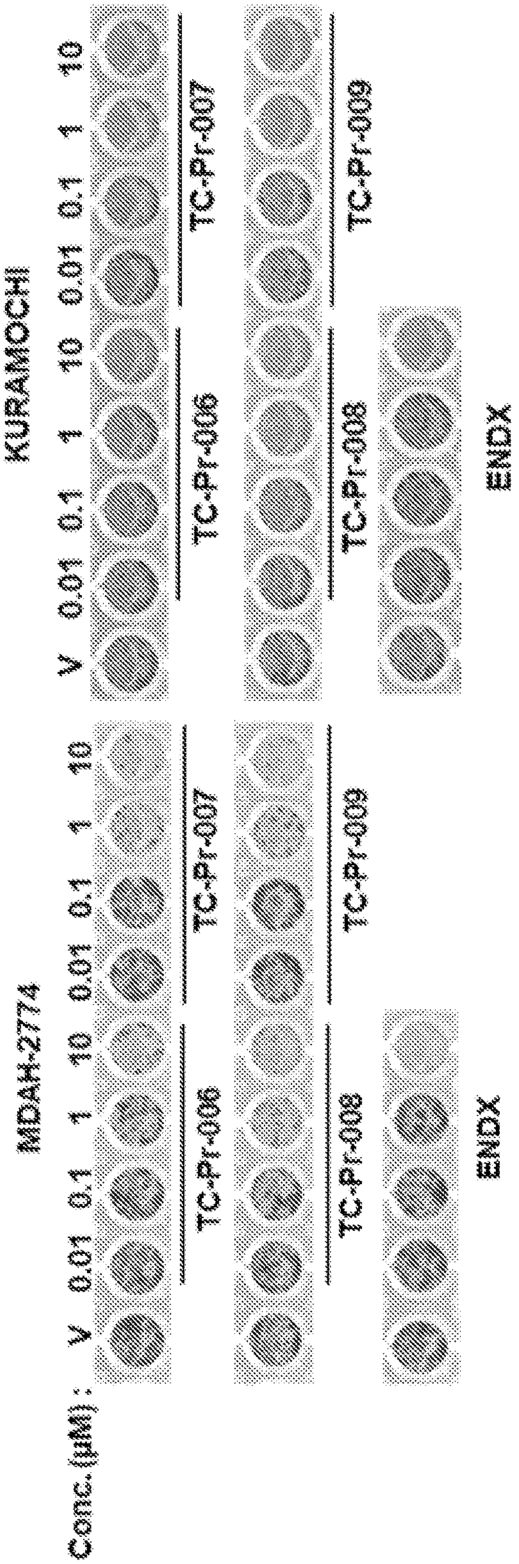
FIG. 5B is an image showing representative CV proliferation assays, indicating the efficacy of the indicated ENDX-PROTAC molecules on the growth of MDAH-2774 (endometrioid) and Kuramochi (high-grade serous) ovarian cancer cells.

Based on the potent anti-proliferative activity of ENDX-PROTACs TC-Pr-006, TC-Pr-007, TC-Pr-008, and TC-Pr-009 in TNBC cells, the efficacy of these compounds for inhibiting the growth of ovarian cancer cells was tested. This analysis utilized KURAMOCHI cells, which represent the high-grade serous subtype (the most malignant form that accounts for 70% of all ovarian cancers and associates with poor clinical outcome) and MDAH-2774 cells, which represent endometrioid ovarian cancer and accounts for 20% of all ovarian cancer. PKCβ1 was confirmed to be expressed in both ovarian cancer cell line models, with MDAH-2774 cells expressing higher amounts of PKCβ1 compared to KURAMOCHI cells (FIG. 5A). As observed with TNBC cells, TC-Pr-007, -008 and -009 also substantially inhibited the growth of these ovarian cancer cells at ≤1 μM concentration. However, ENDX did not inhibit growth until it reached a higher concentration (10 μM; FIGS. 5B and 5C). Taken together, these data indicated that ENDX-PROTACs have additional utility beyond breast cancer.

TABLE 2

Summary of ENDX-PROTAC activity in ovarian cancer cell lines

| Compound | Approximate $IC_{50}$ MDAH-2774 (PKCβ1$^{high}$) 1000 cells/well | KURAMOSHI (PKCβ1$^{low}$) 1000 cells/well |
|---|---|---|
| TC-Pr-003 | No killing | No killing |
| TC-Pr-006 | >10 μM | >10 μM |
| TC-Pr-007 | Between 1 and 10 μM | Between 1 and 10 μM |
| TC-Pr-008 | Between 1 and 10 μM | Between 1 and 10 μM |
| TC-Pr-009 | Between 1 and 10 μM | Between 1 and 10 μM |
| ENDX, NCI | >10 μM | >10 μM |

Example 4—Pharmacokinetic Studies of TC-Pr-009 and TC-Pr-007

ENDX PROTAC 7 and PROTAC 9 pharmacokinetics were characterized in female CD1 mice. Blood samples were collected from mice anesthetized under isoflurane via retro-orbital eye bleed into tubes containing EDTA and immediately chilled on ice. NaF was added to the EDTA collection tubes to help stabilize the drug in whole blood for the second IV and IP studies with ENDX PROTAC 9, and for the IV and oral studies with PROTAC 7. Plasma and red blood cells were separated immediately by centrifugation in a refrigerated centrifuge at 4° C. The plasma was transferred to a separate tube and immediately frozen at −20° C.

For IV dosing, ENDX PROTAC 9 was dissolved in 10% DMSO, 10% PEG 400, and 80% normal saline for a final concentration of 0.2 mg/mL ENDX PROTAC 9 for the 1 mg/kg IV doses. ENDX PROAC 7 was dissolved in 15% DMSO, 9.44% PEG400, and 55% normal saline for a final concentration of 0.19 mg/mL for the 1 mg/kg IV doses. Blood samples (3 mice per time-point) were collected 5 minutes, 15 minutes, 0.5 hour, 1 hour, 2 hours, 4 hours, 8 hours, and 24 hours after administration of the ENDX PROTAC. A second IV study was performed for ENDX PROTAC 9 in which blood samples (3 mice per time-point) were collected 5 minutes, 15 minutes, 1 hour, and 2 hours after administration of ENDX PROTAC 9. For oral dosing, ENDX PROTAC 9 (10 mg/kg) and ENDX PROTAC 7 (10 mg/kg) were suspended in 1 mM ascorbic acid:PEG400, 1:1 v/v for a final concentration of 1.0 mg/mL ENDX PROTAC. Blood samples (three mice per time-point) were collected 15 minutes, 0.5 hour, 1 hour, 2 hours, 4 hours, 6 hours, 8 hours, and 24 hours after administering the ENDX PROTAC. For I.P. dosing, ENDX PROTAC 9 (4 mg/kg) was prepared in 1 mM ascorbic acid:PEG400, 1:1 v/v for a final concentration of 0.4 mg/mL ENDX PROTAC 9. Blood samples (three mice per time-point) were collected 15 minutes, 0.5 hour, 1 hour, 2 hours, 4 hours, 6 hours, 8 hours, and 24 hours after administration. Plasma concentrations of ENDX PROTAC 7 and 9 were measured using UPLC-MS/MS.

Figure 6A:
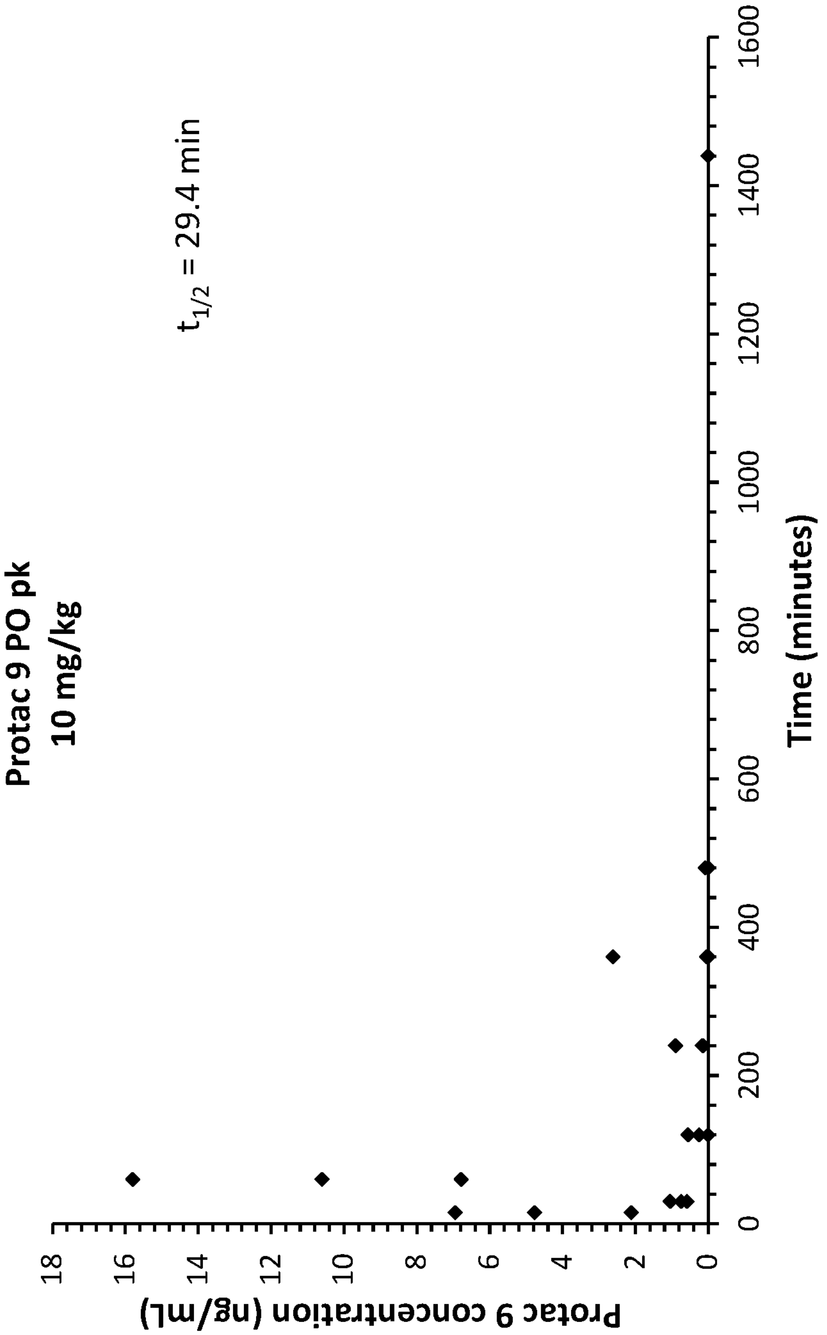
Figure 6B:
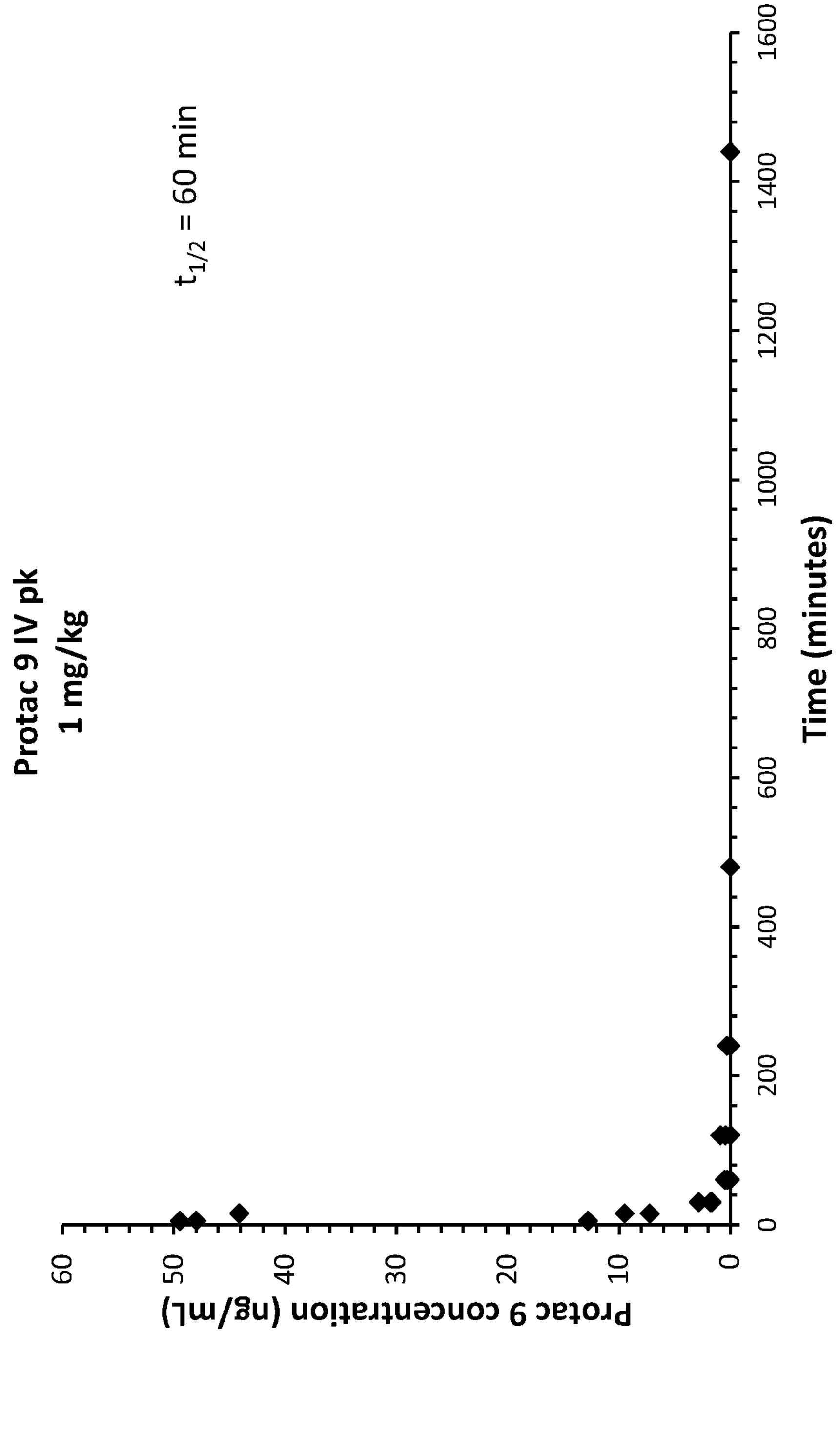
Figure 6C:
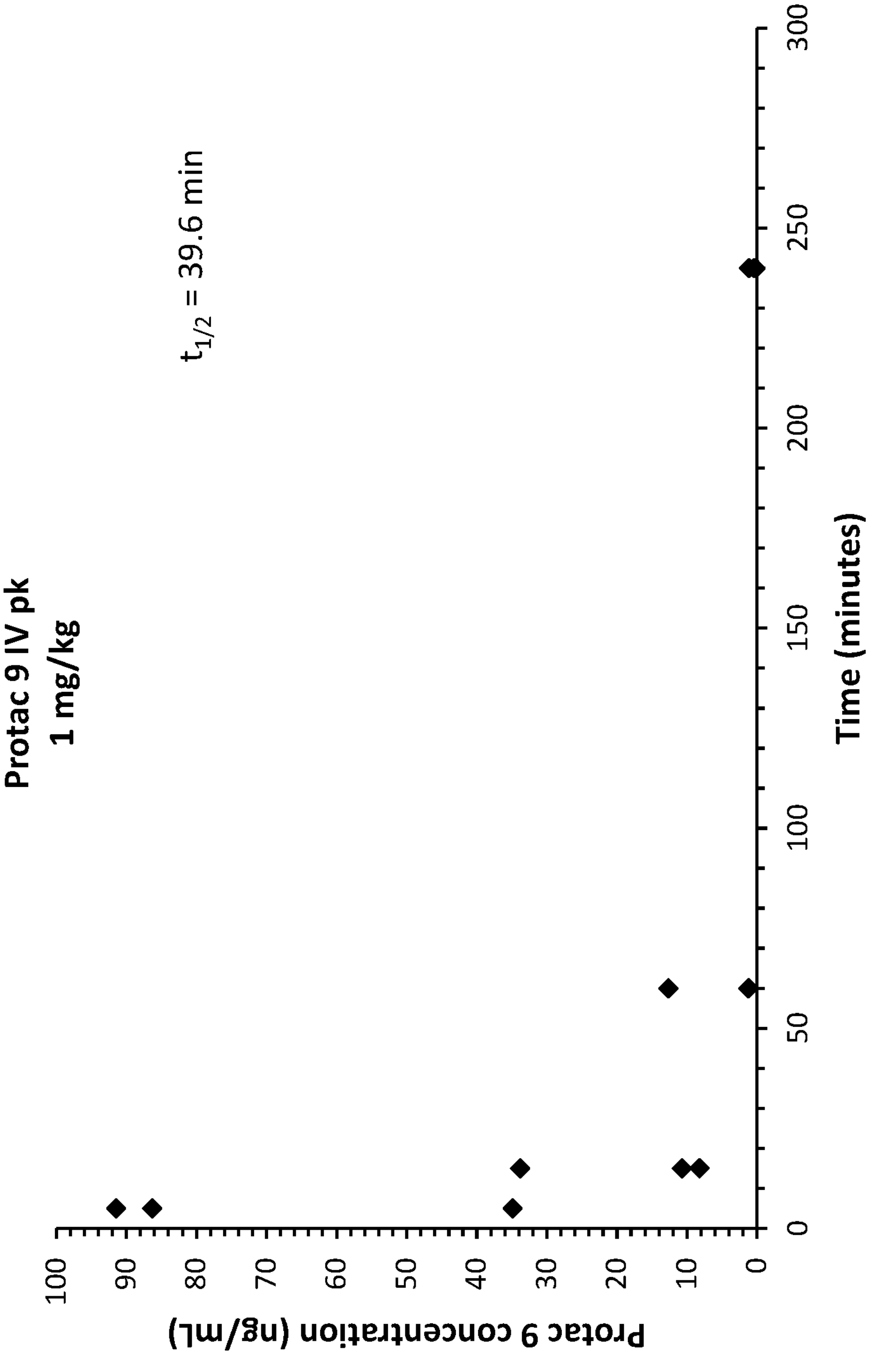
Figure 6D:
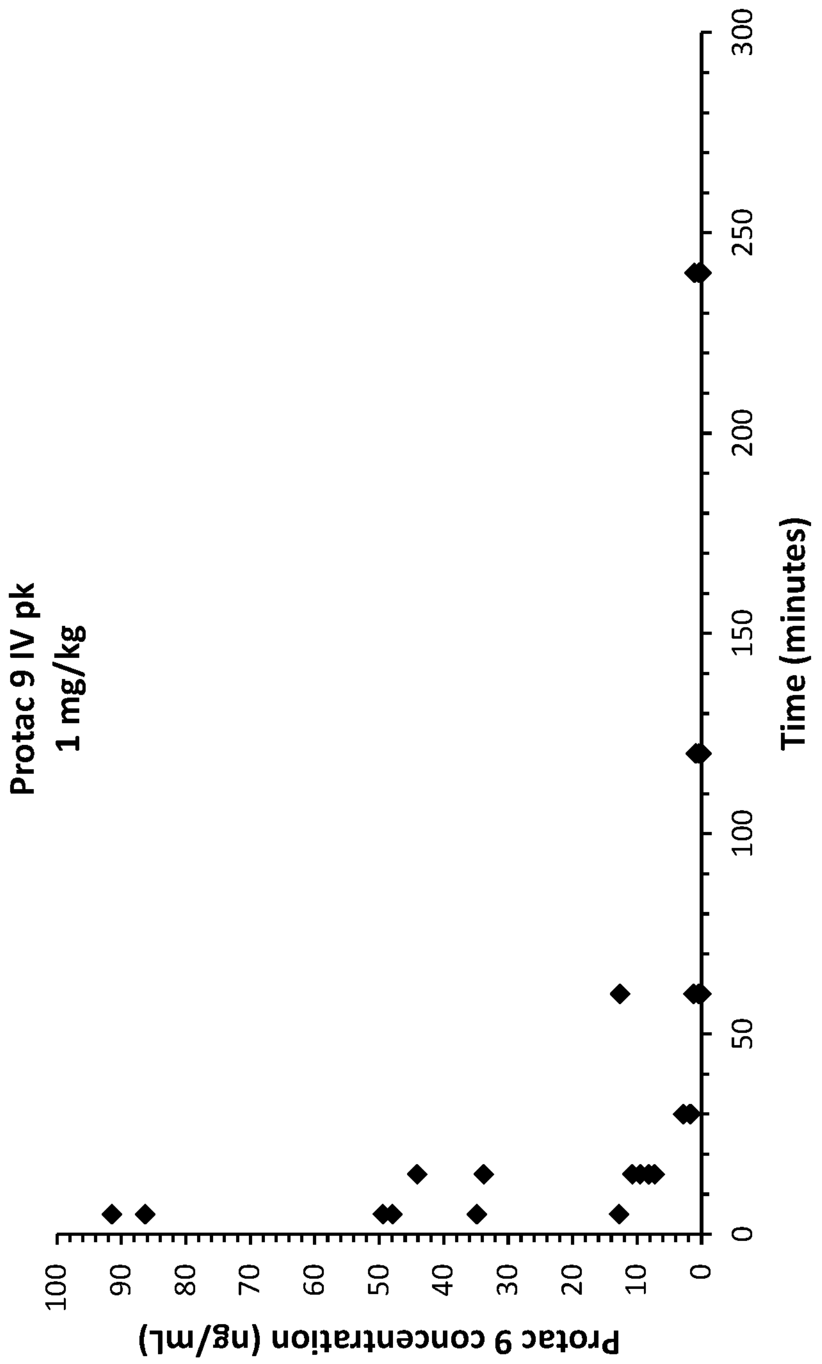
Figure 6E:
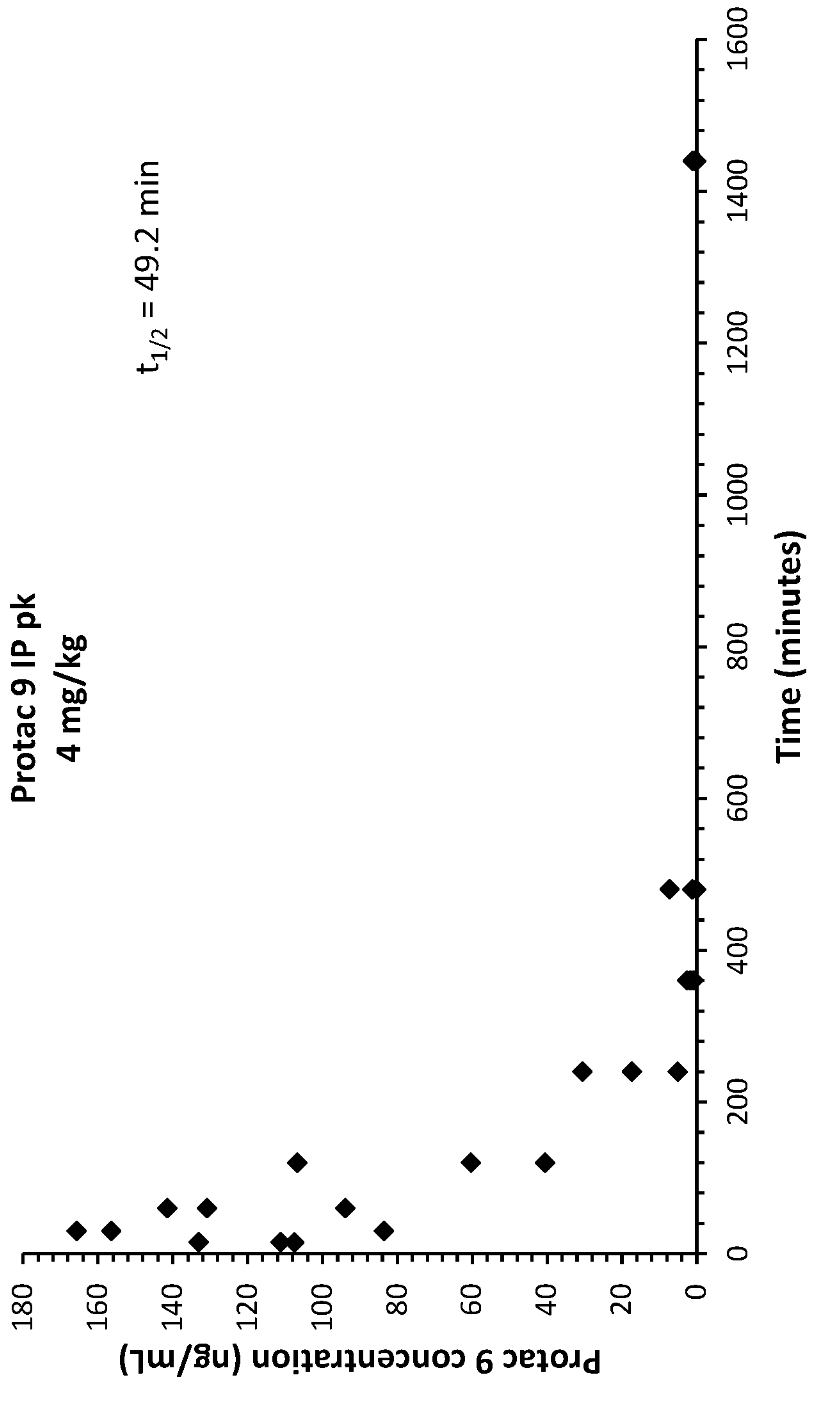

For ENDX PROTAC 9, a peak plasma concentration (47.2 ng/mL) was achieved 5 minutes after I.V. administration in samples collected without added NaF (TABLE 4 and FIG. 6B). The ENDX PROTAC 9 terminal half-life and plasma clearance values were 1 hour and 43.8 L/h*kg. An average peak plasma concentration of 11.06 ng/mL was achieved 1 hour after oral administration of ENDX PROTAC 9 (TABLE 3 and FIG. 6A). Oral bioavailability of PROTAC 9 was higher than that of PROTAC 7, but was still low at 8.8%. Due to concerns regarding the stability of PROTAC 9 in whole blood, a second I.V. study with ENDX PROTAC 9 was performed in which NaF was added to the EDTA collection tubes. In the second study, a peak plasma concentration of 70.9 ng/mL was achieved 5 minutes after I.V. administration of ENDX PROTAC 9 (TABLE 5 and FIG. 6C), suggesting that ENDX PROTAC 9 is indeed unstable in whole blood. The ENDX PROTAC 9 terminal half-life and plasma clearance values were 0.66 h and 28.7 L/h*kg. Combined results are shown in TABLE 6 and FIG. 6D. For I.P. administration of ENDX PROTAC 9, a peak plasma concentration of 135 ng/mL was achieved 30 minutes after dose administration (TABLE 7 and FIG. 6E), and bioavailability of the I.P. dose was high (225%).

Figure 7A:
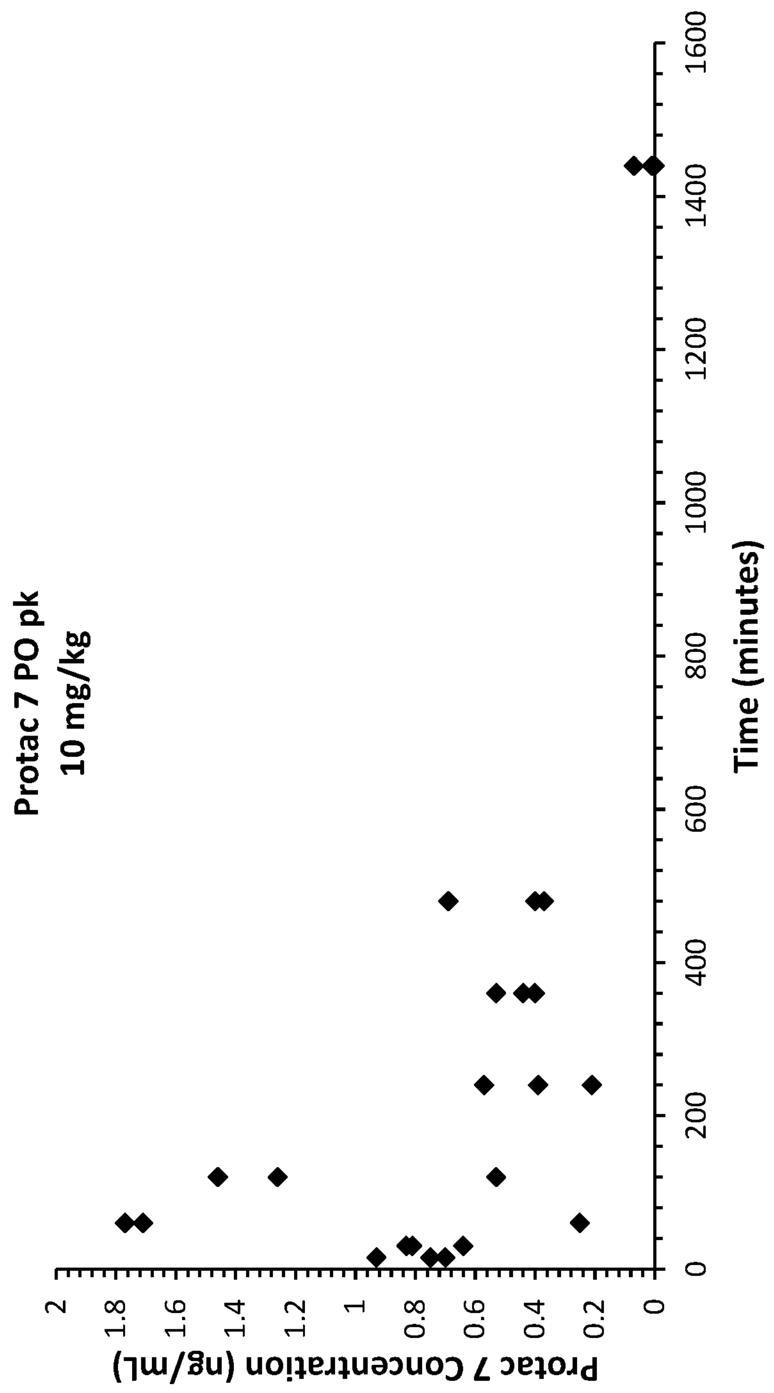
FIGS. 7A and 7B are graphs plotting plasma concentrations of ENDX PROTAC 7 (TC-Pr-007) in mice after PO administration at a dose of 10 mg/kg (FIG. 7A) or after IV administration at a dose of 1 mg/kg (FIG. 7B).
Figure 7B:
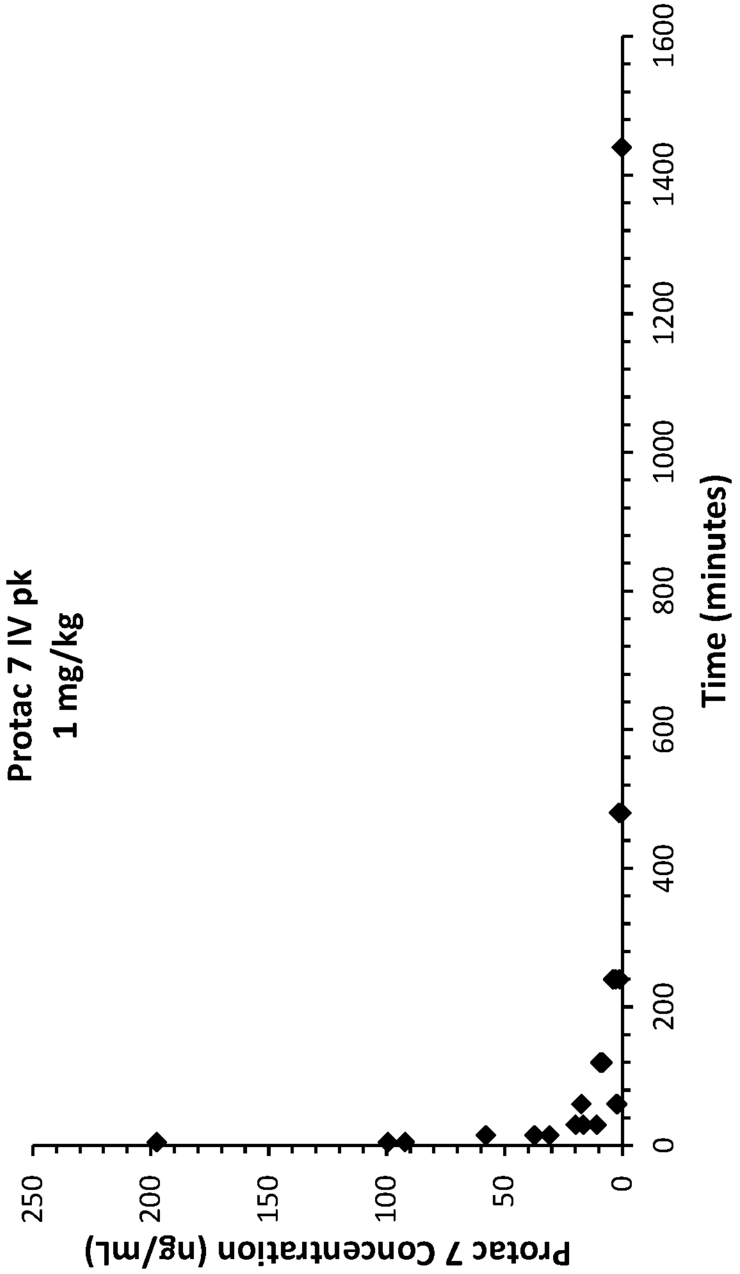

For ENDX PROTAC 7, a peak plasma concentration of 129.7 ng/mL was achieved by 5 minutes after IV administration (TABLE 9 and FIG. 7B), and a peak plasma concentration of 1.24 ng/mL was achieved by 1 hour after oral administration (TABLE 8 and FIG. 7A). The elimination half-life and plasma clearance values following I.V. administration were 5 hours and 7.7 L/h*kg, respectively. Oral bioavailability of PROTAC 7 was low at 0.85%.

TABLE 3

ENDX PROTAC 9 PO pk (10 mg/kg) sample summary

| Time (minutes) | Concentration ENDX PROTAC 9 (ng/ml) |
|---|---|
| 15 | 6.95 |
| 15 | 4.77 |
| 15 | 2.11 |
| 30 | 0.74 |
| 30 | 0.58 |

TABLE 3-continued

ENDX PROTAC 9 PO pk (10 mg/kg) sample summary

| Time (minutes) | Concentration ENDX PROTAC 9 (ng/ml) |
|---|---|
| 30 | 1.05 |
| 60 | 15.8 |
| 60 | 10.6 |
| 60 | 6.78 |
| 120 | 0.25 |
| 120 | BLD* |
| 120 | 0.55 |
| 240 | 0.9 |
| 240 | 0.16 |
| 240 | 0.14 |
| 360 | 2.61 |
| 360 | BLD |
| 360 | 0.05 |
| 480 | 0.08 |
| 480 | BLD |
| 480 | BLD |
| 1440 | BLD |
| 1440 | BLD |
| 1440 | BLD |

*below limit of detection

TABLE 4

ENDX PROTAC 9 IV pk (1 mg/kg) sample summary

| Time (minutes) | Concentration ENDX PROTAC 9 (ng/ml) |
|---|---|
| 5 | 49.449 |
| 5 | 47.9659 |
| 5 | 12.7855 |
| 15 | 44.1034 |
| 15 | 9.4992 |
| 15 | 7.241 |
| 30 | 2.8342 |
| 30 | 1.662 |
| 30 | 1.8075 |
| 60 | 0.5069 |
| 60 | 0.2706 |
| 60 | 0.0179 |
| 120 | 0.8988 |
| 120 | 0.4446 |
| 120 | BLD |
| 240 | BLD |
| 240 | 0.0197 |
| 240 | 0.3141 |
| 480 | 0 |
| 480 | BLD |
| 480 | BLD |
| 1440 | BLD |
| 1440 | 0 |
| 1440 | 0 |

TABLE 5

ENDX PROTAC 9 IV pk (1 mg/kg, second study) sample summary

| Time (minutes) | Concentration ENDX PROTAC 9 (ng/ml) |
|---|---|
| 5 | 86.31 |
| 5 | 91.46 |
| 5 | 34.87 |
| 15 | 8.2 |
| 15 | 33.8 |
| 15 | 10.72 |
| 60 | 1.26 |
| 60 | 12.64 |
| 60 | 1.18 |
| 240 | 0.19 |

TABLE 5-continued

ENDX PROTAC 9 IV pk (1 mg/kg, second study) sample summary

| Time (minutes) | Concentration ENDX PROTAC 9 (ng/ml) |
|---|---|
| 240 | 1.11 |
| 240 | 0.39 |

TABLE 6

ENDX PROTAC 9 IV pk (1 mg/kg) sample summary-all data

| Time (minutes) | Concentration ENDX PROTAC 9 (ng/ml) |
|---|---|
| 5 | 49.449 |
| 5 | 47.9659 |
| 5 | 12.7855 |
| 5 | 86.31 |
| 5 | 91.46 |
| 5 | 34.87 |
| 15 | 44.1034 |
| 15 | 9.4992 |
| 15 | 7.241 |
| 15 | 8.2 |
| 15 | 33.8 |
| 15 | 10.72 |
| 30 | 2.8342 |
| 30 | 1.662 |
| 30 | 1.8075 |
| 60 | 0.5069 |
| 60 | 0.2706 |
| 60 | 0.0179 |
| 60 | 1.26 |
| 60 | 12.64 |
| 60 | 1.18 |
| 120 | 0.8988 |
| 120 | 0.4446 |
| 120 | BLD |
| 240 | BLD |
| 240 | 0.0197 |
| 240 | 0.3141 |
| 240 | 0.19 |
| 240 | 1.11 |
| 240 | 0.39 |
| 480 | 0 |
| 480 | BLD |
| 480 | BLD |
| 1440 | BLD |
| 1440 | 0 |
| 1440 | 0 |

TABLE 7

ENDX PROTAC 9 PO pk (10 mg/kg) sample summary

| Time (minutes) | Concentration ENDX PROTAC 9 (ng/ml) |
|---|---|
| 15 | 107.51 |
| 15 | 111.19 |
| 15 | 133.09 |
| 30 | 165.71 |
| 30 | 156.42 |
| 30 | 83.56 |
| 60 | 141.51 |
| 60 | 93.93 |
| 60 | 130.84 |
| 120 | 60.32 |
| 120 | 106.7 |
| 120 | 40.51 |
| 240 | 17.29 |
| 240 | 5.09 |
| 240 | 30.55 |
| 360 | 1.64 |

TABLE 7-continued

ENDX PROTAC 9 PO pk (10 mg/kg) sample summary

| Time (minutes) | Concentration ENDX PROTAC 9 (ng/ml) |
|---|---|
| 360 | 0.75 |
| 360 | 2.62 |
| 480 | 7.23 |
| 480 | 1.2 |
| 480 | 0.08 |
| 1440 | 1.01 |
| 1440 | 0.33 |
| 1440 | 0.12 |

TABLE 8

ENDX PROTAC 7 PO pk sample summary

| Time (minutes) | Concentration ENDX PROTAC 7 (ng/ml) |
|---|---|
| 15 | 0.75 |
| 15 | 0.7 |
| 15 | 0.93 |
| 30 | 0.83 |
| 30 | 0.64 |
| 30 | 0.81 |
| 60 | 1.77 |
| 60 | 1.71 |
| 60 | 0.25 |
| 120 | 0.53 |
| 120 | 1.46 |
| 120 | 1.26 |
| 240 | 0.57 |
| 240 | 0.21 |
| 240 | 0.39 |
| 360 | 0.53 |
| 360 | 0.4 |
| 360 | 0.44 |
| 480 | 0.69 |
| 480 | 0.37 |
| 480 | 0.4 |
| 1440 | 0.01 |
| 1440 | BLD |
| 1440 | 0.07 |

TABLE 9

ENDX PROTAC 7 IV pk sample summary

| Time (minutes) | Concentration ENDX PROTAC 7 (ng/ml) |
|---|---|
| 5 | 197.46 |
| 5 | 92.23 |
| 5 | 99.51 |
| 15 | 30.96 |
| 15 | 37.27 |
| 15 | 57.95 |
| 30 | 10.89 |
| 30 | 19.85 |
| 30 | 16.62 |
| 60 | 2.19 |
| 60 | 17.43 |
| 60 | 2.59 |
| 120 | 8.35 |
| 120 | 9.53 |
| 120 | 8.69 |
| 240 | 1.22 |
| 240 | 2.9 |
| 240 | 4.1 |
| 480 | 1.51 |
| 480 | 0.53 |
| 480 | 0.38 |
| 1440 | 0.36 |

TABLE 9-continued

| ENDX PROTAC 7 IV pk sample summary | |
|---|---|
| Time (minutes) | Concentration ENDX PROTAC 7 (ng/ml) |
| 1440 | 0.23 |
| 1440 | 0.17 |

Example 5—Synthesis of TC-Pr-009 Analogs

Figure 8A:
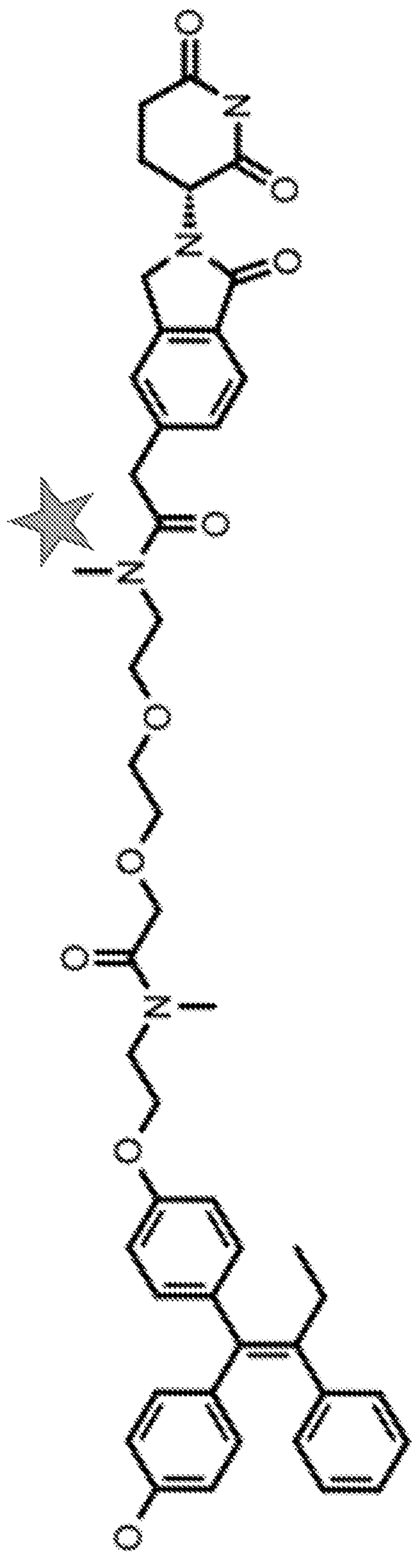
FIGS. 8A-8F show the structures of analogs 1-6, respectively, of ENDX-PROTAC molecule TC-Pr-009. The stars in FIGS. 8A-8F indicate the locations of changes in the molecules, as compared to TC-Pr-009.
Figure 8B:
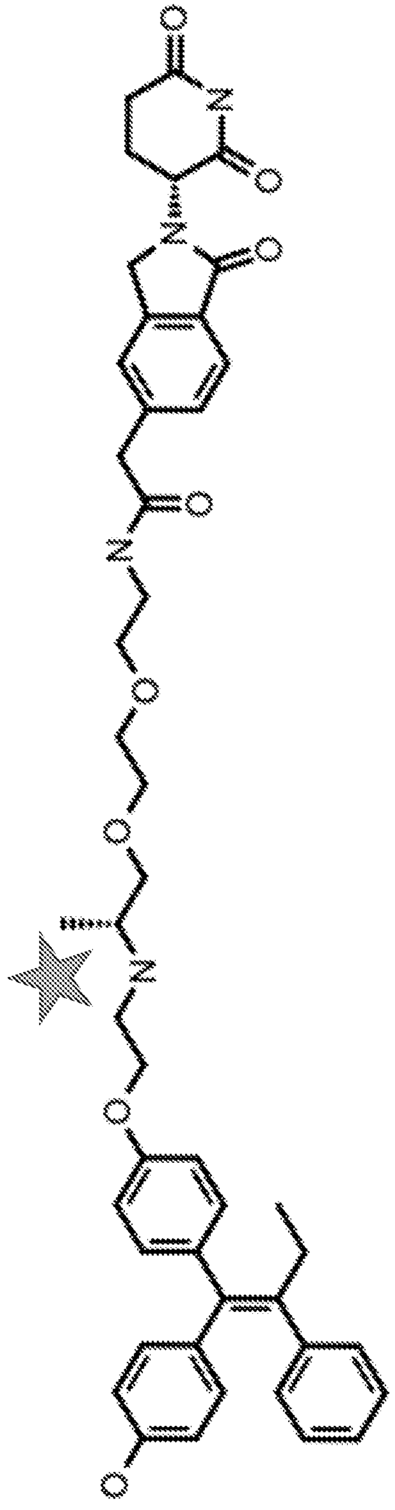
Figure 8C:
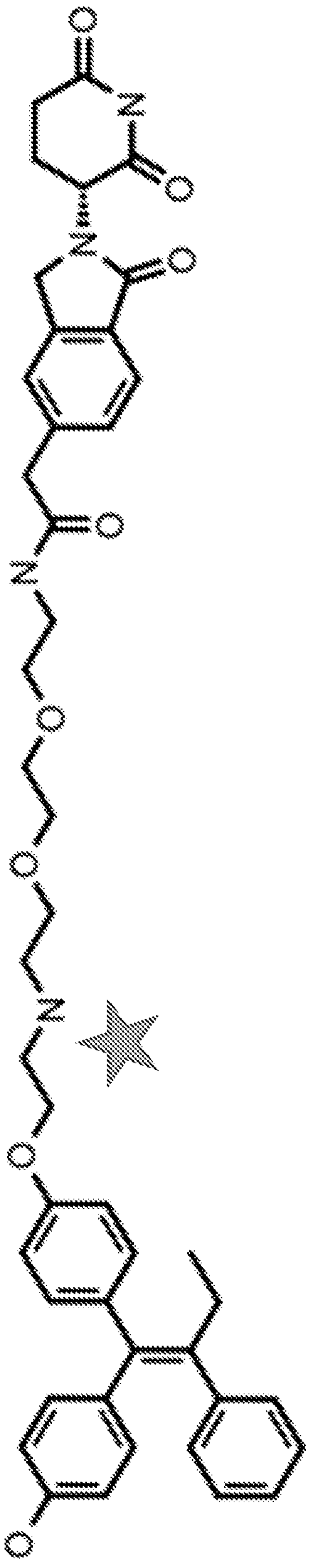
Figure 8D:
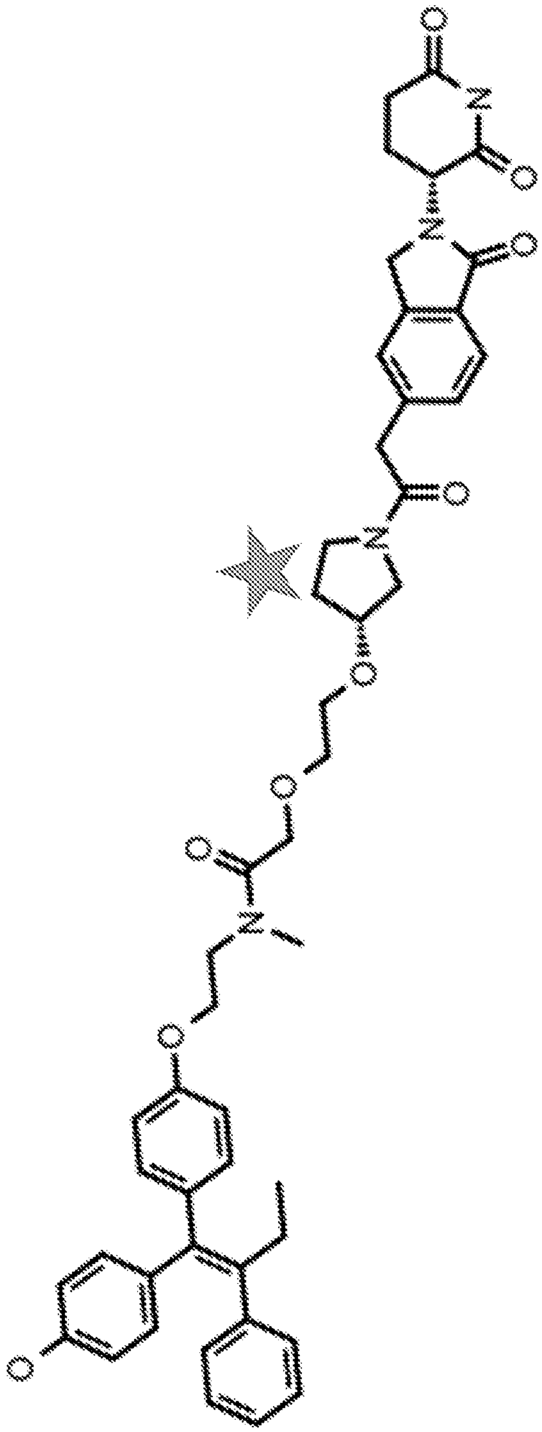
Figure 8E:
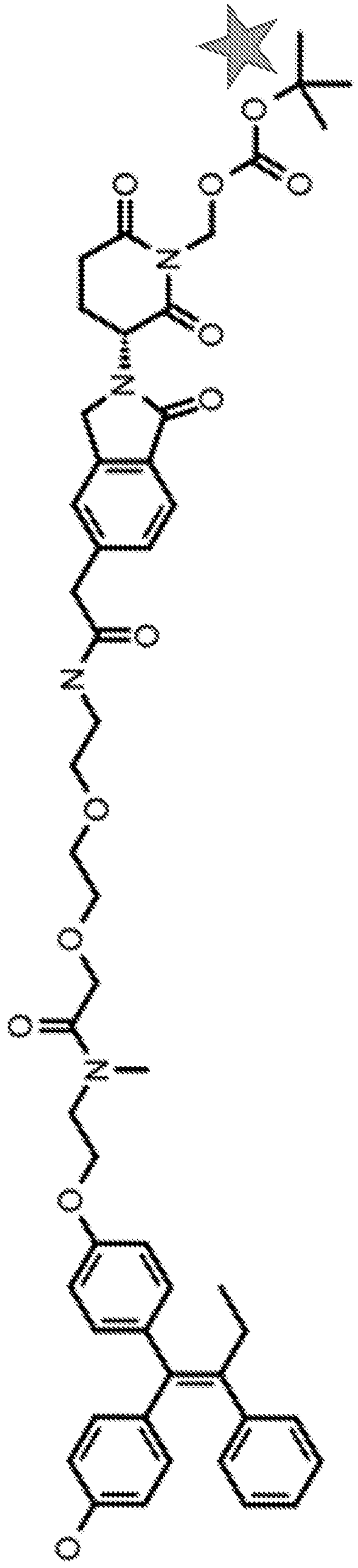
Figure 8F:
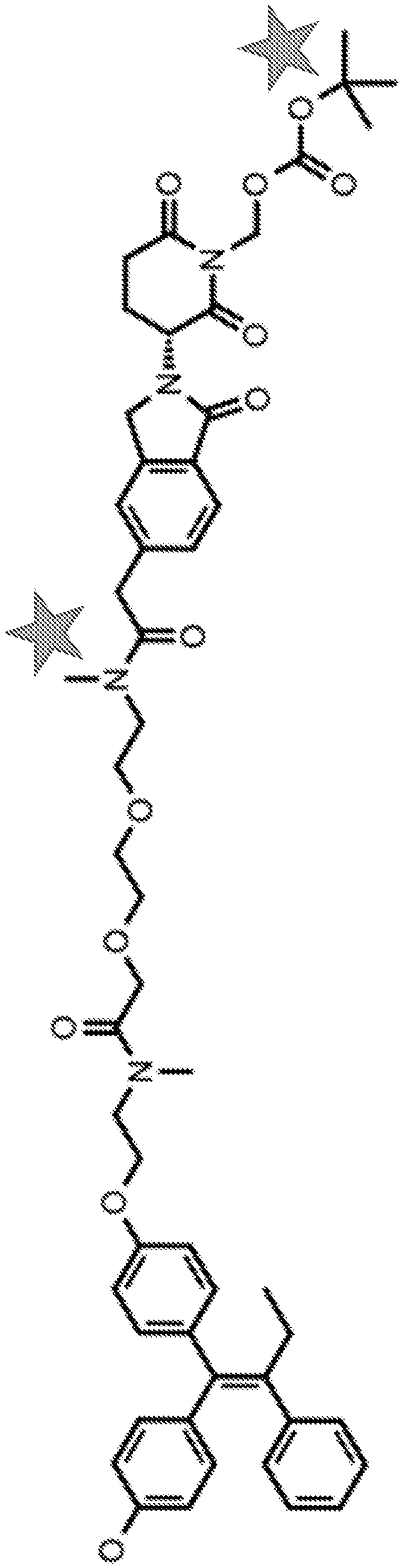
Figure 9A:
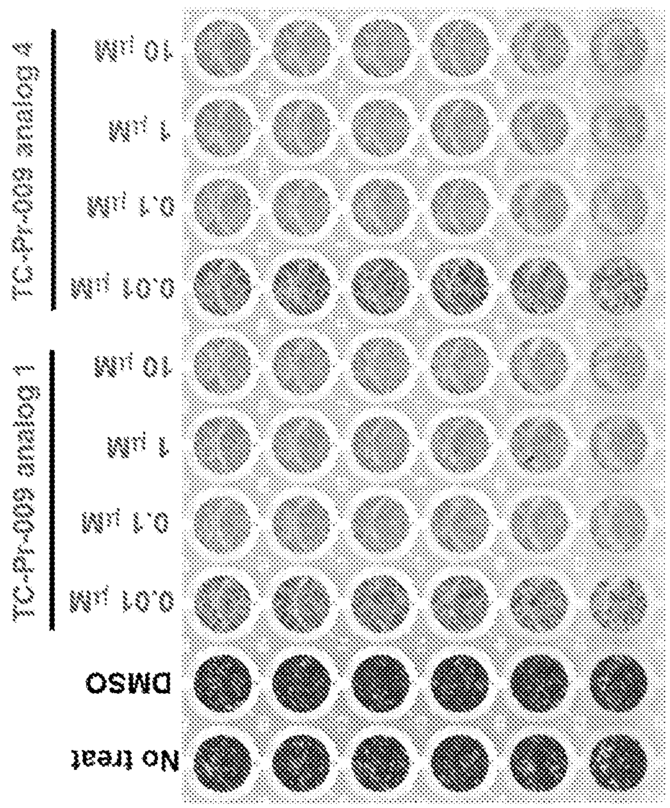
Figure 9C:
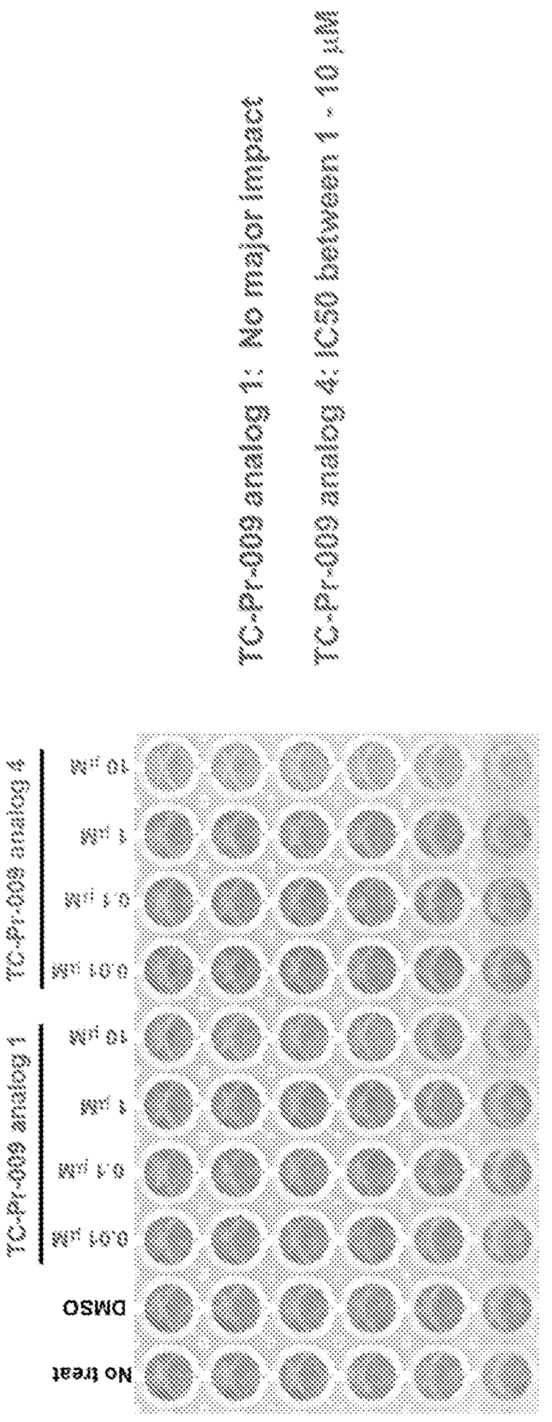
Figure 9E:
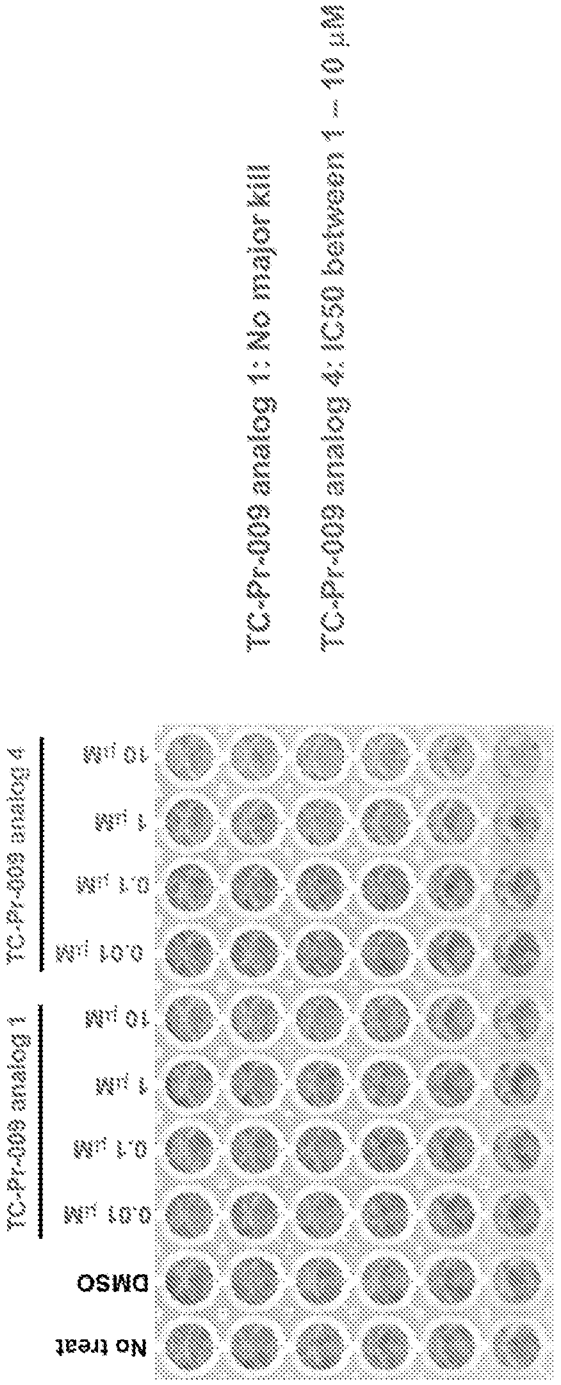
Figure 9G:
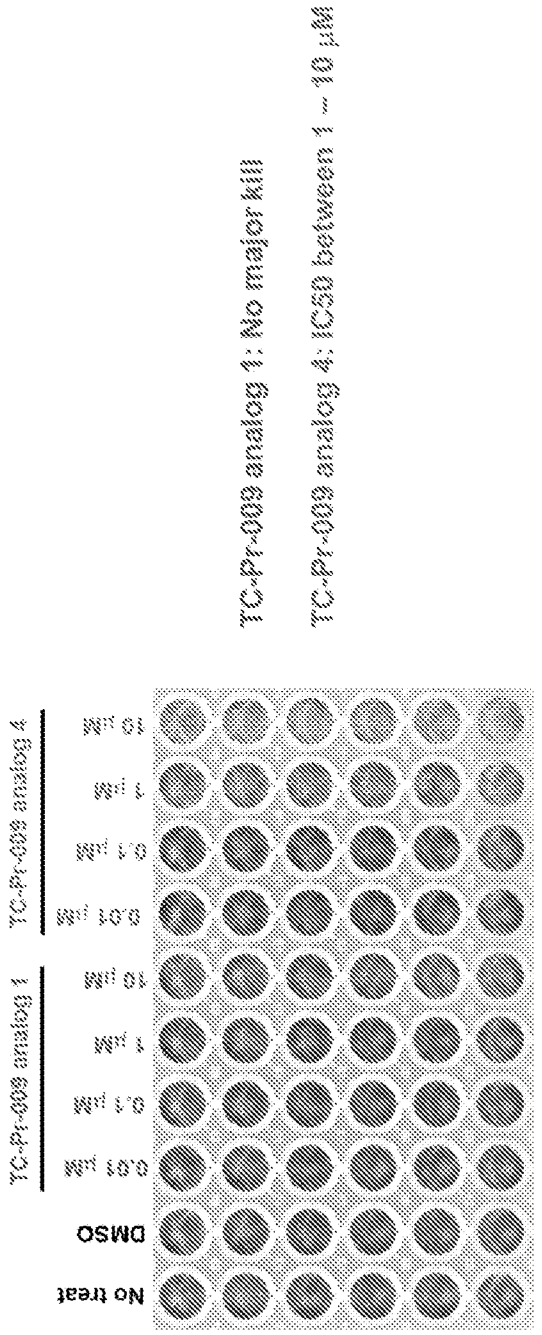
Figure 9I:
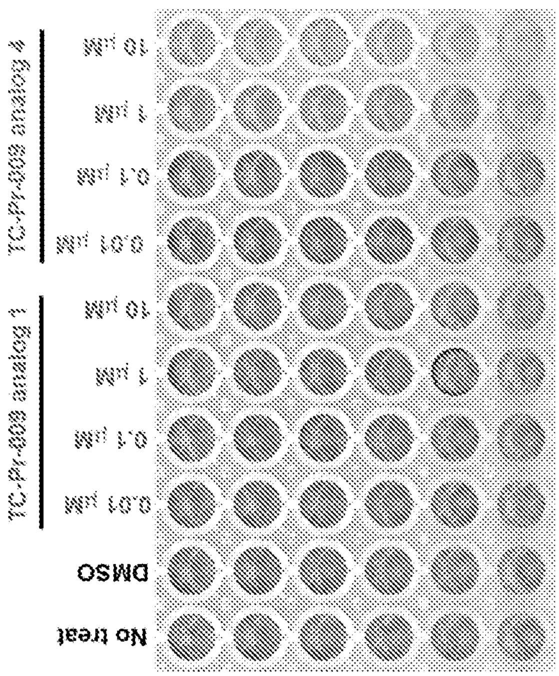

Six analogs of ENDX PROTAC 9 (also referred to as "Pr-9") were synthesized following the general scheme presented in Example 1. The change(s) to the PROTAC 9 structure in each analog included:

(1) addition of a methyl group to the amide on the PROTAC warhead (FIG. 8A), which may help to reduce or prevent degradation of the molecule (referred to as "Pr-9-1");

(2) removal of an amide and addition of an amine and a methyl for a carbonyl group on the ENDX portion of the molecule (FIG. 8B) (referred to as "Pr-9-2");

(3) removal of an amide and addition of an amine on the ENDX portion of the molecule (FIG. 8C) (referred to as "Pr-9-3");

(4) introduction of a cyclic amide on the PROTAC warhead (FIG. 8D) (referred to as "Pr-9-4");

(5) addition of a carbonate group on the PROTAC warhead (FIG. 8E) (referred to as "Pr-9-5"); and (6) addition of a carbonate and addition of a methyl to an amide N on the PROTAC warhead (FIG. 8F) (referred to as "Pr-9-6").

Example 6—Impact of ENDX PROTAC 9 Analogs 1 and 4 on Cellular Proliferation and Expression of PKCβ1, E2F1 and Cyclin D1 in TNBC Cells Cell proliferation rates were determined using CV assays. Two thousand (2000) or 4000 cells per well were plated in 96 well tissue culture plates and treated the following day with a bifunctional compound or control for 6 days in replicates of 6. Cells were fixed with 25% glutaraldehyde for 10 minutes with shaking, washed 5 times with distilled water, stained with a 1% crystal violet solution (solubilized in 25% methanol) for 10 minutes, washed again 5 times and allowed to dry. De-staining was performed using 100 nM sodium citrate in 50% ethanol followed by quantification using a 96 well spectrophotometer set at an absorbance of 550 nM.

TNBC BT549 and MDAMB436 cells were cultured in phenol-red free DMEM/F12 medium supplemented with 10% fetal bovine serum (FBS) and 1% AA. On day 1, cells were plated at a density of $2\times10^5$ BT549 cells or $4\times10^5$ MDAMB436 cells in a 6-well plate (two wells per treatment). The next day, cells were treated with DMSO, 1 μM Pr-9 (positive control), 1 μM Pr-9-1, 1 μM Pr-9-4, or 1 μM ENDX (negative control). Radioimmunoprecipitation Assay (RIPA) protein lysates were collected 24, 48, and 72 hours after treatment.

For western blot analysis, 25 μg of protein lysates were run on Criterion precast 10% Bis-Tris gel, transferred to PVDF membrane, incubated in TBST-5% milk for one hour, and then incubated overnight with PKCβ1 (SC8049, mouse, 1:200), E2F1 (SC251, mouse, 1:250), Cyclin D1 (CS2978, rabbit, 1:1000), or Actin (Sigma A2228, mouse, 1:10,000 or CS8457, rabbit, 1:2000) primary antibodies in TBST-5% BSA solution. Membranes were washed in TBS-T, incubated for one-hour in HRP-linked anti-rabbit or anti-mouse secondary antibodies in TBST-5% milk, and washed in TBS-T. Bands were developed using west-pico or west-femto chemiluminescent substrate reagents.

Figure 10A:
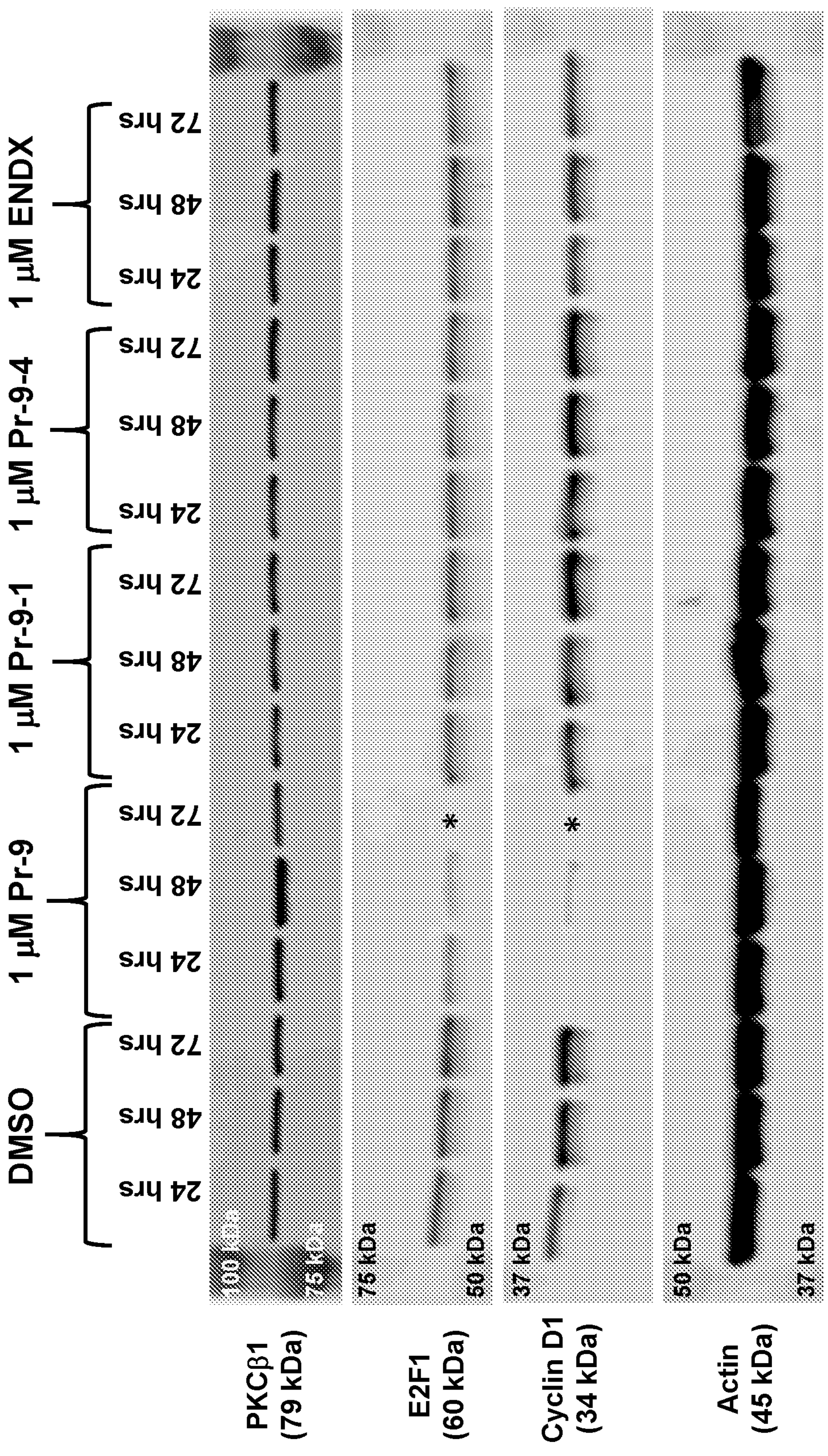
FIGS. 10A and 10B are images of western blots using lysates from BT549 cells (FIG. 10A) or MDAMB436 (FIG. 10B) treated with DMSO, Pr-9, Pr-9 analog 1 (Pr-9-1), Pr-9 analog 4 (Pr-9-4), or ENDX for 24, 48, or 72 hours, showing levels of PKCβ1, E2F1, Cyclin D1, and Actin. The asterisk in FIG. 10A indicates that there was not enough lysate from the 72 hour-treated Pr-9 sample for the E2F1 and Cyclin D1 western blots, but their protein levels were clearly reduced by 48 hours.
Figure 10B:
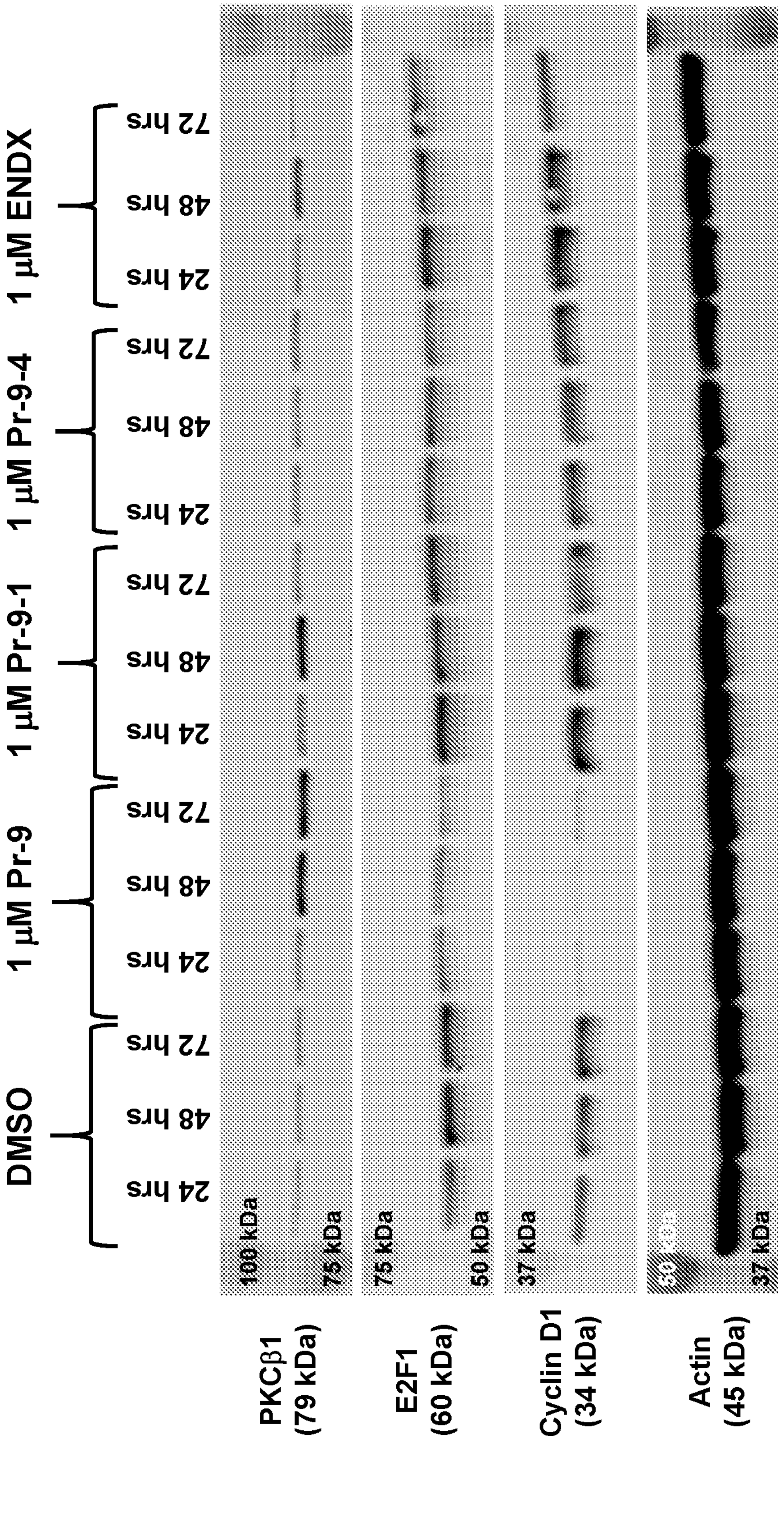

Cell proliferation data showed that Pr-9 analogs 1 and 4 inhibited growth of ER+ MCF7AC1 cells but did not inhibit growth of MDAMB231, BT549, or MDAMB436 TNBC cells as effectively (FIG. 9A-9J). The lack of antitumor activity by Pr-9-1 and Pr-9-4 was associated with lack of impact on PKCβ1, E2F1, and Cyclin D1 protein expression in the BT549 (FIG. 10A) and MDAMB436 (FIG. 10B) models. The findings for Pr9-1 and Pr 9-4 mirrored that seen with ENDX (FIG. 10A and FIG. 10B). In contrast, Pr-9 resulted in reduced protein levels of E2F1 and Cyclin D1, with PKCβ1 protein levels altered to varying extent in these models (FIGS. 10A and FIG. 10B).

Example 7—Impact of PROTAC 7 on the UPR Pathway in MDA-MB-231 Cells

Prolonged protein misfolding or endoplasmic reticulum (ER) stress can activate the apoptosis-inducing unfolded protein response (UPR) pathway, which induces apoptosis signaling primarily through IRE1 and PERK. In the IRE1 pathway, activated IRE1 recruits TRAF2 and ASK1 on the ER membrane and activates the ASK1-dependent apoptosis pathway. The IRE1 pathway also activates the IKK-NFκB pathway through IRE1-TRAF2, which induces the apoptotic response. The proapoptotic Bcl-2 family members, Bax and Bak, interact with IRE1 and promote its RNase/kinase activity. IRE1 also induces ER-localized mRNA degradation. In the PERK pathway, PERK activation leads to phosphorylation of eukaryotic translation initiation factor 2α (eIF2α), leading to activation of ATF4 (a transcription factor; TF), which upregulates the expression of CHOP (another TF), which in turn activates the transcription of proapoptotic factors such as PUMA and NOXA.

Pr-7, Pr-8, and Pr-9 induced apoptosis in MDAMB231 and BT549 cells (FIG. 4A and TABLE 1). Studies were carried out to determine whether the active PROTAC-induced apoptosis might be occurring via activation of UPR signaling. To evaluate the effect of PROTAC 7 (Pr-7) on expression of various proapoptotic polypeptides, triple negative MDAMB231 cells were treated with DMSO, 1 μM Pr-7, or 1 μM ENDX, and mRNA levels were assessed by qRT-PCR at 0-, 1-, 8-, 24-, and 48-hour time points.

Triple negative breast cancer MDA-MB-231 cells were cultured in phenol-red free DMEM/F12 medium supplemented with 10% FBS and 1% AA. Cells were plated at $1\times10^6$ cells per 10 cm dish. The next day, the cells were treated with DMSO, 1 μM Pr-7 or 1 μM ENDX for 1, 8, 24, and 48 hours, and were then processed for RNA and RIPA protein analysis.

In particular, total RNA from tissue samples and cell lines was extracted using the RNEASY® Plus mini kit (Qiagen; Hilden, Germany), cDNA was generated using a ISCRIPT™ cDNA synthesis kit (Bio-Rad; Hercules, CA) and qRT-PCR reactions were set up using PERFECTA® SYBR™ green fast mix reagents (Quanta BioSciences; Beverly, MA) and gene-specific primer sets (IDT; Coralville, IA). The forward and reverse primer sequences for the genes used in this analysis were obtained from the Harvard PrimerBank database. Amplification of HPRT and tubulin was used as an internal control. Relative expression between samples was calculated by the comparative Ct method.

For western blotting, 30 μg of protein lysates were run on Criterion precast 10% Bis-Tris gel, transferred to PVDF membrane, incubated in TBST-5% milk for one hour followed by overnight incubation with phospho-IRE1α (Sigma SAB5700519, rabbit, 1:1000), IRE1α (CS3294, rabbit, 1:1000), phospho-eIF2α (CS3398, rabbit, 1:1000), eIF2α (CS5324, rabbit, 1:1000), CHOP (CS2895, mouse, 1:1000), PUMA (SC374223, mouse, 1:200), NOXA (CS14766, rabbit, 1:1000), E2F1 (SC251, mouse, 1:250), BCL2 (SC7382, 1:200), cleaved PARP (CS5625, rabbit, 1:1000), PARP (CS9542, rabbit, 1:1000), PKCβ1 (SC8049, mouse, 1:200), PKCδ (CS2058, rabbit, 1:1000) and Actin (Sigma A2228, mouse, 1:10,000) primary antibodies in TBST-5% BSA solution. Membranes were washed in TBS-T, incubated for one-hour in HRP-linked anti-rabbit or anti-mouse secondary antibodies in TBST-5% milk, and washed with TBS-T. Bands were developed using west-pico or west-femto chemiluminescent substrate reagents.

Figure 11A:
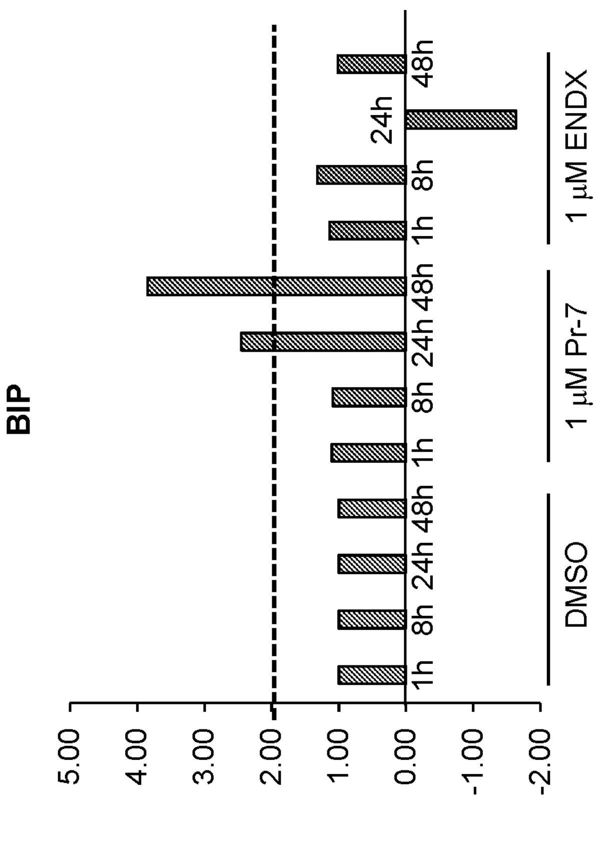
FIGS. 11A-11Q are graphs plotting the levels of various mRNAs in triple negative MDAMB231 cells after treatment for 0, 1, 8, 24, and 48 hours with DMSO, 1 μM Pr-7, or 1 μM ENDX. In particular, levels of mRNAs associated with the unfolded protein response (UPR) were assessed by quantitative reverse transcriptase polymerase chain reaction (qRT-PCR). Results for Pr-7 and ENDX are presented as fold expression relative to the level with DMSO (which was set to 1.0 at each time point). A 2.0-fold change (dashed lines) was considered significant.
Figure 11B:
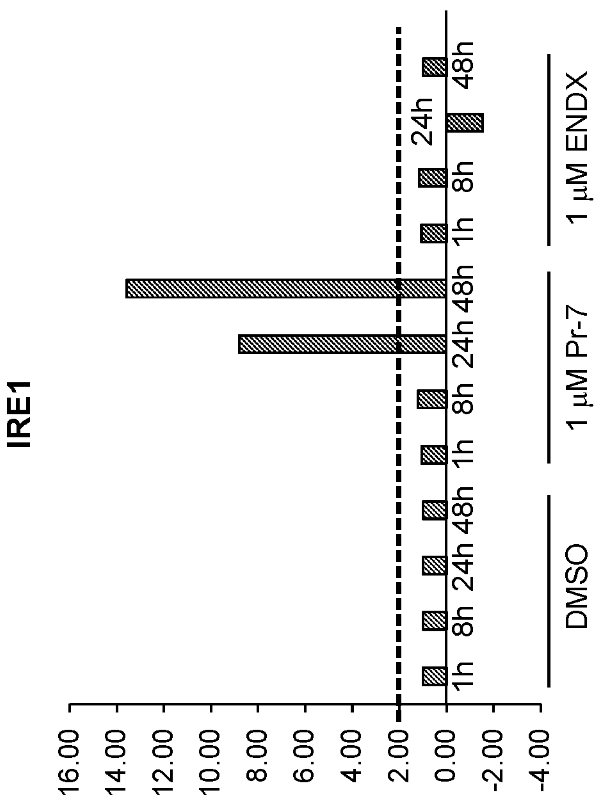
FIG. 11B, IRE1.
Figure 11C:
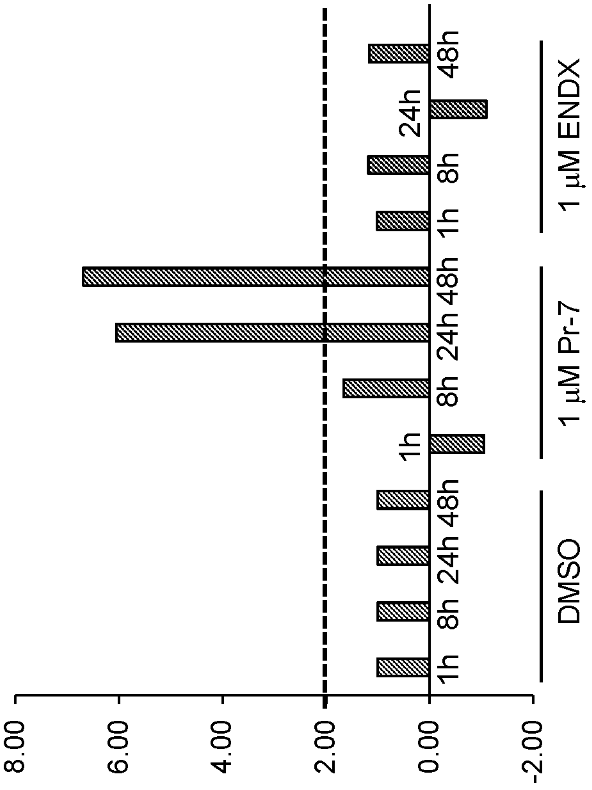
FIG. 11C, Xbp-1.
Figure 11D:
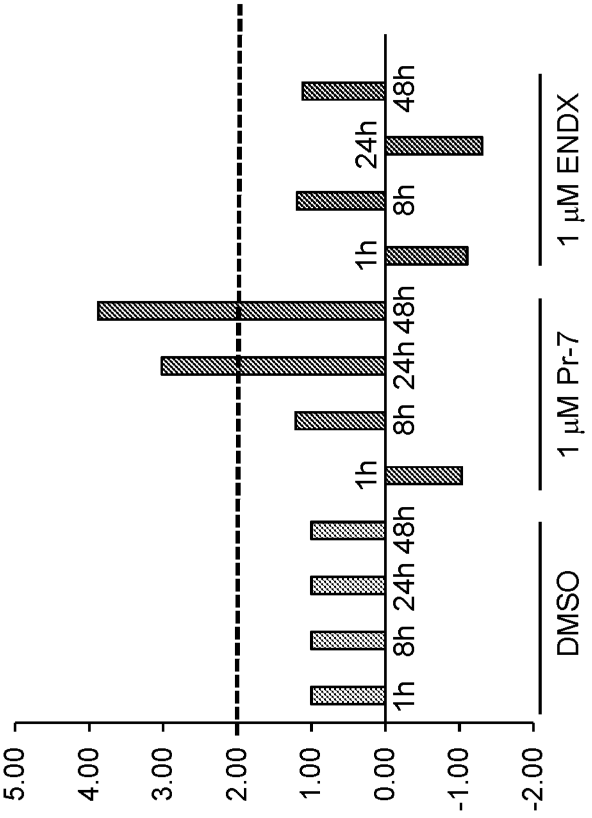
FIG. 11D, Bax.
Figure 11E:
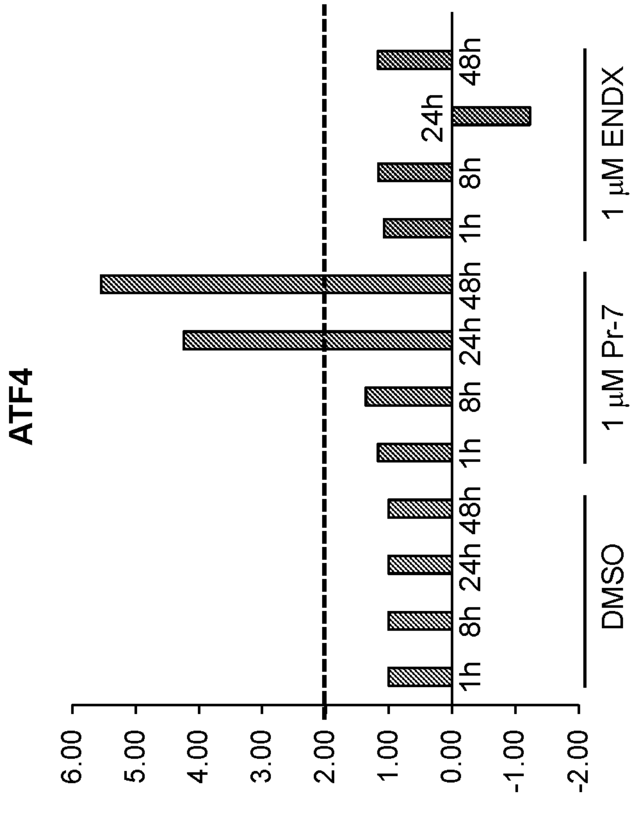
FIG. 11E, ATF4.
Figure 11F:
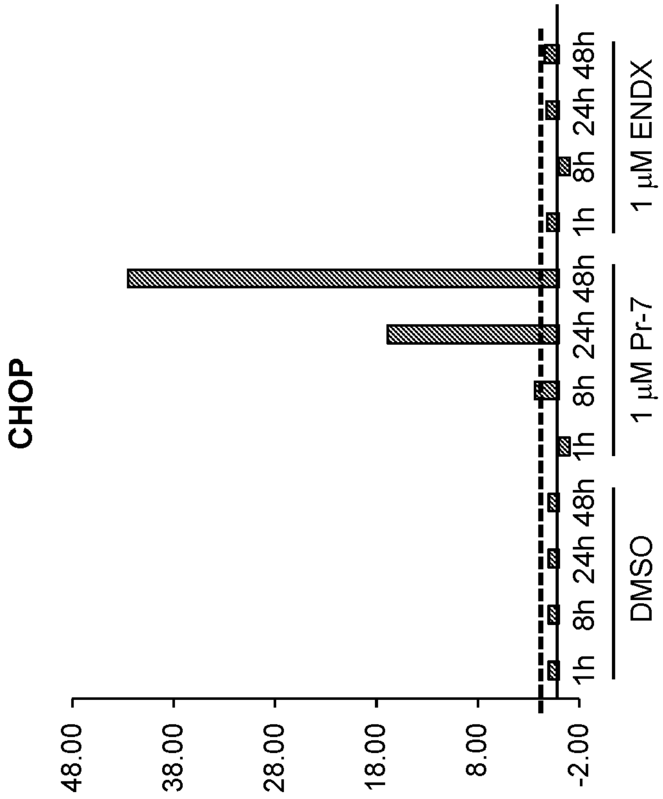
FIG. 11F, CHOP.
Figure 11G:
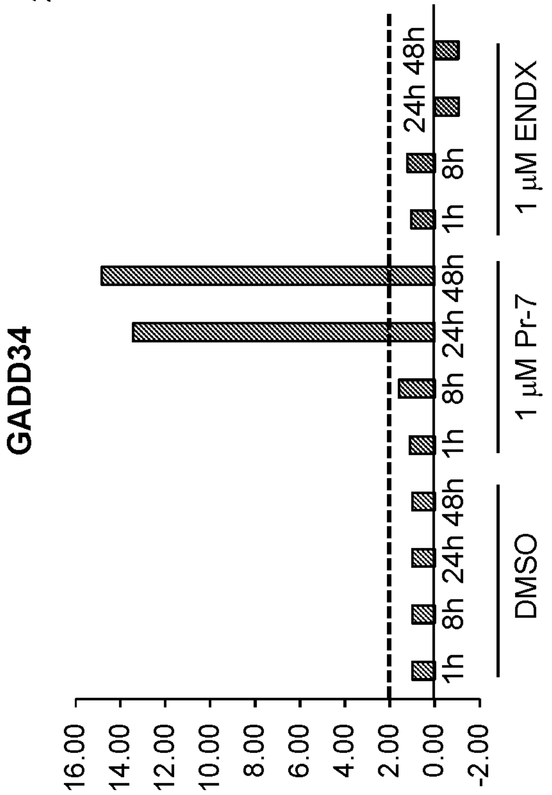
FIG. 11G, GADD34.
Figure 11H:
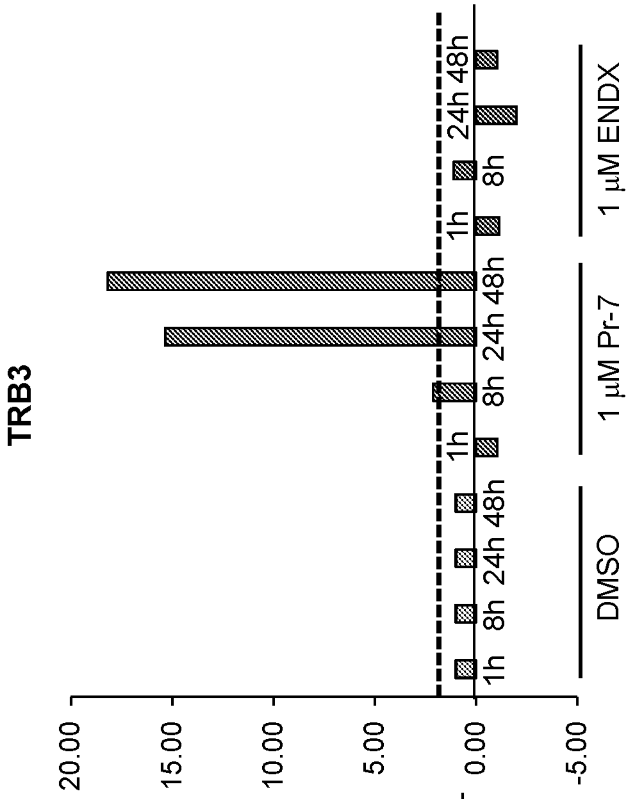
FIG. 11H, TRB3.
Figure 11I:
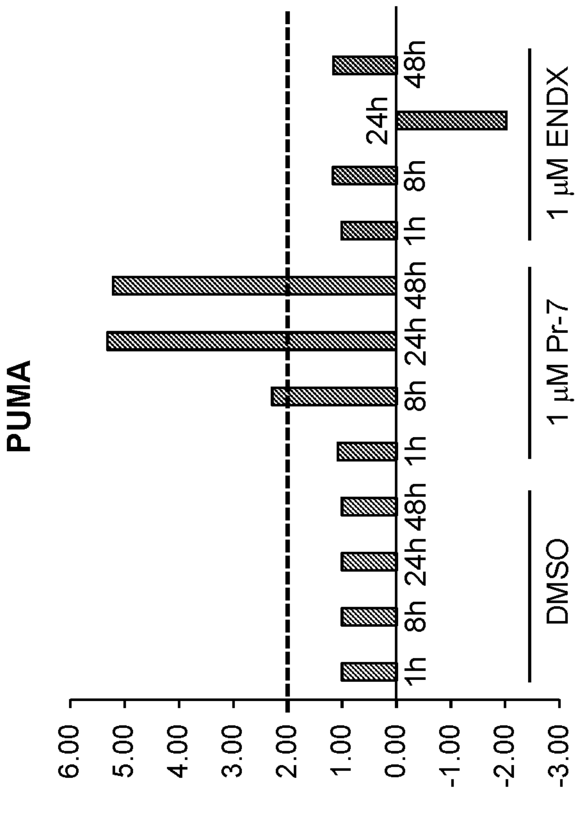
FIG. 11I, PUMA.
Figure 11J:
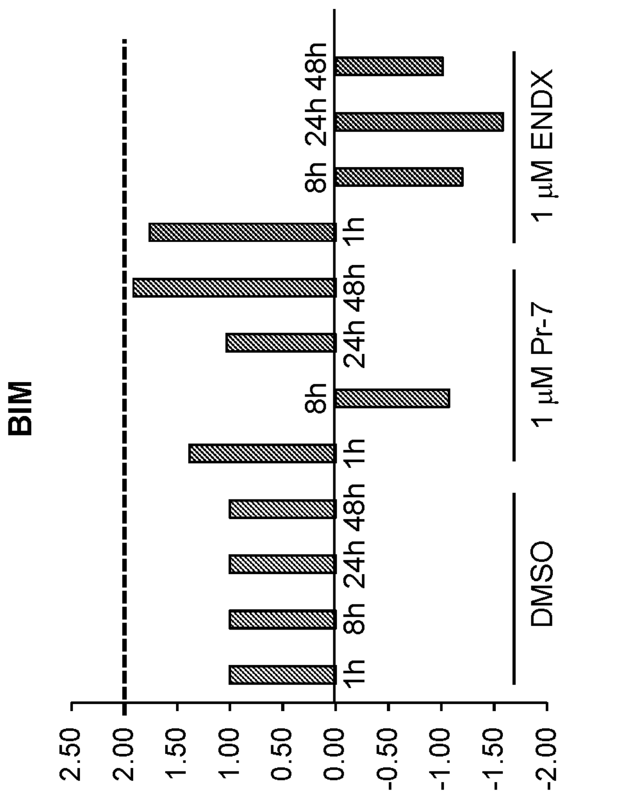
FIG. 11J, BIM.
Figure 11K:
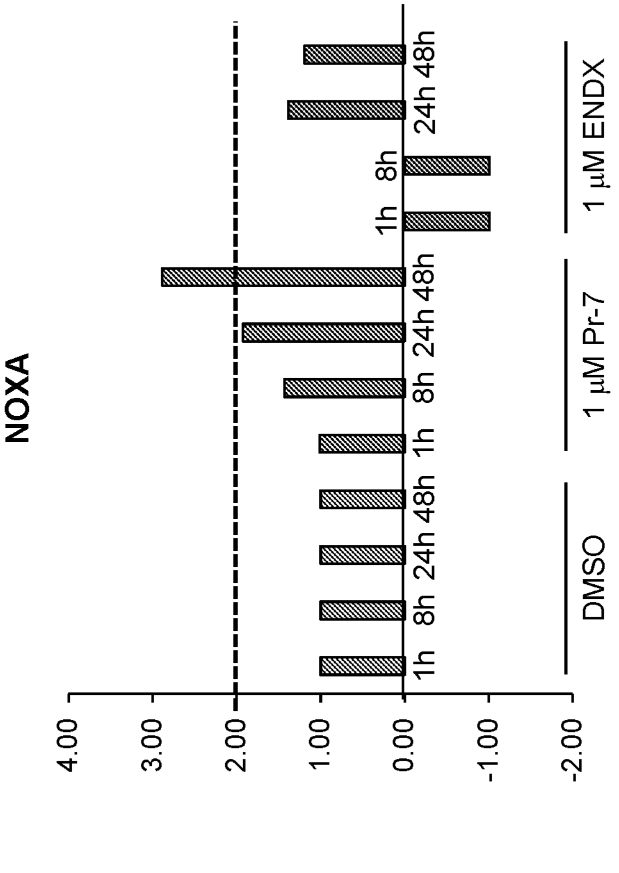
FIG. 11K, NOXA.
Figure 11L:
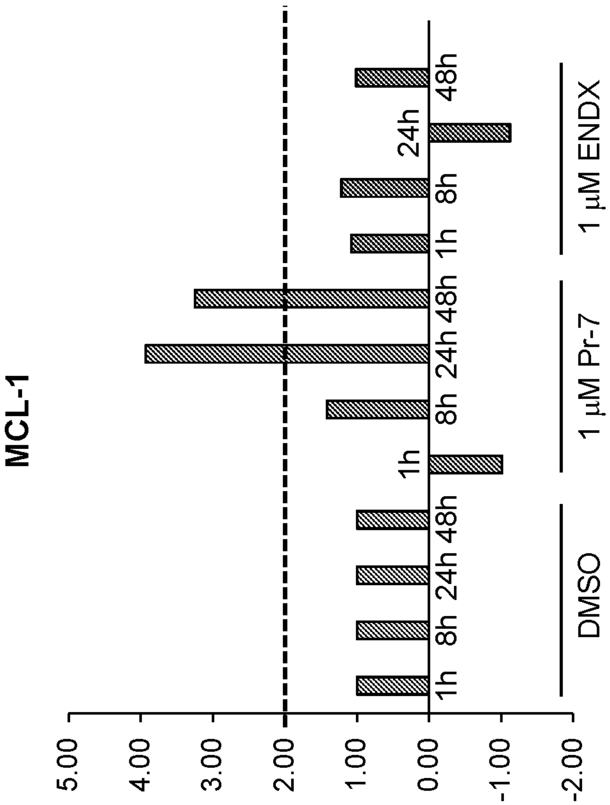
FIG. 11L, MCL-1.
Figure 11N:
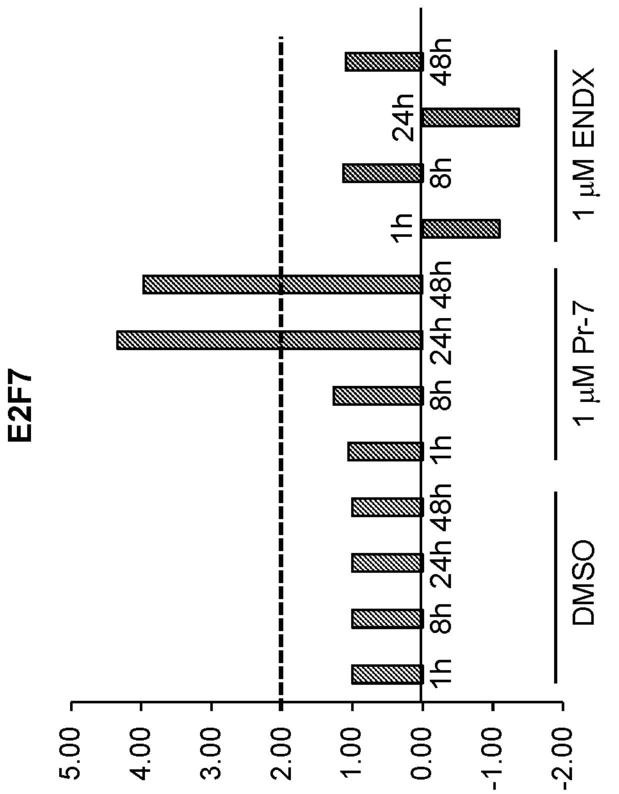
FIG. 11N, E2F7.
Figure 11M:
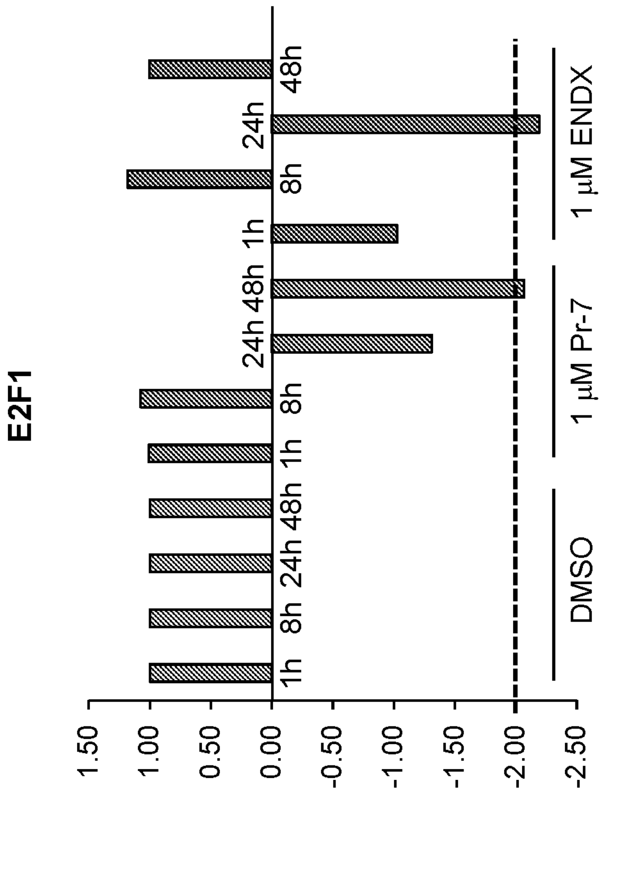
FIG. 11M, E2F1.
Figure 11P:
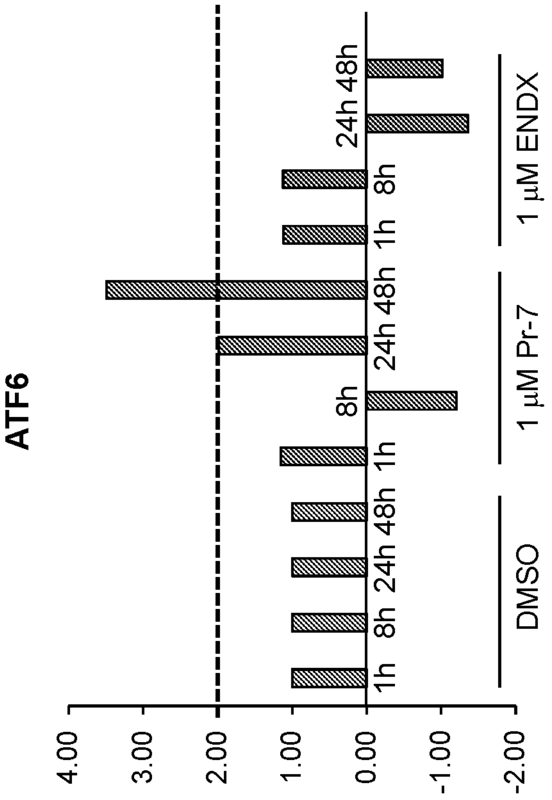
FIG. 11P, ATF6.
Figure 11O:
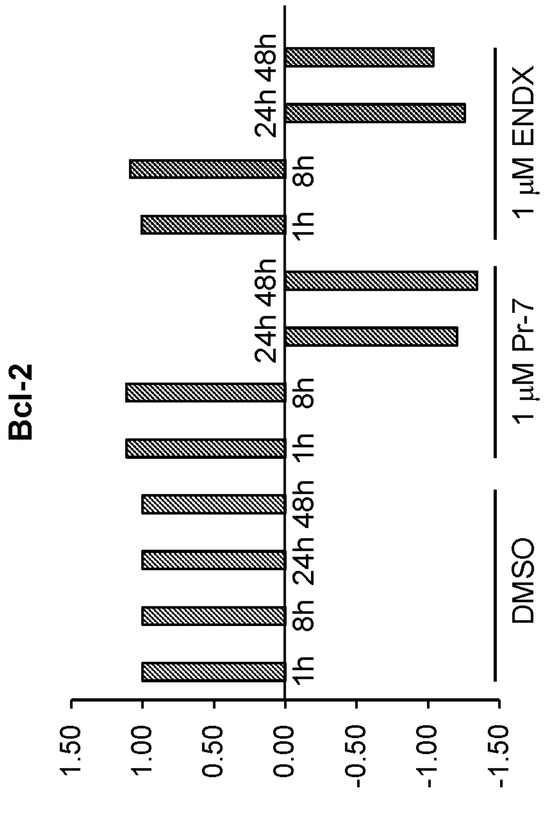
FIG. 11O, Bcl-2.
Figure 11Q:
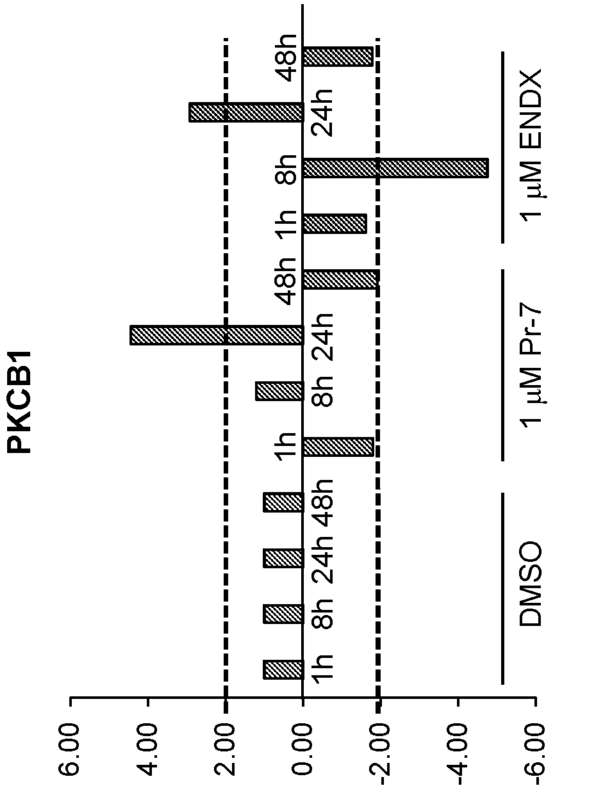
Figure 12A:
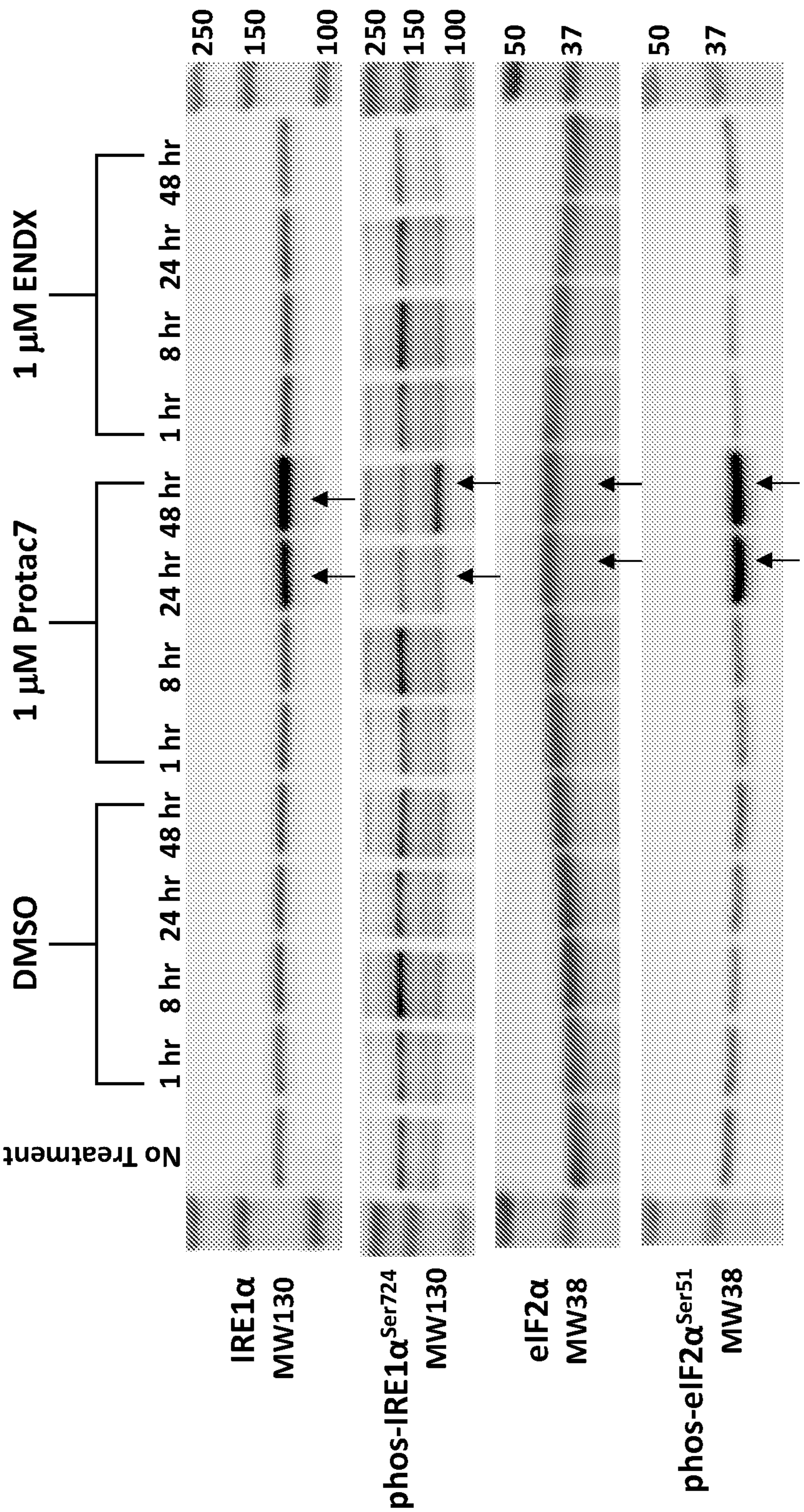
FIGS. 12A-12D are images showing results of western blotting using lysates from MDAMB231 cells after treatment with DMSO, 1 μM Pr-7, or 1 μM ENDX for 1, 8, 24, or 48 hours. Lysates were assessed for levels of various proteins involved in the UPR, including IRE1α, phos-IRE1$\alpha^{Ser724}$, eIF2α, and phos-eIF2$\alpha^{Ser51}$ (FIG. 12A); E2F1, BCL-2, PARP, and cleaved PARP (FIG. 12B); CHOP, PUMA, and NOXA (FIG. 12C); and PKCB1, PKCdelta, and Actin (FIG. 12D).
Figure 12B:
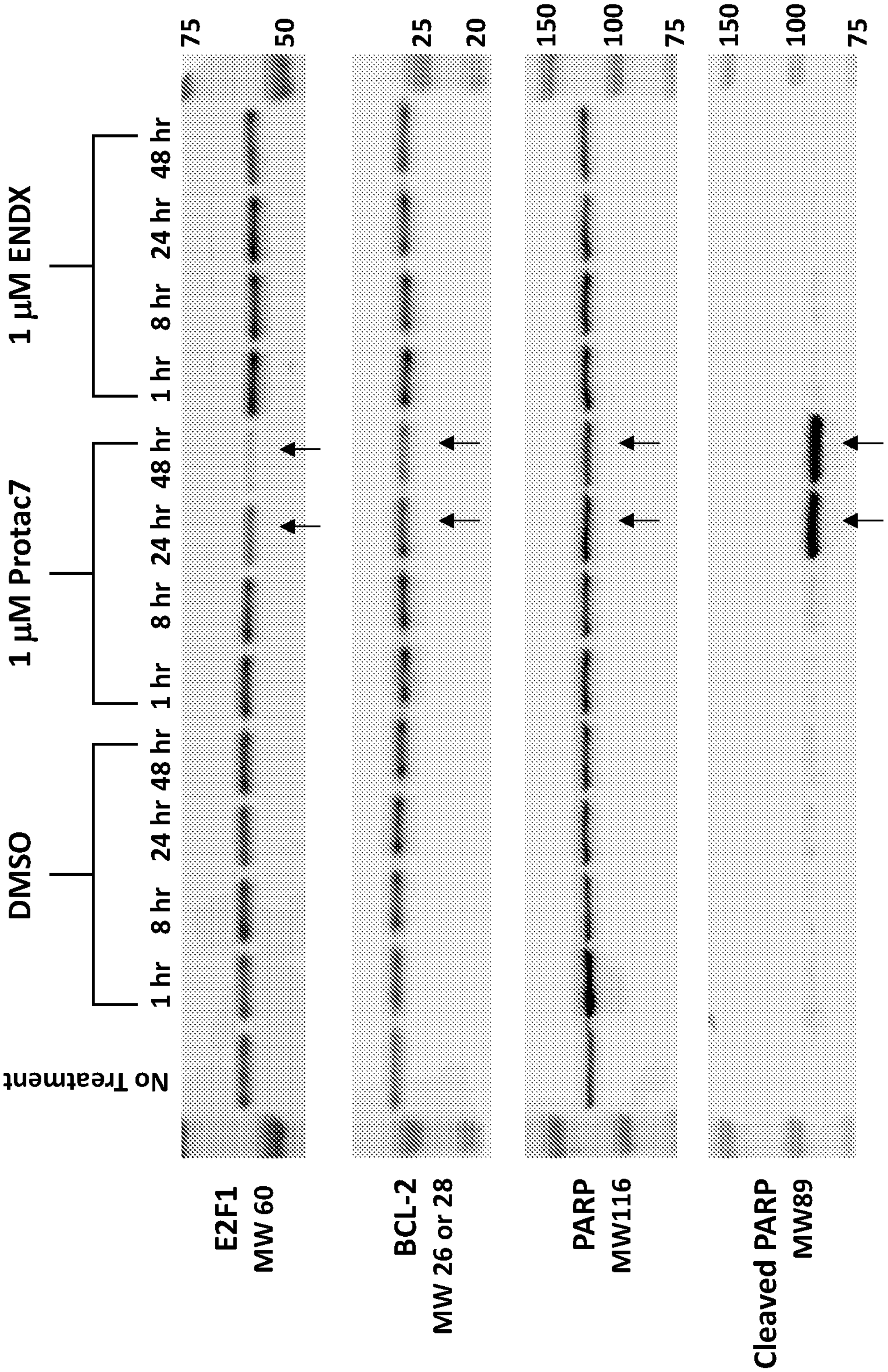
Figure 12C:
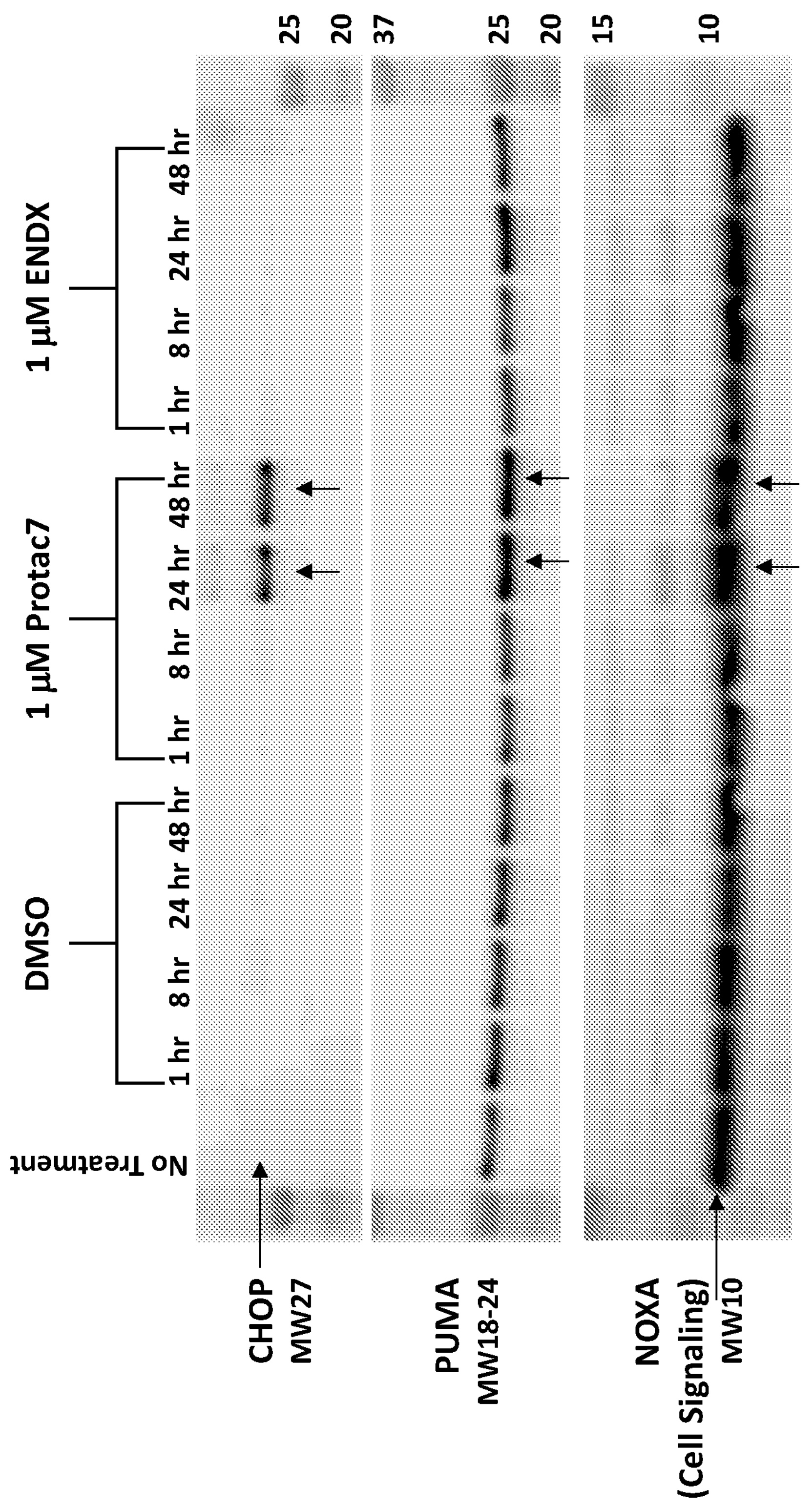
Figure 12D:
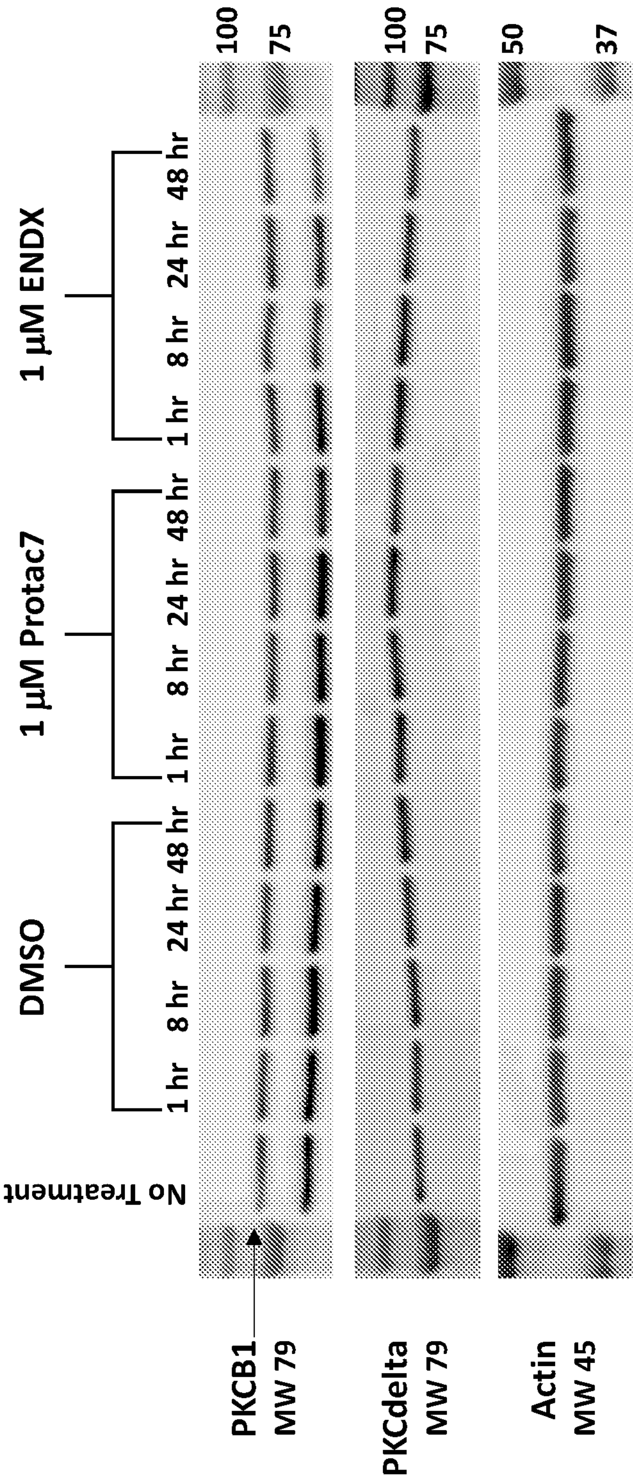

The results of the expression studies are plotted in FIGS. 10A-10Q, with expression levels after Pr-7 and ENDX treatment presented as fold expression relative to DMSO. A 2.0-fold change (dashed lines) was considered significant. The mRNAs evaluated included BIP (FIG. 11A), IRE1 (FIG. 11B), Xbp-1 (FIG. 11C), Bax (FIG. 11D), ATF4 (FIG. 11E), CHOP (FIG. 11F), GADD34 (FIG. 11G), TRB3 (FIG. 11H), PUMA (FIG. 11I), BIM (FIG. 11J), NOXA (FIG. 11K), MCL-1 (FIG. 11L), E2F1 (FIG. 11M), E2F7 (FIG. 11N), Bcl-2 (FIG. 11O), ATF6 (FIG. 11P), and PKCB1 (FIG. 11Q). These studies showed that treatment with PROTAC 7 led to increased mRNA expression for CHOP, MCL-1, PUMA, NOXA, and Xbp-1.

Results of the western blotting studies are shown in FIGS. 12A-12D. Taken together, these studies demonstrated that 1 μM Pr-7 robustly activated multiple components of the ER-stress induced UPR pathway, including CHOP, IRE1α, X-bp1, eIF2α, ATF4, ATF6, PUMA, and NOXA, in MDA-MB-231 cells. In contrast, 1 μM ENDX demonstrated no impact on the UPR pathway. In addition, 1 μM Pr-7 also downregulated expression of the anti-apoptotic protein BCL2, increased PARP cleavage, and activated E2F7, the negative regulator of E2F1. E2F7 is regulated by XBP1s, which along with ATF6 binds to the E2F1 promoter and transcriptionally represses E2F1 gene expression. E2F1 is known to transcriptionally repress the pro-apoptotic PUMA and NOXA genes, and E2F1 downregulation activates PUMA and NOXA. Since E2F1 downregulation appears to be a downstream effect of UPR activation, E2F1 downregulation by Pr-7 has utility as a biomarker of UPR activation.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for killing an estrogen receptor negative (ER−) cancer cell, wherein said method comprises contacting said cell with a bifunctional compound comprising:

(a) a first molecule component capable of interacting with a protein kinase C type beta (PKCβ1) polypeptide, (b) a second molecule component capable of interacting with an E3 ubiquitin ligase polypeptide, and (c) a linker covalently coupling said first molecule component to said second molecule component, wherein said bifunctional compound is a compound of Formula (A:

(A)

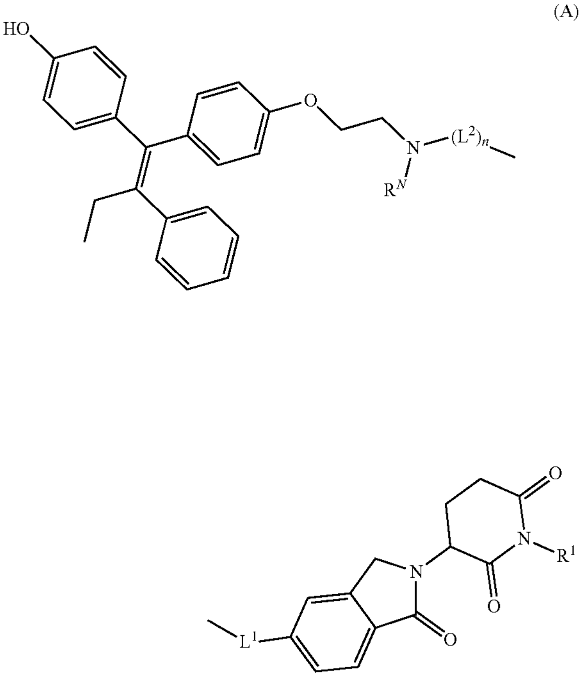

or a pharmaceutically acceptable salt thereof, wherein:

$L^1$ is $C_{1-3}$ alkylene, optionally substituted with 1, 2, or 3 substituents independently selected from OH, $NO_2$, CN, halo, amino, and carboxy;

n is an integer selected from 1 to 10:

each $L^2$ is independently selected from C(═O), N($R^N$), O, (—$C_{1-3}$ alkylene-O—$)_x$, (—O—$C_{1-3}$ alkylene-$)_x$, —$C_{1-3}$ alkylene-, and 4-6 membered heterocycloalkylene, wherein each x is independently an integer from 1 to 10, and wherein said $C_{1-3}$ alkylene and 4-6 membered heterocycloalkylene are each optionally substituted with 1, 2, or 3 substituents independently selected from OH, $NO_2$, CN, halo, amino, and carboxy;

each $R^N$ is independently selected from H and $C_{1-3}$ alkyl; and $R^1$ is selected from H and $C_{1-3}$ alkyl, optionally substituted with a group selected from —OC(═O)O—$C_{1-6}$ alkyl, —OC(═O)$NH_2$, —OC(═O)NH($C_{1-6}$ alkyl), —OC(═O)N($C_{1-6}$ alkyl$)_2$, NHC(═O)O—$C_{1-6}$ alkyl, NHC(═O)$NH_2$, NHC(═O)NH($C_{1-6}$ alkyl), and NHC(═O)N($C_{1-6}$ alkyl$)_2$.

2. The method of claim 1, wherein said cancer cell is a breast cancer cell or an ovarian cancer cell.

3. The method of claim 1, $R^N$ as shown in the compound of Formula (A), independent from $R^N$ in $L^2$ is H.

4. The method of claim 1, wherein said bifunctional compound has an $IC_{50}$ of less than 500 nM in a crystal violet proliferation assay using triple negative cells.

5. The method of claim 4, wherein said triple negative cells are BT549 cells or MDAMB436 cells.

6. The method of claim 1, wherein said bifunctional compound is a compound of Formula (I):

(I)

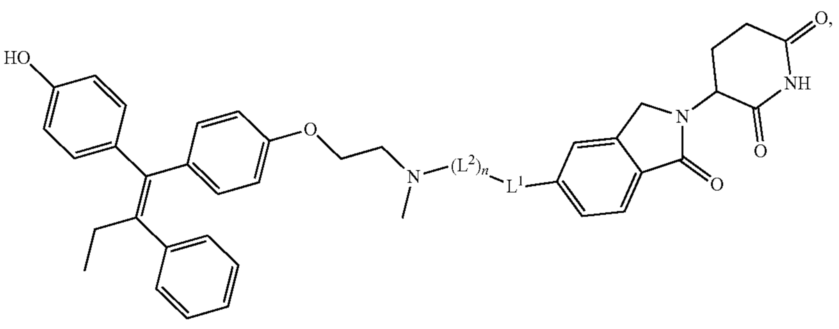

or a pharmaceutically acceptable salt thereof, wherein:

$L^1$ is $C_{1-3}$ alkylene, optionally substituted with 1, 2, or 3 substituents independently selected from OH, $NO_2$, CN, halo, amino, and carboxy;

n is an integer selected from 1 to 10;

each $L^2$ is independently selected from C(=O), $N(R^N)$, O, (—$C_{1-3}$ alkylene-O—$)_x$, (—O—$C_{1-3}$ alkylene-$)_x$, and —$C_{1-3}$ alkylene-, wherein each x is independently an integer from 1 to 10 and each $C_{1-3}$ alkylene is optionally substituted with 1, 2, or 3 substituents independently selected from OH, $NO_2$, CN, halo, amino, and carboxy; and each $R^N$ is independently selected from H and $C_{1-3}$ alkyl;

or wherein said compound has Formula (II):

(II)

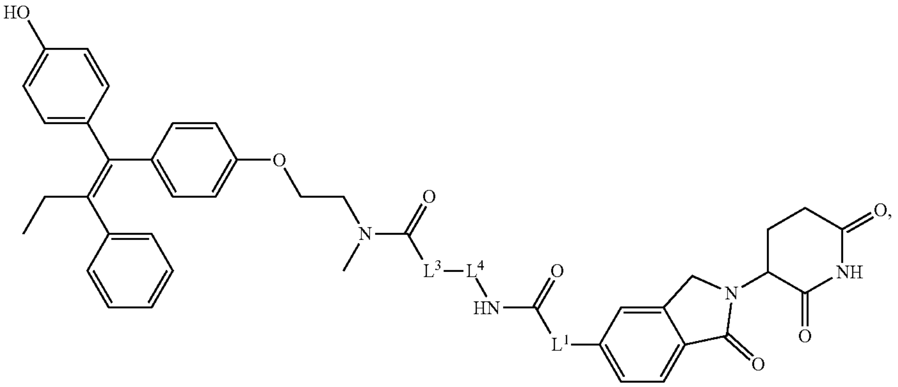

or a pharmaceutically acceptable salt thereof, wherein:

$L^3$ is $C_{1-3}$ alkylene; and $L^4$ is (—O—$C_{1-3}$ alkylene-$)_x$;

or wherein said compound has Formula (III), Formula (IV), or Formula (V):

(III)

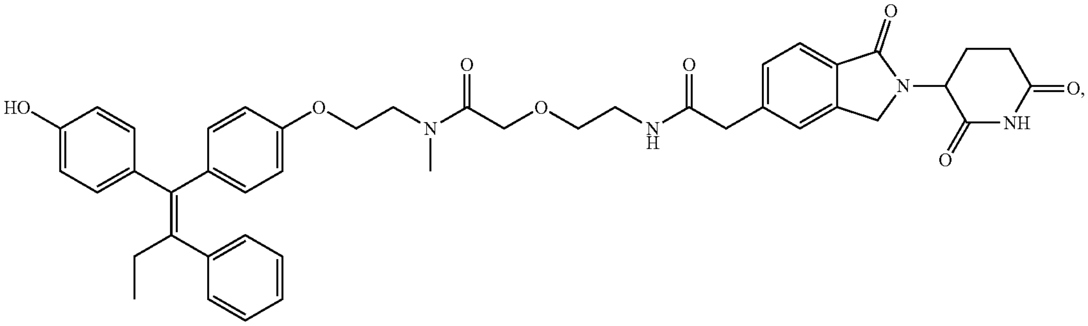

-continued
(IV)
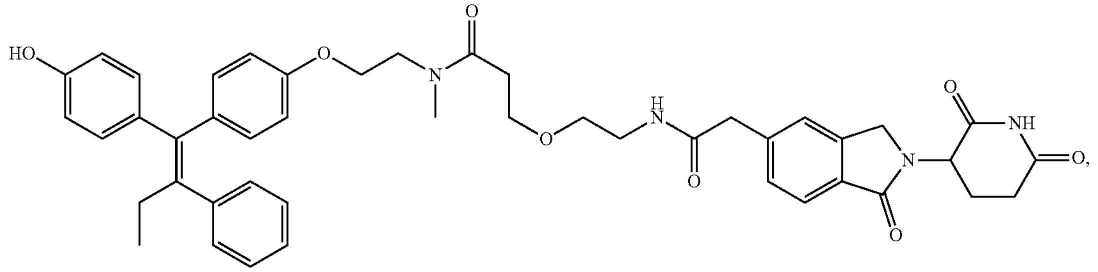
(V)
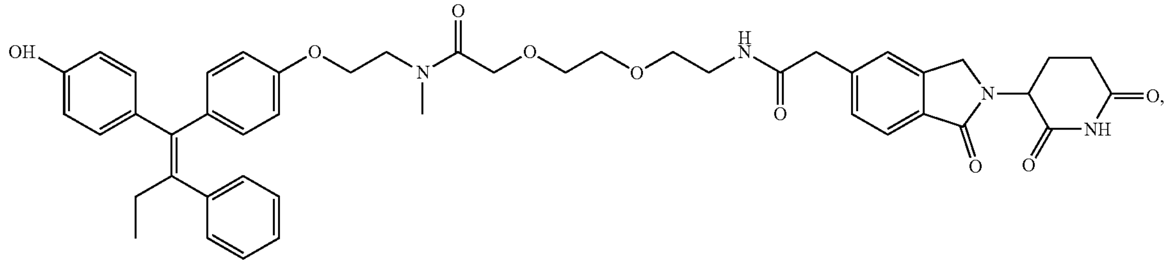
or a pharmaceutically acceptable salt thereof;
or wherein said bifunctional compound has Formula (VI):
(VI)
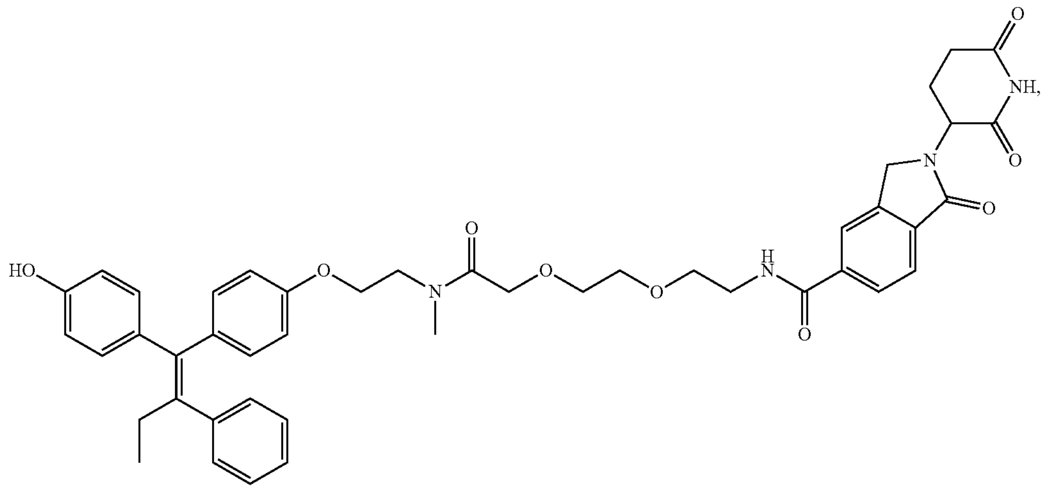
or a pharmaceutically acceptable salt thereof,
or wherein said compound has Formula (VII), Formula (VIII), or Formula (IX):
(VII)
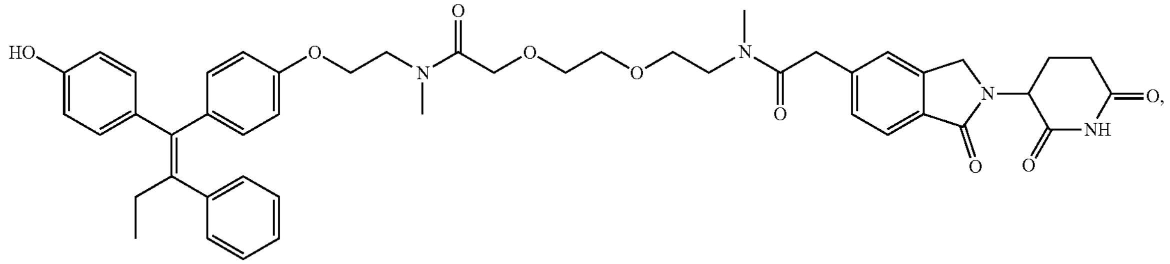

-continued (VIII)

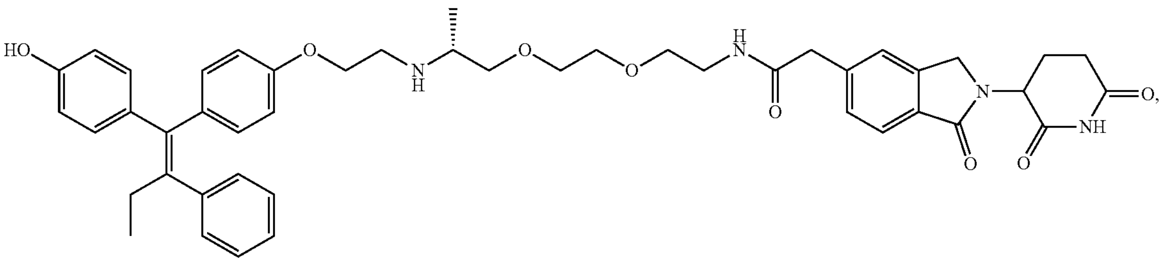

(IX)

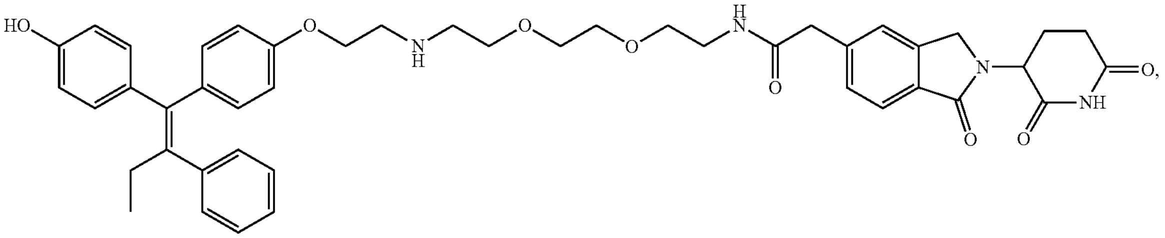

or a pharmaceutically acceptable salt thereof.

7. The method of claim 1, wherein said bifunctional compound is a compound of Formula (B):

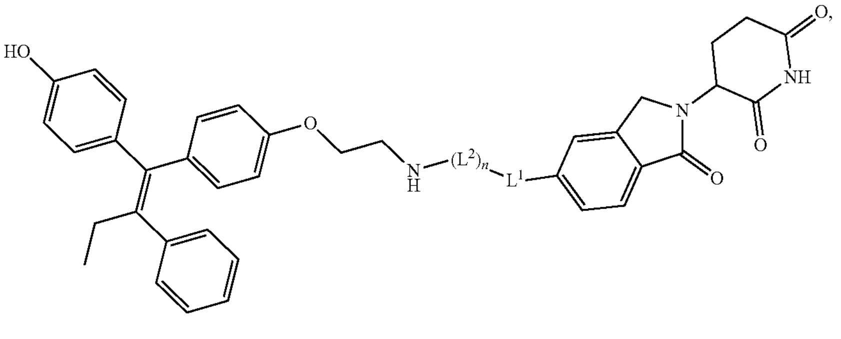

(B)

or a pharmaceutically acceptable salt thereof, wherein:

$L^1$ is $C_{1-3}$ alkylene, optionally substituted with 1, 2, or 3 substituents independently selected from OH, $NO_2$, CN, halo, amino, and carboxy;

n is an integer selected from 1 to 10;

each $L^2$ is independently selected from C(═O), N($R^N$), O, (—$C_{1-3}$ alkylene-O—$)_x$, (—O—$C_{1-3}$ alkylene-$)_x$, —$C_{1-3}$ alkylene-, and 4-6 membered heterocycloalkylene, wherein each x is independently an integer from 1 to 10, wherein said $C_{1-3}$ alkylene and 4-6 membered heterocycloalkylene are each optionally substituted with 1, 2, or 3 substituents independently selected from OH, $NO_2$, CN, halo, amino, and carboxy, and wherein each $R^N$ is independently selected from H and $C_{1-3}$ alkyl, or wherein said bifunctional compound has Formula (X):

(X)

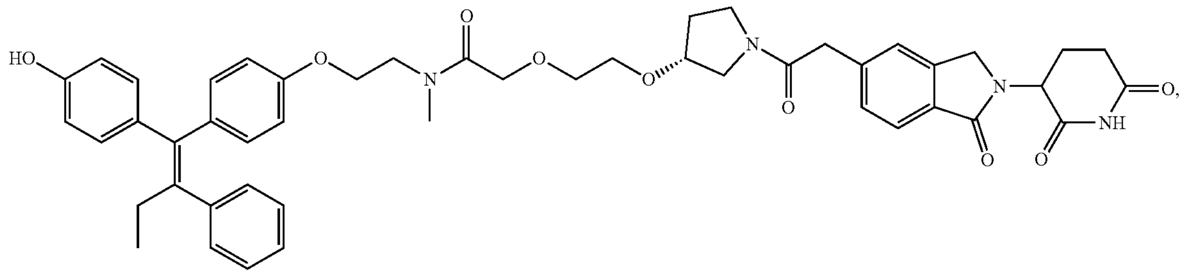

or a pharmaceutically acceptable salt thereof, or wherein said bifunctional compound is a compound of Formula (C):

(C)

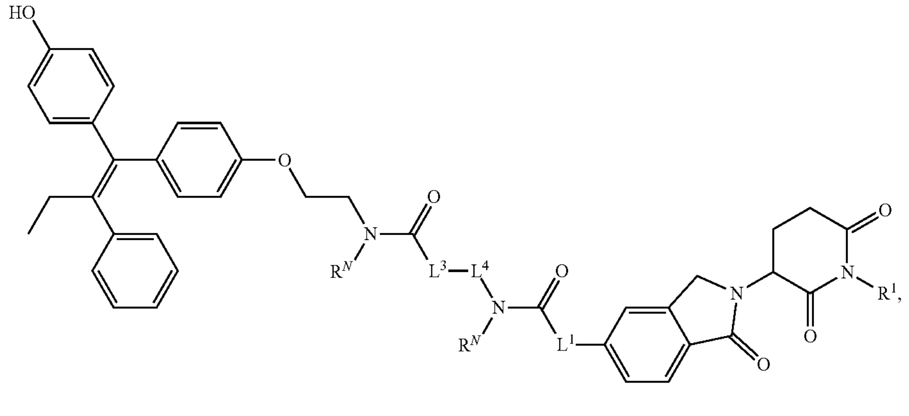

or a pharmaceutically acceptable salt thereof, wherein:

each $R^N$ is independently selected from H and $C_{1-3}$ alkyl;

$L^1$ is $C_{1-3}$ alkylene;

$L^3$ is $C_{1-3}$ alkylene and $L^4$ is (—O—$C_{1-3}$ alkylene-$)_x$; and $R^1$ is $C_{1-3}$ alkyl substituted with —OC(═O)O—$C_{1-6}$ alkyl, or wherein said bifunctional compound has Formula (XI) or Formula (XII):

(XI)

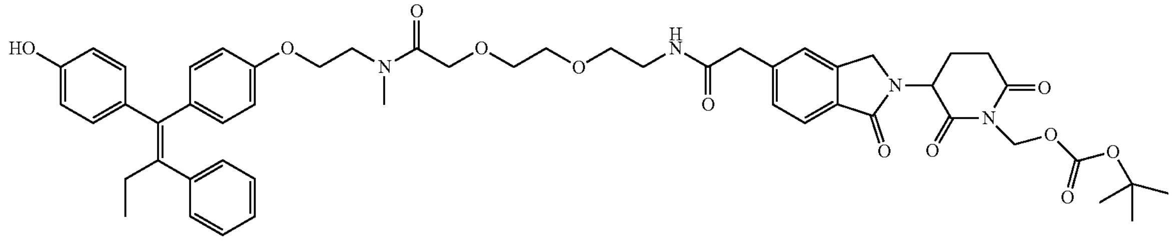

,

-continued (XII)

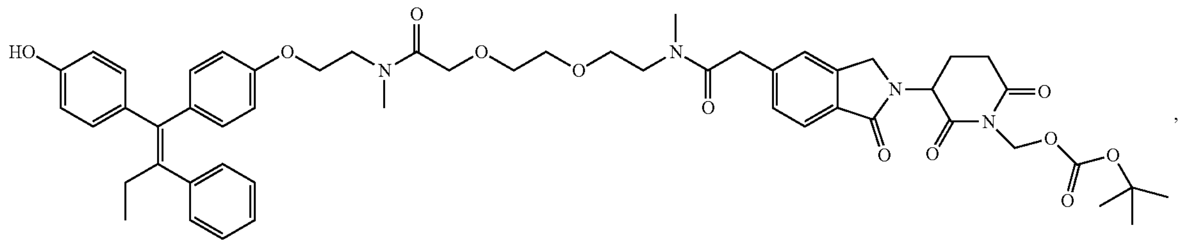

, or a pharmaceutically acceptable salt thereof.

8. The method of claim 1, wherein said ER− cancer cell is in a tumor within a mammal.

9. The method of claim 8, wherein said mammal is a human.

10. A method for treating a mammal identified as having ER− cancer, wherein said method comprises administering to said mammal a composition comprising a bifunctional compound, wherein said bifunctional compound comprises:

(a) a first molecule component capable of interacting with a PKCβ1 polypeptide, (b) a second molecule component capable of interacting with an E3 ubiquitin ligase polypeptide, and (c) a linker covalently coupling said first molecule component to said second molecule component, wherein said bifunctional compound is a compound of Formula (A):

(A)

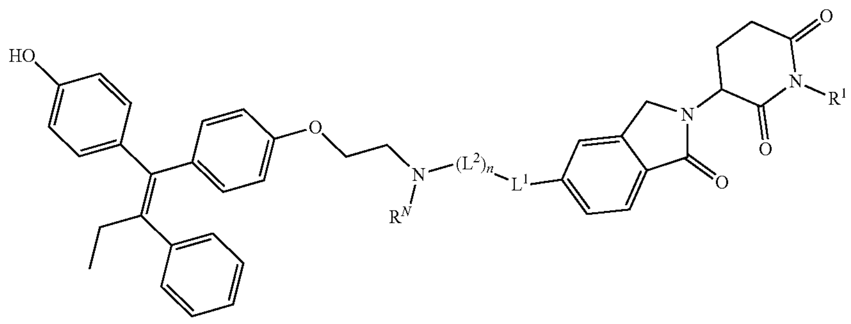

or a pharmaceutically acceptable salt thereof, wherein:

$L^1$ is $C_{1-3}$ alkylene, optionally substituted with 1, 2, or 3 substituents independently selected from OH, $NO_2$, CN, halo, amino, and carboxy;

n is an integer selected from 1 to 10:

each $L^2$ is independently selected from C(═O), N($R^N$), O, (—$C_{1-3}$ alkylene-O—$)_x$, (—O—$C_{1-3}$ alkylene-$)_x$, —$C_{1-3}$ alkylene-, and 4-6 membered heterocycloalkylene, wherein each x is independently an integer from 1 to 10, and wherein said $C_{1-3}$ alkylene and 4-6 membered heterocycloalkylene are each optionally substituted with 1, 2, or 3 substituents independently selected from OH, $NO_2$, CN, halo, amino, and carboxy;

each $R^N$ is independently selected from H and $C_{1-3}$ alkyl; and $R^1$ is selected from H and $C_{1-3}$ alkyl, optionally substituted with a group selected from —OC(═O)O—$C_{1-6}$ alkyl, —OC(═O)$NH_2$, —OC(═O)NH($C_{1-6}$ alkyl), —OC(═O)N($C_{1-6}$ alkyl$)_2$, NHC(═O)O—$C_{1-6}$ alkyl, NHC(═O)$NH_2$, NHC(═O)NH($C_{1-6}$ alkyl), and NHC(═O)N($C_{1-6}$ alkyl$)_2$.

11. The method of claim 10, wherein said cancer is a breast cancer or an ovarian cancer.

12. The method of claim 10, $R^N$ as shown in the compound of Formula (A), independent from $R^N$ in $L^2$, is H.

13. The method of claim 10, wherein said bifunctional compound has an $IC_{50}$ of less than 500 nM in a crystal violet proliferation assay using triple negative cells.

14. The method of claim 13, wherein said triple negative cells are BT549 cells or MDAMB436 cells.

15. The method of claim 10, wherein said bifunctional compound is a compound of Formula (I):

(I)

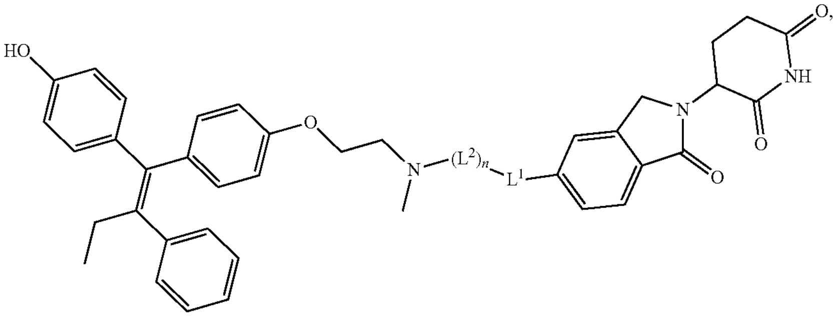

or a pharmaceutically acceptable salt thereof, wherein:

$L^1$ is $C_{1-3}$ alkylene, optionally substituted with 1, 2, or 3 substituents independently selected from OH, $NO_2$, CN, halo, amino, and carboxy;

n is an integer selected from 1 to 10;

each $L^2$ is independently selected from C(=O), N($R^N$), O, (—$C_{1-3}$ alkylene-O—$)_x$, (—O—$C_{1-3}$ alkylene-$)_x$, and —$C_{1-3}$ alkylene-, wherein each x is independently an integer from 1 to 10 and each $C_{1-3}$ alkylene is optionally substituted with 1, 2, or 3 substituents independently selected from OH, $NO_2$, CN, halo, amino, and carboxy; and each $R^N$ is independently selected from H and $C_{1-3}$ alkyl;

or wherein said compound has Formula (II):

(II)

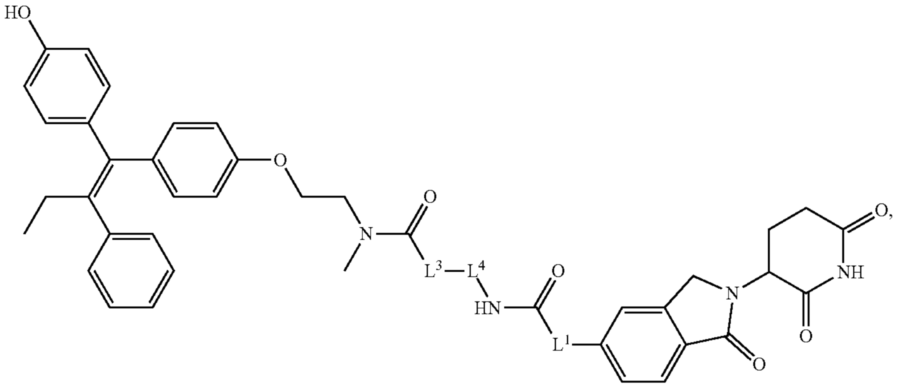

or a pharmaceutically acceptable salt thereof, wherein:

$L^3$ is $C_{1-3}$ alkylene; and $L^4$ is (—O—$C_{1-3}$ alkylene-$)_x$;

or wherein said compound has Formula (III), Formula (IV), or Formula (V):

(III)

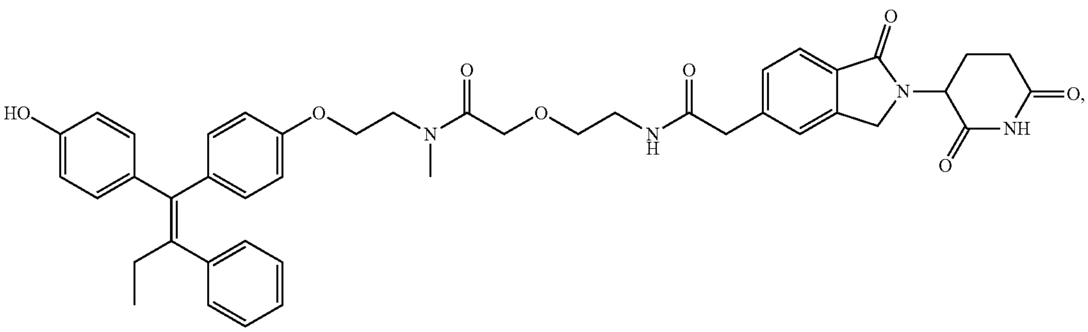

-continued
(IV)
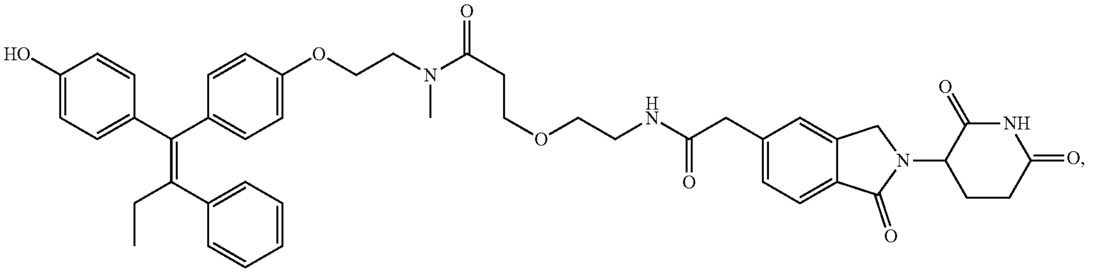
(V)
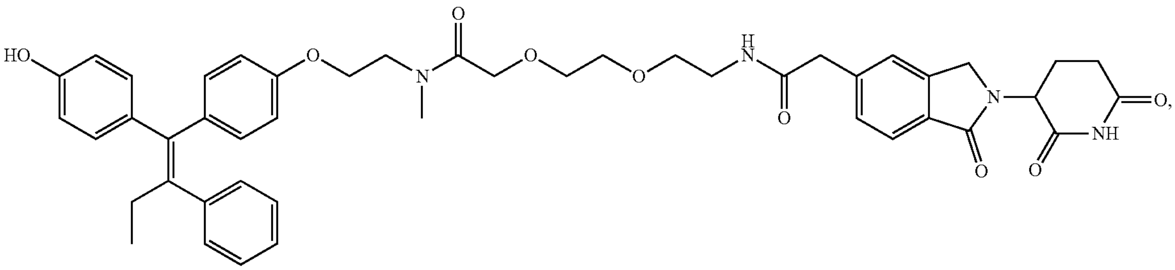
or a pharmaceutically acceptable salt thereof;
or wherein said bifunctional compound has Formula (VI):
(VI)
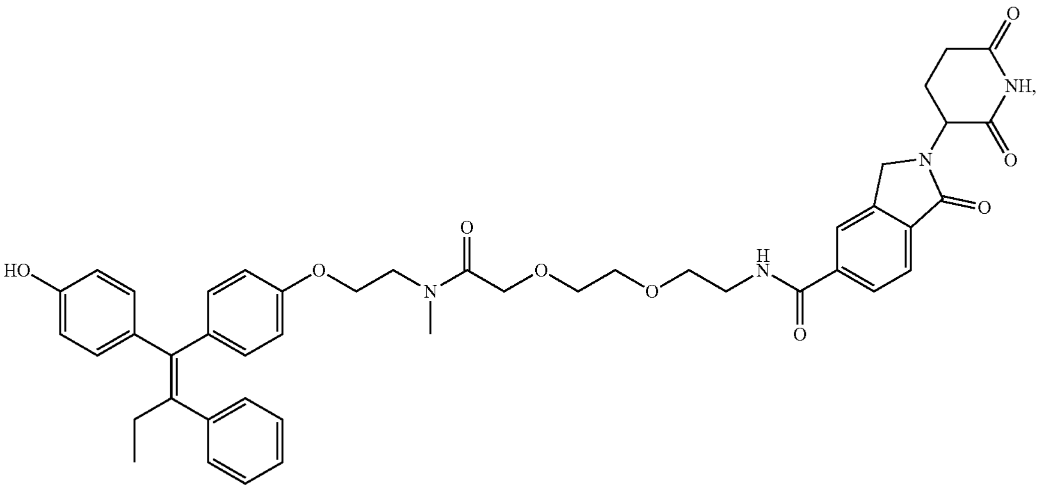
or a pharmaceutically acceptable salt thereof,
or wherein said compound has Formula (VII), Formula (VIII), or Formula (IX):
(VII)
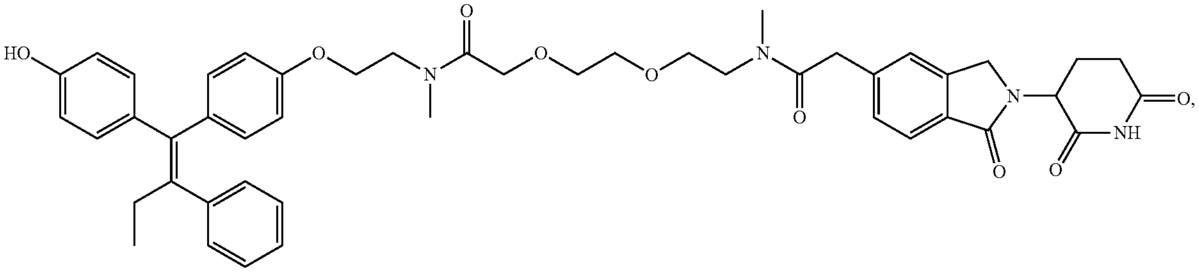

-continued (VIII)

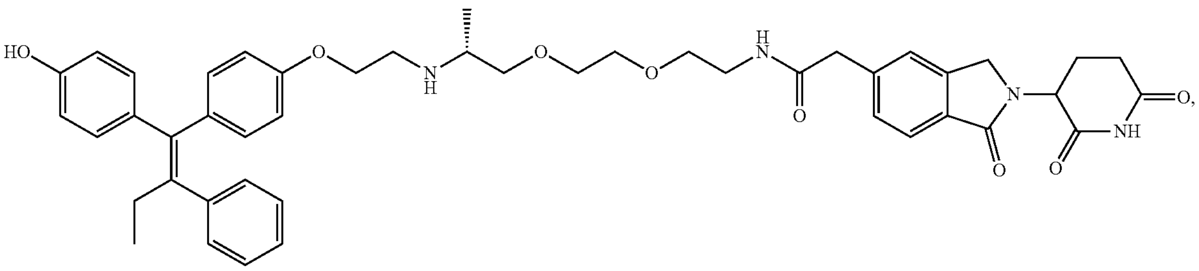

(IX)

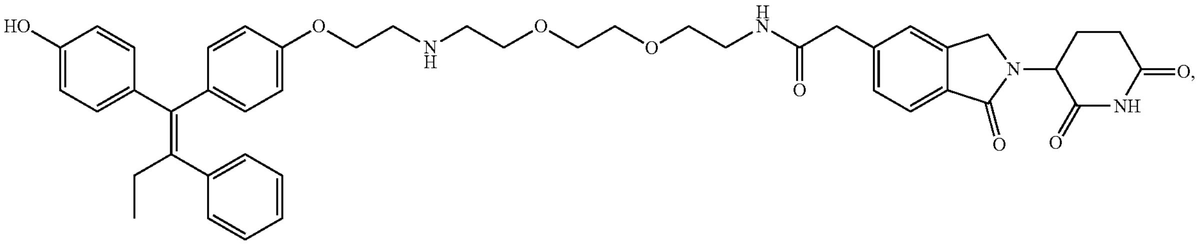

or a pharmaceutically acceptable salt thereof.

16. The method of claim 10, wherein said bifunctional compound is a compound of Formula (B):

(B)

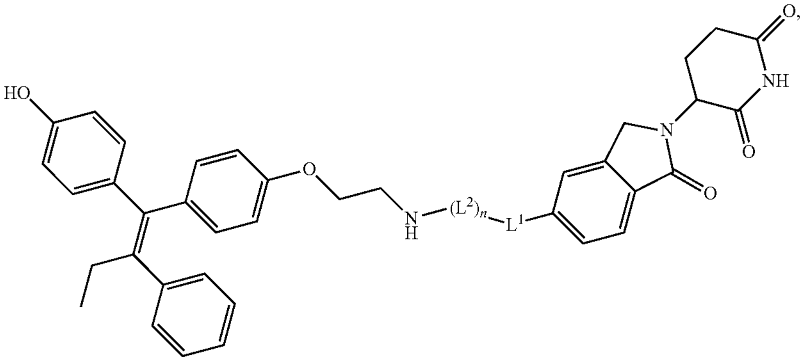

or a pharmaceutically acceptable salt thereof, wherein:

$L^1$ is $C_{1-3}$ alkylene, optionally substituted with 1, 2, or 3 substituents independently selected from OH, $NO_2$, CN, halo, amino, and carboxy;

n is an integer selected from 1 to 10;

each $L^2$ is independently selected from C(=O), N($R^N$), O, (—$C_{1-3}$ alkylene-O—$)_x$, (—O—$C_{1-3}$ alkylene-$)_x$, —$C_{1-3}$ alkylene-, and 4-6 membered heterocycloalkylene, wherein each x is independently an integer from 1 to 10, wherein said $C_{1-3}$ alkylene and 4-6 membered heterocycloalkylene are each optionally substituted with 1, 2, or 3 substituents independently selected from OH, $NO_2$, CN, halo, amino, and carboxy, and wherein each $R^N$ is independently selected from H and $C_{1-3}$ alkyl, or wherein said bifunctional compound has Formula (X):

(X)

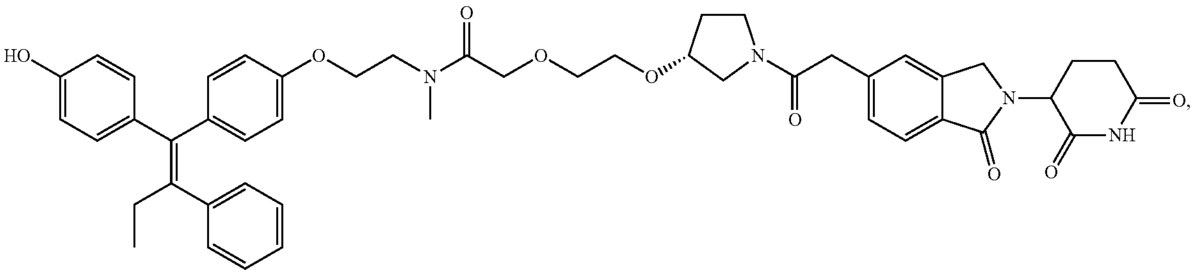

or a pharmaceutically acceptable salt thereof, or wherein said bifunctional compound is a compound of Formula (C):

(C)

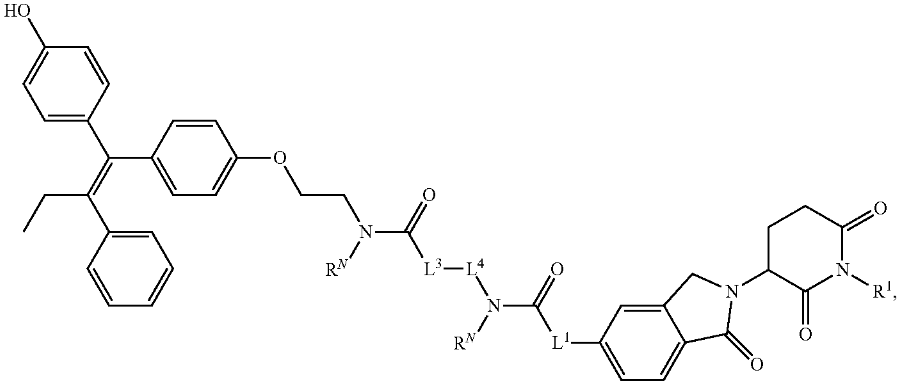

or a pharmaceutically acceptable salt thereof, wherein:

each $R^N$ is independently selected from H and $C_{1-3}$ alkyl;

$L^1$ is $C_{1-3}$ alkylene;

$L^3$ is $C_{1-3}$ alkylene and $L^4$ is $(—O—C_{1-3}\text{ alkylene-})_x$; and $R^1$ is $C_{1-3}$ alkyl substituted with $—OC(=O)O—C_{1-6}$ alkyl, or wherein said bifunctional compound has Formula (XI) or Formula (XII):

(XI)

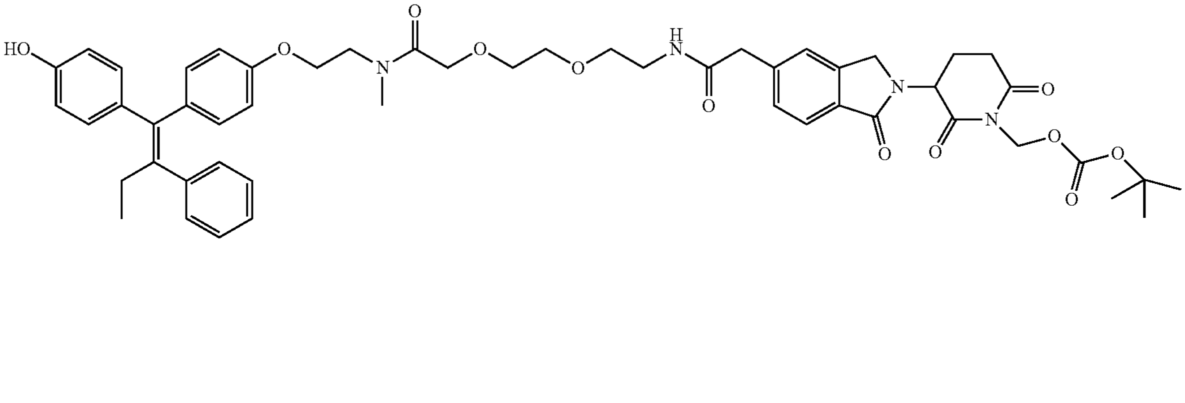

,

-continued (XII)

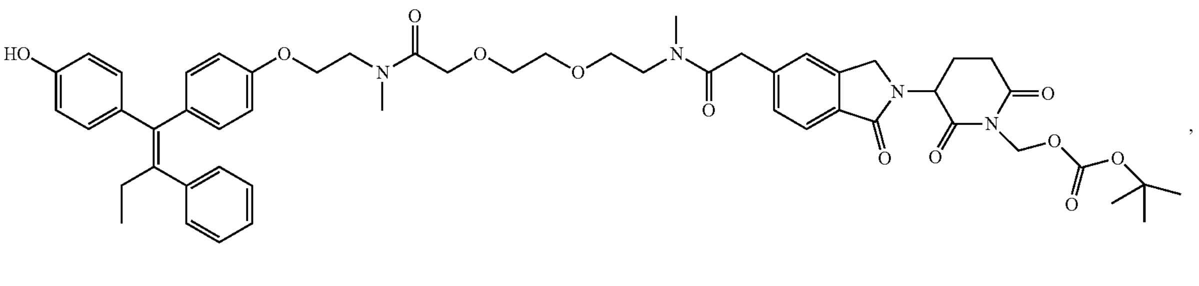

or a pharmaceutically acceptable salt thereof.

17. The method of claim 10, wherein said mammal is a human.

18. A compound of Formula (A):

(A)

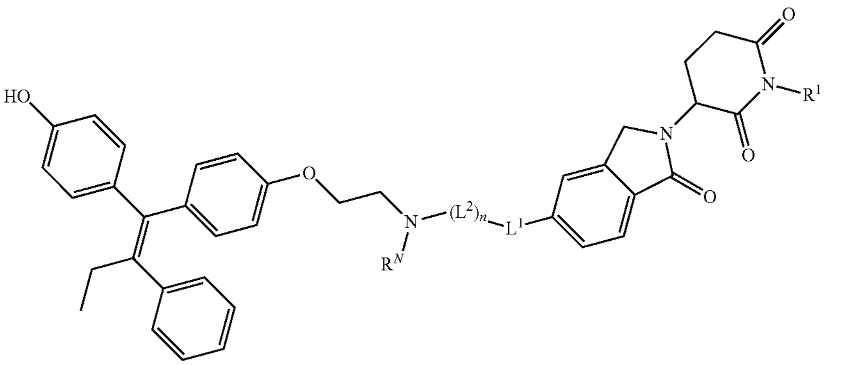

or a pharmaceutically acceptable salt thereof, wherein:

$L^1$ is $C_{1-3}$ alkylene, optionally substituted with 1, 2, or 3 substituents independently selected from OH, $NO_2$, CN, halo, amino, and carboxy;

n is an integer selected from 1 to 10;

each $L^2$ is independently selected from C(═O), $N(R^N)$, O, $(—C_{1-3}$ alkylene-O—$)_x$, $(—O—C_{1-3}$ alkylene-$)_x$, $—C_{1-3}$ alkylene-, and 4-6 membered heterocycloalkylene, wherein each x is independently an integer from 1 to 10, and wherein said $C_{1-3}$ alkylene and 4-6 membered heterocycloalkylene are each optionally substituted with 1, 2, or 3 substituents independently selected from OH, $NO_2$, CN, halo, amino, and carboxy;

each $R^N$ is independently selected from H and $C_{1-3}$ alkyl; and $R^1$ is selected from H and $C_{1-3}$ alkyl, optionally substituted with a group selected from —OC(═O)O—$C_{1-6}$ alkyl, —OC(═O)$NH_2$, —OC(═O)NH($C_{1-6}$ alkyl), —OC(═O)N($C_{1-6}$ alkyl)$_2$, NHC(═O)O—$C_{1-6}$ alkyl, NHC(═O)$NH_2$, NHC(═O)NH($C_{1-6}$ alkyl), and NHC(═O)N($C_{1-6}$ alkyl)$_2$.

19. The compound of claim 18, wherein said compound has Formula (I):

(I)

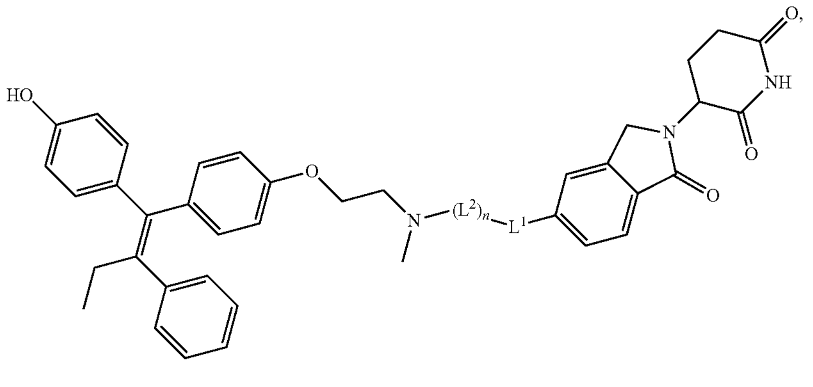

or a pharmaceutically acceptable salt thereof, wherein:

$L^1$ is $C_{1-3}$ alkylene, optionally substituted with 1, 2, or 3 substituents independently selected from OH, $NO_2$, CN, halo, amino, and carboxy;

n is an integer selected from 1 to 10;

each $L^2$ is independently selected from C(═O), N($R^N$), O, (—$C_{1-3}$ alkylene-O—$)_x$, (—O—$C_{1-3}$ alkylene-$)_x$, and —$C_{1-3}$ alkylene-, wherein each x is independently an integer from 1 to 10 and each $C_{1-3}$ alkylene is optionally substituted with 1, 2, or 3 substituents independently selected from OH, $NO_2$, CN, halo, amino, and carboxy; and each $R^N$ is independently selected from H and $C_{1-3}$ alkyl;

or wherein said compound has Formula (II):

(II)

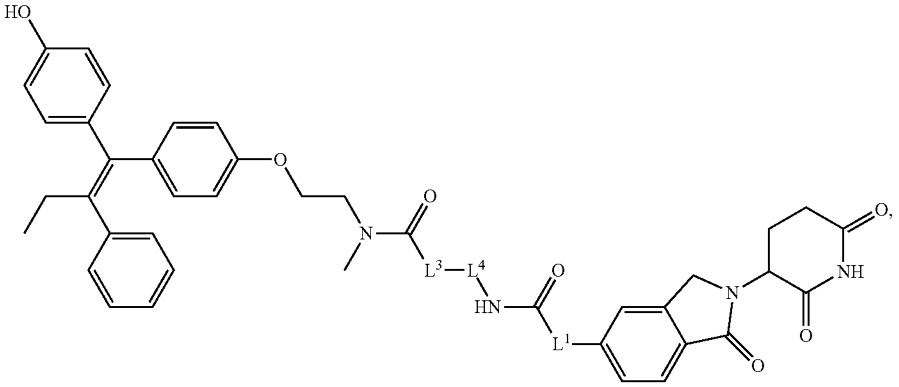

or a pharmaceutically acceptable salt thereof, wherein:

$L^3$ is $C_{1-3}$ alkylene; and $L^4$ is (—O—$C_{1-3}$ alkylene-$)_x$;

or wherein said compound has Formula (III), Formula (IV), or Formula (V):

(III)

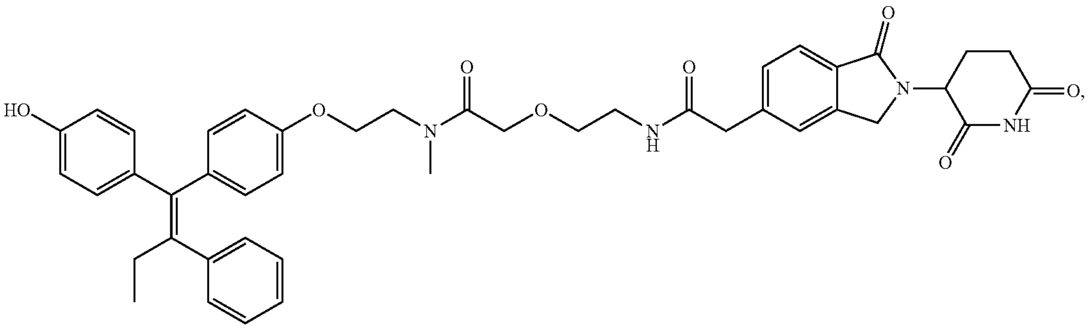

(IV)

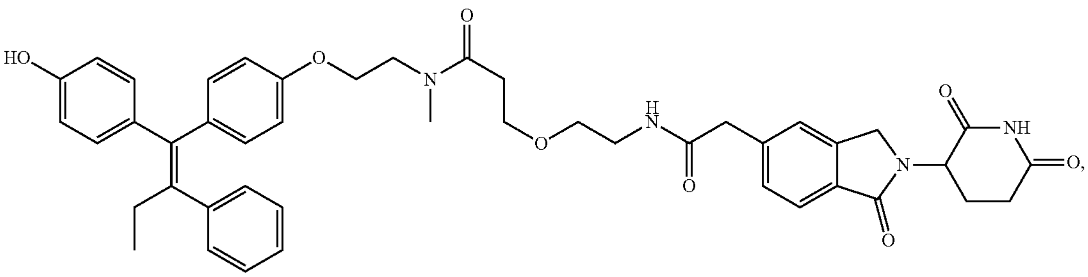

-continued
(V)
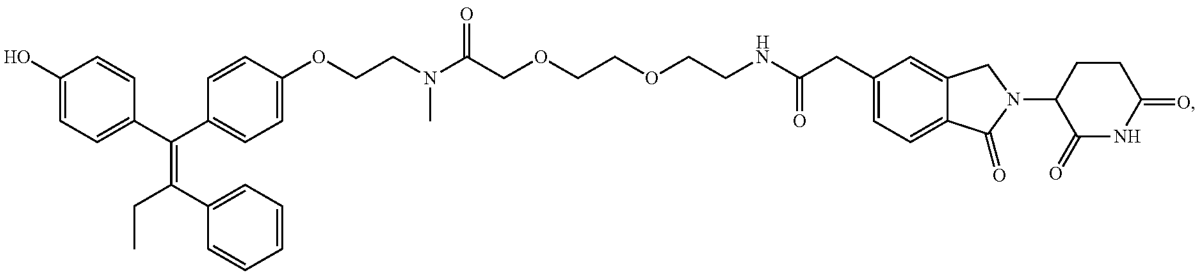
or a pharmaceutically acceptable salt thereof:
or wherein said compound has Formula (VI):
(VI)
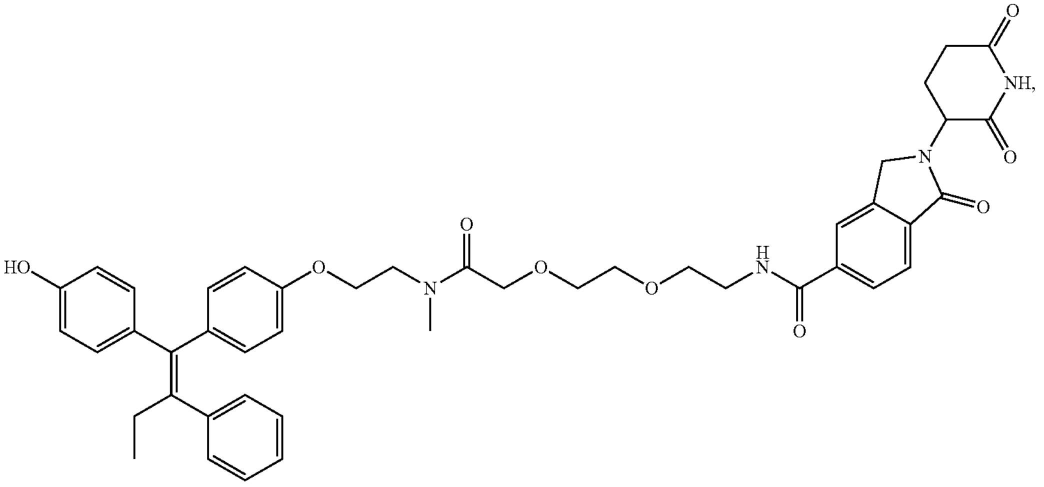
or a pharmaceutically acceptable salt thereof,
or wherein said compound has Formula (VII), Formula (VIII), or Formula (IX):
(VII)
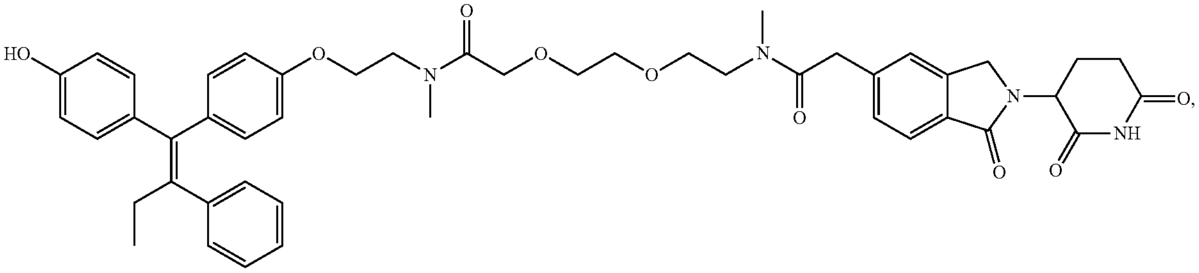

-continued (VIII)

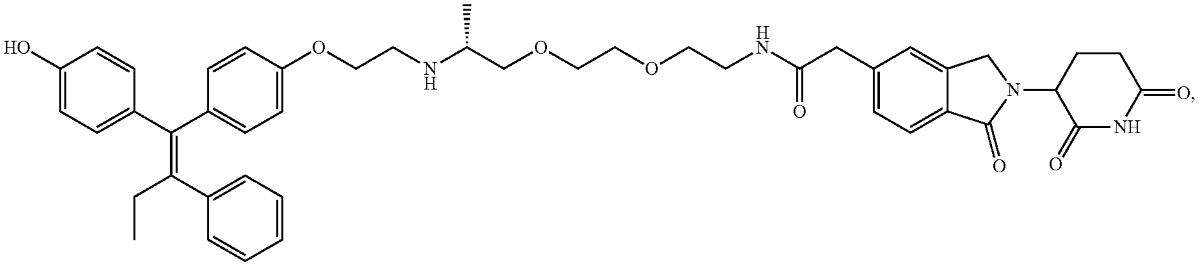

(IX)

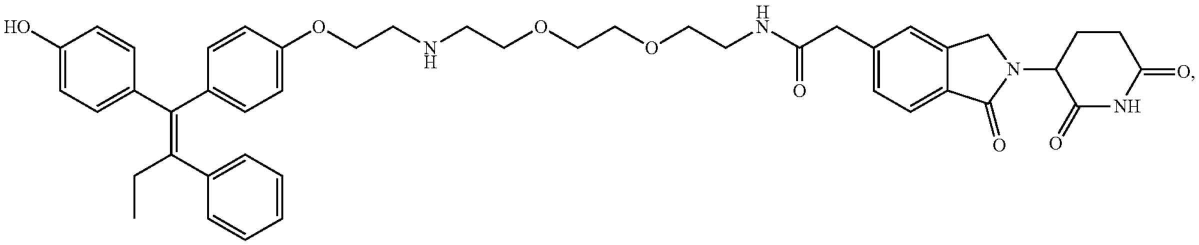

or a pharmaceutically acceptable salt thereof.

20. The compound of claim 18, wherein said compound has Formula (B):

(B)

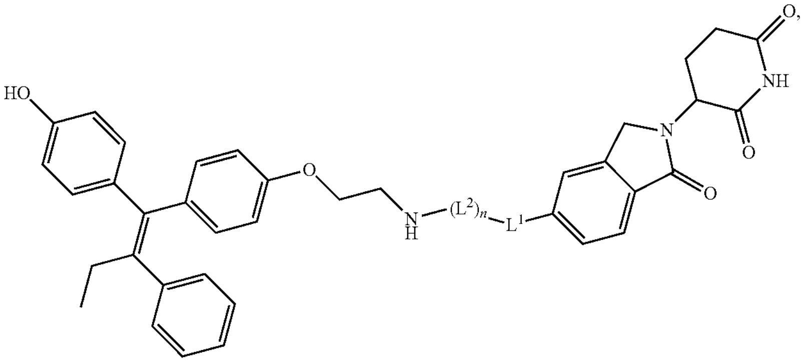

or a pharmaceutically acceptable salt thereof, wherein:

$L^1$ is $C_{1-3}$ alkylene, optionally substituted with 1, 2, or 3 substituents independently selected from OH, $NO_2$, CN, halo, amino, and carboxy;

n is an integer selected from 1 to 10;

each $L^2$ is independently selected from C(=O), $N(R^N)$, O, (—$C_{1-3}$ alkylene-O—)$_x$, (—O—$C_{1-3}$ alkylene-)$_x$, —$C_{1-3}$ alkylene-, and 4-6 membered heterocycloalkylene, wherein each x is independently an integer from 1 to 10, wherein said $C_{1-3}$ alkylene and 4-6 membered heterocycloalkylene are each optionally substituted with 1, 2, or 3 substituents independently selected from OH, $NO_2$, CN, halo, amino, and carboxy, and wherein each $R^N$ is independently selected from H and $C_{1-3}$ alkyl, or wherein said bifunctional compound has Formula (X):

(X)

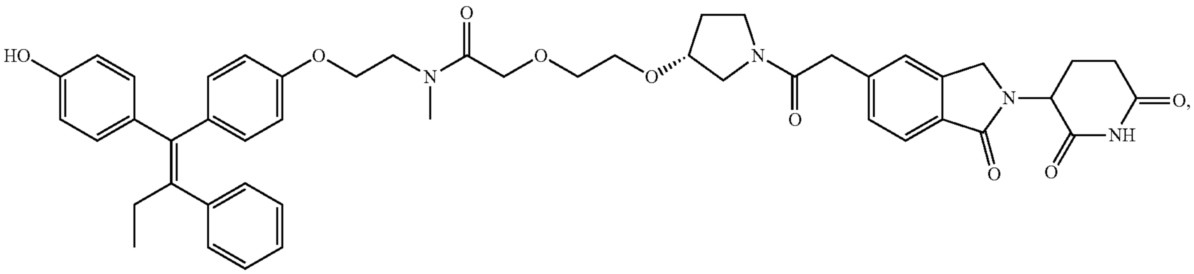

or a pharmaceutically acceptable salt thereof, or wherein said bifunctional compound is a compound of Formula (C):

(C)

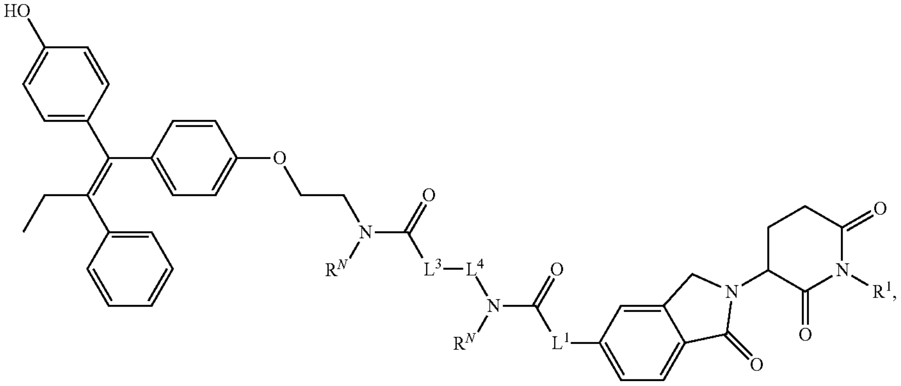

or a pharmaceutically acceptable salt thereof, wherein:

each $R^N$ is independently selected from H and $C_{1-3}$ alkyl;

$L^1$ is $C_{1-3}$ alkylene;

$L^3$ is $C_{1-3}$ alkylene and $L^4$ is $(—O—C_{1-3}\ alkylene-)_x$; and $R^1$ is $C_{1-3}$ alkyl substituted with $—OC(═O)O—C_{1-6}$ alkyl, or wherein said bifunctional compound has Formula (XI) or Formula (XII):

(XI)

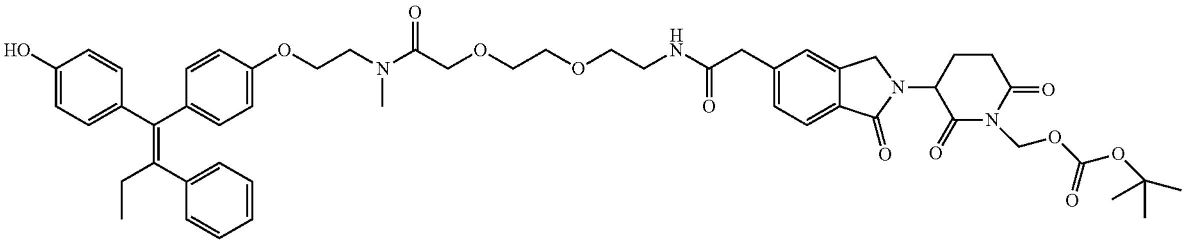

,

-continued
(XII)
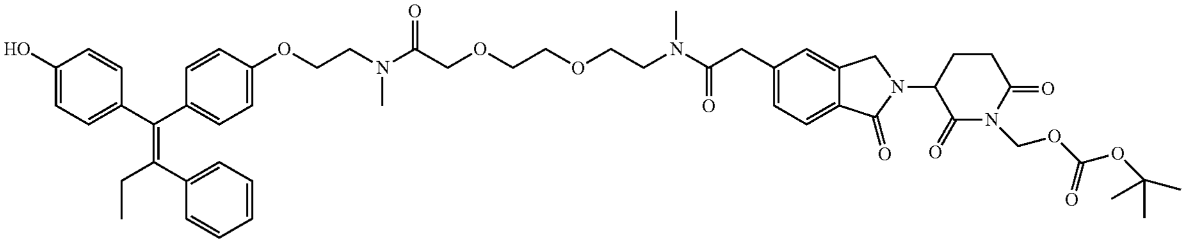
,
or a pharmaceutically acceptable salt thereof.
21. A composition comprising a pharmaceutically acceptable carrier and a bifunctional compound of claim 18.
* * * * *